(12) United States Patent
Barbier et al.

(10) Patent No.: US 8,653,068 B2
(45) Date of Patent: Feb. 18, 2014

(54) FILAMIN A BINDING ANTI-INFLAMMATORY AND ANALGESIC

(75) Inventors: Lindsay Burns Barbier, Palo Alto, CA (US); Hoau-Yan Wang, Philadelphia, PA (US); Nan-Horng Lin, Vernon Hills, IL (US); Andrei Blasko, San Bruno, CA (US)

(73) Assignee: Pain Therapeutics, Inc., Austin, TX (US)

( * ) Notice: Subject to any disclaimer, the term of this patent is extended or adjusted under 35 U.S.C. 154(b) by 0 days.

(21) Appl. No.: 12/610,091

(22) Filed: Oct. 30, 2009

(65) Prior Publication Data

US 2011/0105487 A1     May 5, 2011

(51) Int. Cl.
*A61K 31/535* (2006.01)
*A61K 31/505* (2006.01)
*A61K 31/44* (2006.01)

(52) U.S. Cl.
USPC .................. 514/228.8; 514/269; 514/278

(58) Field of Classification Search
None
See application file for complete search history.

(56) References Cited

U.S. PATENT DOCUMENTS

| | | | |
|---|---|---|---|
| 5,852,029 | A | 12/1998 | Fisher et al. |
| 5,869,496 | A | 2/1999 | Hale et al. |
| 6,060,469 | A | 5/2000 | Baker et al. |
| 7,049,321 | B2 | 5/2006 | Fisher et al. |
| 7,951,815 | B2 | 5/2011 | Sundermann et al. |
| 2004/0192916 | A1 | 9/2004 | Buschmann et al. |
| 2007/0015783 | A1 | 1/2007 | Sundermann et al. |
| 2007/0117824 | A1* | 5/2007 | Berk et al. ............ 514/278 |

FOREIGN PATENT DOCUMENTS

WO     WO 2010/051476 A1     5/2010

OTHER PUBLICATIONS

Anderson (Chem and Biol 10:787-797, 2003).*
Thiel (Nature Biotechnol 2:513-519, 2004).*
STN Search Report (Accession No. 2007:564923).*
Tondeur et al (Bulletin de la Societe Chimique de France 10:2493-2499. 1964—based on the attached STN Search Report (Accession No. 1965:29665)).*
CAS RN 1070805-65-0 (Nov. 4, 2008).*
ZINC12342403 Compound Summary—NCBI PubChem Chemical Database, (Nov. 2007).
Written Opinion and Preliminary Report for PCT/US2009/062823.
Written Opinion and Preliminary Report for PCT/US2009/062860.

* cited by examiner

*Primary Examiner* — Craig Ricci
(74) *Attorney, Agent, or Firm* — Husch Blackwell, LLP

(57) ABSTRACT

A compound or its pharmaceutically acceptable salt, composition and method are disclosed that can provide analgesia and reduce inflammation. A contemplated compound has a structure that corresponds to Formula A, wherein the R group substituents, d, e, f, k, n, m, D, E, F, K, G, P, Q, W, and Z are defined within.

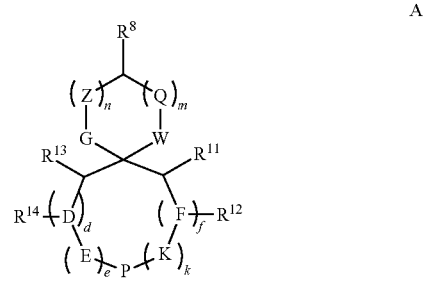

5 Claims, No Drawings

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial sequence
<220> FEATURE:
<223> OTHER INFORMATION: chemically synthesized FLNA sequence that
      corresponds to amino acid residue positions 2561-2565 of the FLNA
      protein

<400> SEQUENCE: 1

Val Ala Lys Gly Leu
1               5
```

FILAMIN A BINDING ANTI-INFLAMMATORY AND ANALGESIC

CROSS-REFERENCE TO RELATED APPLICATION

This applications claims priority from application Ser. No. 12/435,304 that was filed on May 4, 2009, as well as Ser. No. 12/263,257 that was filed on Oct. 31, 2008, whose disclosures are incorporated herein by reference.

TECHNICAL FIELD

This invention contemplates a composition and related method for providing long-lasting analgesia and reducing inflammation. More particularly, a compound, composition and method are described that utilize a small molecule to bind filamin A, to reduce inflammation and to preserve Gi/o signaling by the mu opioid receptor, known to interact with filamin A. Preferably, the compound reduces inflammation, preserves mu opioid receptor-Gi/o signaling and also functions as a mu opioid receptor agonist. Most preferably, the compound binds filamin A with picomolar or sub-picomolar affinity.

BACKGROUND OF THE INVENTION

Best known for cross-linking cytoplasmic actin into dynamic scaffolds to control cell motility, filamins are large cytoplasmic proteins increasingly found to regulate cell signaling by interacting with over 30 different receptors and signaling molecules (Feng et al., 2004 Nat Cell Biol 6:1034-1038; Stossel et al., 2001 Nature 2:138-145), including the mu opioid receptor (MOR) (Onoprishvili et al, 2003 Mol Pharmacol 64:1092-1100). Filamins are dimerized through the last carboxy-terminal repeat near the transmembrane regions, allowing an intracellular V-shaped structure that is critical for function. There are three mammalian isoforms: filamin A (FLNA), B and C.

FLNA controls cell motility by controlling the cycle of actin polymerization and depolymerization, allowing cells to move and to migrate. As actin depolymerization is linked to the inflammatory response, binding to FLNA suppresses inflammation by slowing actin polymerization and cell motility. Femtomolar naloxone and its inactive isomer, both known to bind FLNA (Wang et al., 2008 PLoS One 3:e1554), have been shown to reduce the microglial inflammatory response; i.e., pro-inflammatory factors and reactive oxygen species, of lipopolysaccaride-activated microglial cells (Liu et al, 2000 JPET 293:607-617; Qin et al., 2005 FASEB J 19:550-557). The glial inflammatory response has been implicated in neuropathic pain (Hutchinson et al., 2008 Eur J Neurosci 28:20-29) as well as the inflammatory neurotoxicity of neurodegenerative disease (Liu et al., 2003 JPET 304:1-7).

A second function of binding to FLNA is a beneficial regulation of opioid receptor signaling; i.e., a maintenance of coupling to Gi and Go proteins. MOR preferentially couples to pertussis toxin-sensitive G proteins, Gi/o (inhibitory/other), and inhibits the adenylyl cyclase/cAMP pathway (Laugwitz et al., 1993 Neuron 10:233-242; Connor et al., 1999 Clin Exp Pharmacol Physiol 26:493-499). Analgesia results from these MOR-linked inhibitory G protein (Gi/o) signaling cascades and related ion channel interactions that suppress cellular activities by hyperpolarization.

Adaptive responses of opioid receptors contribute to the development of analgesic tolerance and physical dependence, and possibly also to components of opioid addiction. A critical adaptive response of the MOR is a switch in G protein coupling from its native Gi/o proteins to stimulatory Gs proteins, resulting in opposite effects on the cell upon activation as well as analgesic tolerance and physical dependence (Wang et al., 2005 Neuroscience 135:247-261). Prevention of this G protein coupling switch by agents that bind filamin A (Wang et al, 2008 PLoS One 3:e1554), a scaffolding protein known to interact with MOR, can alleviate unwanted adaptive responses to continued opioid administration.

A chronic opioid-induced switch to Gs coupling by MOR can cause excitatory signaling, by activation of adenylyl cyclase, in place of the usual inhibitory signaling or inhibition of adenylyl cyclase (Crain et al., 1992 Brain Res 575:13-24; Crain et al., 2000 Pain 84:121-131; Gintzler et al., 2001 Mol Neurobiol 21:21-33; Wang et al., 2005 Neuroscience 135: 247-261). This switch in G protein coupling from Gi/o to Gs (Wang et al., 2005 Neuroscience 135:247-261; Chakrabarti et al., 2005 Mol Brain Res 135:217-224) may be a result of the decreased efficiency of coupling to the native G proteins, the usual index of desensitization (Sim et al., 1996 J Neurosci 16:2684-2692) and still commonly considered the reason for analgesic tolerance.

The chronic opioid-induced MOR-G protein coupling switch is accompanied by stimulation of adenylyl cyclase II and IV by MOR-associated G$\beta\gamma$ dimers (Chakrabarti et al., 1998 Mol Pharmacol 54:655-662; Wang et al., 2005 Neuroscience 135:247-261). The interaction of the G$\beta\gamma$ dimer with adenylyl cyclase had previously been postulated to be the sole signaling change underlying the excitatory effects of opiates (Gintzler et al., 2001 Mol Neurobiol 21:21-33). It has further been shown that the G$\beta\gamma$ that interacts with adenylyl cyclases originates from the Gs protein coupling to MOR and not from the Gi/o proteins native to MOR (Wang et al., 2006 J Neurobiol 66:1302-1310).

Thus, MORs are normally inhibitory G protein-coupled receptors that couple to Gi or Go proteins to inhibit adenylyl cyclase and decrease production of the second messenger cAMP, as well as to suppress cellular activities via ion channel-mediated hyperpolarization. Opioid analgesic tolerance and dependence are also associated with that switch in G protein coupling by MOR from Gi/o to Gs (Wang et al., 2005 Neuroscience 135:247-261). This switch results in activation of adenylyl cyclase that provides essentially opposite, stimulatory, effects on the cell.

Controlling this switch in G protein coupling by MOR is the scaffolding protein FLNA, and compounds that bind a particular segment of FLNA with high affinity, like naloxone (NLX) and naltrexone (NTX), can prevent this switch (Wang et al, 2008 PLoS One 3:e1554) and the associated analgesic tolerance and dependence (Wang et al., 2005 Neuroscience 135:247-261). This switch in G protein coupling also occurs acutely, though transiently, and is potentially linked to the acute rewarding or addictive effects of opioid drugs, through CREB activation as a result of increased cAMP accumulation (Wang et al., 2009 PLoS ONE 4 (1):e4282).

Ultra-low-dose NLX or NTX have been shown to enhance opioid analgesia, minimize opioid tolerance and dependence (Crain et al., 1995 Proc Natl Acad Sci USA 92:10540-10544; Powell et al. 2002. JPET 300:588-596), as well as to attenuate the addictive properties of opioids (Leri et al., 2005 Pharmacol Biochem Behav 82:252-262; Olmstead et al., 2005 Psychopharmacology 181:576-581). An ultra-low dose of opioid antagonist was an amount initially based on in vitro studies of nociceptive dorsal root ganglion neurons and on in vivo mouse studies. It has long been hypothesized that ultra-low-dose opioid antagonists enhance analgesia and alleviate tolerance/dependence by blocking the excitatory signaling opioid receptors that underlie opioid tolerance and hyperalgesia (Crain et al., 2000 *Pain* 84:121-131). Later research has shown that the attenuation of opioid analgesic tolerance, dependence and addictive properties by ultra-low-dose, defined herein, naloxone or naltrexone, occurs by preventing the MOR-Gs coupling that results from chronic opiate administration (Wang et al., 2005 *Neuroscience* 135:247-261), and that the prevention of MOR-Gs coupling is a result of NLX or NTX binding to filamin A at approximately 4 picomolar affinity (Wang et al, 2008 *PLoS One* 3:e1554).

Found in all cells of the brain, CREB is a transcription factor implicated in addiction as well as learning and memory and several other experience-dependent, adaptive (or maladaptive) behaviors (Carlezon et al., 2005 *Trends Neurosci* 28:436-445). In general, CREB is inhibited by acute opioid treatment, an effect that is completely attenuated by chronic opioid treatment, and activated during opioid withdrawal (Guitart et al., 1992 *J Neurochem* 58:1168-1171). However, a regional mapping study showed that opioid withdrawal activates CREB in locus coeruleus, nucleus accumbens and amygdala but inhibits CREB in lateral ventral tegemental area and dorsal raphe nucleus (Shaw-Luthman et al., 2002 *J Neurosci* 22:3663-3672).

In the striatum, CREB activation has been viewed as a homeostatic adaptation, attenuating the acute rewarding effects of drugs (Nestler, 2001 *Am J Addict* 10:201-217; Nestler, 2004 *Neuropharmacology* 47:24-32). This view is supported by nucleus accumbens overexpression of CREB or a dominant-negative mutant respectively reducing or increasing the rewarding effects of opioids in the conditioned place preference test (Barot et al., 2002 *Proc Natl Acad Sci USA* 99:11435-11440). In conflict with this view, however, is the finding that reducing nucleus accumbens CREB via antisense attenuated cocaine reinforcement as assessed in self-administration (Choi et al., 2006 *Neuroscience* 137:373-383). Clearly, CREB activation is implicated in addiction, but whether it directly contributes to the acute rewarding effects of drugs or initiates a homeostatic regulation thereof appears less clear.

The several-fold increase in pS$^{133}$CREB reported by Wang et al., 2009 *PLoS ONE* 4 (1):e4282 following acute, high-dose morphine may indicate acute dependence rather than acute rewarding effects. However, the transient nature of the MOR-Gs coupling correlating with this CREB activation suggests otherwise. In fact, the correlation of pS$^{133}$CREB with the Gs coupling by MOR following this acute high-dose morphine exposure, as well as the similar treatment effects on both, suggest that this alternative signaling mode of MOR can contribute to the acute rewarding or addictive effects of opioids. This counterintuitive notion can explain the apparent paradox that ultra-low-dose NTX, while enhancing the analgesic effects of opioids, decreases the acute rewarding or addictive properties of morphine or oxycodone as measured in conditioned place preference or self-administration and reinstatement paradigms.

In considering analgesic tolerance, opioid dependence, and opioid addiction together as adaptive regulations to continued opioid exposure, a treatment that prevents MOR's signaling adaptation of switching its G protein partner can logically attenuate these seemingly divergent behavioral consequences of chronic opioid exposure.

Even though ultra-low-dose NTX blocks the conditioned place preference to oxycodone or morphine (Olmstead et al., 2005 *Psychopharmacology* 181:576-581), its co-self-administration only reduces the rewarding potency of these opioids but does not abolish self-administration outright (Leri et al., 2005 *Pharmacol Biochem Behav* 82:252-262). It is possible that a direct stimulatory effect on VTA neurons, as opposed to the proposed disinhibition via inhibition of GABA interneurons (Spanagel et al., 1993 *Proc Natl Acad Sci USA* 89:2046-2050), can play some role in opioid reward. A MOR-Gs coupling mediation of reward, increasing with increasing drug exposure, is in keeping with current theories that the escalation of drug use signifying drug dependence can not indicate a "tolerance" to rewarding effects but instead a sensitization to rewarding effects (Zernig et al., 2007 *Pharmacology* 80:65-119).

The results reported in Wang et al., 2009 *PLoS ONE* 4 (1):e4282 demonstrated that acute, high-dose morphine causes an immediate but transient switch in G protein coupling by MOR from Go to Gs similar to the persistent switch caused by chronic morphine. Ultra-low-dose NLX or NTX prevented this switch and attenuated the chronic morphine-induced coupling switch by MOR. The transient nature of this acute altered coupling suggests the receptor eventually recovers and couples to its native G protein.

With chronic opioid exposure, the receptor can lose the ability to recover and continue to couple to Gs, activating the adenylyl cyclase/cAMP pathway, upregulating protein kinase A, and phosphorylating CREB as one downstream effector example. The persistently elevated phosphorylated CREB can then shape the expression of responsive genes including those closely related to drug addiction and tolerance. Importantly, the equivalent blockade of Gs coupling and pS$^{133}$CREB by the pentapeptide binding site of naloxone (NLX) and naltrexone (NTX) on FLNA further elucidates the mechanism of action of ultra-low-dose NLX and NTX in their varied effects.

These data further strengthen the regulation of MOR-Gs coupling by FLNA and that binding to FLNA or using a FLNA peptide decoy for MOR can prevent the altered MOR coupling, thereby attenuating tolerance, dependence and addictive properties associated with opioid drugs.

The combination of ultra-low-dose opioid antagonists with opioid agonists formulated together in one medication has been shown to alleviate many of these undesirable aspects of opioid therapy (Burns, 2005 *Recent Developments in Pain Research* 115-136, ISBN: 81-308-0012-8). This approach shows promise for an improvement in analgesic efficacy, and animal data suggests reduced addictive potential. The identification of the cellular target of ultra-low-dose NLX or NTX in their inhibition of mu opioid receptor-Gs coupling as a pentapeptide segment of filamin A (Wang et al., 2008 *PLoS ONE* 3 (2):e1554) has led to development of assays to screen against this target to create a new generation of pain therapeutics that can provide long-lasting analgesia with minimal tolerance, dependence and addictive properties. Importantly, the non-opioid cellular target of ultra-low-dose NLX or NTX, FLNA, provides potential for developing either a therapeutic combination of which one component is not required to be ultra-low-dose, or a single-entity novel analgesic.

The present invention identifies a compound that binds to filamin A (FLNA; the high-affinity binding site of naloxone [NLX] and naltrexone [NTX]), to reduce cell motility and inflammation as well as to prevent the Gi/o-to-Gs coupling switch of MOR and is similar to or more active than DAMGO in activating MOR.

BRIEF SUMMARY OF THE INVENTION

The present invention contemplates an analgesic compound, a composition containing that compound and a method of reducing pain in a host mammal in need thereof by administering a composition containing such a compound. A compound that corresponds in structure to Formula A is contemplated

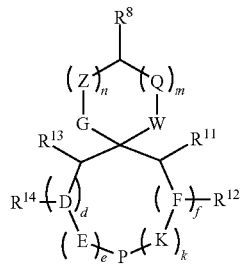

A

In Formula A, G, P and W are selected from the group consisting of $NR^{20}$, $NR^2$, $NR^7$, $CH_2$, S and O, where $R^2$ and $R^7$ are the same or different and are H, $C(H)_v(D)_h$ where each of v and h is 0, 1, 2 or 3 and v+h=3, $C(H)_q(D)_r$-aliphatic $C_1$-$C_{11}$ hydrocarbyl where each of q and r is 1, or 2 and q+r=0, 1 or 2, aliphatic $C_1$-$C_{12}$ hydrocarbyl sulfonyl [—$S(O)_2$-aliphatic $C_1$-$C_{12}$ hydrocarbyl] or aliphatic $C_1$-$C_{12}$ hydrocarboyl [acyl; —C(O)-aliphatic $C_0$-$C_{11}$ hydrocarbyl], and $R^{20}$ is X-circle A-$R^1$ as defined hereinafter, with the provisos that i) only one of G, P and W is $NR^{20}$, ii) one of G, P and W must be $NR^{20}$, and iii) P is $NR^2$ when other than $NR^{20}$. X is $SO_2$, C(O), $CH_2$, $CD_2$, OC(O), NHC(NH) or NHC(O), preferably $SO_2$, C(O) or $CH_2$, and most preferably $SO_2$ Q is $CHR^9$ or C(O) and Z is $CHR^{10}$ or C(O), and preferably, only one of Q and Z is C(O). Each of d, e, f and k is either zero or one and the sum of (d+e+f+k)=2. D and F are the same or different and are CH or CD, and E and K are the same or different and are $CH_2$, CHD or $CD_2$. Each of m and n is zero or one and the sum of m+n is 1 or 2, preferably 1.

Circle A is an aromatic or heteroaromatic ring system that contains one ring or two fused rings, and preferably contains a single ring. $R^1$ represents up to three substituents, $R^{1a}$, $R^{1b}$, and $R^{1c}$, that themselves can be the same or different, wherein each of those three groups, $R^{1a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl, hydroxy-, trifluoromethyl-(-$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [$S(O)_2NR^3R^4$], wherein the amido nitrogen in either amide group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl or heteroaryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur.

$R^8$, $R^9$, and $R^{10}$ are each H, which is preferred, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms.

$R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited in this paragraph (herein). A pharmaceutically acceptable salt of a compound of Formula A and all of the remaining formulas disclosed herein is contemplated.

In one preferred embodiment, a compound of Formula A corresponds in structure to Formula B.

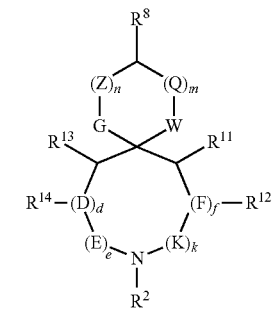

B

In a compound that corresponds in structure to Formula B, G and W are selected from the group consisting of $NR^{20}$, $NR^7$, $CH_2$, S and O, where $R^2$ and $R^7$ are the same or different and are H, $C(H)_v(D)_h$ where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl, and $R^{20}$ is X-circle A-$R^1$ as defined hereinafter, with the provisos that only one of G and W is $NR^{20}$ and that one of G and W must be $NR^{20}$. X is $SO_2$, C(O), $CH_2$, $CD_2$, OC(O), NHC(NH) or NHC(O); Q is $CHR^9$ or C(O); and Z is $CHR^{10}$ or C(O). Each of d, e, f and k is either zero or one and the sum of (d+e+f+k)=2. D and F are the same or different and are CH or CD and E and K are the same or different and are $CH_2$, CHD or $CD_2$. $R^2$ is preferably H, $C(H)_v(D)_h$ where each of v and h is 0, 1, 2 or 3 and v+h=3, $C(H)_q(D)_r$-aliphatic $C_1$-$C_5$ hydrocarbyl where each of q and r is 0, 1, or 2 and q+r=0, 1 or 2, $C_1$-$C_6$ aliphatic acyl [—C(O)—$C_0$-$C_5$ aliphatic], or a $C_1$-$C_6$ aliphatic sulfonyl [—$S(O)_2$—$C_0$-$C_5$ aliphatic].

Circle A is an aromatic or heteroaromatic ring system that contains one ring or two fused rings, preferably one ring; and group $R^1$ is H or represents up to three substituents, $R^{1a}$, $R^{1b}$, and $R^{1c}$, that themselves can be the same or different, in which each of those three groups, $R^{1a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl (acyl), hydroxy-, trifluoromethyl-(-$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate, carboxamide or sulfonamide wherein the amido nitrogen in either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl or heteroaryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur.

Groups $R^8$, $R^9$, and $R^{10}$ are each H, which is preferred, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms.

Groups $R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited in this paragraph (herein). A pharmaceutically acceptable salt of a compound of Formula B is also contemplated.

In another preferred embodiment, a compound of Formula A corresponds in structure to Formula C.

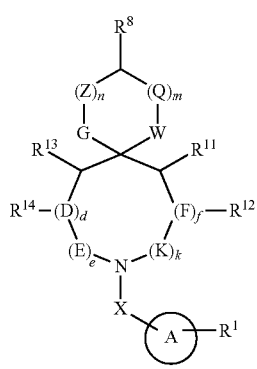

C

In a compound that corresponds in structure to Formula C, G and W are selected from the group consisting of $NR^2$, $NR^7$, $CH_2$, S and O, where $R^2$ and $R^7$ are the same or different and are H, $C(H)_v(D)_h$ where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, aliphatic $C_1$-$C_{12}$ hydrocarbyl, aliphatic $C_1$-$C_{12}$ hydrocarbyl sulfonyl or aliphatic $C_1$-$C_{12}$ hydrocarboyl, with the proviso that that one of G and W must be $NR^2$ or $NR^7$. X is $SO_2$, C(O), $CH_2$, $CD_2$, OC(O), NHC(NH) or NHC(O); Q is $CHR^9$ or C(O); and Z is $CHR^{10}$ or C(O), and preferably, only one of Q and Z is C(O).

Each of d, e, f and k is either zero or one and the sum of (d+e+f+k)=2; D and F are the same or different and are CH or CD; E and K are the same or different and are $CH_2$, CHD or $CD_2$; and each of m and n is zero or one and the sum of m+n is 1 or 2.

Circle A is an aromatic or heteroaromatic ring system that contains a single ring or two fused rings; and group $R^1$ is H or represents up to three substituents, $R^{1a}$, $R^{1b}$, and $R^{1c}$, that themselves can be the same or different, in which each of the three groups, $R^{1a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl, hydroxy-, trifluoromethyl-(-$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate, carboxamide or sulfonamide wherein the amido nitrogen in either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl or heteroaryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur. Groups $R^8$, $R^9$, and $R^{10}$ are each H, or two of $R^8$, $R^9$, and $R^{10}$ are H and one is a is a $C_1$-$C_8$ hydrocarbyl group that is unsubstituted or is substituted with up to three atoms that are the same or different and are oxygen or nitrogen atoms; and groups $R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited herein (in this subparagraph). A pharmaceutically acceptable salt of a compound of Formula C is also contemplated.

A preferred compound of Formulas A and B has the structure of Formula I

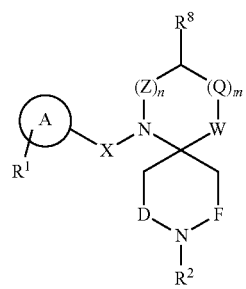

I where X, W, Z, Q, n, m, circle A, $R^1$, $R^2$, $R^8$ and the R groups therein defined are as described previously, and D and F are the same or different and are $CH_2$, CHD or $CD_2$.

In another preferred embodiment, a compound of Formulas A and B has the structure of Formula II

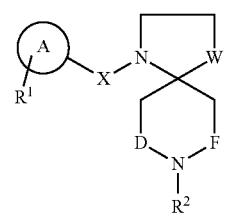

II where X, W, circle A, $R^1$, $R^2$ and the R groups therein defined are as described previously, and D and F are the same or different and are $CH_2$, CHD or $CD_2$.

In a further preferred embodiment, a compound of Formulas A and B has the structure of Formula III

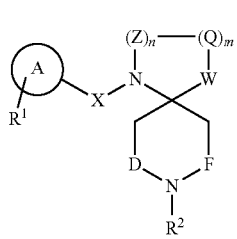

III where X, W, Z, Q, n, m, circle A, $R^1$, $R^2$ and the R groups therein defined are as described previously, and D and F are the same or different and are $CH_2$, CHD or $CD_2$.

In a still further preferred embodiment, a compound of Formulas A and C has the structure of Formula IV

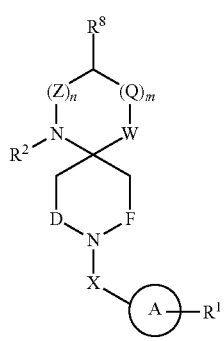

where X, W, Z, Q, n, m, circle A, $R^1$, $R^2$, $R^8$ and the R groups therein defined are as described previously, and D and F are the same or different and are $CH_2$, CHD or $CD_2$.

In yet another preferred embodiment, compound of Formulas A and C has the structure of Formula V

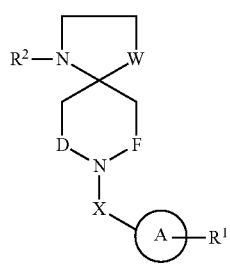

where X, W, circle A, $R^1$, $R^2$ and the R groups therein defined are as described previously, and D and F are the same or different and are $CH_2$, CHD or $CD_2$.

In still another preferred embodiment, compound of Formulas A and C has the structure of Formula VI

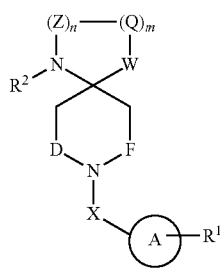

where X, W, Z, Q, n, m, circle A, $R^1$, $R^2$ and the R groups therein defined are as described previously, and D and F are the same or different and are $CH_2$, CHD or $CD_2$.

In each of the above compounds of Formulas A, B, C and I-VI, it is preferred that X is C(O), $CH_2$, $CD_2$, or $SO_2$, and separately preferred that W is $NR^7$, $CH_2$, S or O. It is also preferred that one of Q and Z be C(O) and the other be $CH_2$.

It is further separately preferred that wherein circle A is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, and benzopyrimidinyl.

As can be seen from the above definitions, a contemplated compound can contain deuterated carbon atoms on either side of the "X" substituent. Deuterated compounds can be useful in studying the mechanism of drug interactions with living organisms for the elucidation of metabolic and biosynthetic pathways. Deuteration can also extend the half-life of a contemplated compound in vivo because a C-D bond is stronger than a C—H bond thereby requiring more energy input for bond cleavage. See, Blake et al., 1975 J. Pharm. Sci. 64 (3):367-391; and Nelson et al., 2003 Drug Metab. Dispos. 31 (12):1481-1498, and the citations therein. Contemplated deuterated compounds are prepared using well-known reactions.

A pharmaceutical composition is also contemplated. That composition comprises an above compound of Formulas A, B, C, and I-VI or its pharmaceutically acceptable salt dissolved or dispersed in a physiologically tolerable carrier. The compound is present in an effective analgesic amount. The composition is preferably in solid form as in a tablet of capsule.

A method of reducing one or both of pain and inflammation in a host mammal in need thereof is also contemplated. That method comprises administering to that host mammal a pharmaceutical composition as disclosed above. The host mammal for such a method is selected from the group consisting of a primate, a laboratory rodent, a companion animal, and a food animal. A composition can be administered a plurality of times over a period of days, as well as administered a plurality of times in one day. That administration can be perorally or parenterally.

The present invention has several benefits and advantages.

One benefit is anti-inflammatory action combined with analgesia by a compound with a novel mechanism of action for both that does not have a narcotic structure.

An advantage of the invention is that analgesia can be provided by administration of a contemplated composition either perorally or parenterally.

A further benefit of the invention is that as indicated by the initial data, a contemplated compound provides the analgesic effects characteristic of opioid drugs but does not cause analgesic tolerance or dependence.

Another advantage of the invention as also indicated by the initial data is that a contemplated compound provides the analgesic effects characteristic of opioid drugs and does not have the addictive potential of opioid drugs.

Still further benefits and advantages will be apparent to a skilled worker from the description that follows.

Abbreviations and Short Forms

The following abbreviations and short forms are used in this specification.

"MOR" means μ opioid receptor
"FLNA" means filamin A
"NLX" means naloxone
"NTX" means naltrexone
"Gi/o" means G protein inhibitory/other subtype, inhibits adenylyl cyclase "Gs" means G protein stimulatory subtype, stimulates adenylyl cyclase "Gβγ" means G protein beta gamma subunit "cAMP" means cyclic adenosine monophosphate "CREB" means cAMP Response Element Binding protein "IgG" means Immunoglobulin G

DEFINITIONS

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed hereinafter to be subsumed within the aliphatic groups. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups, substituents, moieties or radicals, as discussed hereinafter. An aralkyl substituent group such as benzyl is deemed an aromatic group as being an aromatic ring bonded to an X group, where X is $CH_2$. A substituent group containing both an aliphatic ring and an aromatic ring portion such as tetralin (tetrahydronaphthalene) that is linked directly through the aliphatic portion to the depicted ring containing the W group is deemed a non-aromatic, hydrocarbyl group. On the other hand, a similar group bonded directly via the aromatic portion, is deemed to be a substituted aromatic group. Where a specific aliphatic hydrocarbyl substituent group is intended, that group is recited; i.e., $C_1$-$C_4$ alkyl, methyl or dodecenyl. Exemplary hydrocarbyl groups contain a chain of 1 to about 12 carbon atoms, and preferably 1 to about 8 carbon atoms, and more preferably 1 to 6 carbon atoms of an alkyl group.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, isoamyl, hexyl, octyl, decyl, dodecyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups. On the other hand, a hydrocarbyl group containing a —C(O)— functionality is referred to as a hydrocarboyl (acyl) and that containing a —C(O)O— is a hydrocarboyloxy group inasmuch as there is no ambiguity. Exemplary hydrocarboyl and hydrocarboyloxy groups include acyl and acyloxy groups, respectively, such as acetyl and acetoxy, acryloyl and acryloyloxy.

Carboxyl-related linking groups between the central spiro ring system and an aromatic or heteroaromatic ring system, circle A, include several types of ester and amide bonds. Illustrative of such bonds are sulfonamide, sulfonate and thiosulfonate esters that can be formed between a $SO_2$-containing group and an amine, oxygen or sulfur atom, respectively. Amide, ester and thioester links can be formed between an aromatic or heteroaromatic ring containing a C(O) group and a nitrogen, oxygen or sulfur atom, respectively. Similarly, a guanidino linker can be formed between an aromatic or heteroaromatic ring containing a NHC(NH) group and a nitrogen, a urethane, carbonate or thiocarbonate can be formed between an aromatic or heteroaromatic ring containing a OC(O) group and a nitrogen, oxygen or sulfur, respectively. A compound containing a urea linker, urethane linker or isothiourea linker [NHC(O)S] can be formed between an aromatic or heteroaromatic ring containing a NHC(O) group and a nitrogen, oxygen or sulfur, respectively.

A "carboxyl" substituent is a —C(O)OH group. A $C_1$-$C_6$ hydrocarbyl carboxylate is a $C_1$-$C_6$ hydrocarbyl ester of a carboxyl group. A carboxamide is a —C(O)NR$^3$R$^4$ substituent, where the R groups are defined elsewhere. Similarly, a sulfonamide is a —S(O)$_2$NR$^3$R$^4$ substituent, where the R groups are defined hereinafter. Illustrative R$^3$ and R$^4$ groups that together with the depicted nitrogen of a carboxamide form a 5-7-membered ring that optionally contains 1 or 2 additional hetero atoms that independently are nitrogen, oxygen or sulfur, include morpholinyl, piperazinyl, oxathiazolyl, 1,2,3-triazolyl, 1,2,4-triazolyl, pyrazolyl, 1,2,4-oxadiazinyl and azepinyl groups.

As a skilled worker will understand, a substituent that cannot exist such as a $C_1$ alkenyl or alkynyl group is not intended to be encompassed by the word "hydrocarbyl", although such substituents with two or more carbon atoms are intended.

The term "aryl", alone or in combination, means a phenyl, naphthyl or other radical as recited hereinafter that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy) phenyl, 4-fluorophenyl, 4-chlorophenyl, 4-hydroxyphenyl, and the like. The term "arylhydrocarbyl", alone or in combination, means a hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O-arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

As used herein, the term "binds" refers to the adherence of molecules to one another, such as, but not limited to, peptides or small molecules such as the compounds disclosed herein, and opioid antagonists, such as naloxone or naltrexone.

As used herein, the term "selectively binds" refers to binding as a distinct activity. Examples of such distinct activities include the independent binding to FLNA or a FLNA peptide, and the binding of a compound discussed above to a MOR.

As used herein, the term "FLNA-binding compound" refers to a compound that binds to the scaffolding protein filamin A, or more preferably to a polypeptide comprising residues -Val-Ala-Lys-Gly-Leu- (SEQ ID NO:1) of the FLNA sequence that correspond to amino acid residue positions 2561-2565 of the FLNA protein sequence as noted in the sequence provided at the web address: UniProtKB/Swiss-Prot entry P21333, FLNA-HUMAN, Filamin-A protein sequence. A FLNA-binding compound can inhibit the MOR-Gs coupling caused by agonist stimulation of the µ opioid receptor via interactions with filamin A, preferably in the $24^{th}$ repeat region. When co-administered with an opioid agonist, a FLNA-binding compound can enhance the analgesic effects and improve the treatment of pain.

As used herein, the term "candidate FLNA-binding compound" refers to a substance to be screened as a potential FLNA-binding compound. In preferred instances a FLNA-binding compound is also an opioid agonist. Additionally, a FLNA-binding compound can function in a combinatory manner similar to the combination of an opioid agonist and ultra-low-dose antagonist, wherein both FLNA and MOR are targeted by a single entity.

As used herein, the term "opioid receptor" refers to a G protein coupled receptor, located in the central nervous system that interacts with opioids. More specifically, the µ opioid receptor is activated by morphine causing analgesia, sedation, nausea, and many other side effects known to one of ordinary skill in the art.

As used herein, the term "opioid agonist" refers to a substance that upon binding to an opioid receptor can stimulate the receptor, induce G protein coupling and trigger a physiological response. More specifically, an opioid agonist is a morphine-like substance that interacts with MOR to produce analgesia.

As used herein, the term "opioid antagonist" refers to a substance that upon binding to an opioid receptor inhibits the function of an opioid agonist by interfering with the binding of the opioid agonist to the receptor.

As used herein an "analgesia effective amount" refers to an amount sufficient to provide analgesia or pain reduction to a recipient host.

As used herein an "inflammation effective amount" refers to an amount sufficient to provide reduction of inflammation to a recipient host.

As used herein the term "ultra-low-dose" or "ultra-low amount" refers to an amount of compound that when given in combination with an opioid agonist is sufficient to enhance the analgesic potency of the opioid agonist. More specifically, the ultra-low-dose of an opioid antagonist is admixed with an opioid agonist in an amount about 1000- to about 10,000,000-fold less, and preferably about 10,000- to about 1,000,000-fold less than the amount of opioid agonist.

As used herein an "FLNA-binding effective amount" refers to an amount sufficient to perform the functions described herein, such as reduction or prevention of inflammation, inhibition of MOR-Gs coupling, prevention of the cAMP desensitization measure, inhibition of CREB $S^{133}$ phosphorylation and inhibition of any other cellular indices of opioid tolerance and dependence, which functions can also be ascribed to ultra-low-doses of certain opioid antagonists such as naloxone or naltrexone. When a polypeptide or FLNA-binding compound of the invention interacts with FLNA, an FLNA-binding effective amount can be an ultra-low amount or an amount higher than an ultra-low-dose as the polypeptide or FLNA-binding compound will not antagonize the opioid receptor and compete with the agonist, as occurs with known opioid antagonists such as naloxone or naltrexone in amounts greater than ultra-low-doses. More preferably, when a polypeptide or VAKGL-binding compound of the present invention both interacts with FLNA and is an agonist of the mu opioid receptor, an FLNA-binding effective amount is an amount higher than an ultra-low-dose and is a sufficient amount to activate the mu opioid receptor.

As used herein the phrase "determining inhibition of the interaction of MOR with a Gs protein" refers to monitoring the cellular index of opioid tolerance and dependence caused by chronic or high-dose administration of opioid agonists to mammalian cells. More specifically, the mu opioid receptor-Gs coupling response can be identified by measuring the presence of the Gαs (stimulatory) subunit, the interaction of MOR with the G protein complexes and formation of Gs-MOR coupling, the interaction of the Gβγ protein with adenylyl cyclase types II and IV, loss of inhibition or outright enhancement of cAMP accumulation, and the activation of CREB via phosphorylation of $S^{133}$.

As used herein the term "naloxone/naltrexone positive control" refers to a positive control method comprising steps discussed in a method embodiment, wherein the candidate FLNA-binding compound is a known opioid antagonist administered in an ultra-low amount, preferably naloxone or naltrexone.

As used herein the term "FLNA-binding compound negative control" refers to a negative control method comprising steps discussed in a method embodiment, wherein the candidate FLNA-binding compound is absent and the method is carried out in the presence of only opioid agonist.

As used herein the term "pharmacophore" is not meant to imply any pharmacological activity. The term refers to chemical features and their distribution in three-dimensional space that constitutes and epitomizes the preferred requirements for molecular interaction with a receptor (U.S. Pat. No. 6,034,066).

DETAILED DESCRIPTION OF THE INVENTION

It should be understood that the present disclosure is to be considered as an exemplification of the present invention, and is not intended to limit the invention to the specific embodiments illustrated. It should be further understood that the title of this section of this application ("Detailed Description of the Invention") relates to a requirement of the United States Patent Office, and should not be found to limit the subject matter disclosed herein.

The present invention contemplates a compound that binds to FLNA and also stimulates MOR, a composition containing that compound and method of its use to provide one or both of pain relief and reduction of inflammation. A contemplated compound can suppress inflammation and inhibit MOR-Gs coupling through interactions with FLNA and/or MOR.

In another aspect of the present invention, a contemplated compound inhibits or prevents the morphine-induced Gs protein coupling by MOR. That prevention of MOR-Gs coupling is believed to occur by preserving a particular interaction of filamin A and MOR. Downstream effects of preventing the MOR-Gs coupling include inhibition of cAMP accumulation and of cAMP Response Element Binding protein (CREB) activation in a manner resembling the activity of ultra-low-dose opioid antagonists naloxone and naltrexone.

In another aspect of the present invention, a FLNA-binding compound prevents or inhibits the MOR-Gs coupling while itself activating MOR.

The data collected in organotypic striatal slice cultures demonstrate that after 7 days of twice daily 1-hour exposures to oxycodone, MOR in striatum switch from Go to Gs coupling (compare vehicle to oxycodone conditions). In contrast, a compound contemplated herein does not cause a switch to Gs coupling despite its ability to stimulate MOR as previously assessed by GTPγS binding that is blocked by beta-funaltrexamine, a specific MOR antagonist. These data imply that these compounds provide the analgesic effects characteristic of opioid drugs but do not cause analgesic tolerance or dependence, and do not have the addictive potential of opioid drugs.

A compound contemplated by the present invention binds to an above-defined FLNA polypeptide as well as stimulates MOR. A contemplated compound corresponds in structure to Formula A

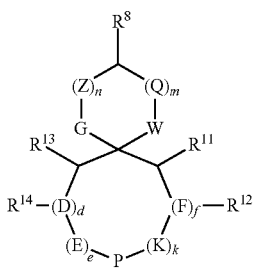

A

In Formula A, each of G, P and W is selected from the group consisting of $NR^{20}$, $NR^2$, $NR^7$, $CH_2$, S and O, where $R^7$ and $R^2$ are the same or different and are H, $C(H)_v(D)_h$ where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, aliphatic $C_1$-$C_{12}$ hydrocarbyl, aliphatic $C_1$-$C_{12}$ hydrocarbyl sulfonyl or aliphatic $C_1$-$C_{12}$ hydrocarboyl (acyl), and $R^{20}$ is X-circle A-$R^1$ as defined hereinafter, with the provisos that i) only one of G, P and W is $NR^{20}$, ii) one of G, P and W must be $NR^{20}$, and iii) when P is other than $NR^{20}$, K is $NR^2$.

X is $SO_2$, C(O), $CH_2$, $CD_2$, OC(O), NHC(NH) or NHC(O), preferably $SO_2$, C(O) or $CH_2$, and most preferably $SO_2$. Q is $CHR^9$ or C(O) and Z is $CHR^{10}$ or C(O), and preferably, only one of Q and Z is C(O).

Each of d, e, f and k is either zero or one and the sum of (d+e+f+k)=2; D and F are the same or different and are CH or CD; and E and K are the same or different and are $CH_2$, CHD or $CD_2$.

Each of m and n is zero or one and the sum of m+n is 1 or 2, preferably 1.

Circle A is an aromatic or heteroaromatic ring system that preferably contains a single ring, but can also contain two fused rings. $R^1$ is H or represents up to three substituents, $R^{1a}$, $R^{1b}$, and $R^{1c}$, that themselves can be the same or different, wherein each of those three groups, $R^{1a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl, hydroxy-, trifluoromethyl-(-$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate [C(O)O—$C_1$-$C_7$ hydrocarbyl], carboxamide [$C(O)NR^3R^4$] or sulfonamide [$S(O)_2NR^3R^4$], wherein the amido nitrogen in either amide group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl or heteroaryl group and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur.

$R^8$, $R^9$, and $R^{10}$ are each H, which is preferred, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms.

$R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited herein (in this subparagraph).

A pharmaceutically acceptable salt of a compound of Formula A and all of the remaining formulas disclosed herein is also contemplated.

In preferred embodiments, a compound of Formula A corresponds in structure to either Formula B or Formula C.

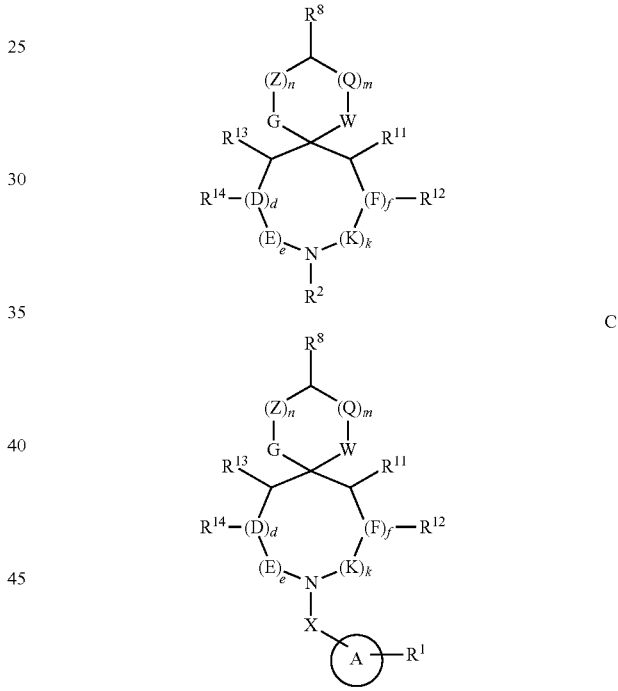

B

C

In a compound that corresponds in structure to Formula B, G and W are selected from the group consisting of $NR^{20}$, $NR^7$, $CH_2$, S and O, where $R^2$ and $R^7$ are the same or different and are $C(H)_v(D)_h$ where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl, and $R^{20}$ is X-circle A—$R^1$, with the provisos that only one of G and W is $NR^{20}$ and that one of G and W must be $NR^{20}$. In a compound that corresponds in structure to Formula C, G and W are selected from the group consisting of $NR^2$, $NR^7$, $CH_2$, S and O, where $R^2$ and $R^7$ are the same or different and are $C(H)_v(D)_h$ where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl. In both of Formulas B and C, X, Z, Q, d, e, f, g, n, m, circle A, and all of the R groups not otherwise defined in this paragraph are as defined previously.

A preferred compound of one or more of Formulas A, B and C includes the following:

C0144M-2

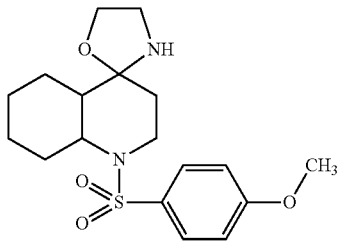

C0145M-3

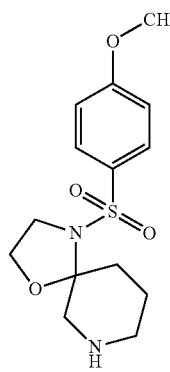

C0152M-4

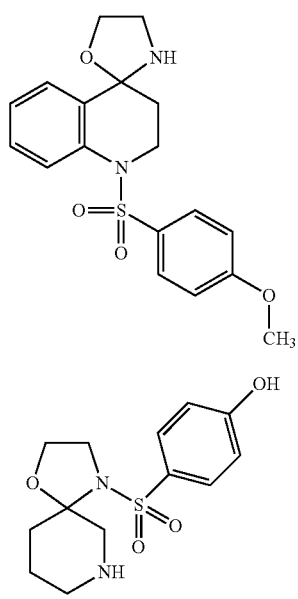

C0153M-3

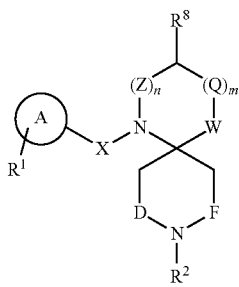

In one embodiment, a preferred compound of Formulas A and B has the structure of Formula I

I

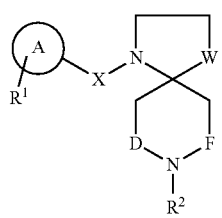

where X, W, Z, Q, n, m, circle A, $R^1$, $R^2$, $R^8$ and the R groups therein defined are as described previously, and D and F are the same or different and are $CH_2$, CHD or $CD_2$.

In another preferred embodiment where $R^8$ is H, one of n and m is zero and the remaining Z or Q is $CH_2$, a compound of Formulas A, B and I has the structure of Formula II

II

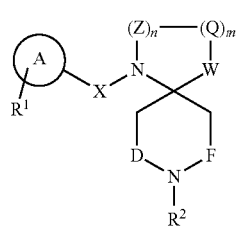

where X, W, circle A, $R^1$, $R^2$ and the R groups therein defined are as described previously, and D and F are the same or different and are $CH_2$, CHD or $CD_2$.

In a further preferred embodiment, where $R^8$ is H, a compound of Formulas A, B and I has the structure of Formula III

III

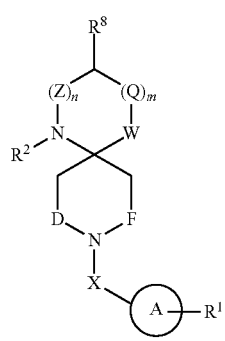

where X, W, Z, Q, circle A, $R^1$, $R^2$ and the R groups therein defined are as described previously, each of m and n is one so m+n=2, and F are the same or different and are $CH_2$, CHD or $CD_2$.

In a still further preferred embodiment, a compound of Formulas A and C has the structure of Formula IV

IV where X, W, Z, Q, n, m, circle A, $R^1$, $R^2$, $R^8$ and the R groups therein defined are as described previously, and D and F are the same or different and are $CH_2$, CHD or $CD_2$.

In yet another preferred embodiment where $R^8$ is H, one of n and m is zero and the remaining Z or Q is $CH_2$, and D and F are the same or different and are $CH_2$, CHD or $CD_2$, a compound of Formulas A, C and IV has the structure of Formula V

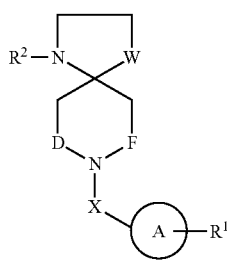

V

In still another preferred embodiment, where $R^8$ is H, a compound of Formulas A, C and I has the structure of Formula VI

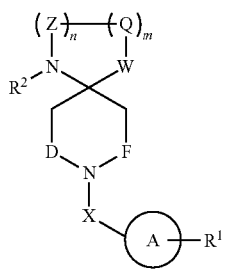

VI where X, W, Z, Q, circle A, $R^1$, $R^2$ and the R groups therein defined are as described previously, each of m and n is one so m+n=2, and D and F are the same or different and are $CH_2$, CHD or $CD_2$.

Again, a pharmaceutically acceptable salt of all of the compounds of Formulas A, B, C, and I-VI is contemplated. It is also noted that the previously mentioned preferences regarding apply to X, W, Z, Q, d, e, f, k, n, m, circle A, and all of the R groups apply to a compound of Formulas A, B, C, and I-VI.

In a compound of Formulas A, B and I, II and III, for enhanced potency as a MOR agonist, it is preferred that $R^1$ have a Hammett sigma value for a para-position substituent that is about −0.7 to about zero, and more preferably, a Hammett sigma value for a para-position substituent that is about −0.3 to about −0.1. An $R^2$ group is preferably a H or $C_1$-$C_6$ hydrocarbyl, with a cyclopropylmethyl group being preferred.

In a compound of Formulas A, C and IV, V and VI, for enhanced potency as a MOR agonist, $R^1$ preferably has a Hammett sigma value for a para-position substituent that is greater than −0.2, and more preferably, a Hammett sigma value for a para-position substituent that is zero or positive (greater than zero). For enhanced specificity, it is also preferred that G and W are both $NR^2$ or $NR^7$ and that $R^2$ and $R^7$ both be H, so that both G and W are NH, and that one of Z and Q being C(O).

Hammett sigma values are well known in organic chemistry and those values for para-position substituents reflect both electron donation or withdrawal via an inductive effect, but also are understood to reflect a resonance effect. It is noted that the recited para-position sigma value is utilized regardless of the actual position of the substituent on the aromatic ring. For Hammett sigma values see, for example, U.S. Pat. No. 7,473,477, U.S. Pat. No. 5,811,521, U.S. Pat. No. 4,746,651, and U.S. Pat. No. 4,548,905. A list of Hammett sigma values can be found in J. Hine, *Physical Organic Chemistry*, $2^{nd}$ ed., McGraw-Hill Book Co., Inc., New York page 87 (1962) and at the web site: wiredchemist.com/chemistry/data/hammett_sigma_constants.

A contemplated aromatic ring (aryl) system of circle A of one of the contemplated compounds preferably contains a single aromatic ring, but can also contain two fused aromatic rings. An illustrative circle A aromatic ring system is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, and benzopyrimidinyl.

An illustrative single-ringed aryl or heteroaryl group of a circle A group or of a substituent of circle A, MAr, is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl and isothiazolyl groups.

Phenyl, pyridinyl and furanyl are a preferred aromatic or heteroaromatic ring system of circle A, with phenyl being more preferred. Phenyl, pyridinyl and furanyl are also preferred single-ringed aryl or heteroaryl groups, Ar, of a MAr substituent, with phenyl being particularly preferred.

X and Y can form a sulfonamido, a carboxamido, a urea, a guanidino or methylene linkage from the circle A ring system to a depicted nitrogen atom of the central spiro rings.

Examining a compound of the above formulas more closely, it is seen that that formula defines a double ringed, substituted spiro compound that can have two six-membered rings or one six- and one five-membered ring, as when one of "m" and "n" is one and the other zero. One of those rings (the lower ring in the formulas) contains one nitrogen atom in the 6-membered ring and the remaining ring atoms are carbons. The ring that can contain 5- or 6-ring atoms (upper ring in the formulas) can contain one ring nitrogen and four or five carbons, or two nitrogens, a nitrogen and a sulfur or a nitrogen and an oxygen atom along with three or four ring carbons. Illustrative central spiro rings are shown below where wavy lines are used to indicate the presence of covalent bonds to other entities, and where $R^7$ is defined above and $R^8$ is H for clarity.

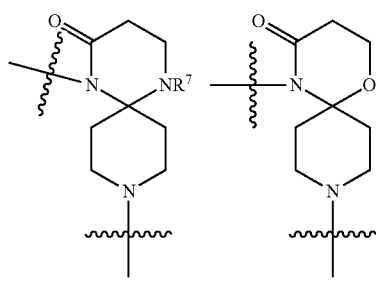

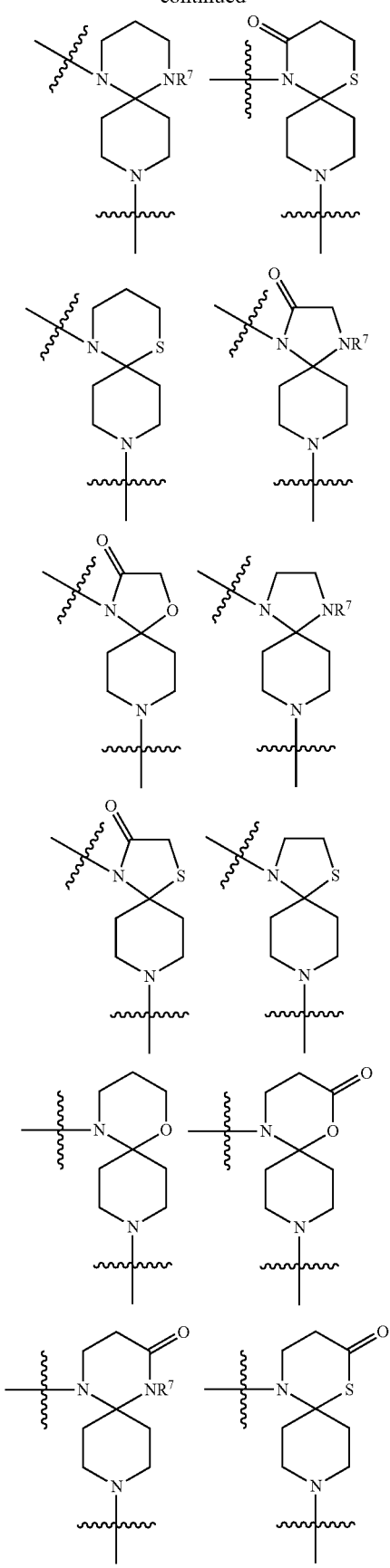
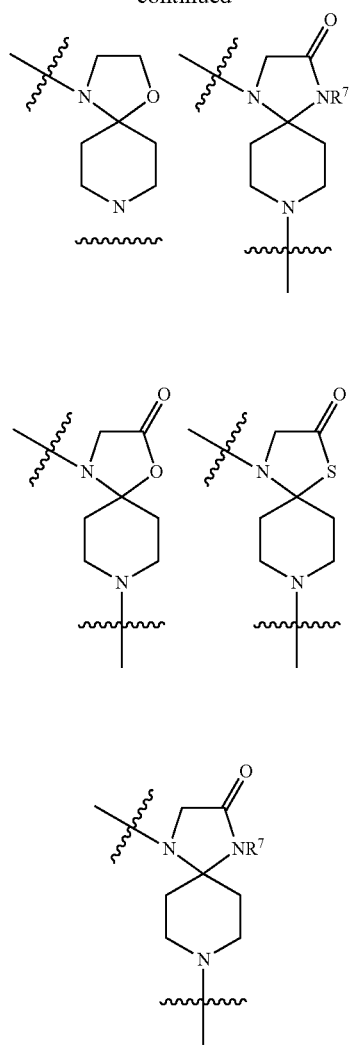
Illustrative compounds of Formula A in which d and e are each zero and $R^{11}$, $R^{12}$ and $R^{13}$ are each H have asymmetric spiro ring structures a few of which are shown below with wavy lines indicating the presence of covalent bonds to other entities, and $R^7$ is defined above and $R^8$ is again H for clarity.
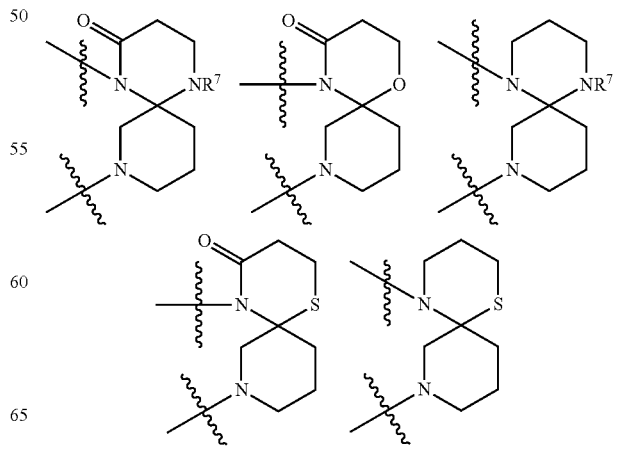

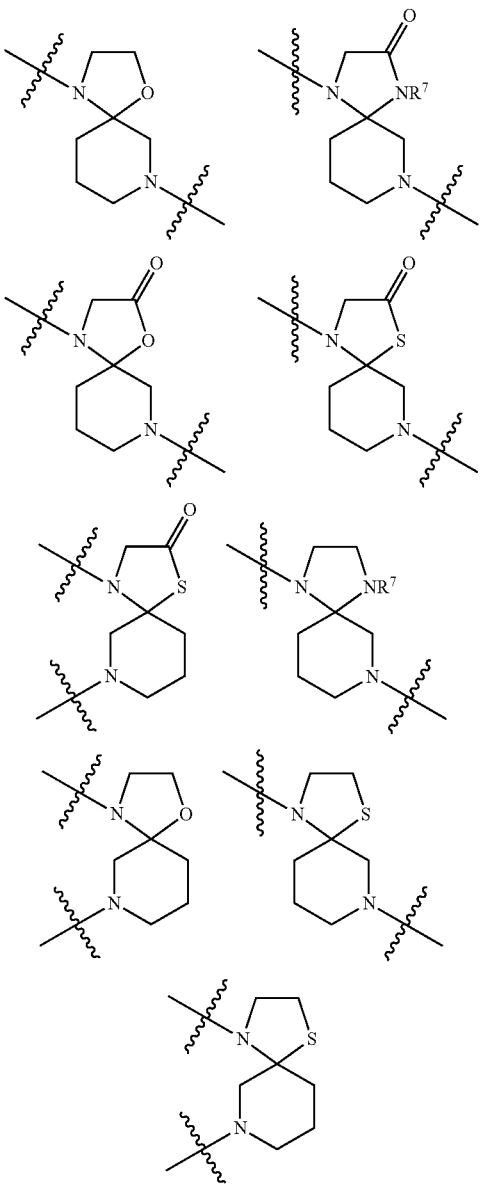

A particularly preferred compound of Formulas A and B, and that embodies one or more of the above separate preferences is a compound whose structure corresponds to that of Formula I

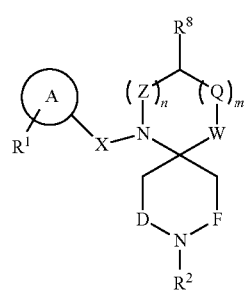

I

A particularly preferred compound of Formula I is selected from the group consisting of

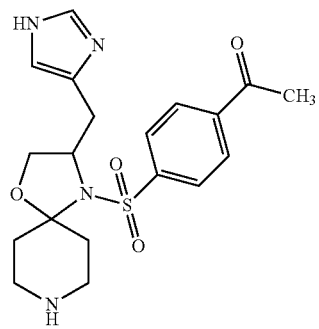

C0079M-7

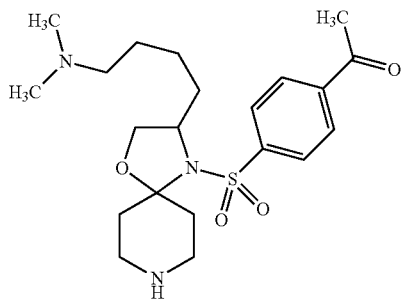

C0080M-6

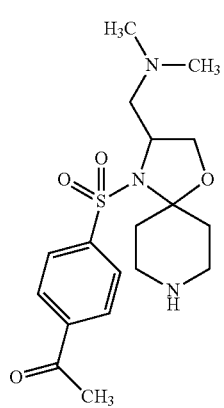

C0081M-7

In preferred practice for the compounds of Formulas A, B and C, n is zero, e and g are both zero and $R^{11}$, $R^{12}$ and $R^{13}$ are all H, so the central ring is a spiro 5,6-ring system whose 6-membered ring is unsubstituted and in which the spiro bonds are in the 4-position relative to the nitrogen of the 6-membered ring. It is separately preferred that W be O or $NR^7$. It is also preferred that X be $SO_2$ (sulfonyl).

The aromatic substituent, the circle A, is linked to one nitrogen atom of the spiro rings by a X group that is $SO_2$, C(O), $CH_2$, $CD_2$, OC(O), NHC(NH) or NHC(O), preferably $SO_2$, C(O), $CH_2$, or $CD_2$, and most preferably $SO_2$. The resulting aromatic substituent is thereby linked to the spiro ring portion by a sulfonamide, an amide, a methylene, a urea or a urethane linkage. Aryl sulfonamide bridges, aryl amide bridges and phenylmethylene bridges (benzyl compounds) are preferred, with aryl sulfonamides being particularly preferred.

C0108M
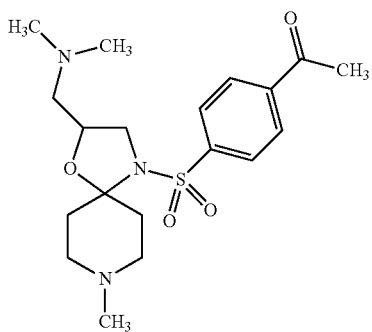
C0109 M
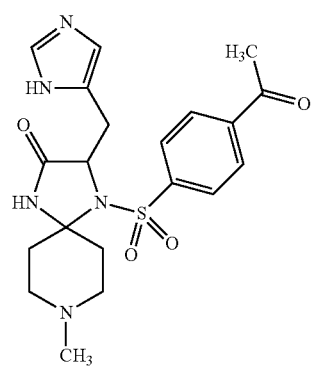
C0111 M
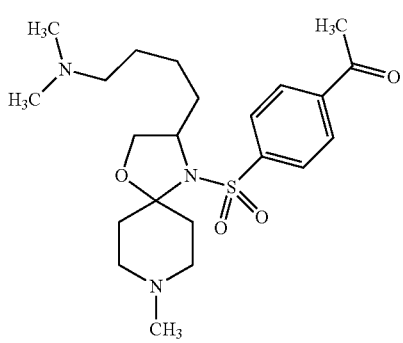
C0118M
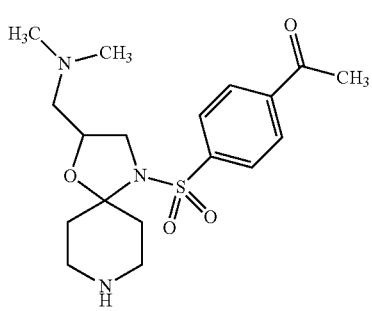
C0119M
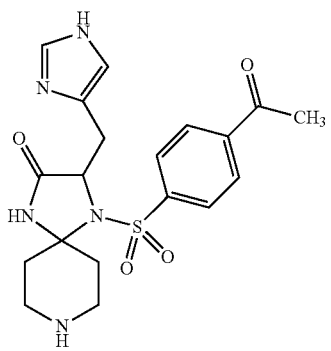
C0128M
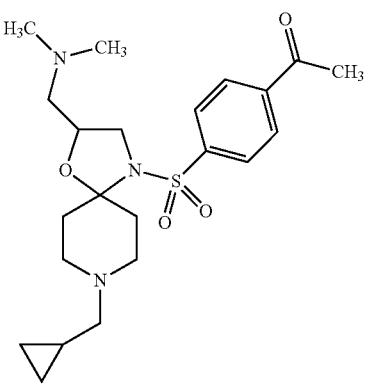
C0129M
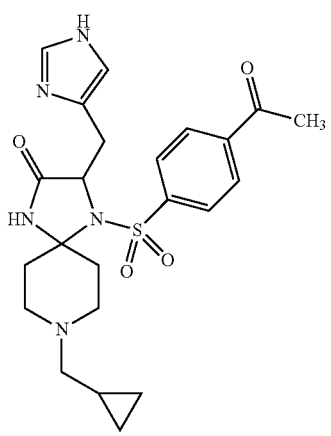
In another embodiment, a contemplated compound corresponds in structure to Formula II
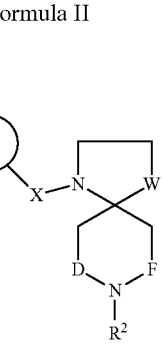
II Here, particularly preferred compounds include those selected from the group consisting of
C0027
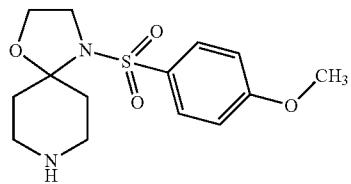
C0043
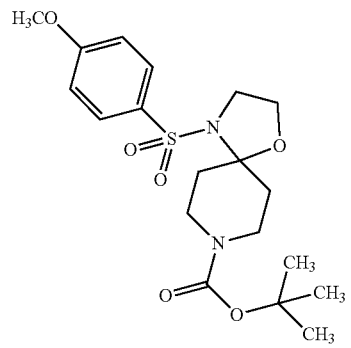
C0046
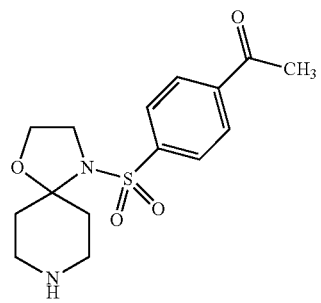
C0053-3
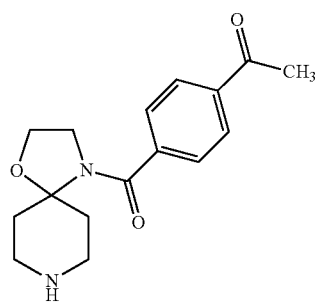
C0086M
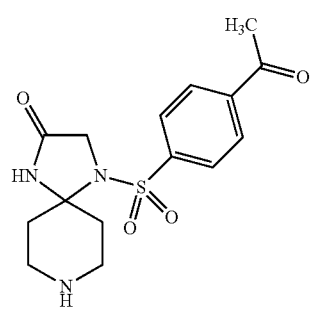
-continued
C0088M
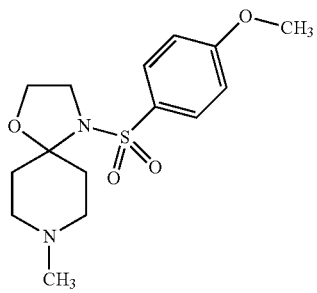
C0091M
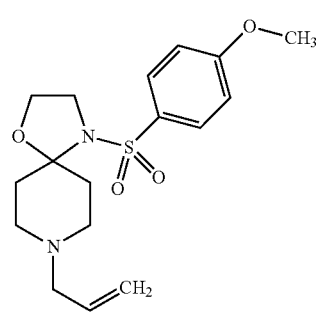
C0092M
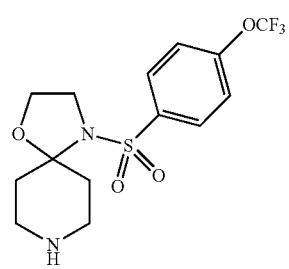
C0093M
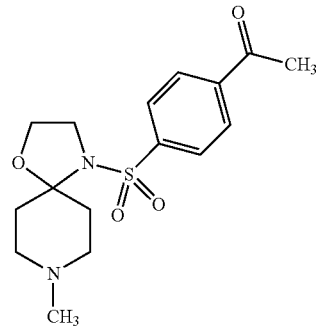
C0097M
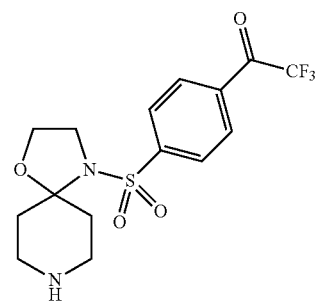

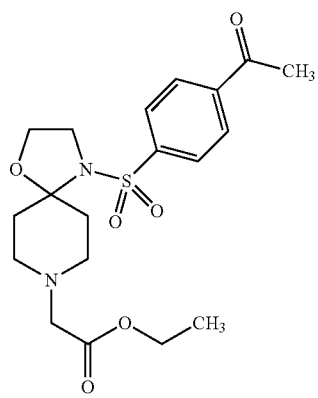
C0099M
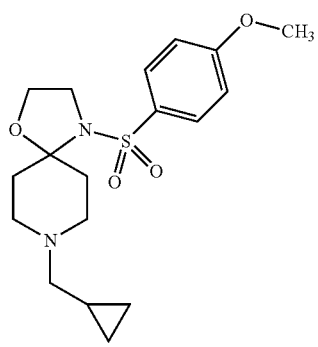
C0090M
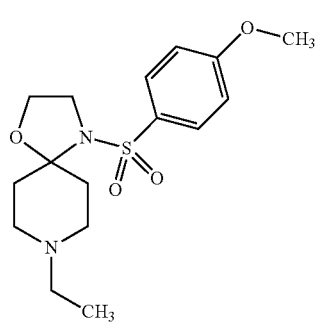
C0089M
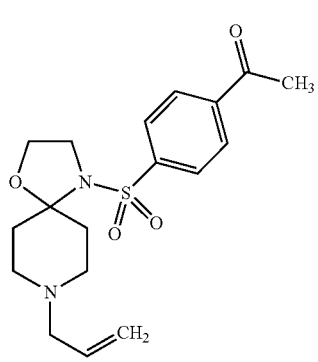
C0096M
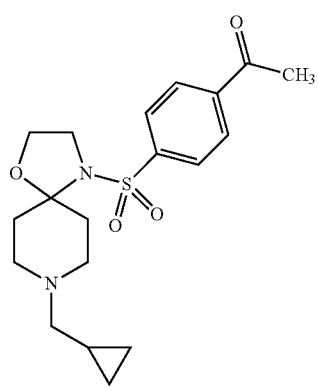
C0095M
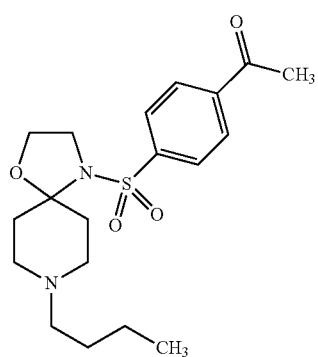
C0101M US 8,653,068 B2
31
-continued
32
-continued
C0100M
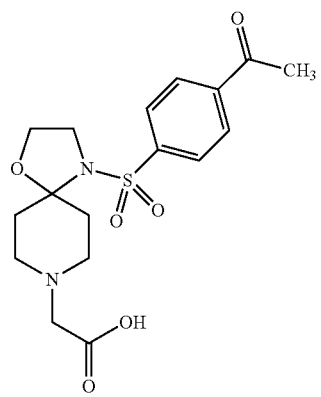
C0134M
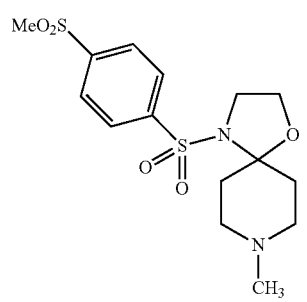
C0106M
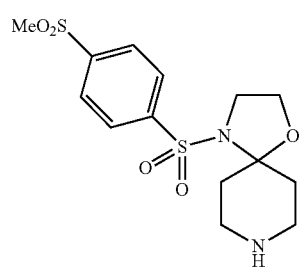
C0135M
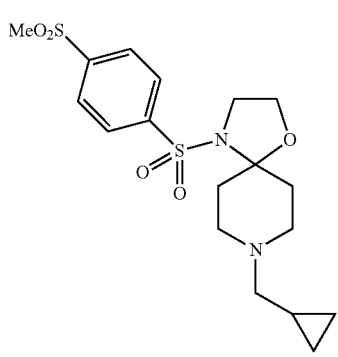
C0116M
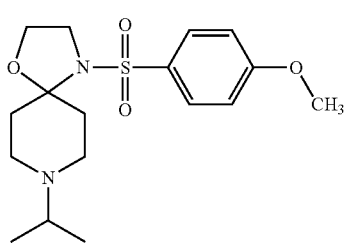
C0143M-2
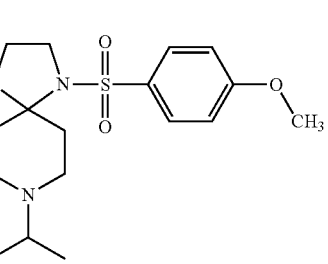
C0126M
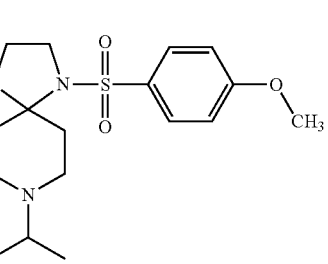
C0149M-2
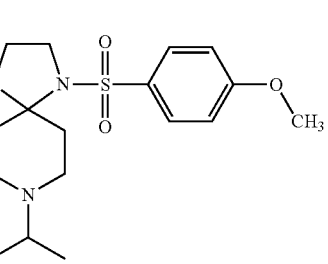
C0133M

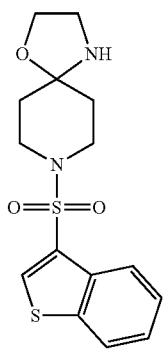
C0150M-2
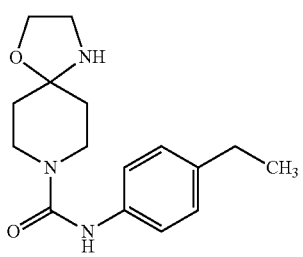
C0151M-2
In a further embodiment, a particularly preferred compound of Formulas A and B is a compound of Formula III
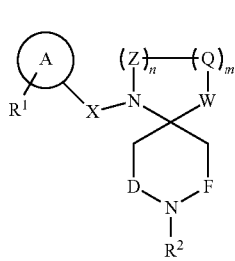
III
A particular compound of Formula III is selected from the group consisting of
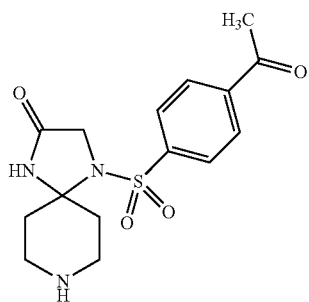
C0086M
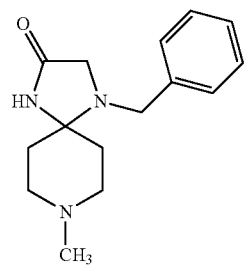
C0104 M
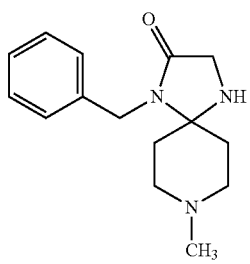
C0105 M
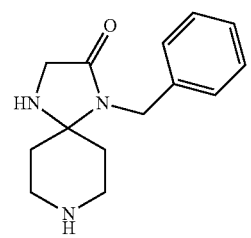
C0114M
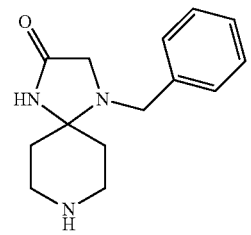
C0115M
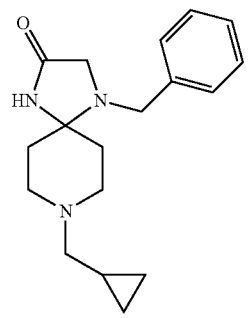
C0125 M

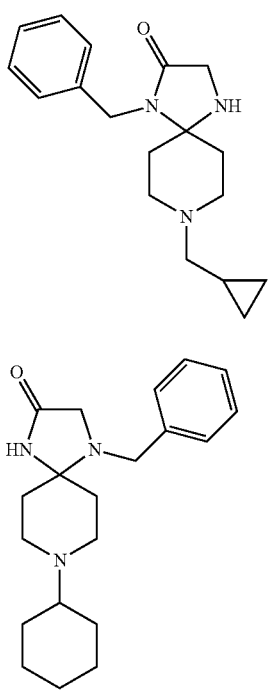

C0124M

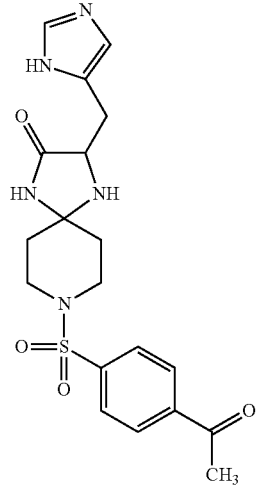

C0098M

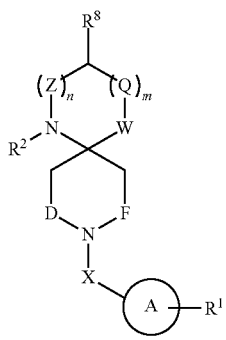

C0137M(P7)

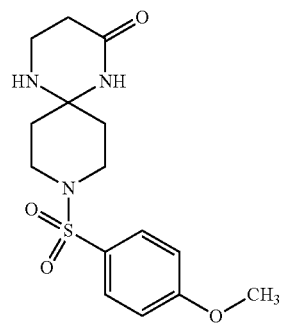

C0142M

In a further embodiment, a particularly preferred compound of Formulas A and C is a compound of Formula IV

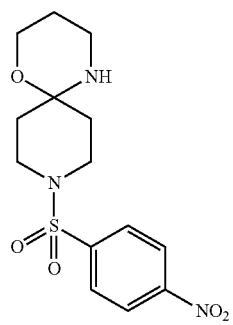

IV

In yet another embodiment, a particularly preferred compound of Formulas A and C is a compound of Formula V

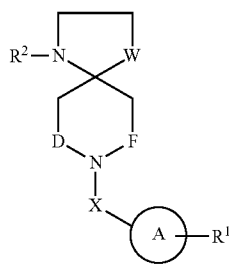

V

A particularly preferred compound of Formula IV has the structure

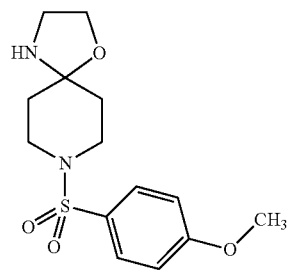

C0037-2

A particularly preferred compound of Formula V corresponds in structure to

C0026

-continued
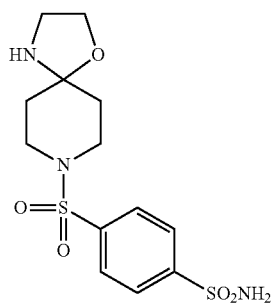
C0034-3
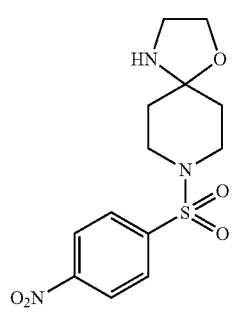
C0040
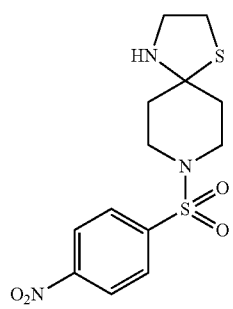
C0044
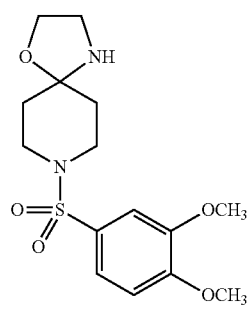
C0049-2
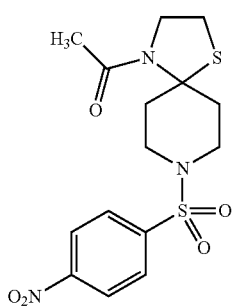
C0050
-continued
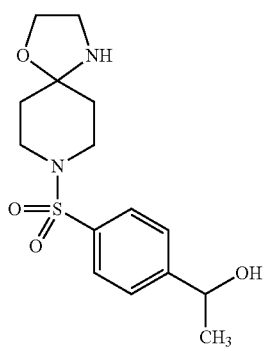
C0055-4
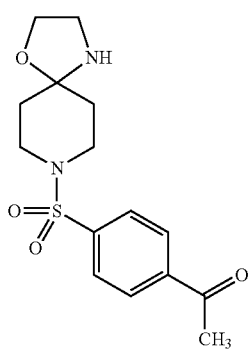
C0055
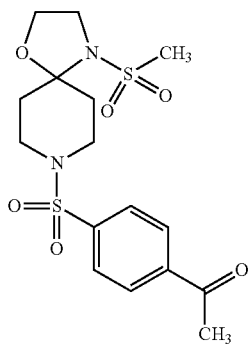
C0056
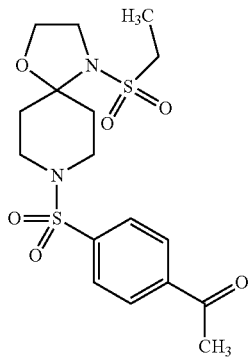
C0058

C0059
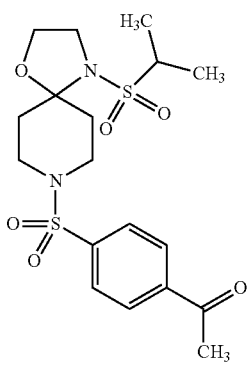
C0144M-2
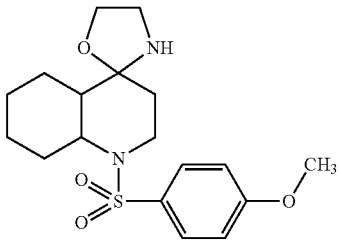
C0060
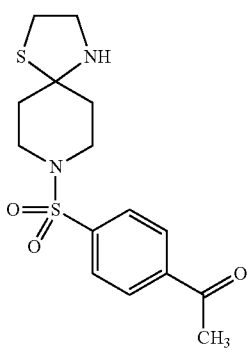
C0149M-2
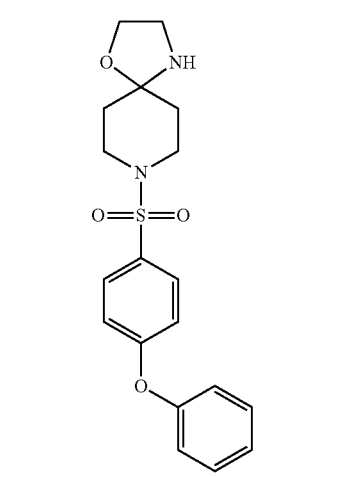
C0077-2
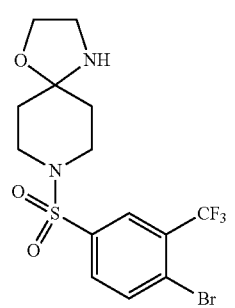
C0078-2
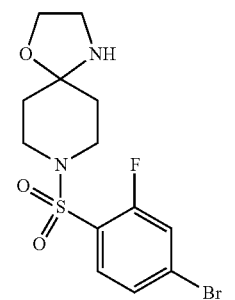
C0150M-2
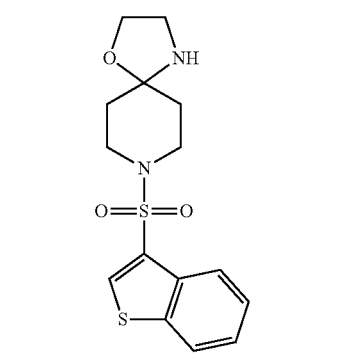
C0143M-2
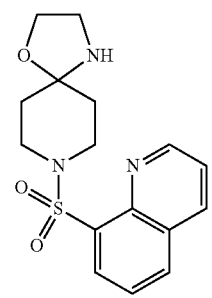
C0151M-2
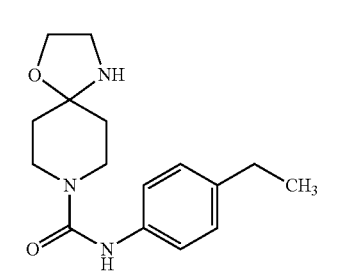

-continued

C0152M-2

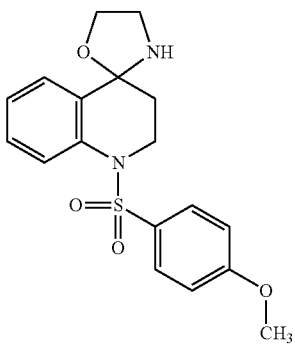

In still another preferred embodiment, compound of Formulas A and C has the structure of Formula VI

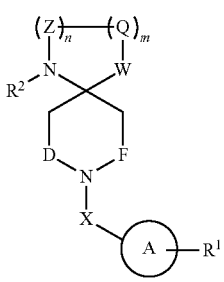

VI

A particularly preferred compound of Formula VI corresponds in structure to

C0066

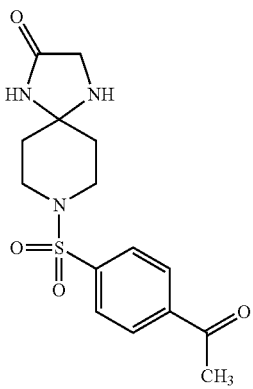

C0083M

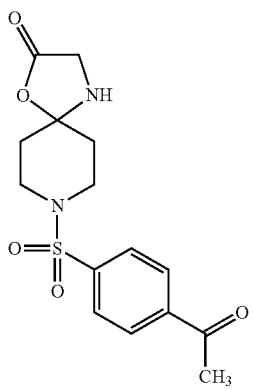

-continued

C0087M

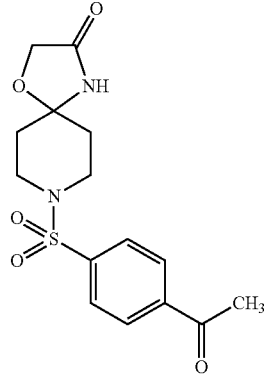

C0136M

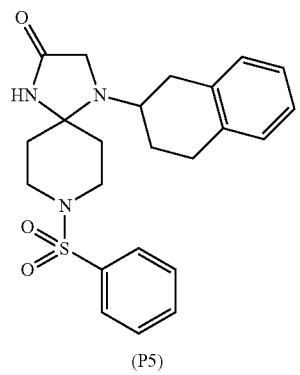

(P5)

The present invention also contemplates a method of treatment to reduce one or both of pain and inflammation in a treated mammal. A compound of Formulas A, B, C, I, II, III, IV, V and VI or its pharmaceutically acceptable salt present in an analgesic effective amount dissolved or dispersed in a physiologically tolerable diluent can be and preferably is used in such a treatment. Such compositions and methods are discussed further hereinafter.

In another aspect, a contemplated compound is selected in part using a method for determining the ability of a candidate FLNA-binding compound, other than naloxone or naltrexone, to inhibit the interaction of the mu opioid receptor with filamin A (FLNA) and thereby prevent the mu opioid receptor from coupling to Gs proteins (Gs). That method comprises the steps of: (a) admixing the candidate FLNA-binding compound (alone if such FLNA-binding compound also stimulates MOR or with a MOR agonist otherwise) with mammalian cells that contain the mu opioid receptor and FLNA in their native conformations and relative orientations, the opioid agonist being present in an agonist effective amount and/or being administered in a repeated, chronic manner the FLNA-binding compound being present in an FLNA-binding effective amount; and (b) determining inhibition of the interaction of the mu opioid receptor with the G protein by analysis of the presence or the absence of the Gαs subunit of Gs protein, wherein the absence of the Gαs subunit indicates inhibition of the interaction of the mu opioid receptor with the Gs protein.

In one aspect, the analysis of Gs protein coupling by the mu opioid receptor and downstream effects elicited by admixing mammalian cells with a before-defined compound can be conducted by any one or more of several methods such as for example co-immunoprecipitation of Gα proteins with MOR, Western blot detection of MOR in immunoprecipitates, and densitometric quantification of Western blots.

Pharmaceutical Composition

A compound of the invention can be provided for use by itself, or as a pharmaceutically acceptable salt. Although substituent groups can provide an acid functionality, a contemplated compound of any of Formulas A-C and Formulas I-VI is an amine and can typically be used in the form of a pharmaceutically acceptable acid addition salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Other compounds useful in this invention that contain acid functionalities can also form salts. Examples include salts with alkali metals or alkaline earth metals, such as sodium, potassium, calcium or magnesium or with organic bases or basic quaternary ammonium salts.

The reader is directed to Berge, 1977 *J. Pharm. Sci.* 68 (1):1-19 for lists of commonly used pharmaceutically acceptable acids and bases that form pharmaceutically acceptable salts with pharmaceutical compounds.

In some cases, the salts can also be used as, an aid in the isolation, purification or resolution of the compounds of this invention. In such uses, the acid used and the salt prepared need not be pharmaceutically acceptable.

A contemplated composition can be used in the manufacture of a medicament that is useful at least for lessening or reducing pain in a mammal that is in need, such as somatic, visceral, neuropathic or sympathetic pain, including musculoskeletal pain, inflammatory pain, burn pain, and pain from syndromes such as fibromyalgia and complex regional pain syndrome (CRPS). A contemplated composition can also be used in the manufacture of a medicament that is useful in reducing inflammation. Inasmuch as pain and inflammation are not always coincident, a contemplated composition is referred to as being used to reduce one or both of pain and inflammation, or a similar phrase.

A contemplated pharmaceutical composition contains an analgesia effective amount of a compound Formulas A, B or C and of Formulas I-VI or a pharmaceutically acceptable salt thereof dissolved or dispersed in a physiologically tolerable carrier. Such a composition can be administered to mammalian cells in vitro as in a cell culture, or in vivo as in a living, host mammal in need.

A contemplated composition is typically administered a plurality of times over a period of days. More usually, a contemplated composition is administered a plurality of times in one day.

As is seen from the data that follow in the table below, a contemplated compound is active in the assays studied at micromolar amounts. In the laboratory mouse tail flick test, orally administered morphine exhibited an $A_{50}$ value of 61.8 (52.4-72.9) mg/kg, and a mean maximum antinociception amount of about 43% at 56 mg/kg at about 20 minutes. Several orally administered compounds whose structures are shown in the Table of Correspondence hereinafter were compared at various dosages to determine a maximal amount of pain relief (antinociception amount) and the time after administration that that maximal pain relief occurred. Data from those studies are shown below.

| Compound Number | Maximum Antinociception (%) | Dosage (mg/kg) | Time to Max. (minutes) |
| --- | --- | --- | --- |
| Morphine | 43 | 56 | 20 |
| C0027 | 70 | 56 | 20 |
| C0066 | 55 | 56 | 20 |
| C0134M | 50 | 56 | 30 |
| C0108M | 50 | 56 | 20 |
| C0090 | 35 | 56 | 20 |
| C0089 | 30 | 56 | 20 |

It is thus seen that the contemplated compounds are quite active and potent, and that a skilled worker can readily determine an appropriate dosage level to achieve a desired amount of pain reduction, particularly in view of the relative activity of a contemplated compound compared to orally administered morphine.

A contemplated pharmaceutical composition can be administered orally (perorally), parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal in need of treatment and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where in vitro mammalian cell contact is contemplated, a CNS tissue culture of cells from an illustrative mammal is often utilized, as is illustrated hereinafter. In addition, a non-CNS tissue preparation that contains opioid receptors such as guinea pig ileum can also be used.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, in vials or ampules.

EXAMPLES

The present invention is described in the following examples which are set forth to aid in the understanding of the invention, and should not be construed to limit in any way the invention as defined in the claims which follow thereafter.

The experiments described herein were carried out on organotypic striatal slices from male Sprague Dawley rats (200 to 250 g) purchased from Taconic (Germantown, N.Y.). Rats were housed two per cage and maintained on a regular 12-hour light/dark cycle in a climate-controlled room with food and water available ad libitum and sacrificed by rapid decapitation. All data are presented as mean±standard error of the mean. Treatment effects were evaluated by two-way ANOVA followed by Newman-Keul's test for multiple comparisons. Two-tailed Student's t test was used for post hoc pairwise comparisons. The threshold for significance was $p<0.05$.

The following Table of Correspondence shows the structures of the compounds discussed herein and their identifying numbers.

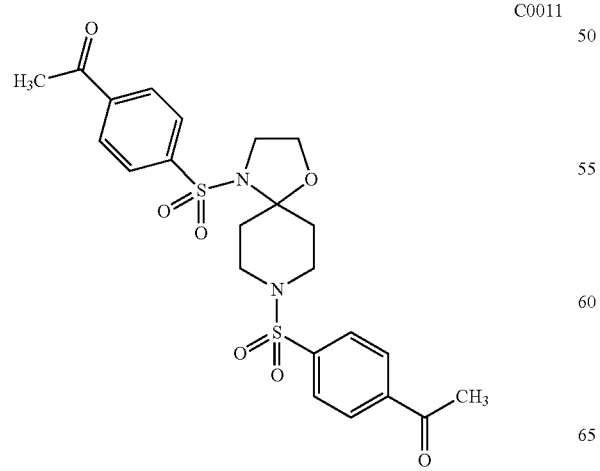

C0011

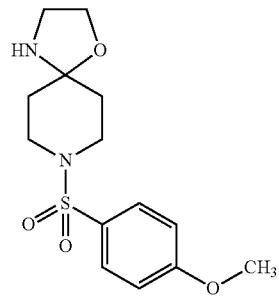

C0026

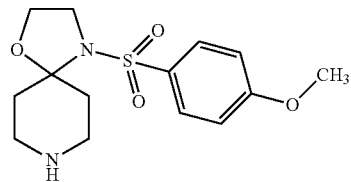

C0027

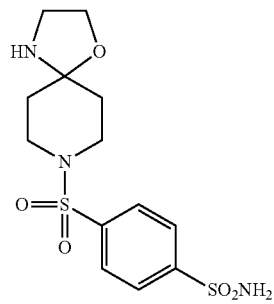

C0034-3

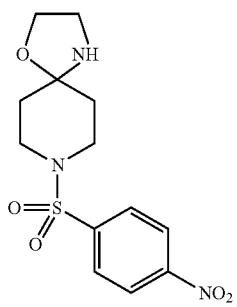

C0037-2

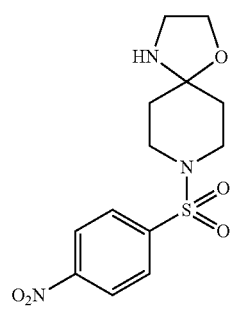

C0040

C0043
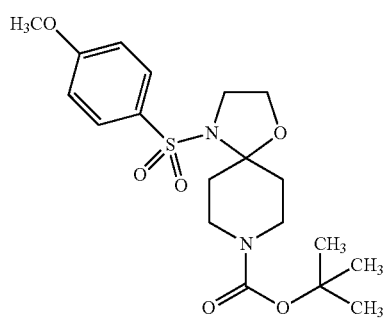
C0044
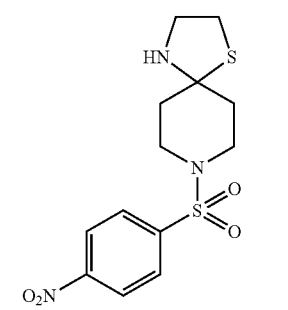
C0046
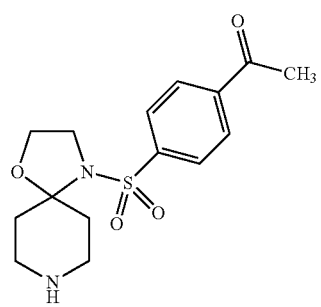
C0049-2
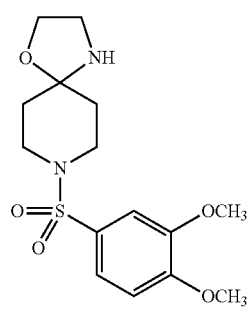
C0050
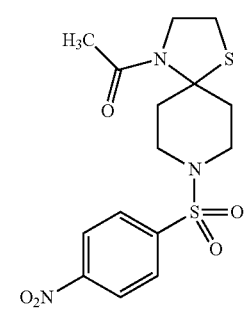
C0055-4
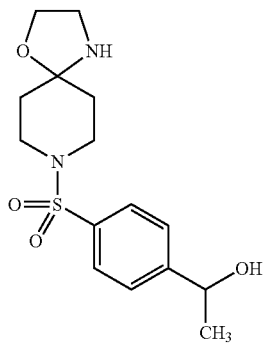
C0055
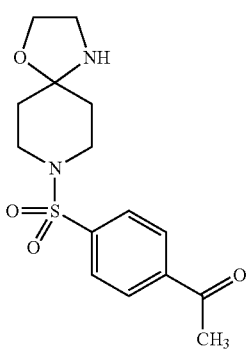
C0056
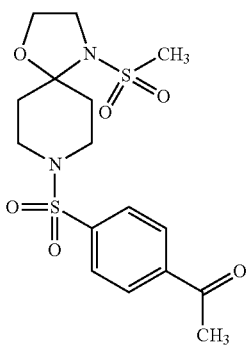
C0058
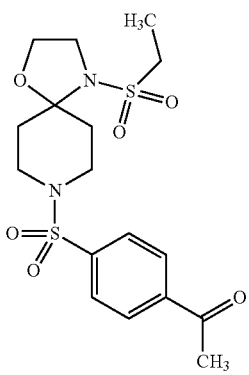

-continued
C0059
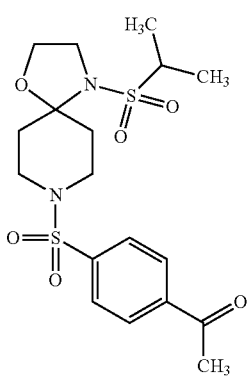
C0060
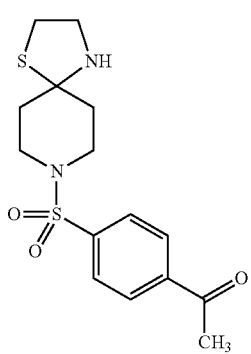
C0062-3
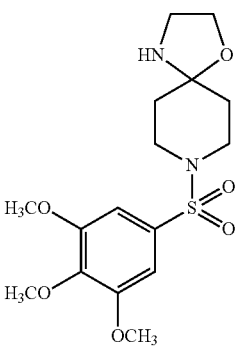
C0066
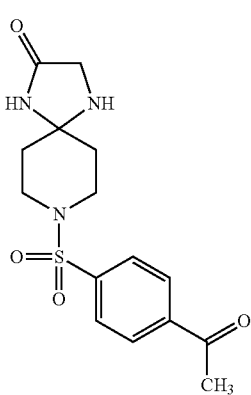
-continued
C0062-3
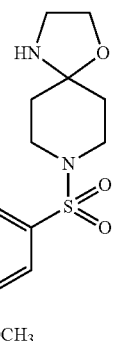
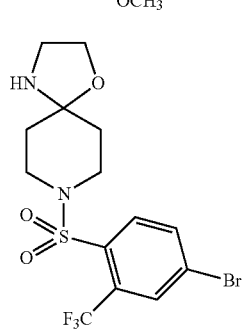
C0068-2
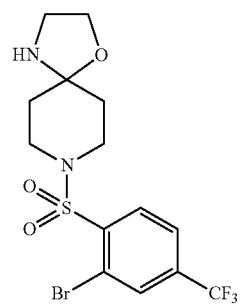
C0071-2
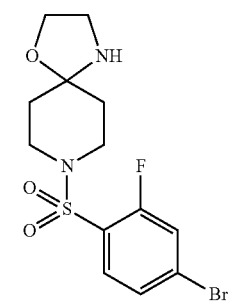
C0078-2
C0079M-7
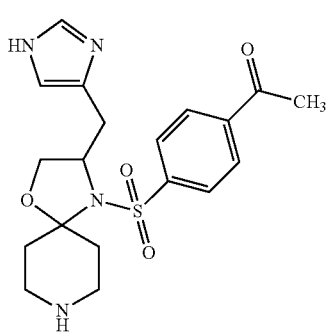

C0080M-6
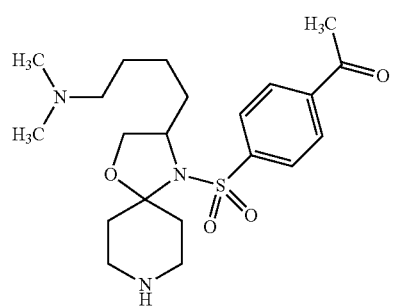
C0081M-7
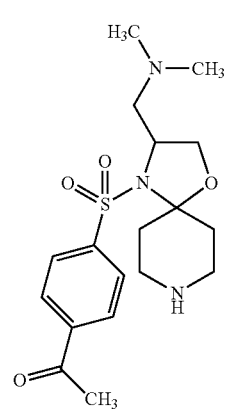
C0083M
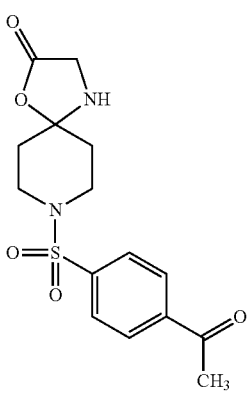
C0086M
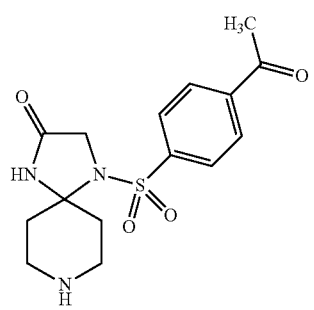
C0087M
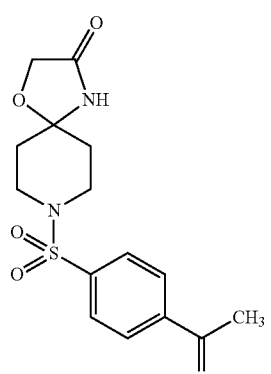
C0088M
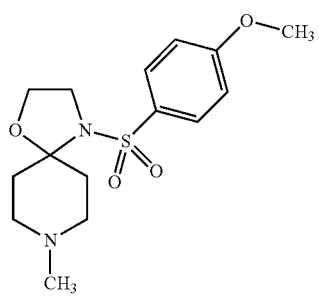
C0089M
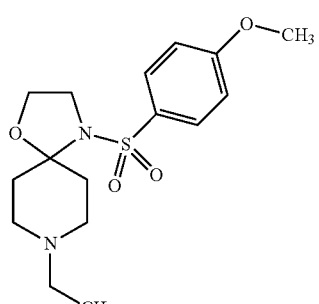
C0090M
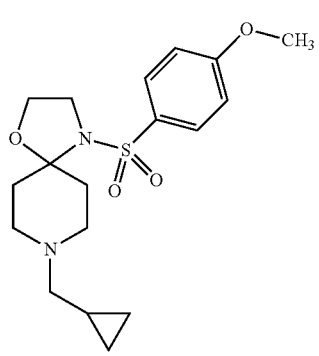
C0091M
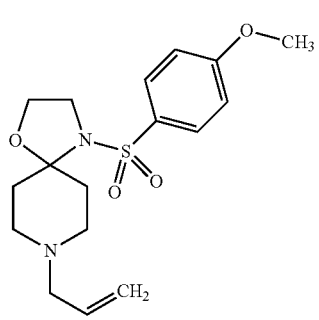

-continued
C0092M
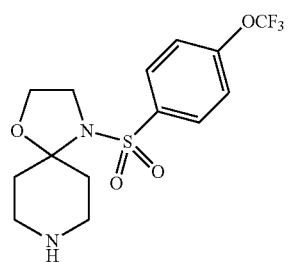
C0093M
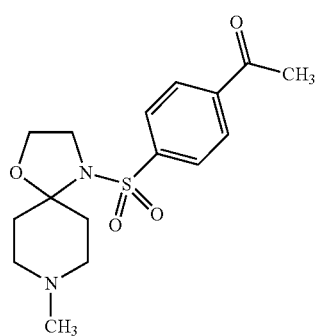
C0094M
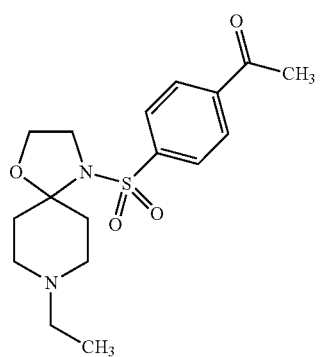
C0095M
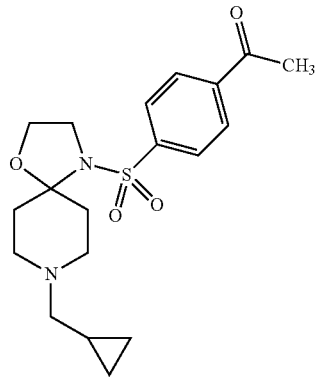
-continued
C0096M
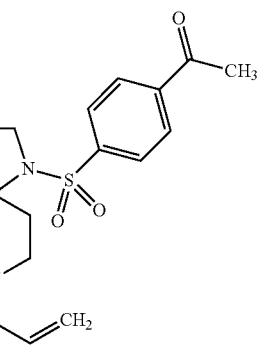
C0097M
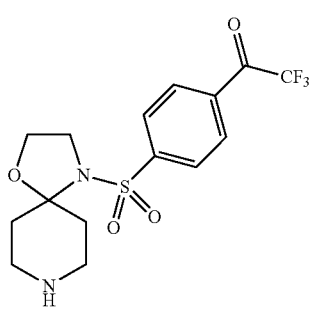
C0099M
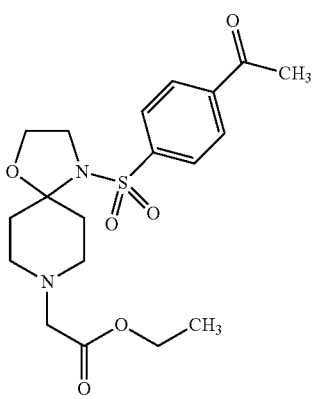
C0100M
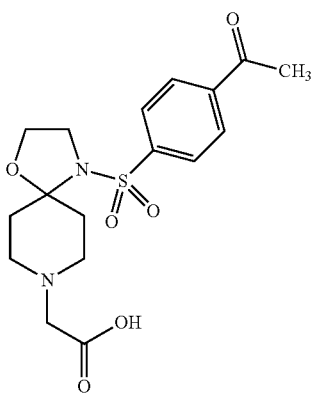

US 8,653,068 B2
| | |
|---|---|
| C0101M 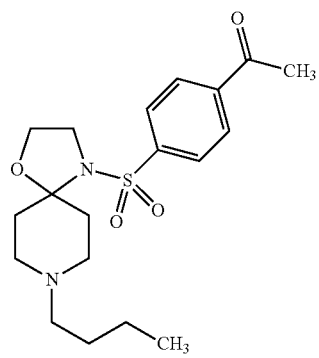 | C0119M 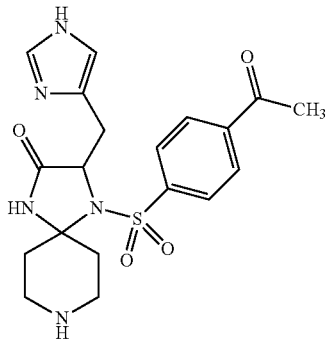 |
| C0102M 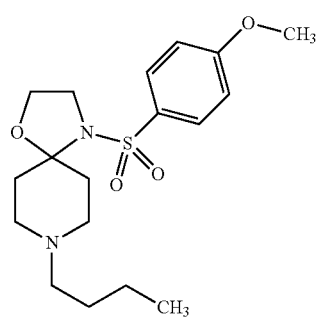 | C0125M 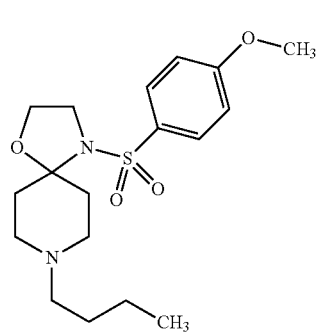 |
| C0104M 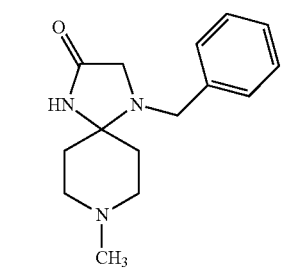 | C0126M 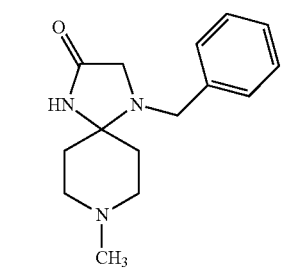 |
| C0105M 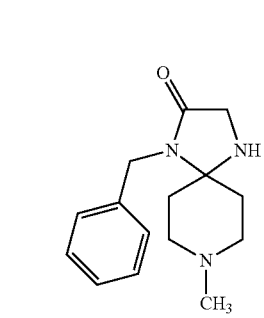 | C0128M 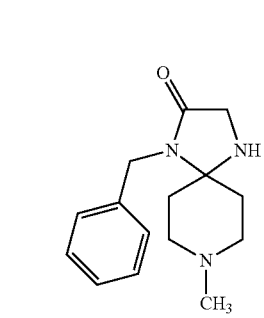 |
| C0118M 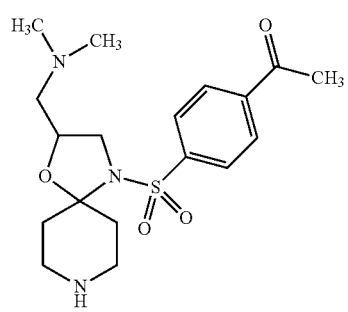 | |

C0133M
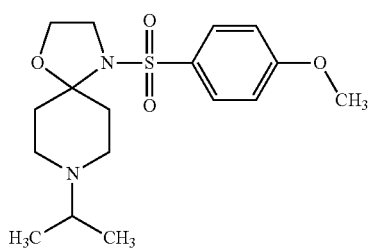
C0134M
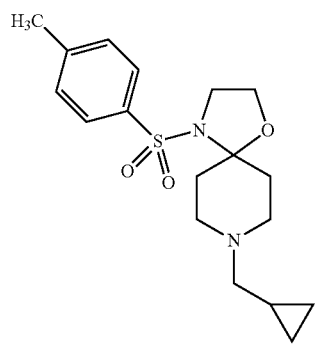
C0135M
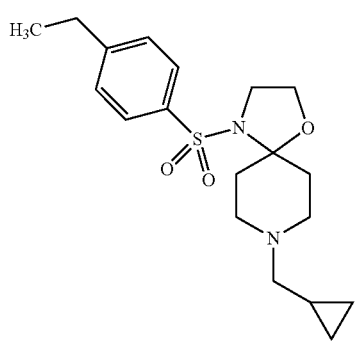
C0136M (P5)
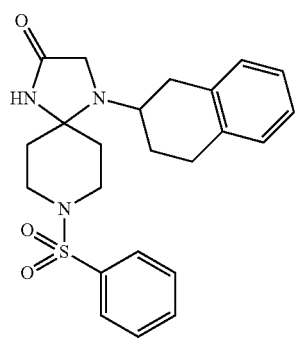
C0137M P7
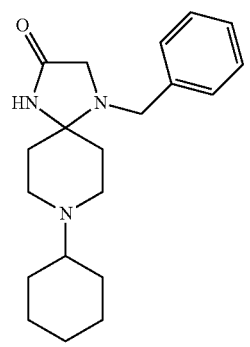
C0142M
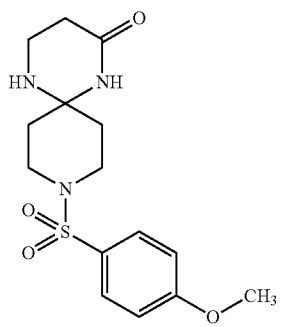
C0143M-2
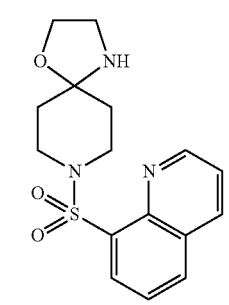
C0144M-2
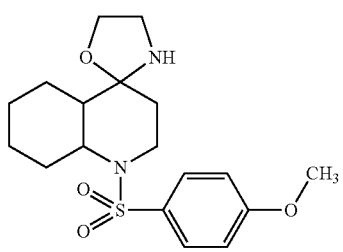
C0145M-3
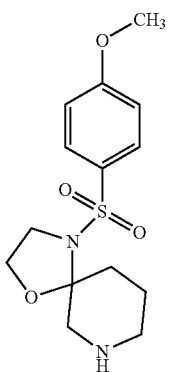

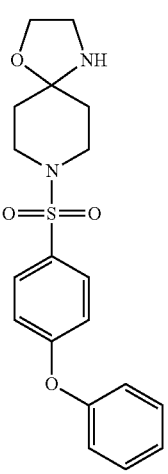

C0149M-2

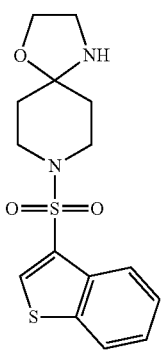

C0150M-2

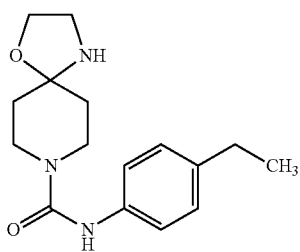

C0151M-2

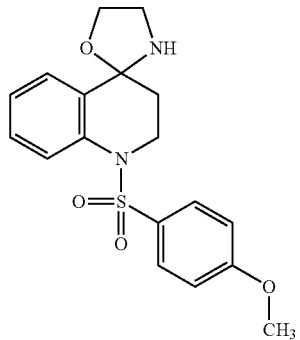

C0152M-4

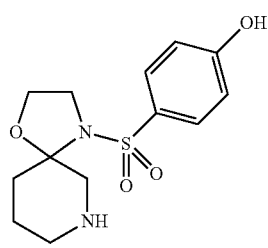

C0153M-3

Tables A-AE hereinafter illustrate several further contemplated compounds having various linking groups X, central spiro ring systems and aromatic ring systems, circle A, and wherein the wavy lines indicate the place of bonding between the circle A ring system and the central spiro ring system. Substituents on the aromatic or heteroaromatic ring systems are omitted for added clarity with the understanding that one to three substituents, $R^{1a-c}$, can be present bonded to each of the ring systems as discussed previously.

TABLE A

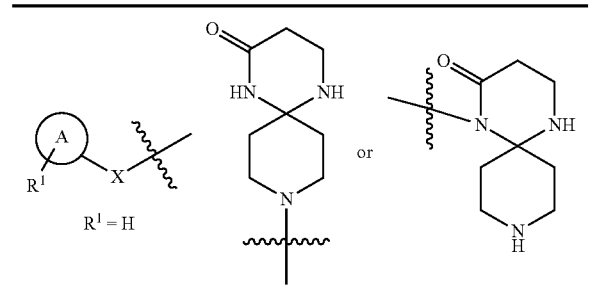

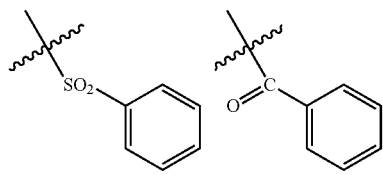

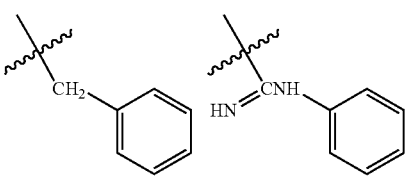

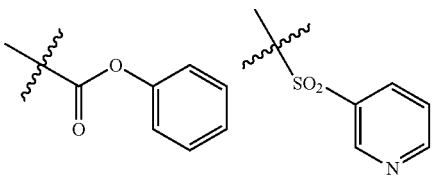 [SMILES: *C(=O)Oc1ccccc1 ; *S(=O)(=O)c1cccnc1]

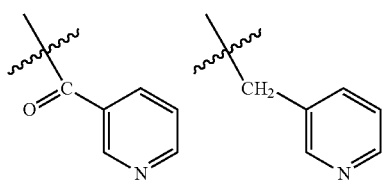 [SMILES: *C(=O)c1cccnc1 ; *Cc1cccnc1]

TABLE A-continued
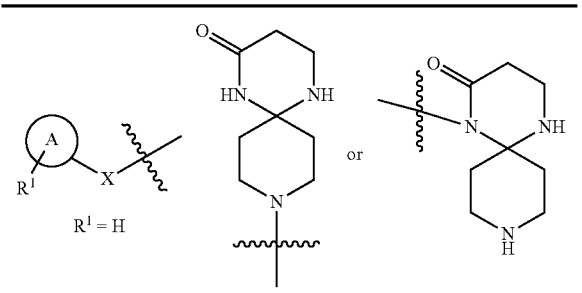
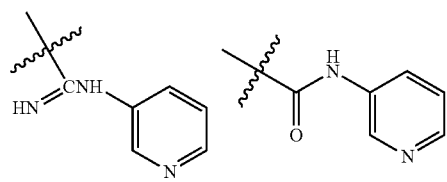
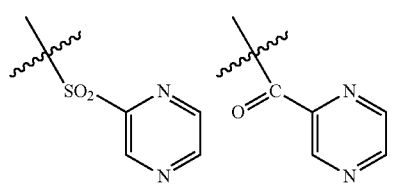
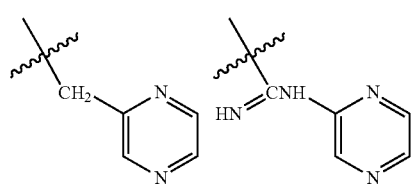
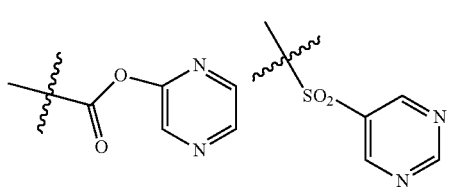
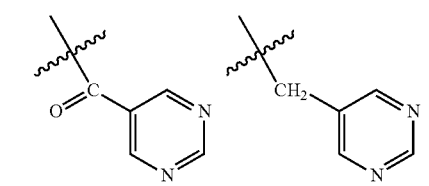 [SMILES: *C(=O)c1cncnc1 ; *Cc1cncnc1]
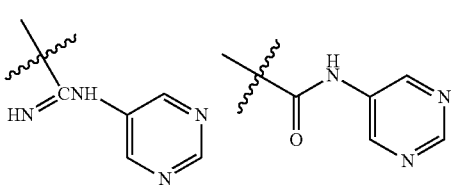
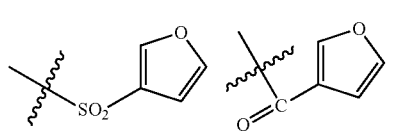
TABLE A-continued
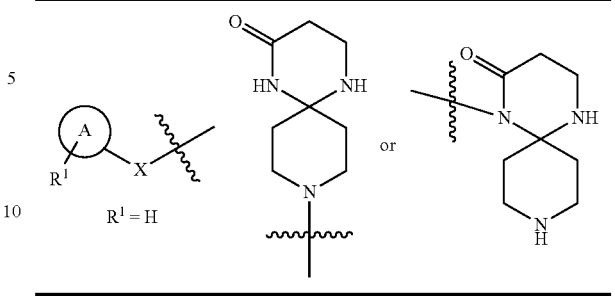
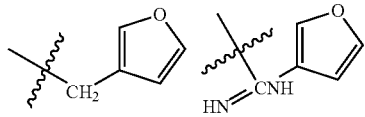
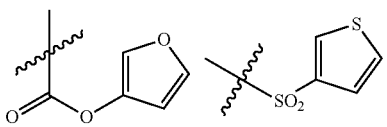
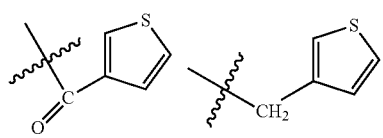 [SMILES: *C(=O)c1ccsc1 ; *Cc1ccsc1]
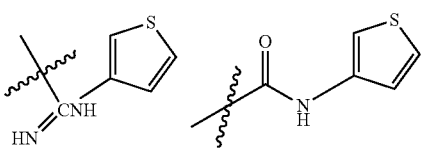
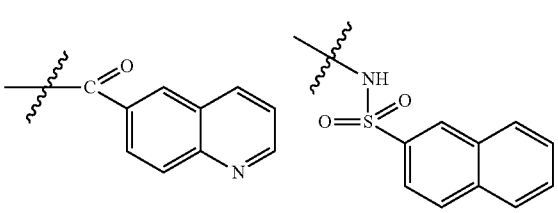
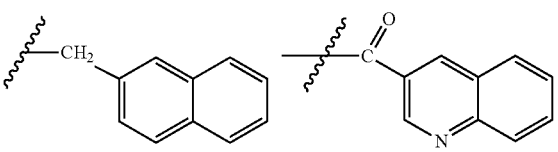 [SMILES: *Cc1ccc2ccccc2c1 ; *C(=O)c1cnc2ccccc2c1]
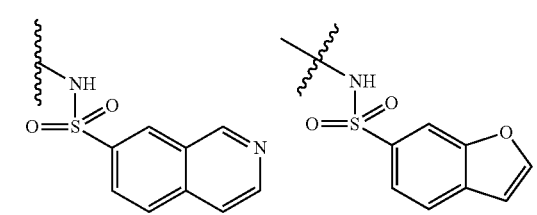
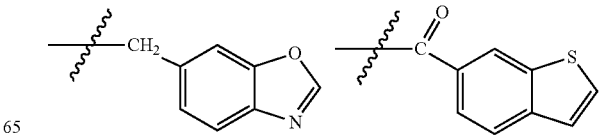

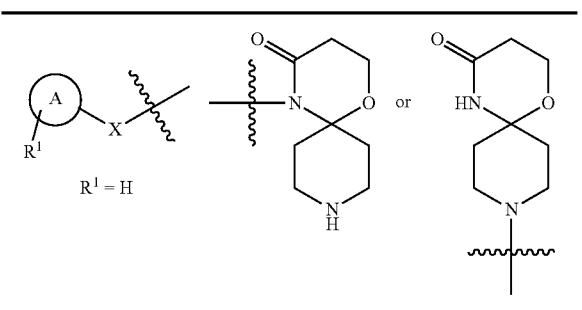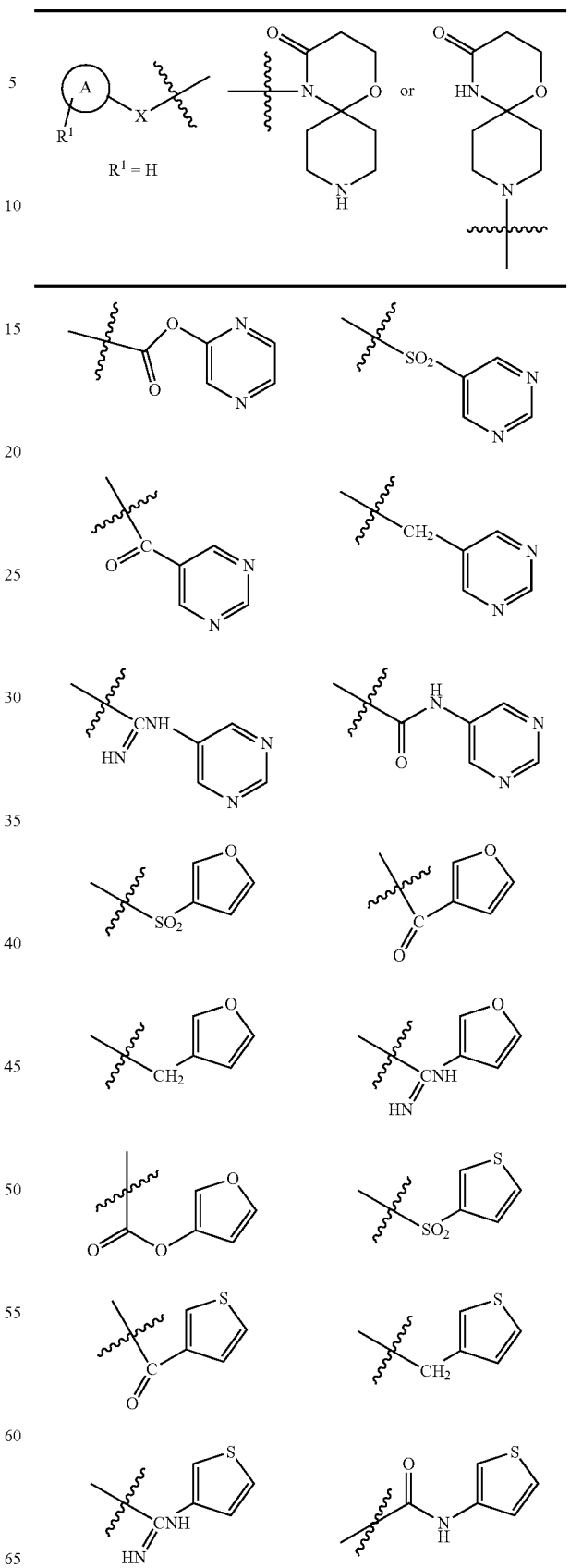

TABLE B-continued
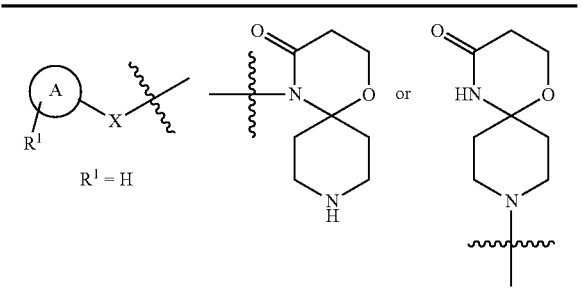
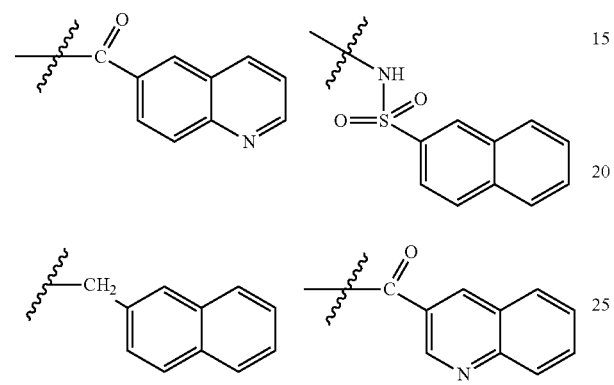
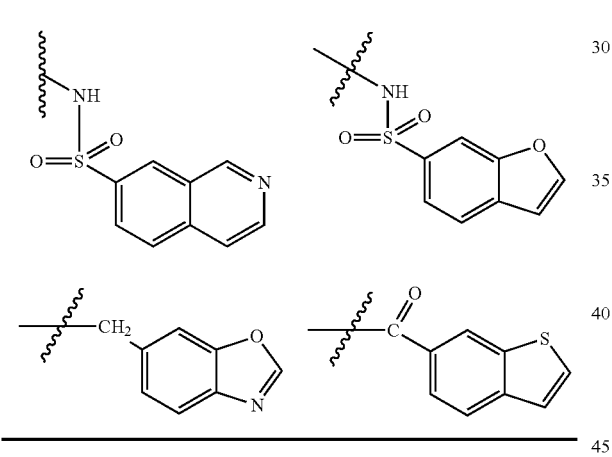
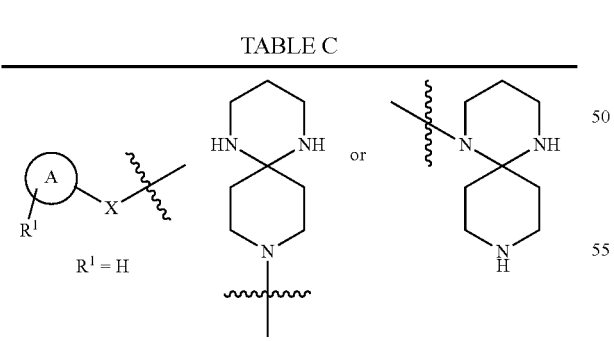
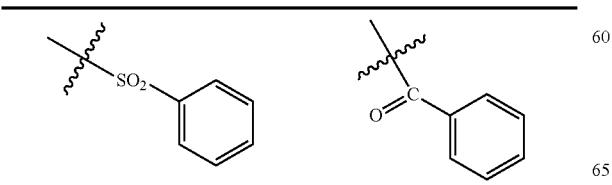
TABLE C
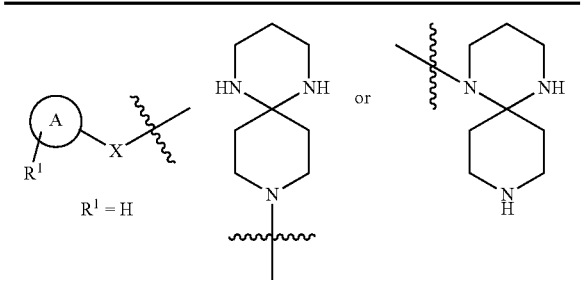
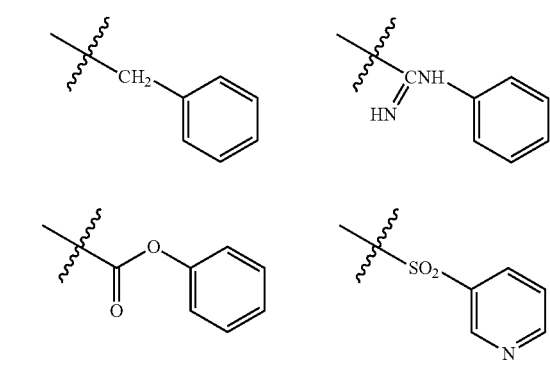
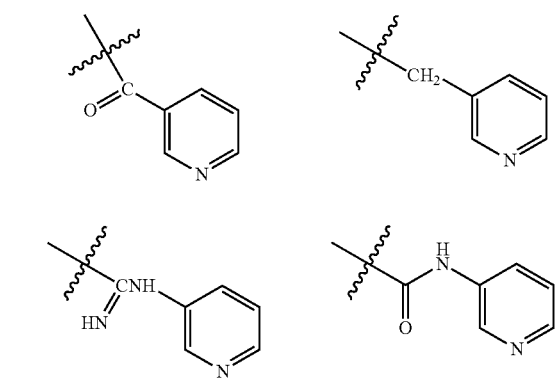
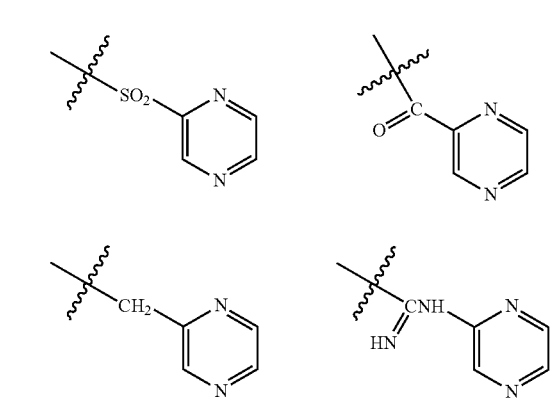
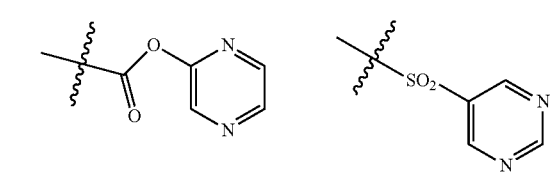
TABLE C-continued

TABLE C-continued
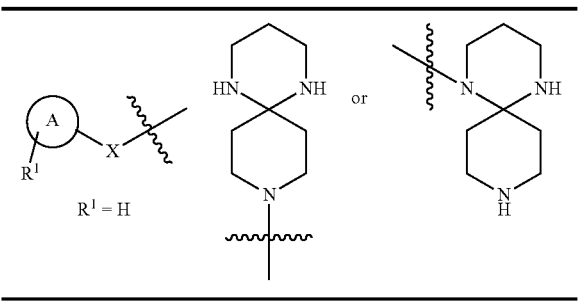
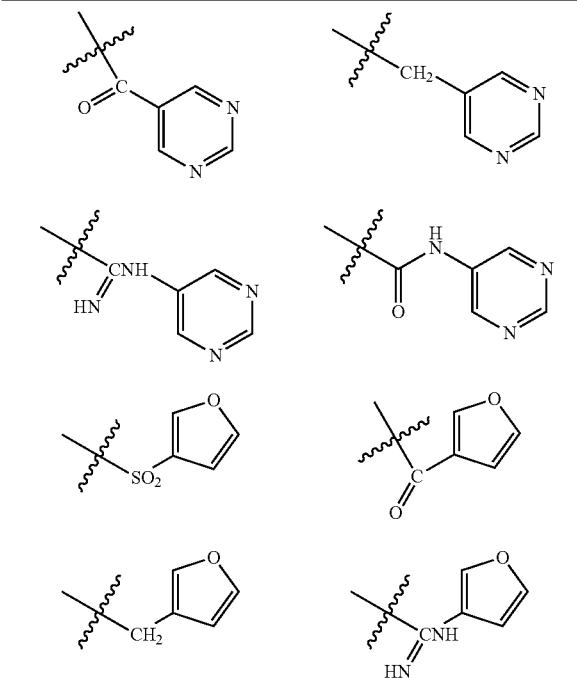
TABLE C-continued
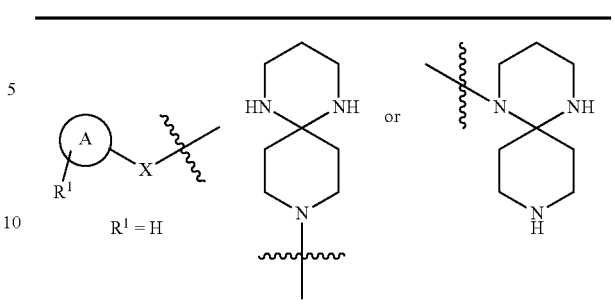
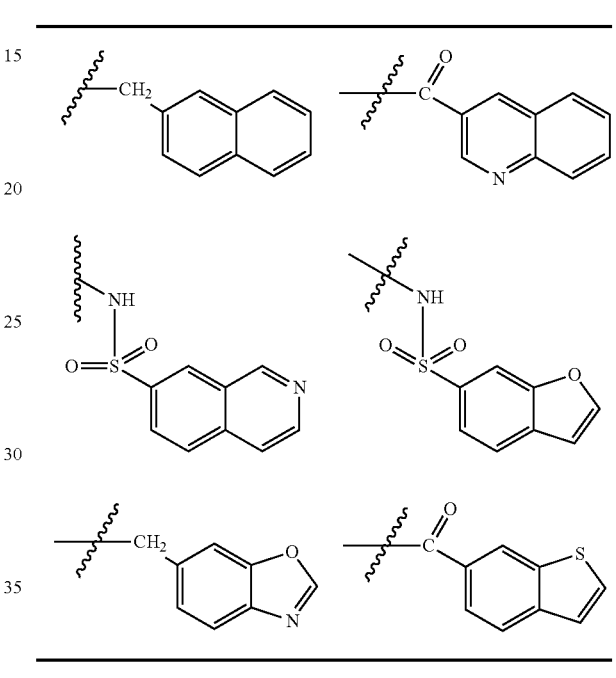
TABLE D
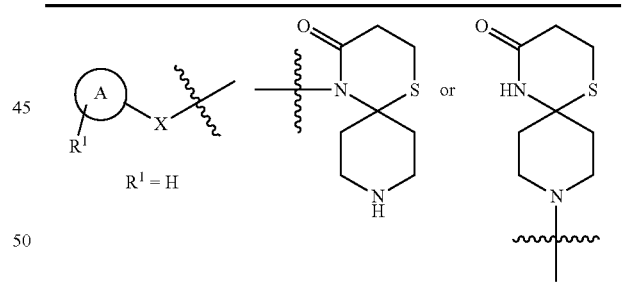
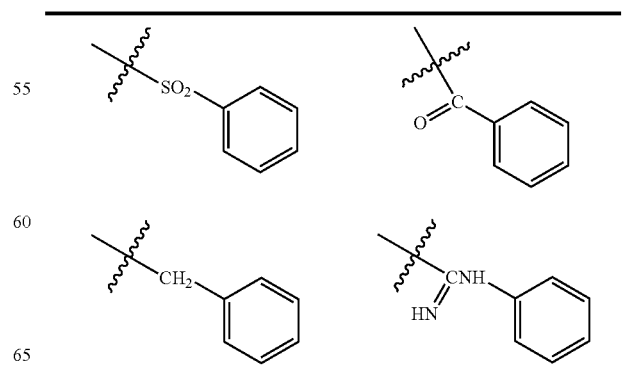

TABLE D-continued
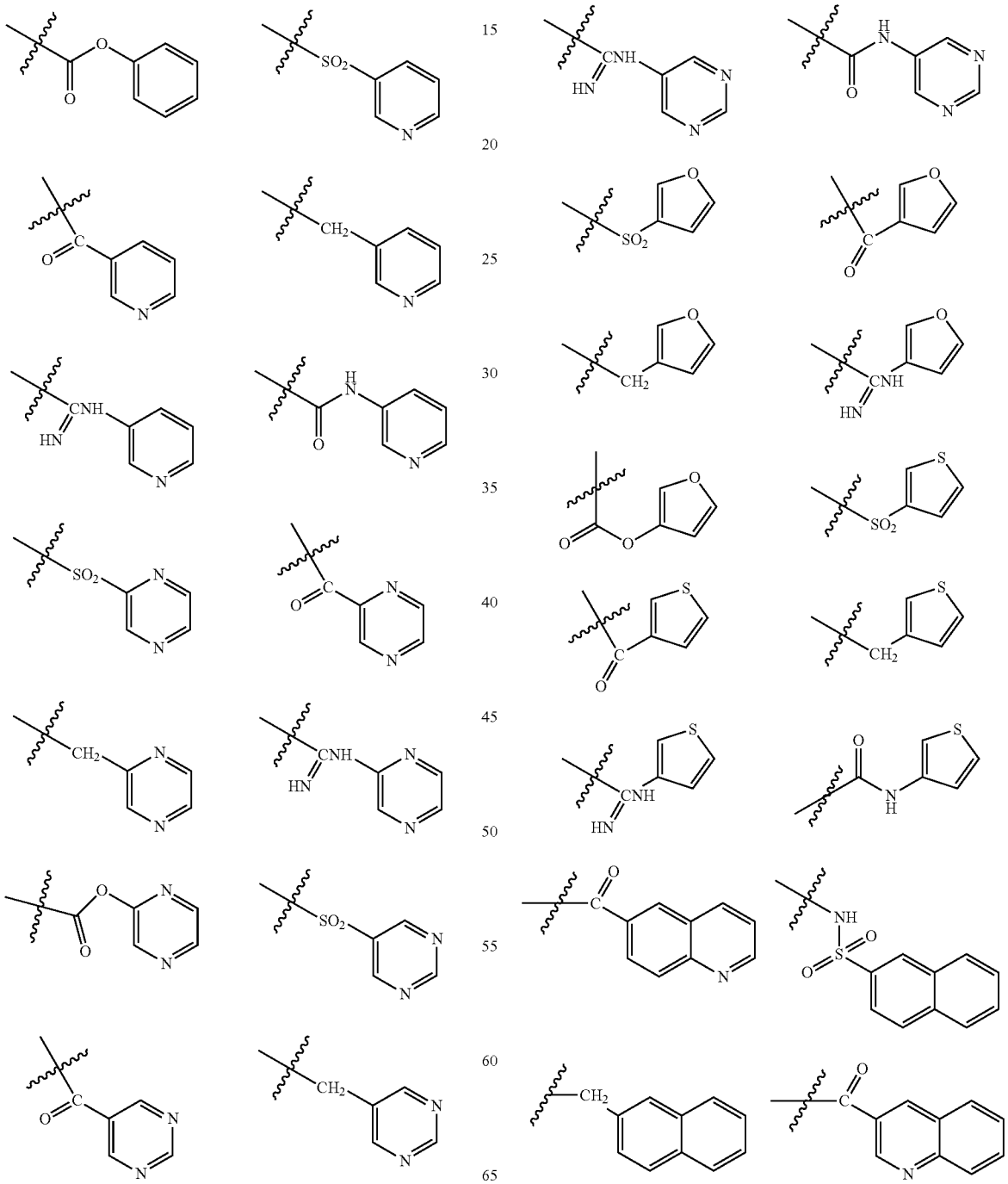

TABLE D-continued
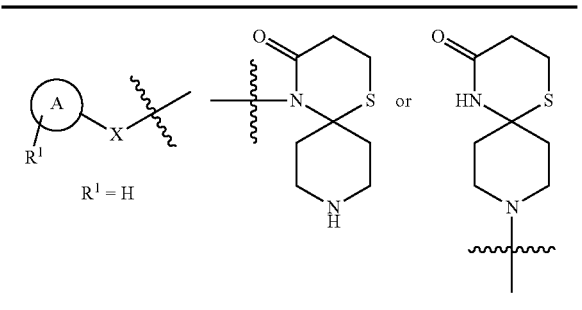
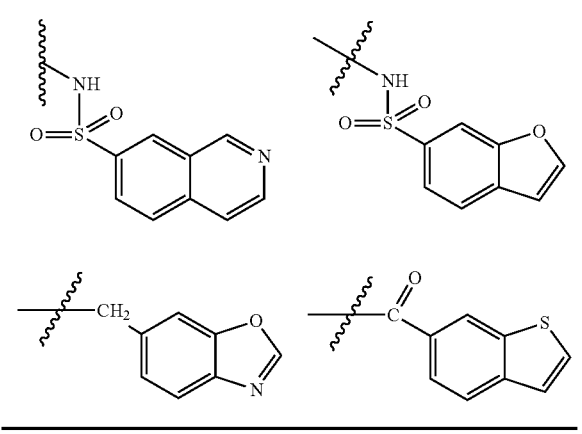
TABLE E
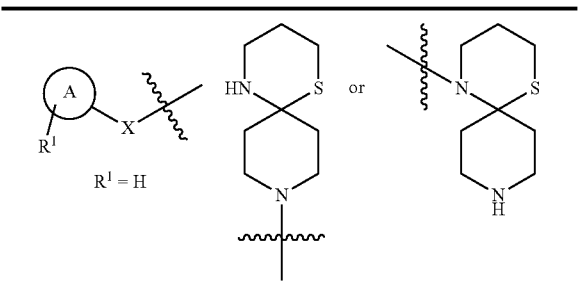
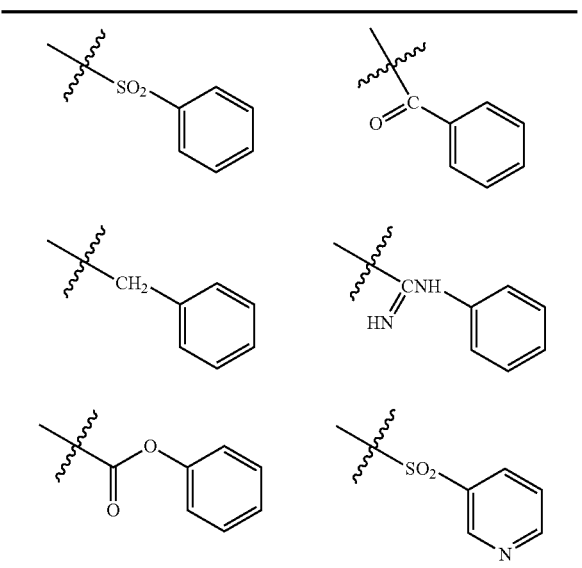
TABLE E-continued
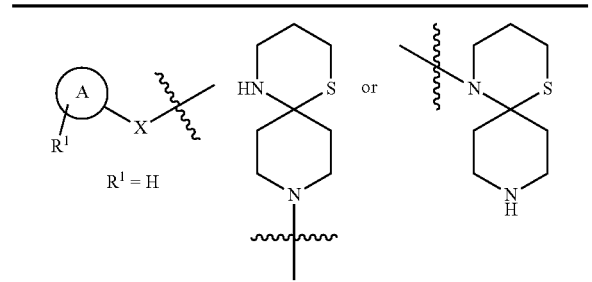
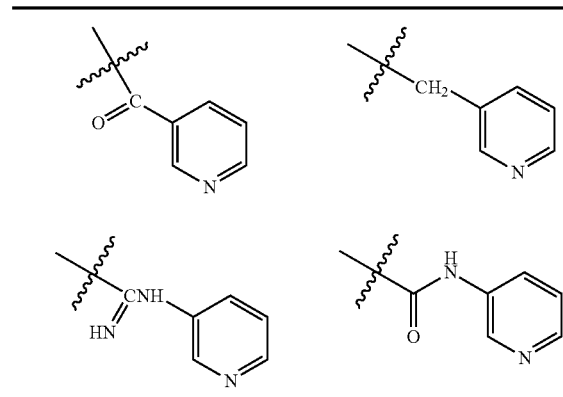
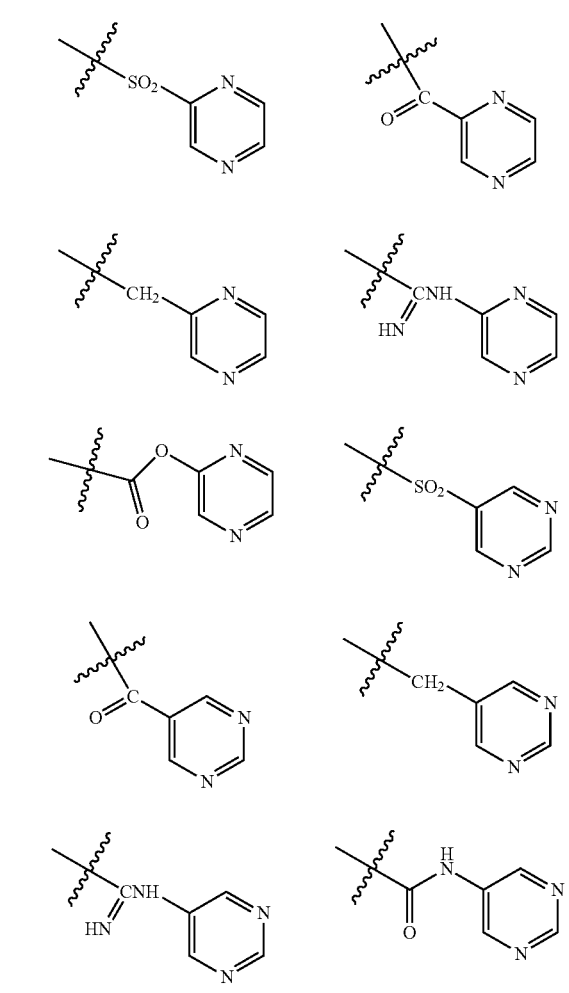

TABLE E-continued
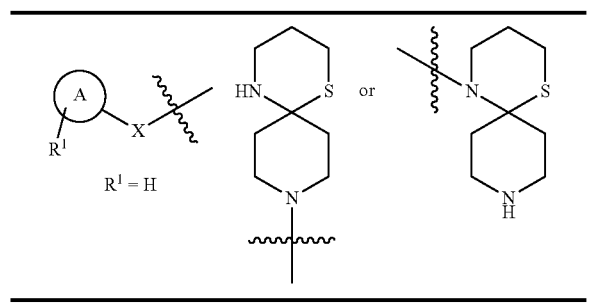
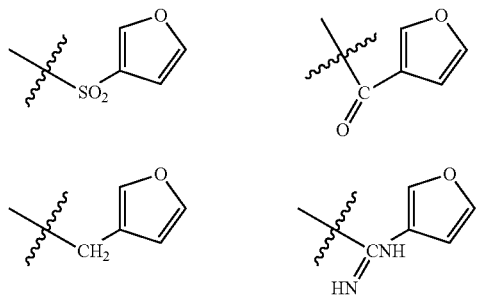
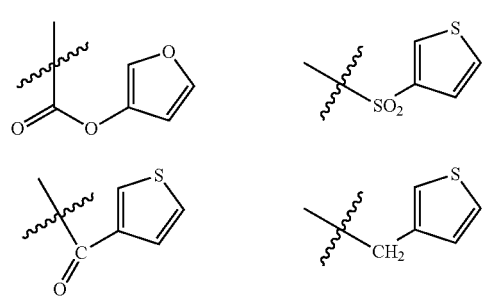
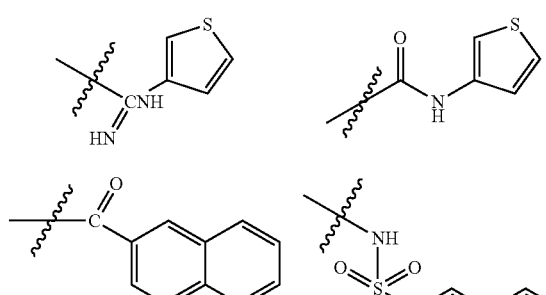
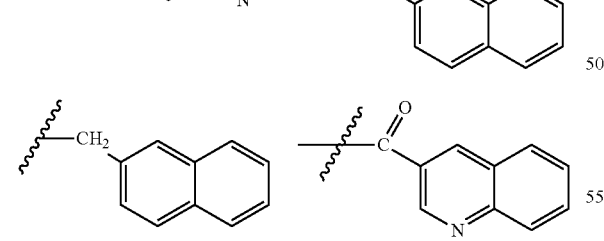
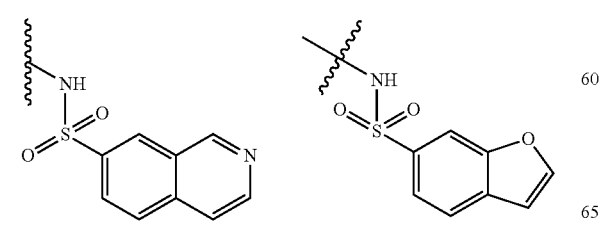
TABLE E-continued
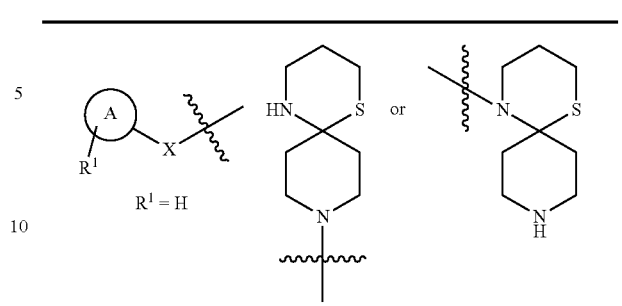
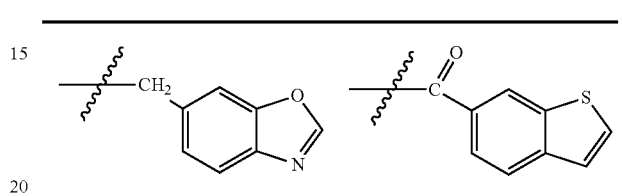
TABLE F
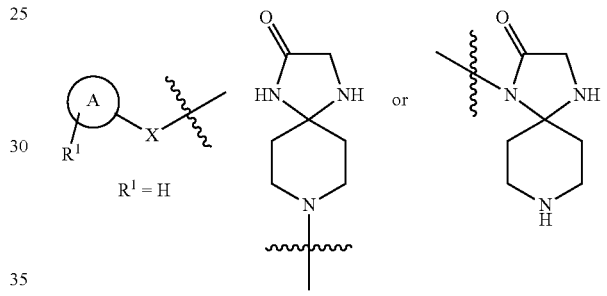
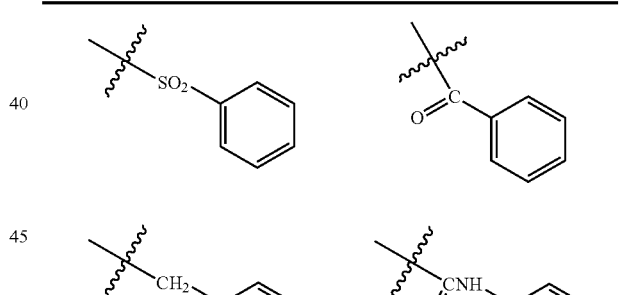
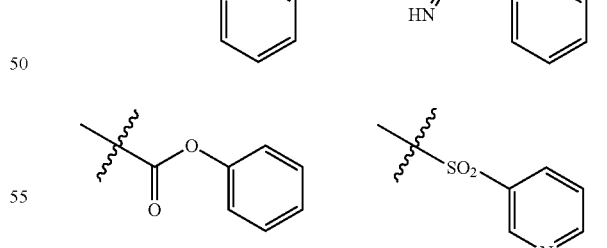
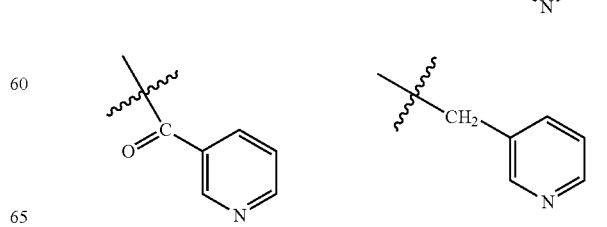

TABLE F-continued
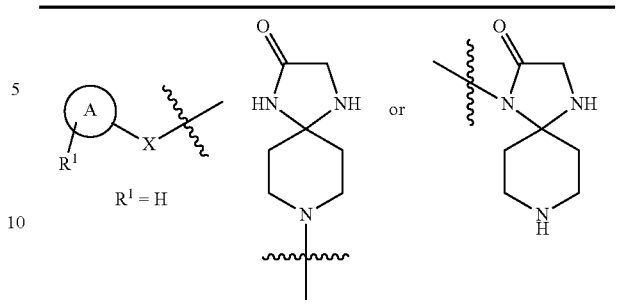
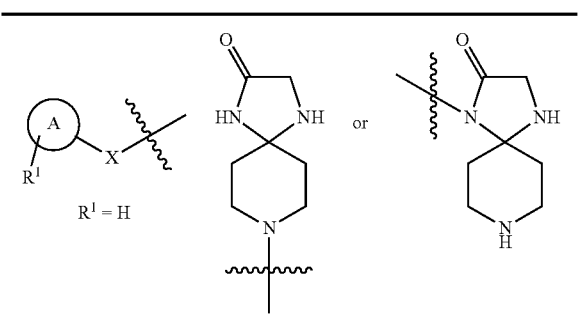
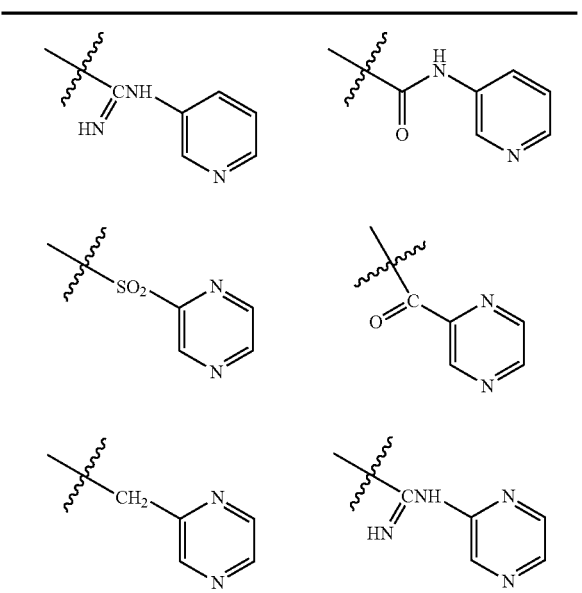
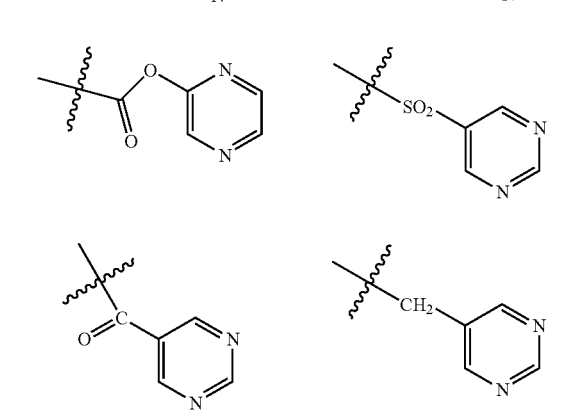
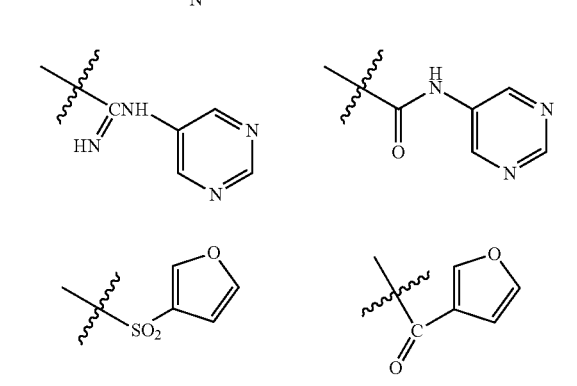
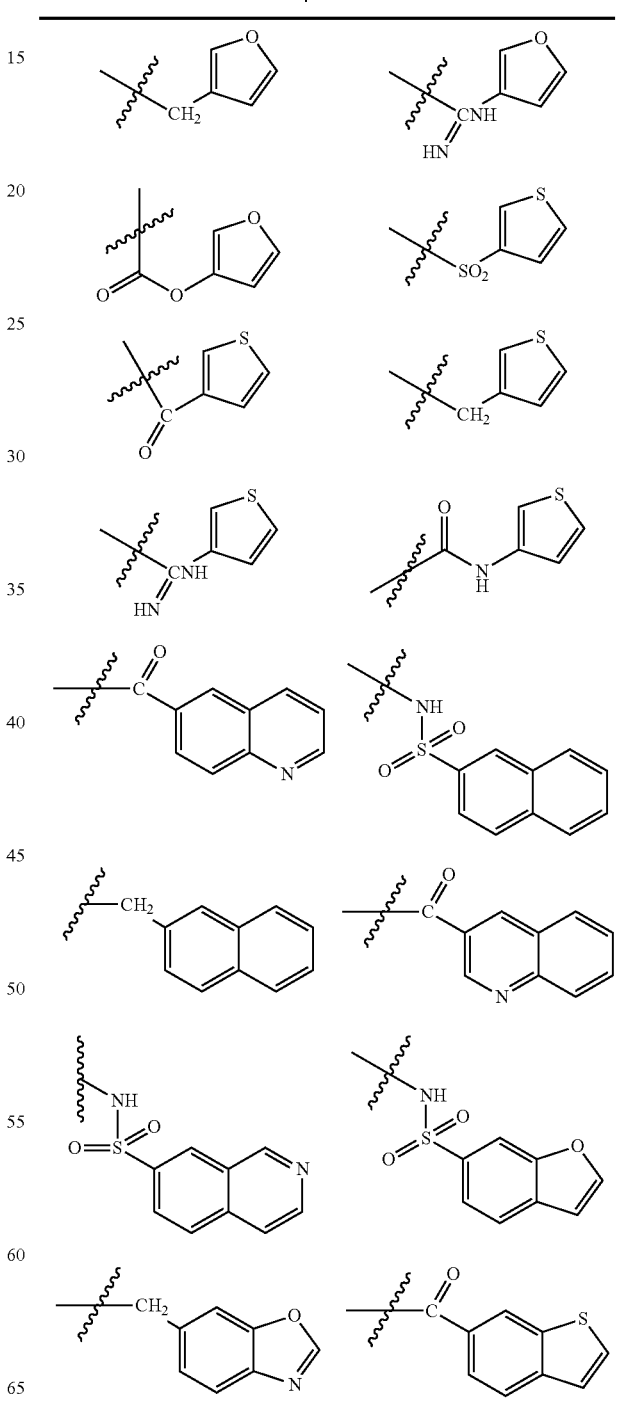

TABLE G
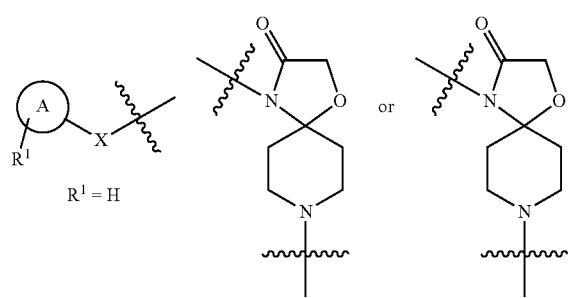
R¹ = H
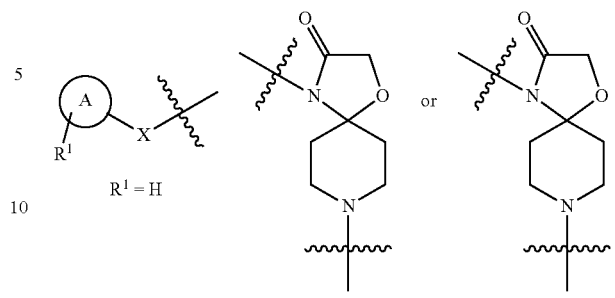
R¹ = H
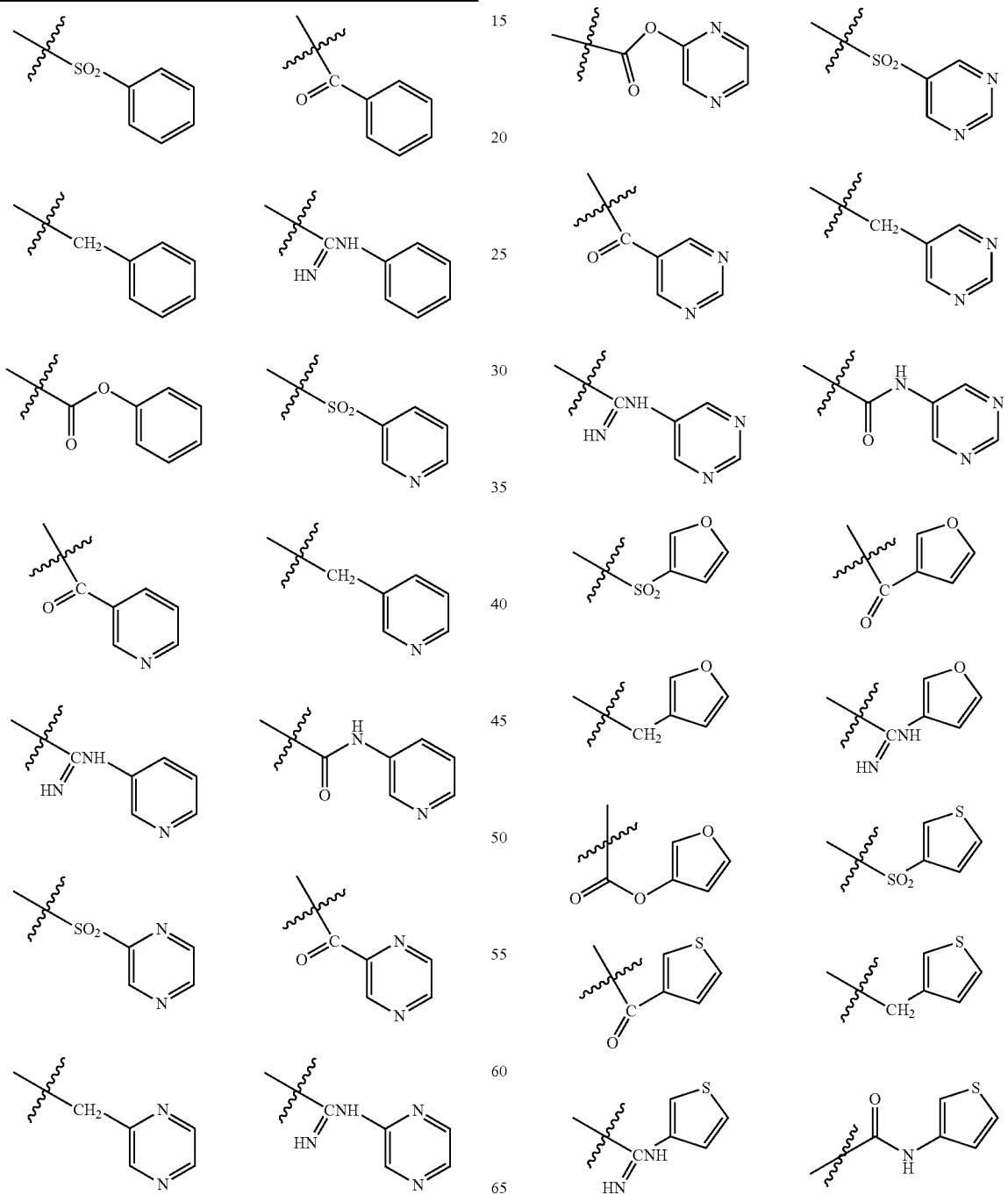

TABLE G-continued
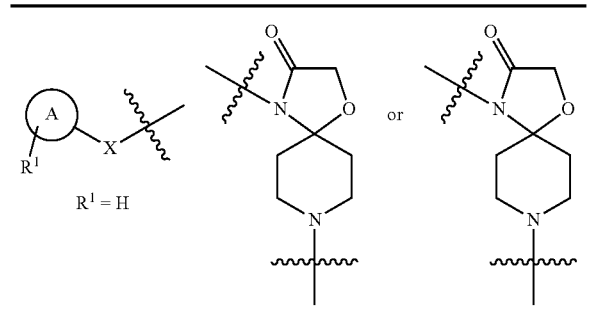
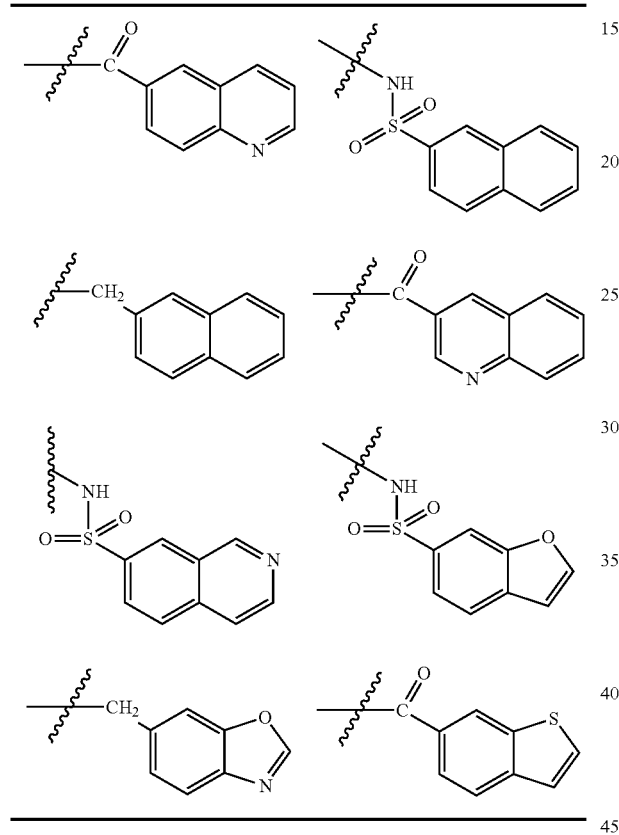
TABLE H
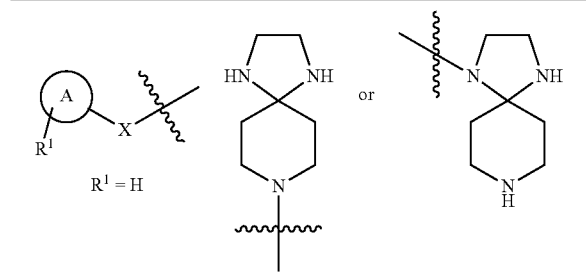
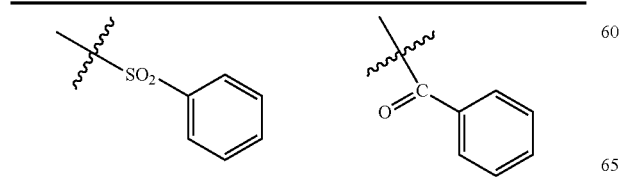
TABLE H-continued
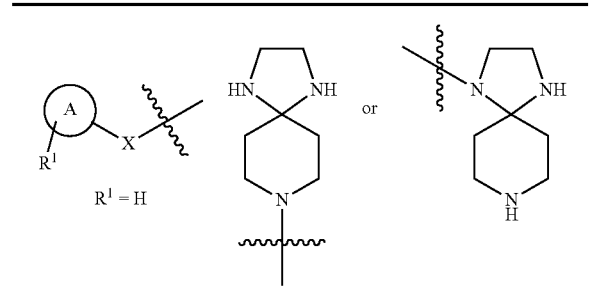
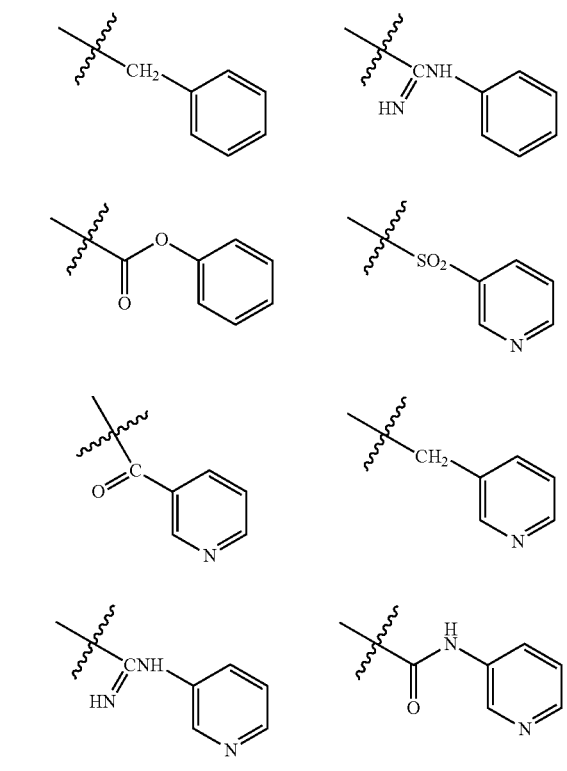
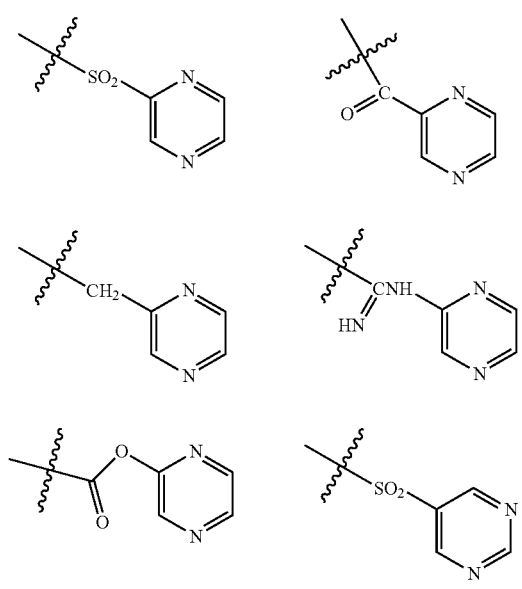

TABLE H-continued
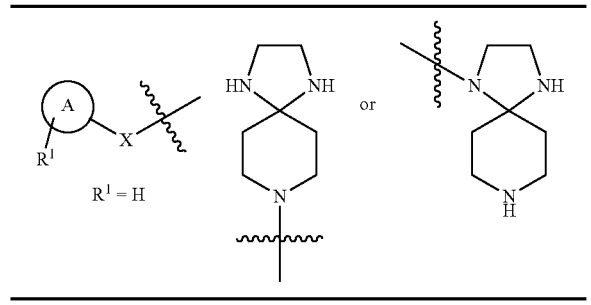
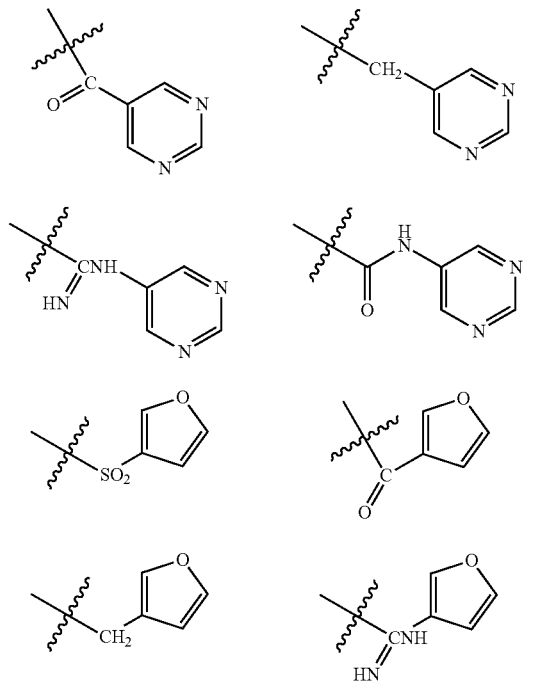
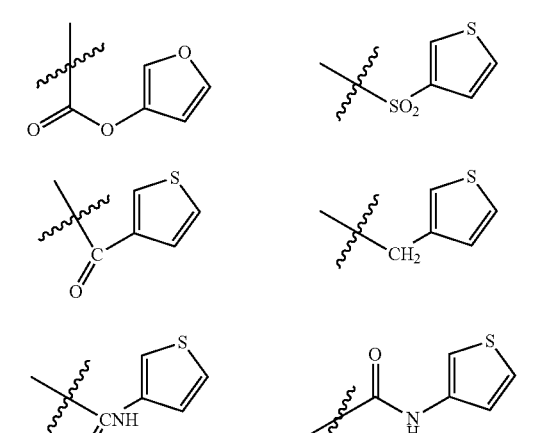
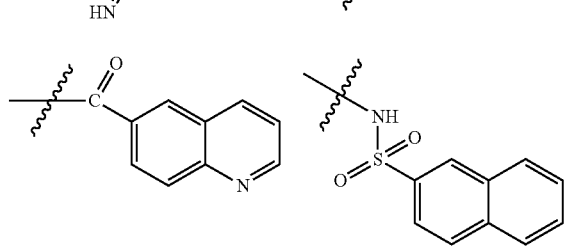
TABLE H-continued
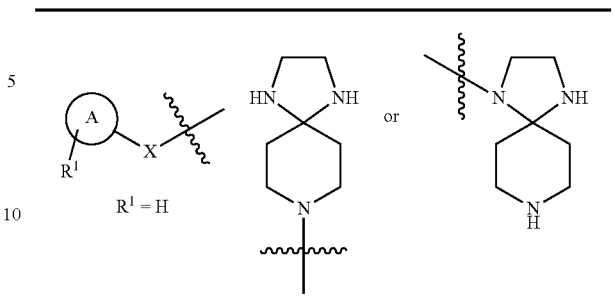
TABLE I
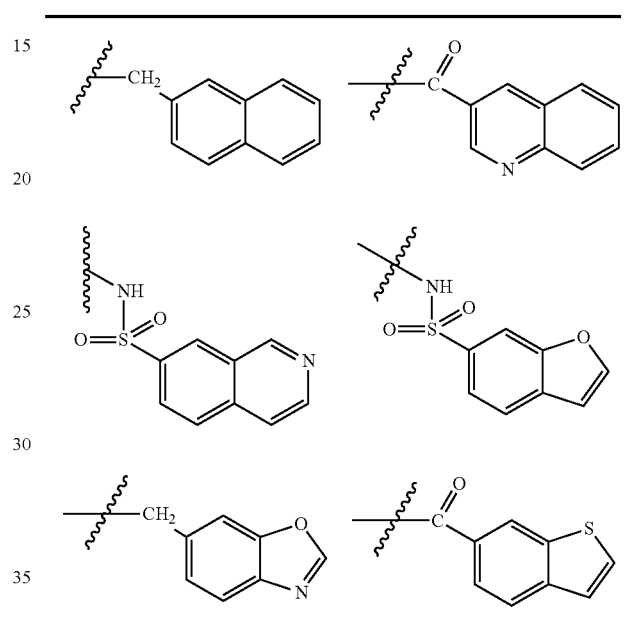
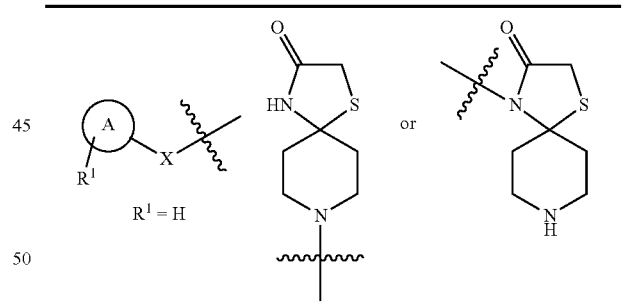
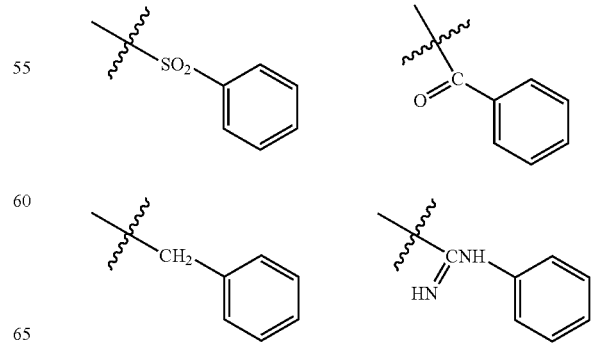

TABLE I-continued
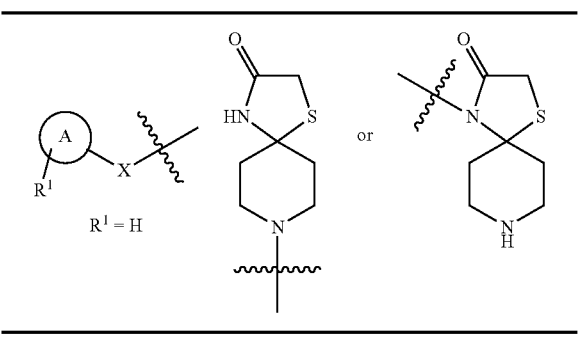
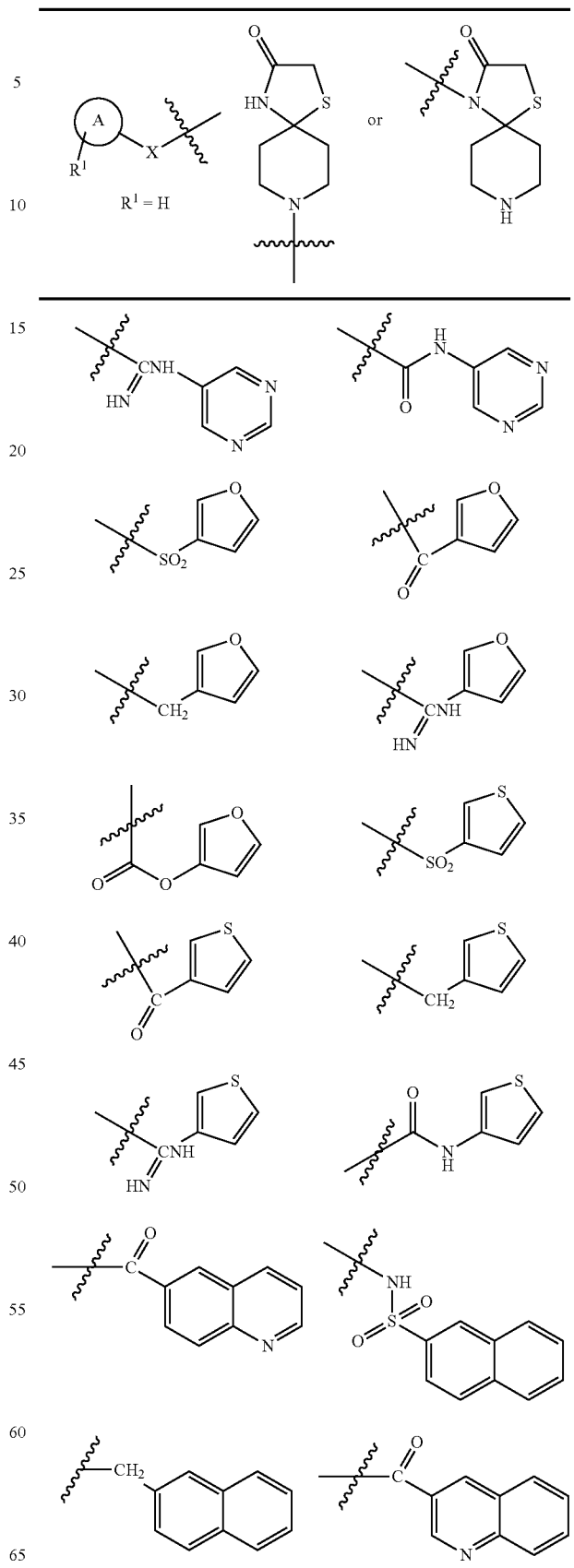

TABLE I-continued
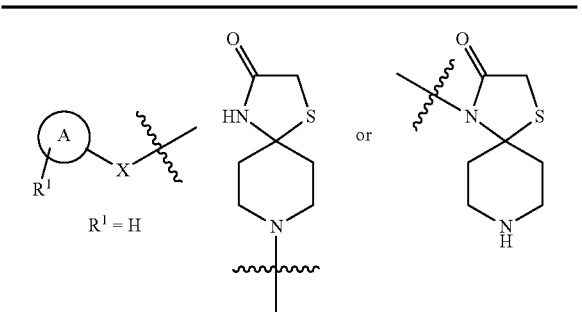
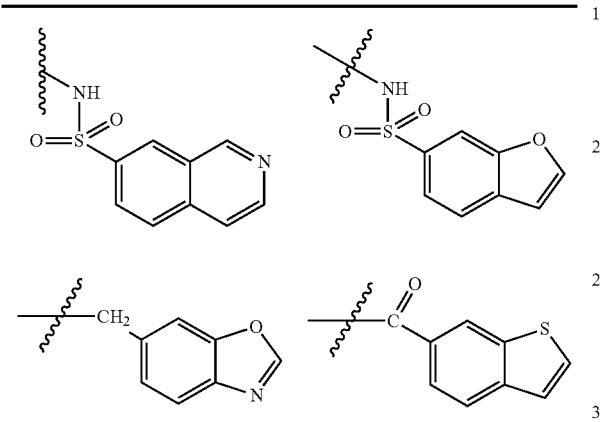
TABLE J
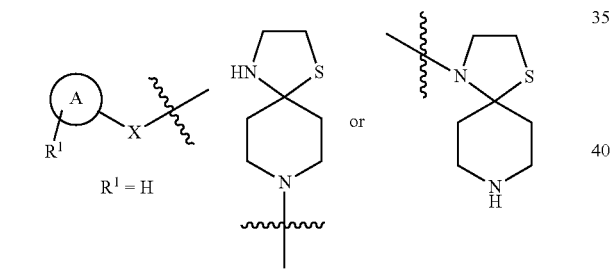
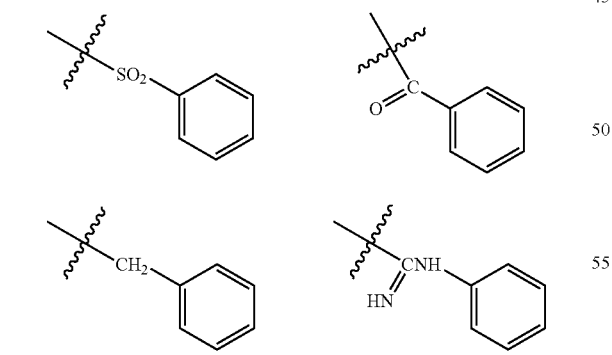
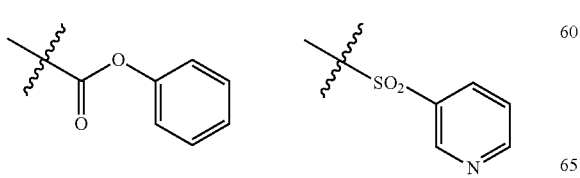
TABLE J-continued
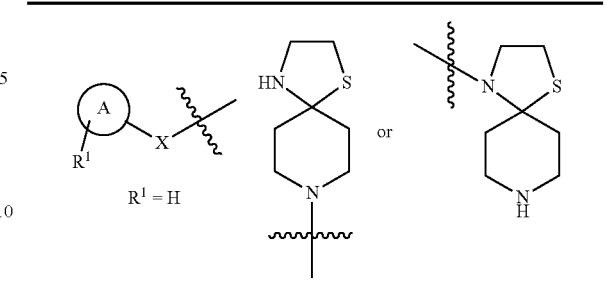
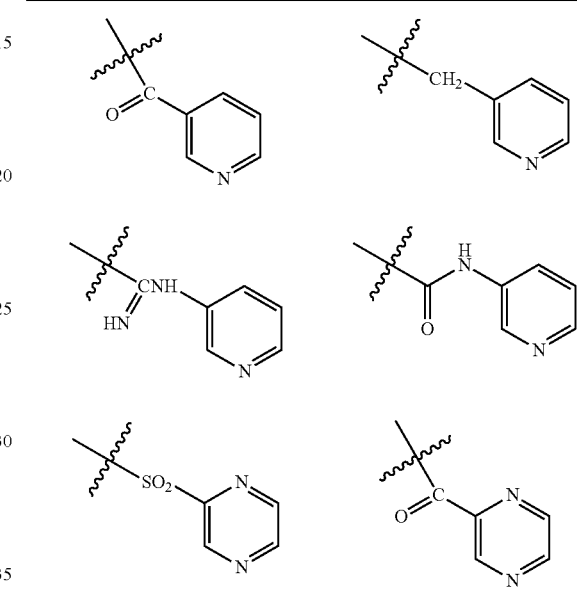

TABLE J-continued
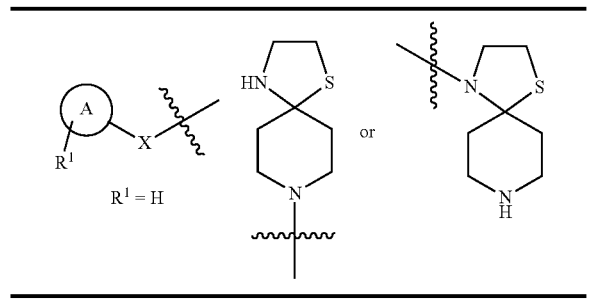
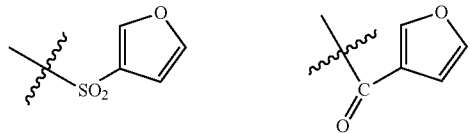
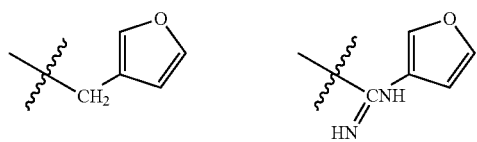
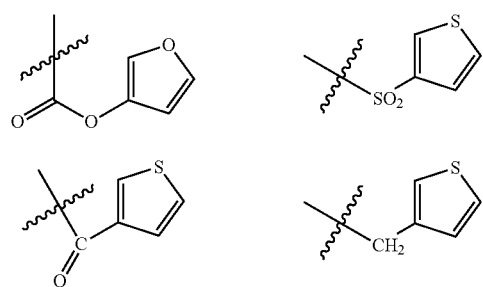
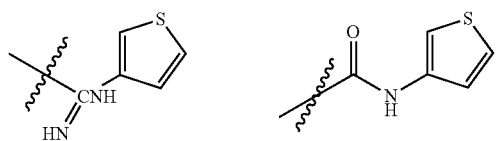
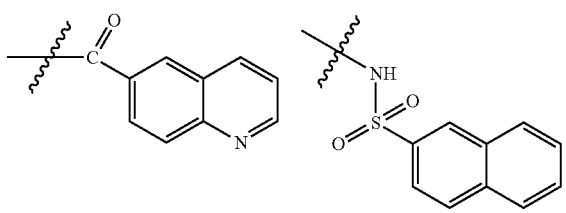
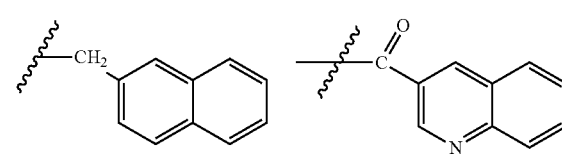
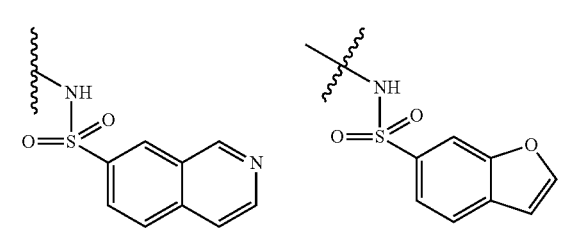
TABLE J-continued
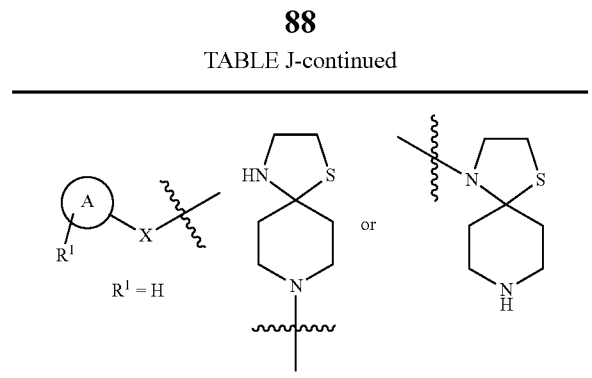
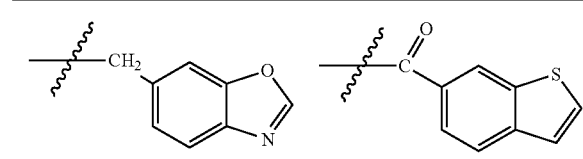
TABLE K
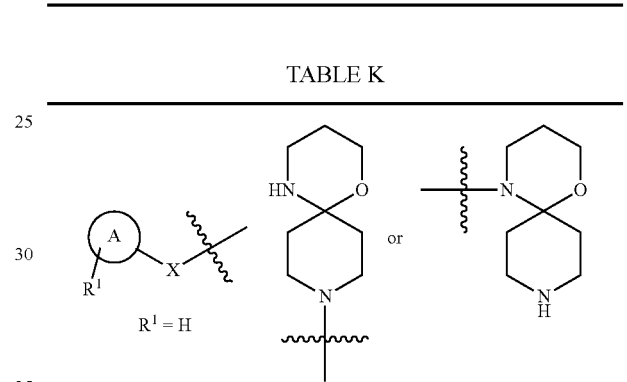
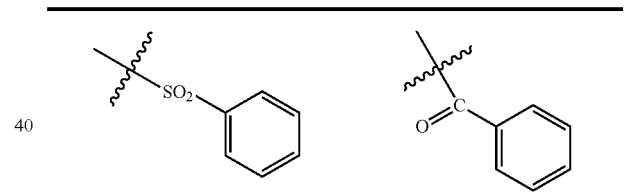
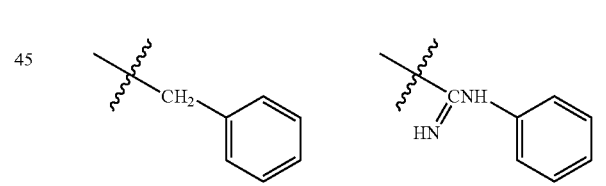
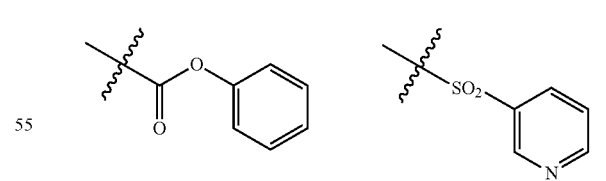
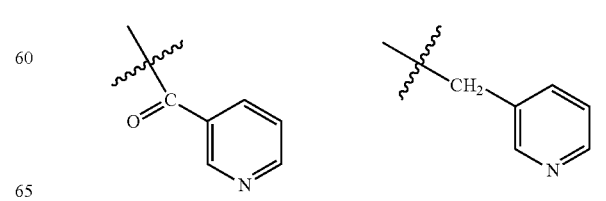

TABLE K-continued
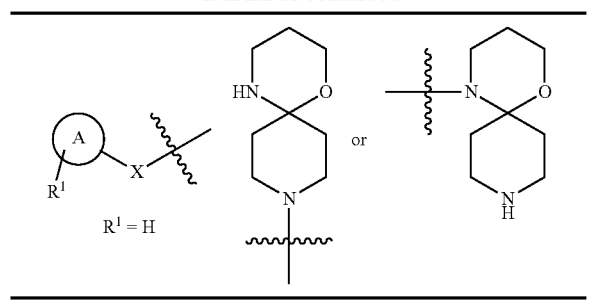
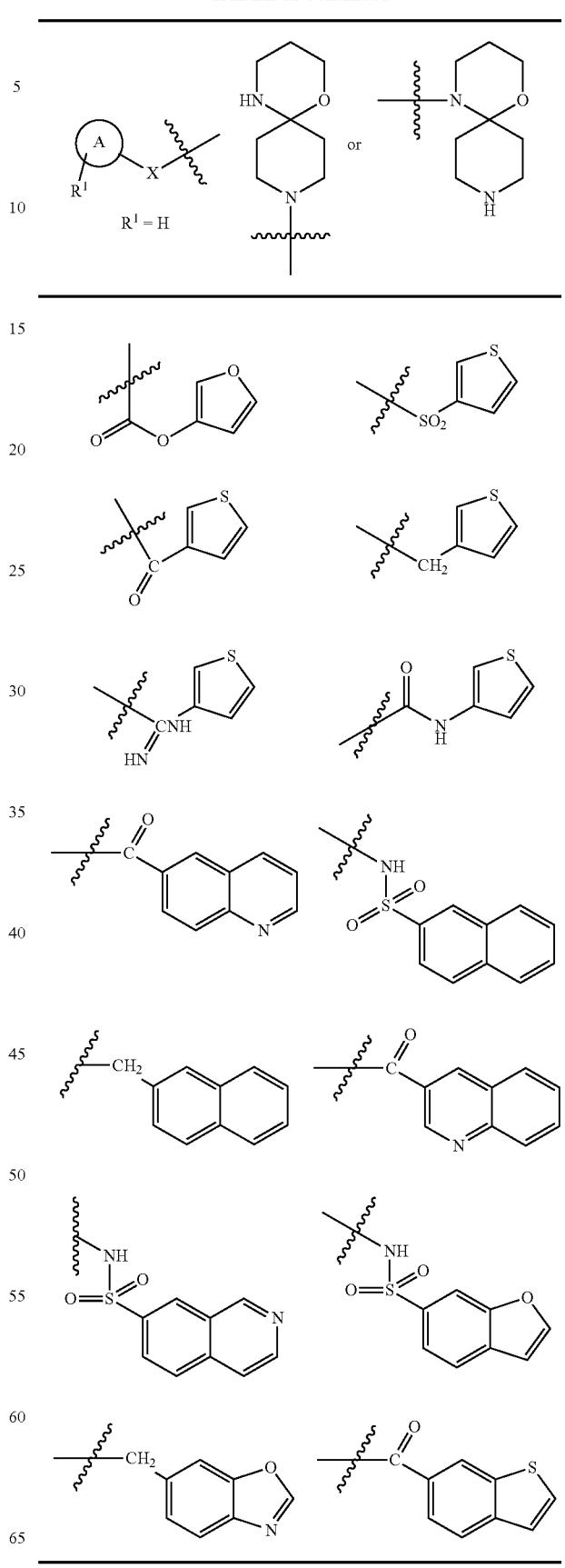

TABLE L
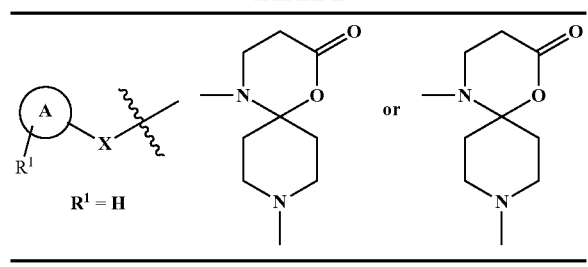
R¹ = H
TABLE L-continued
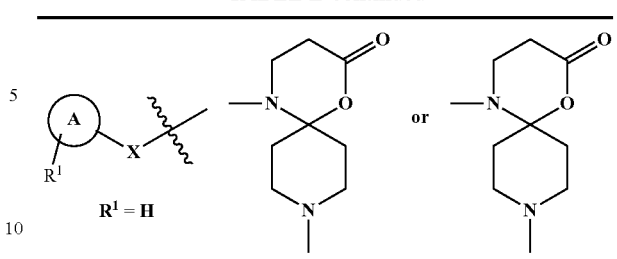
R¹ = H
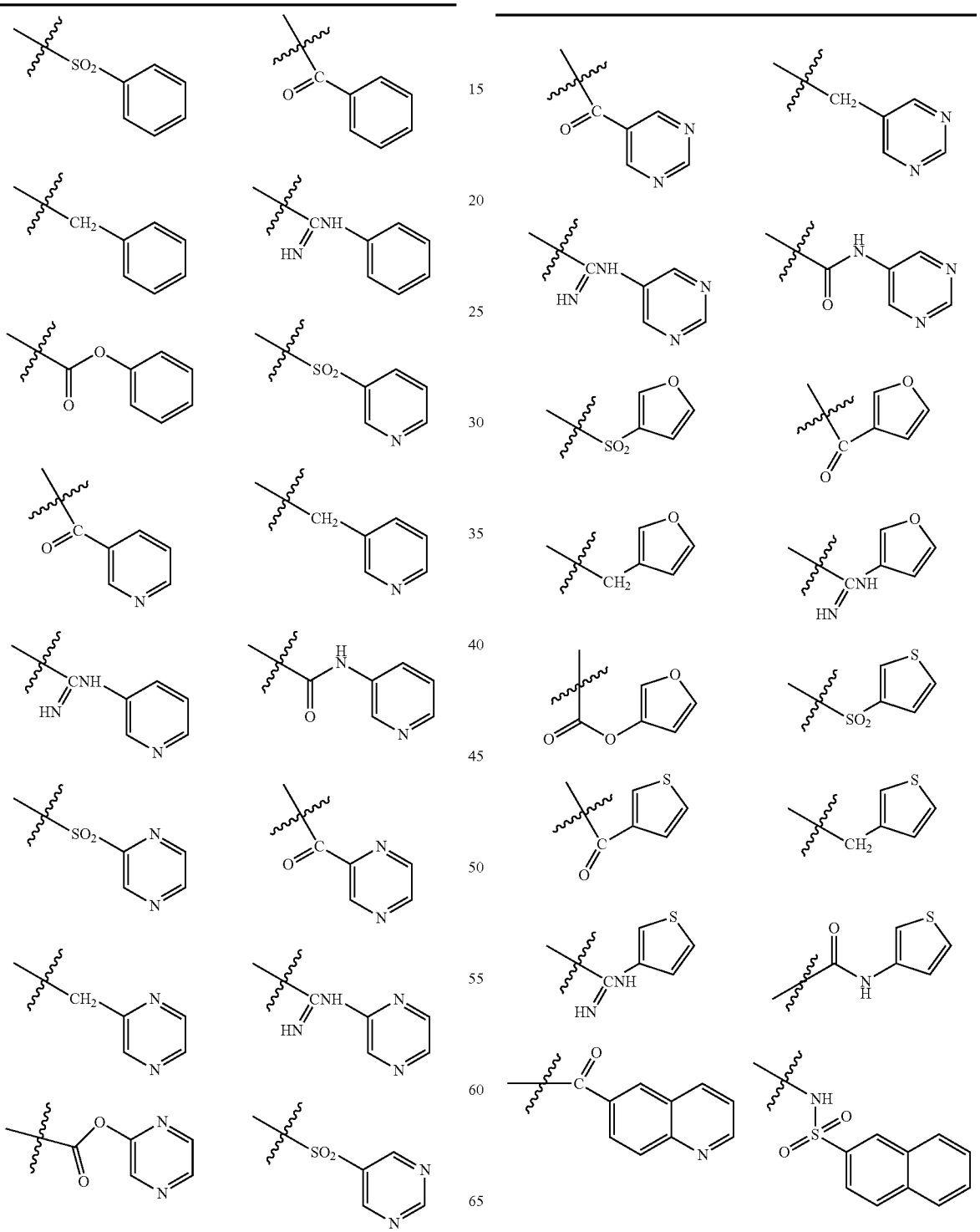

TABLE L-continued
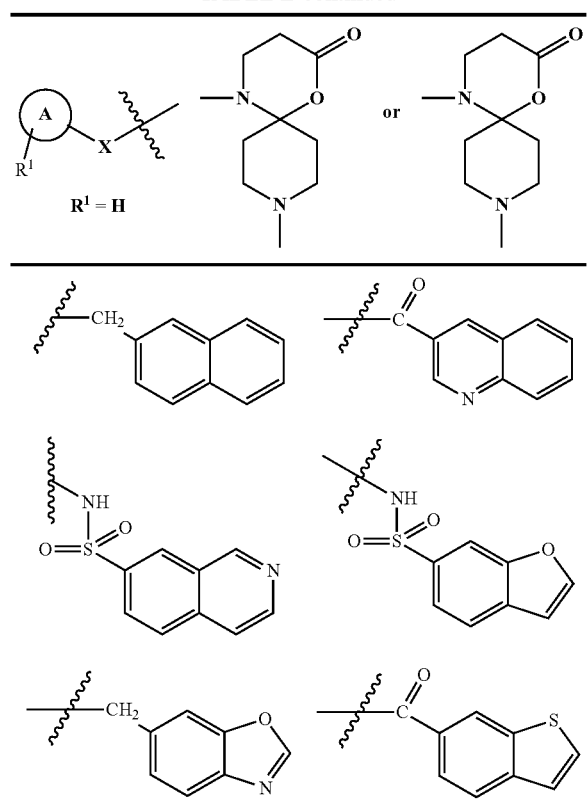
TABLE M
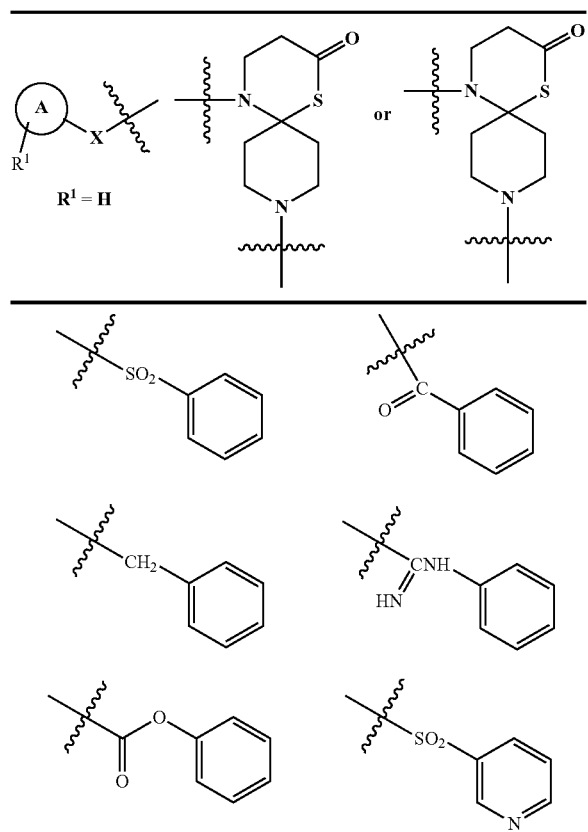
TABLE M-continued
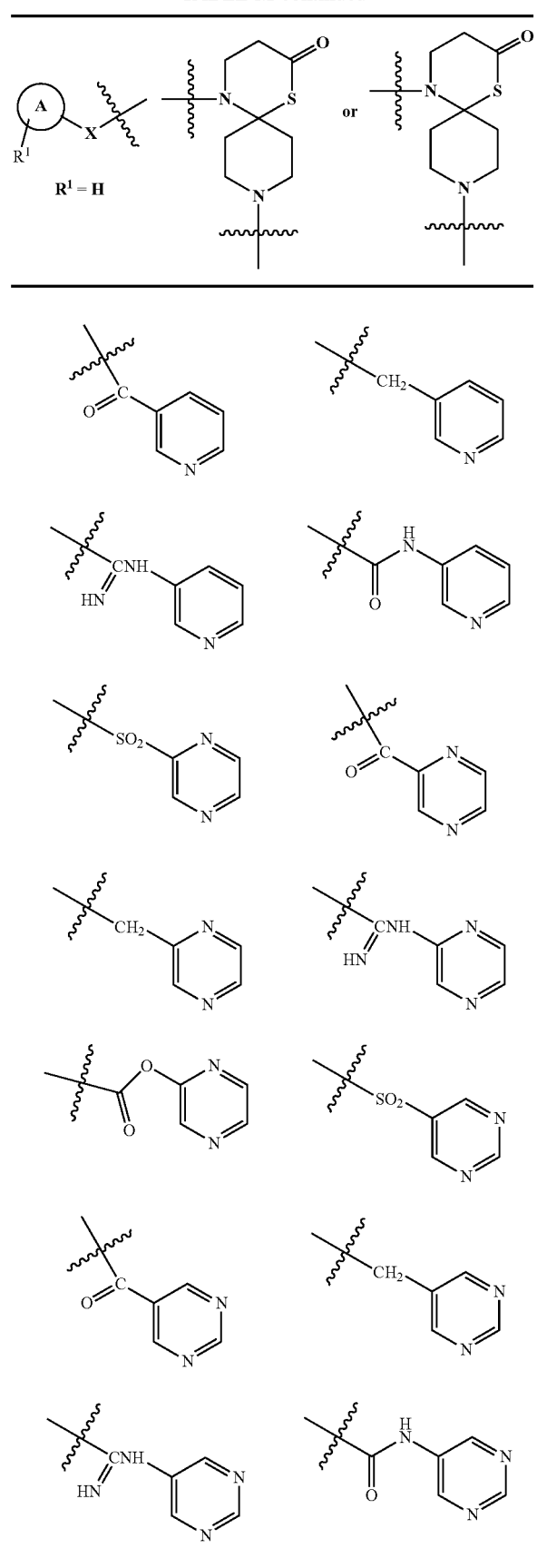

TABLE M-continued
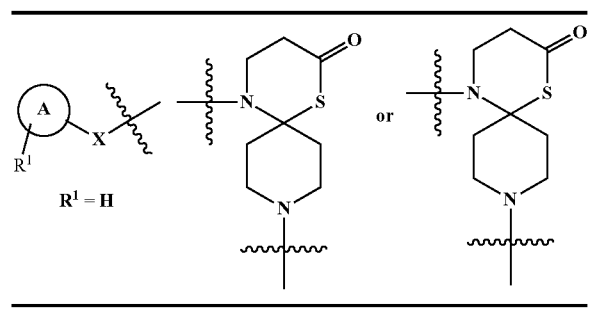
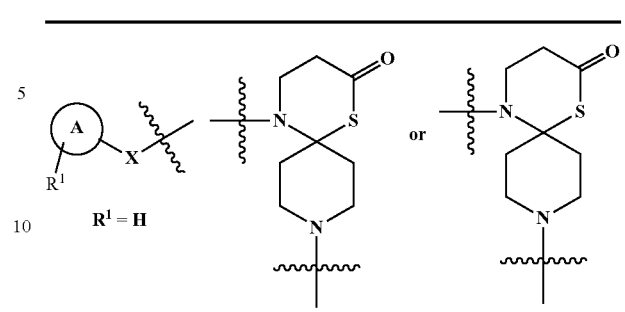
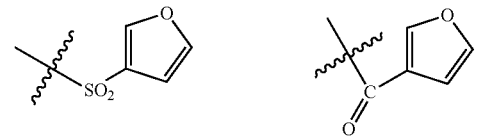
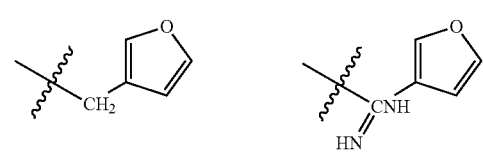
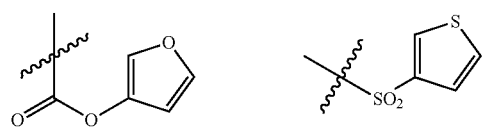
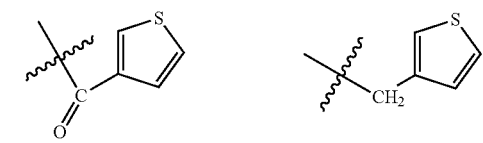
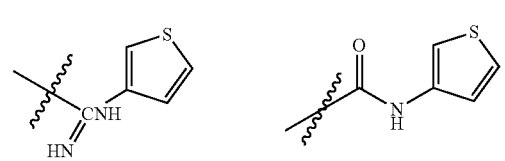
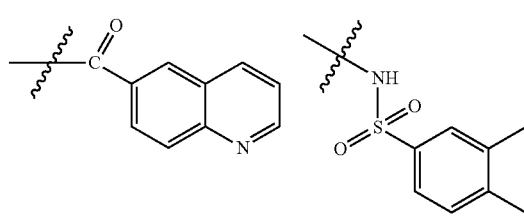
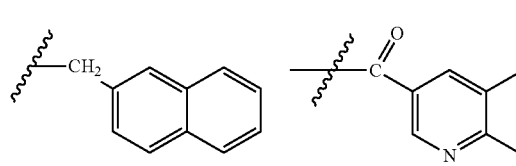
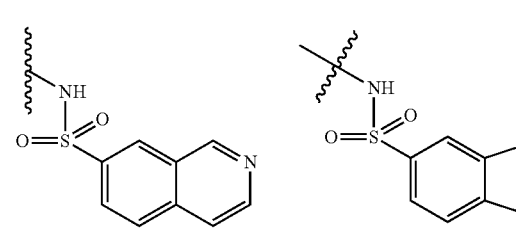
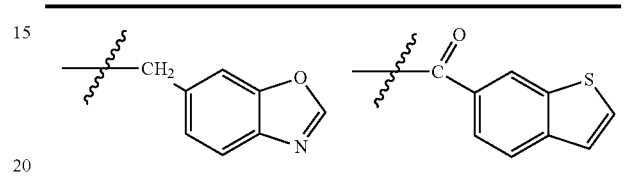
TABLE N
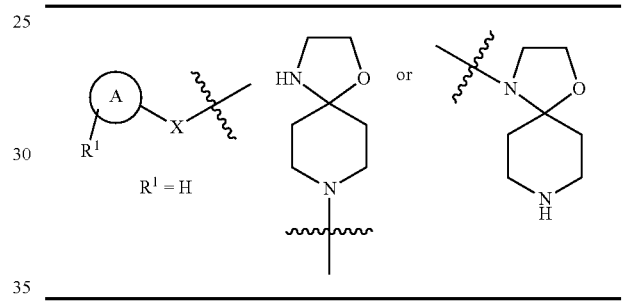
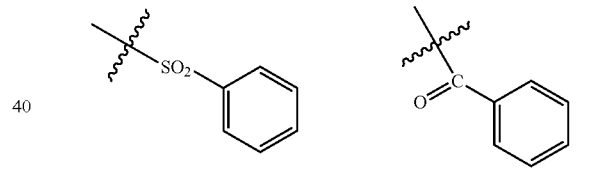
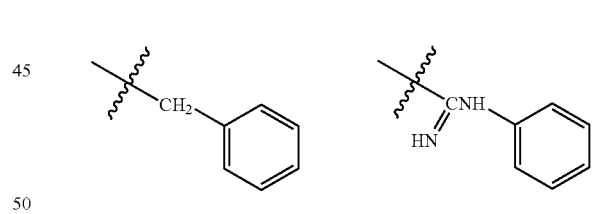
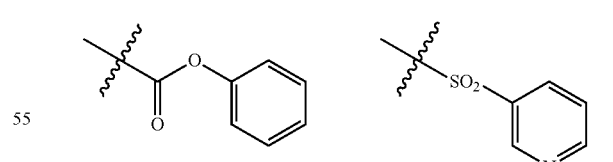
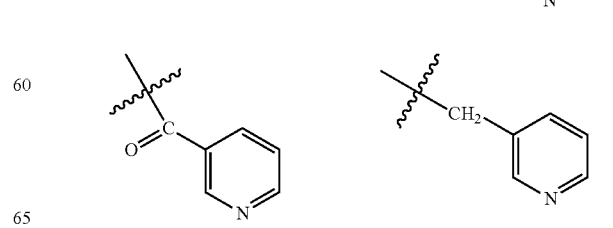

TABLE N-continued
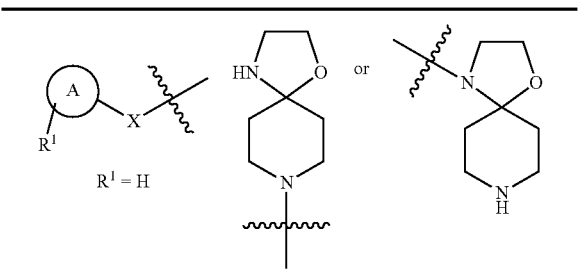
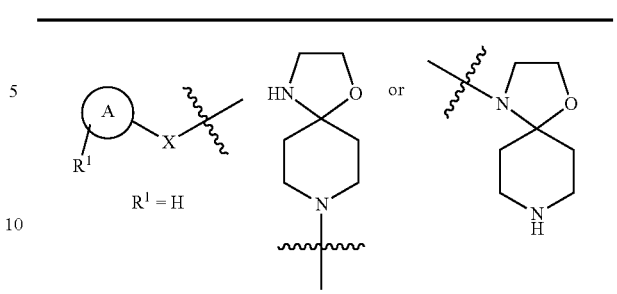
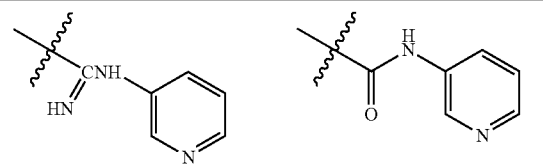
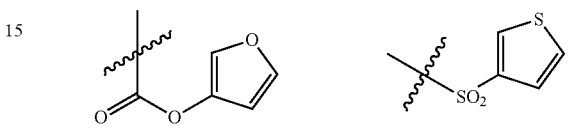
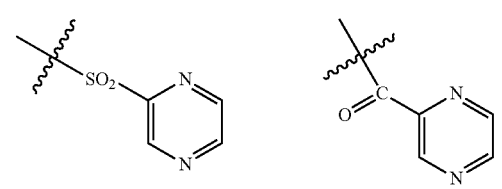
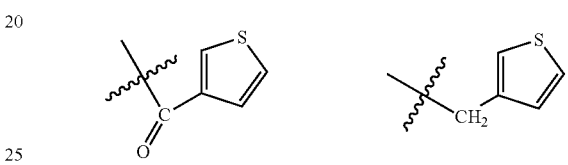
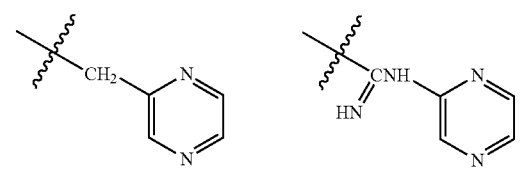
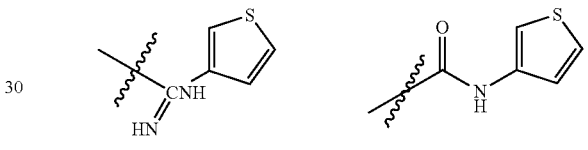
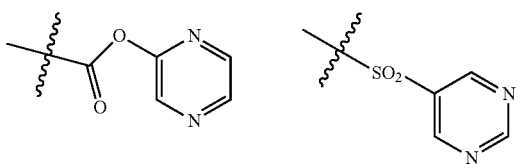
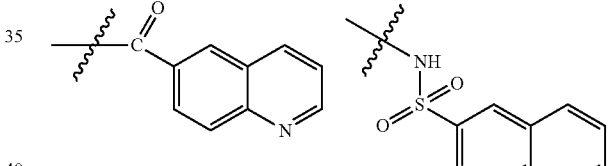
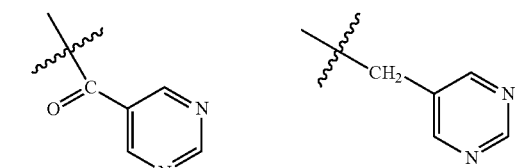
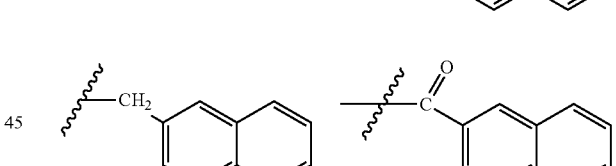
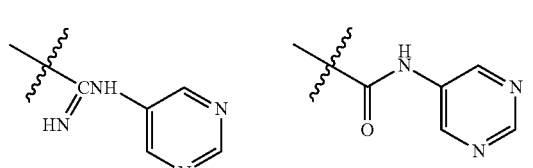
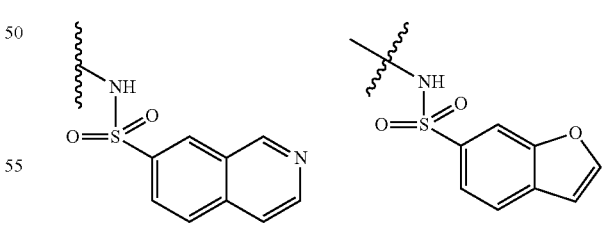
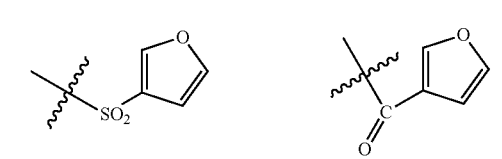
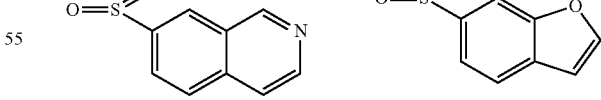
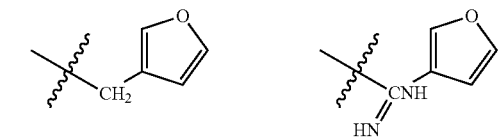
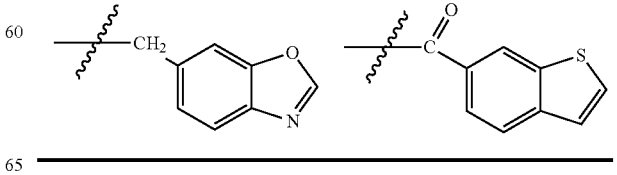

TABLE O
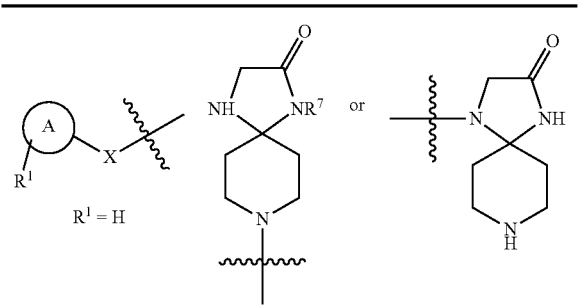
R¹ = H
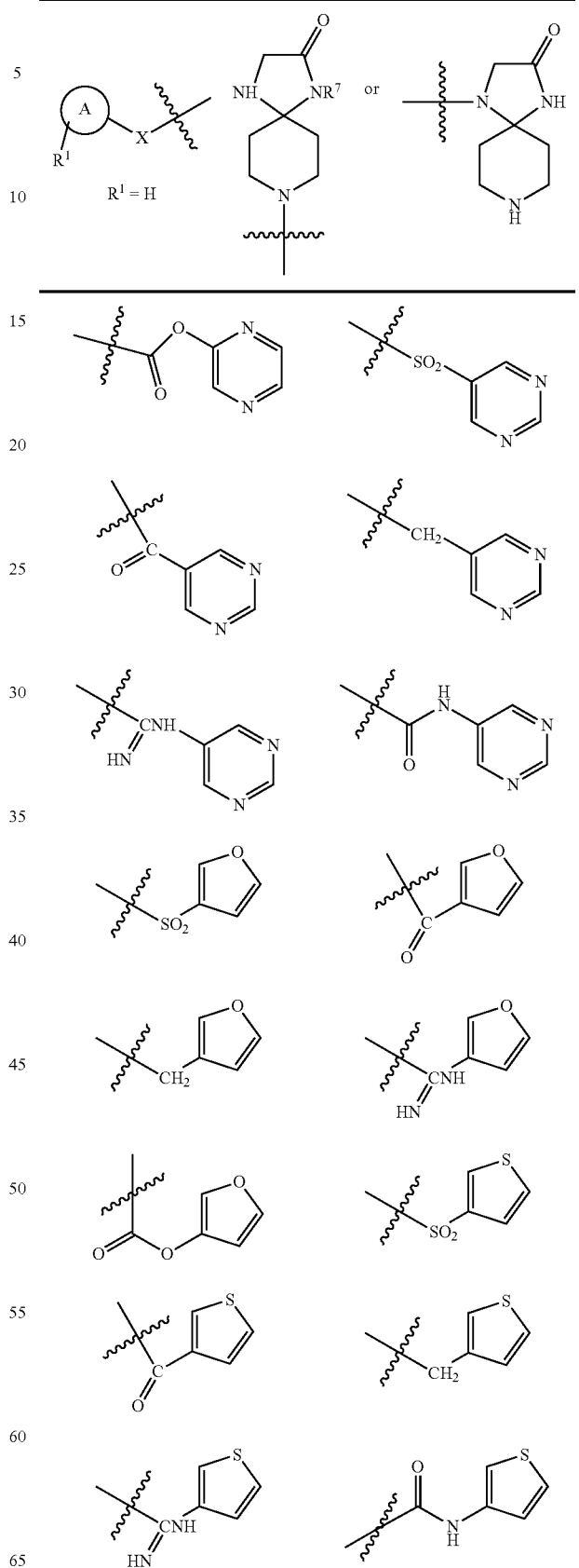

TABLE O-continued
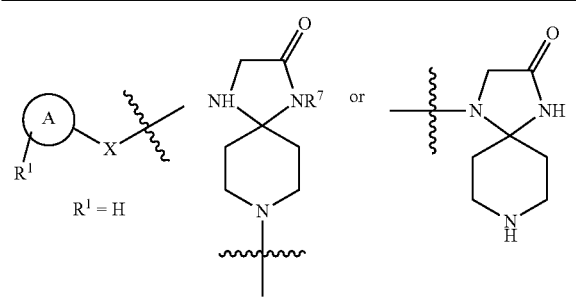
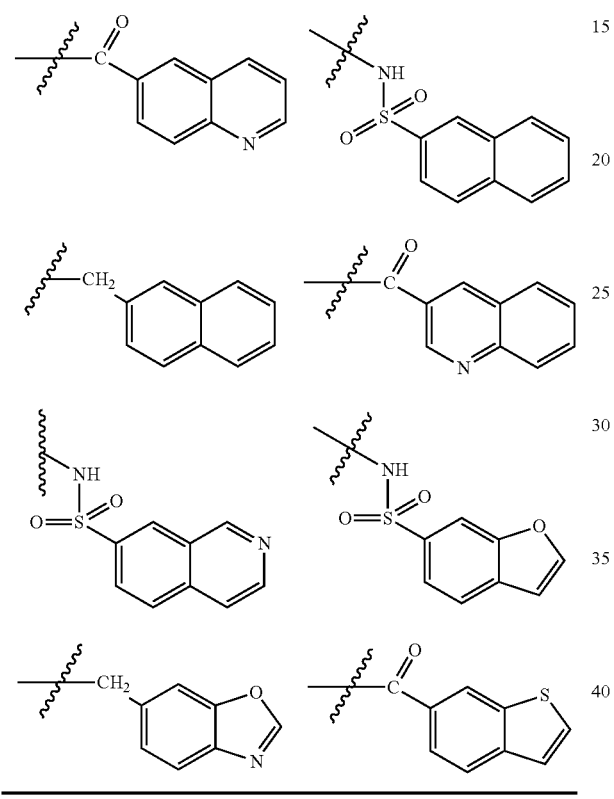
TABLE P
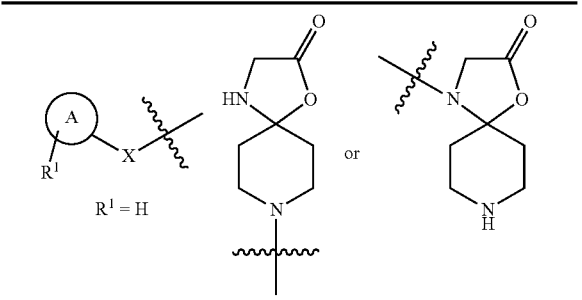
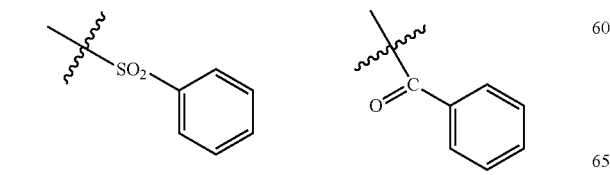
TABLE P-continued
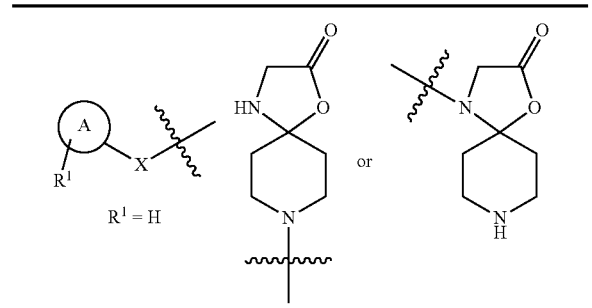
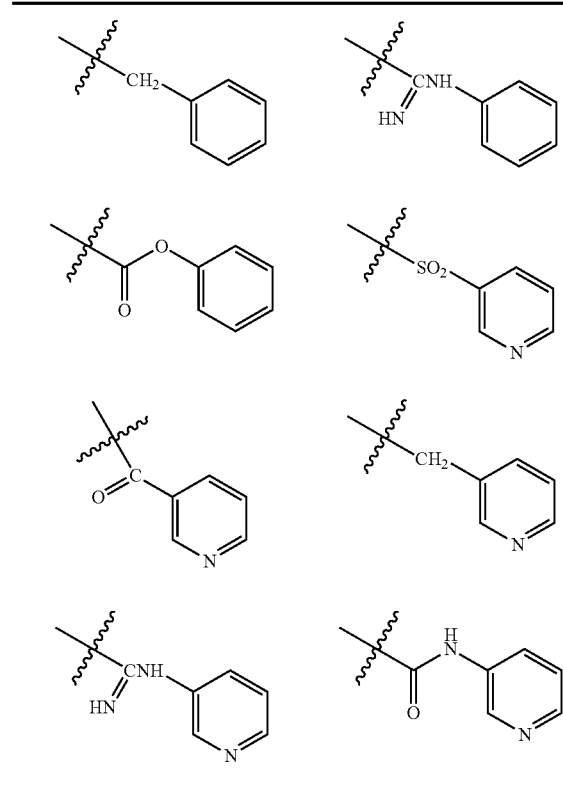
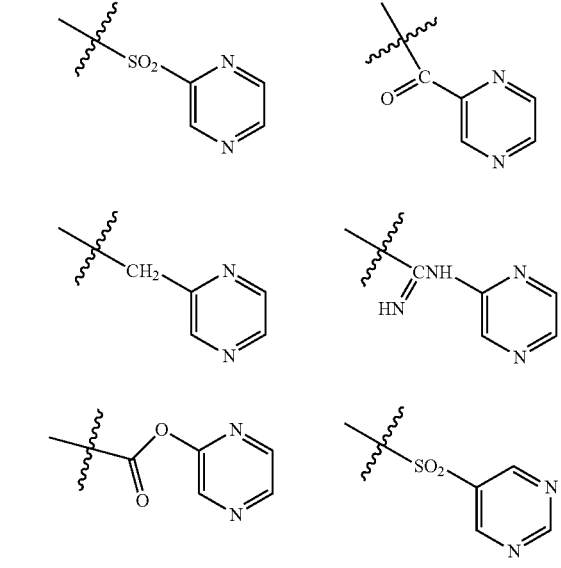

TABLE P-continued
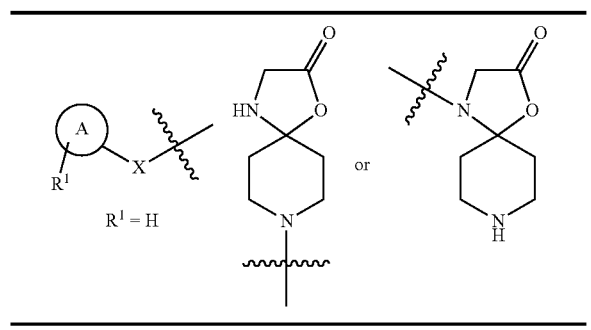
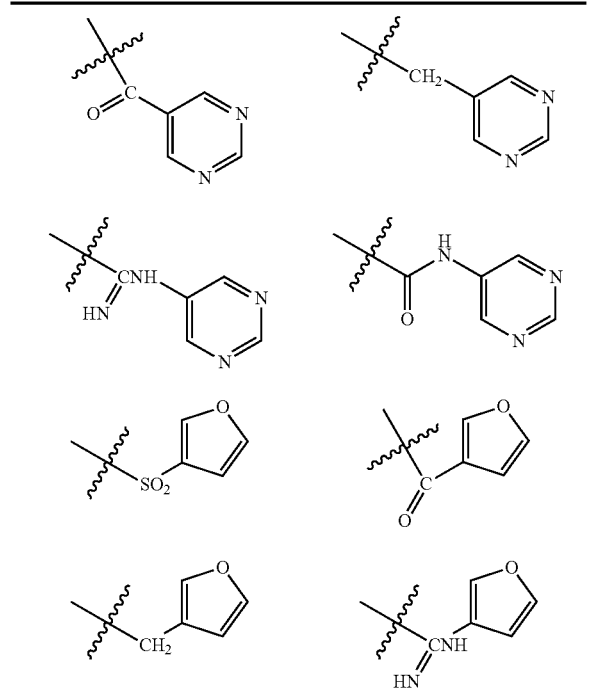
TABLE P-continued
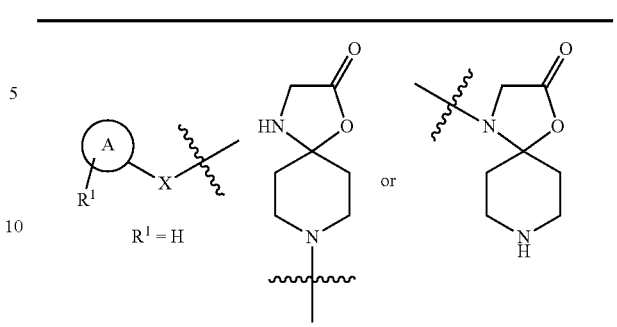
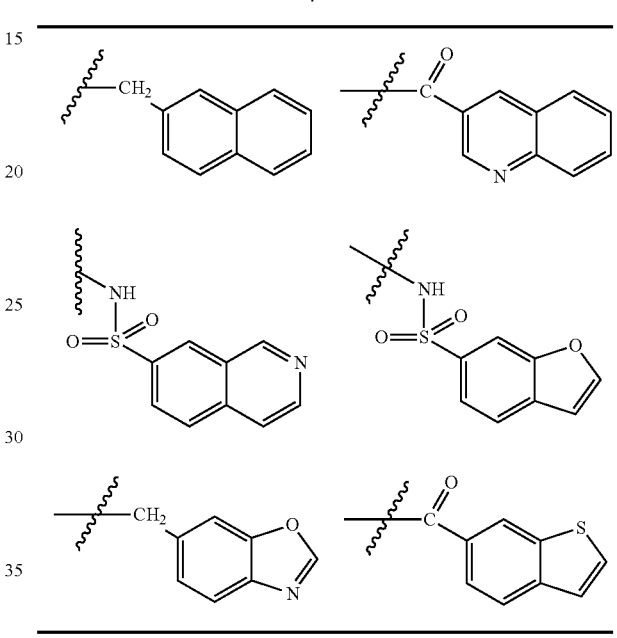
TABLE Q
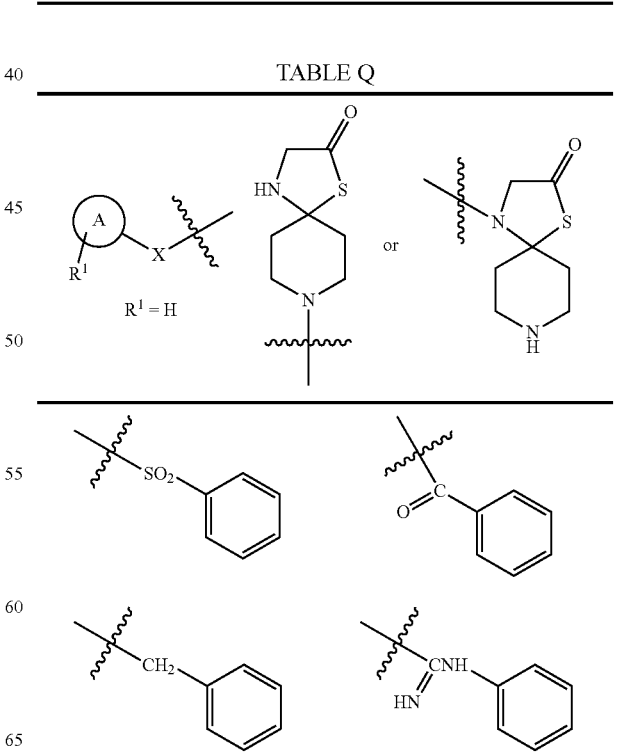

TABLE Q-continued
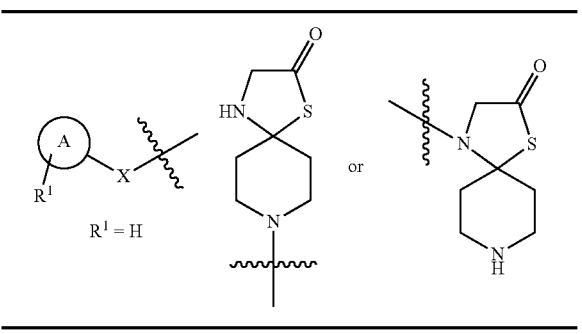
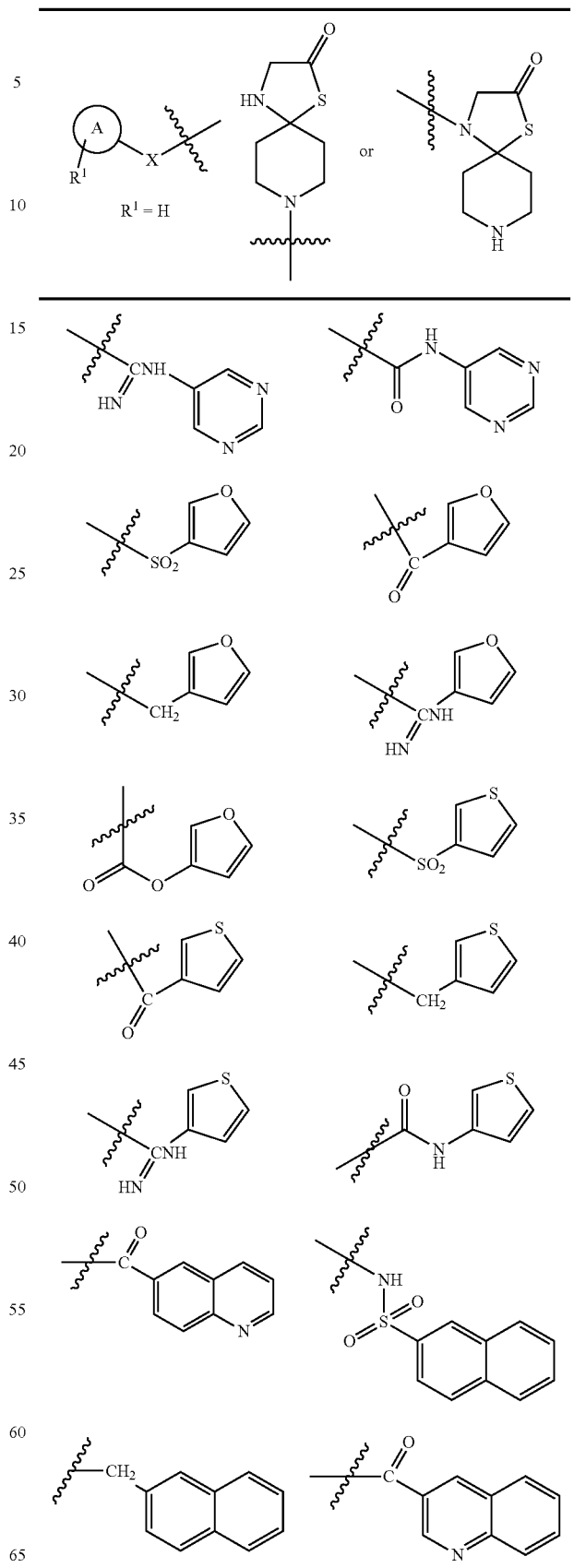

TABLE Q-continued
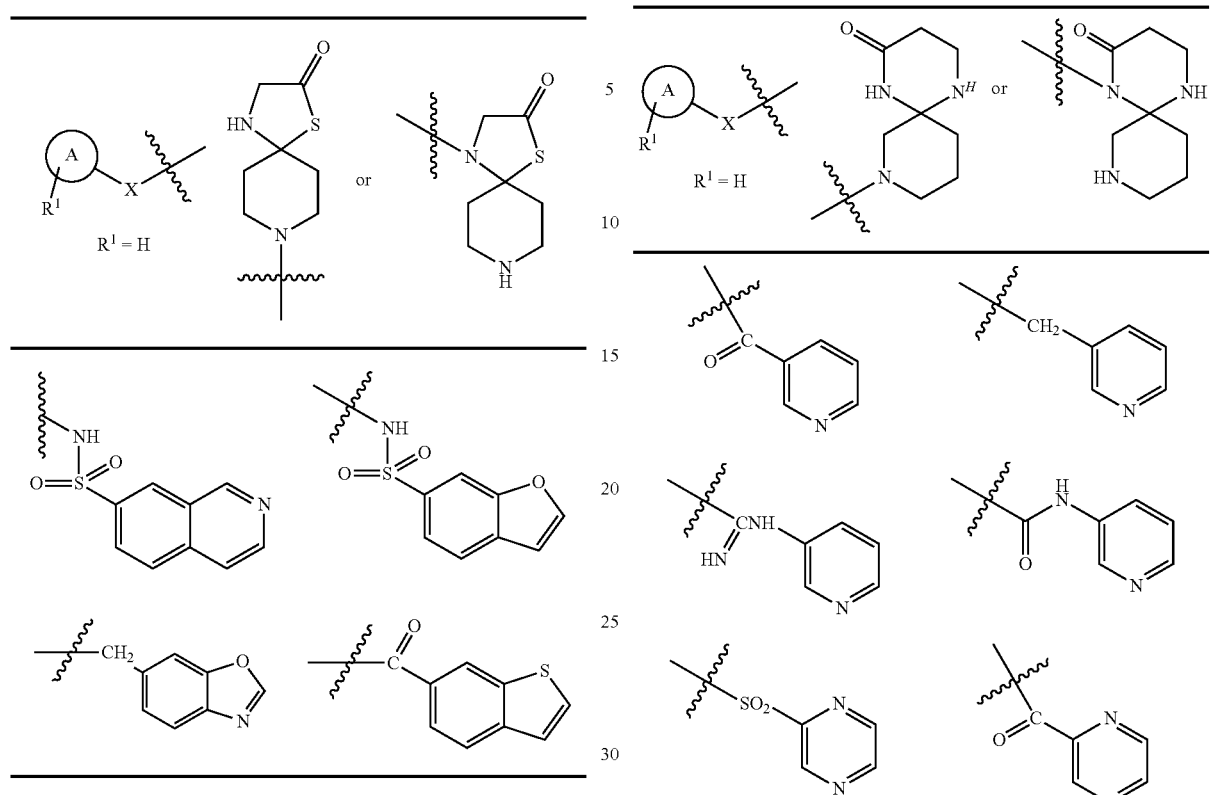
TABLE R
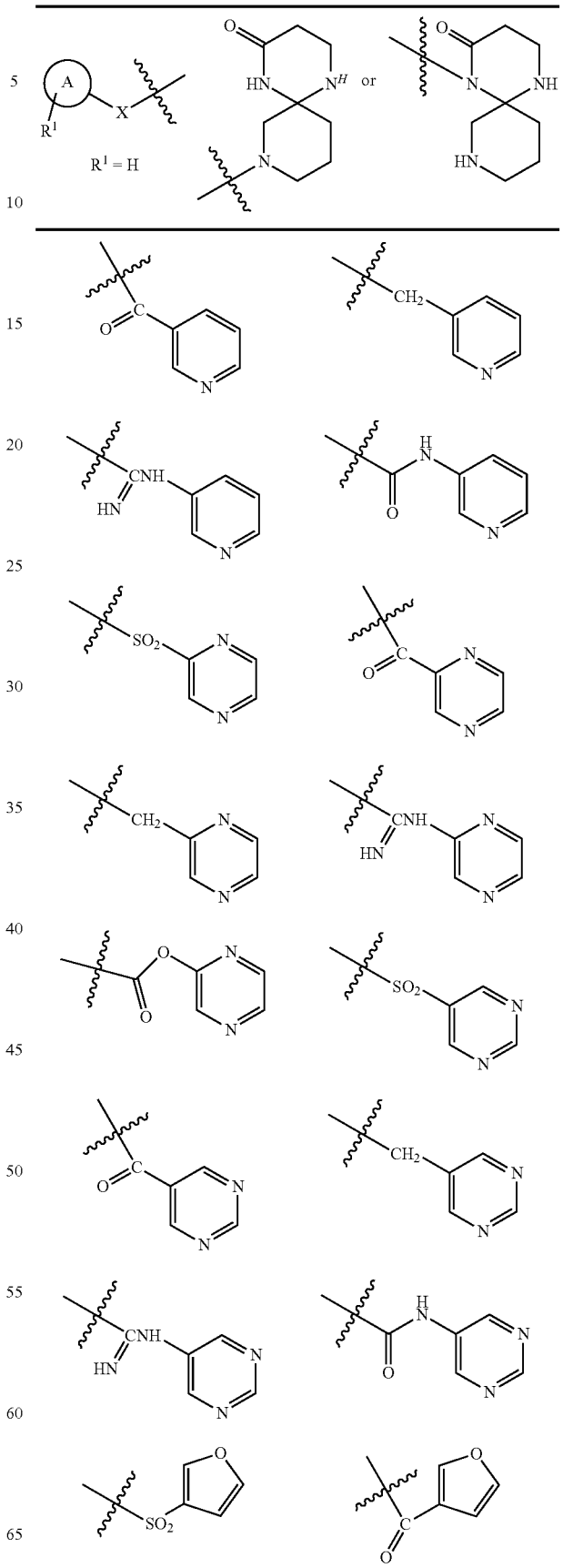

TABLE R-continued
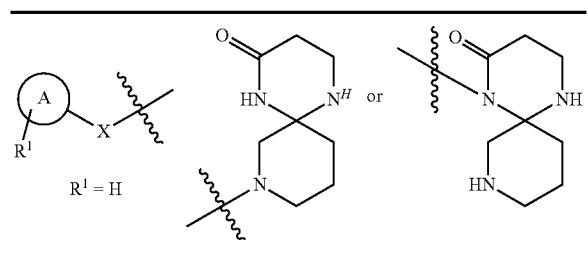
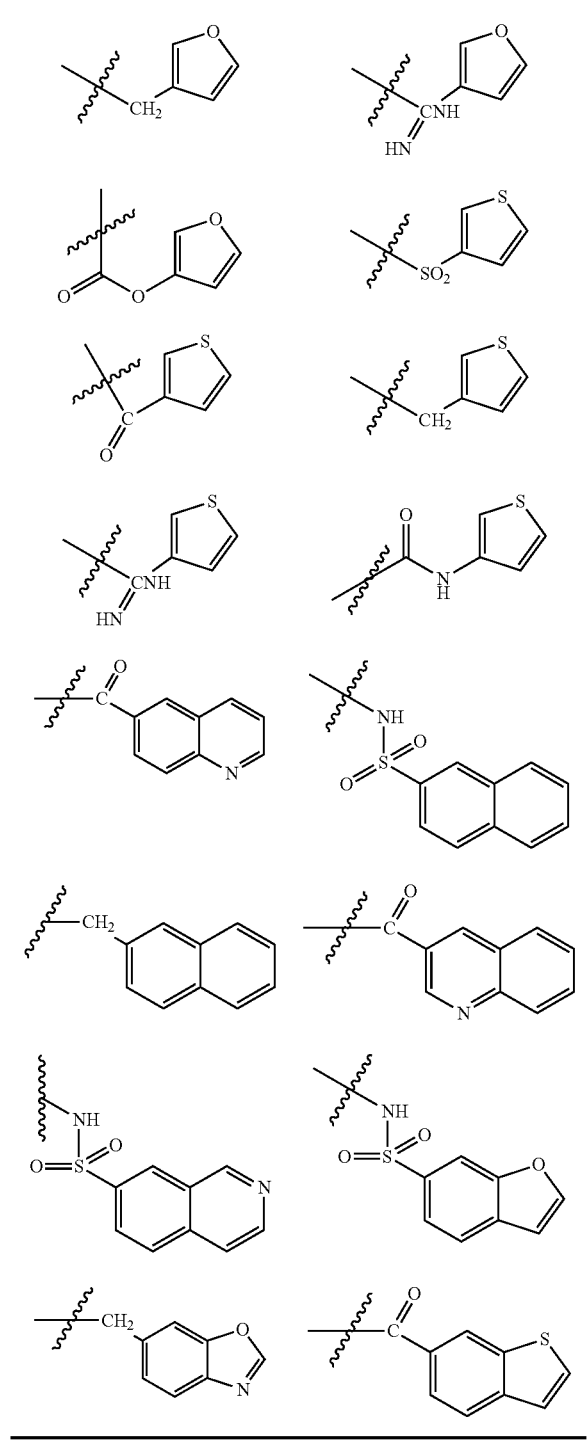
TABLE S
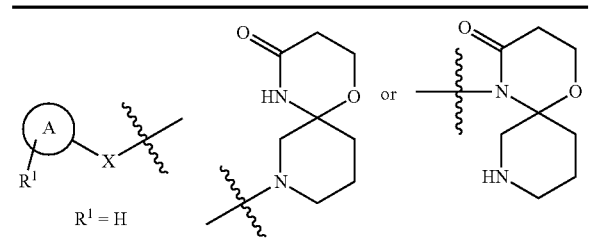
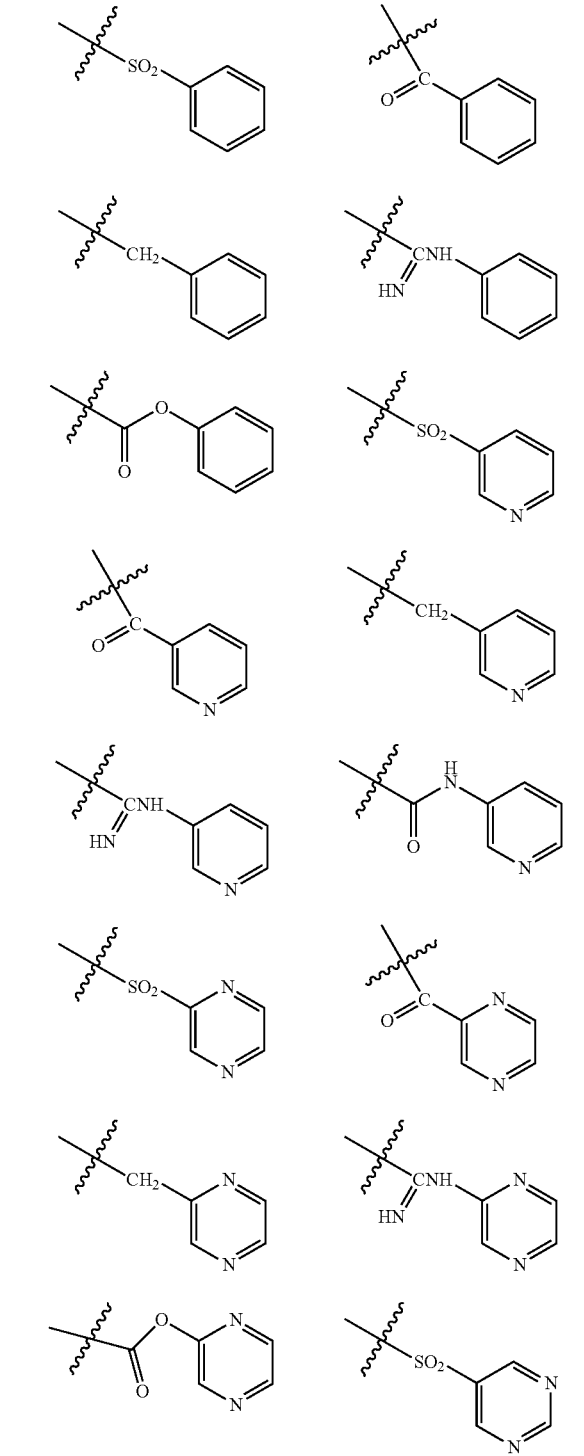

TABLE S-continued
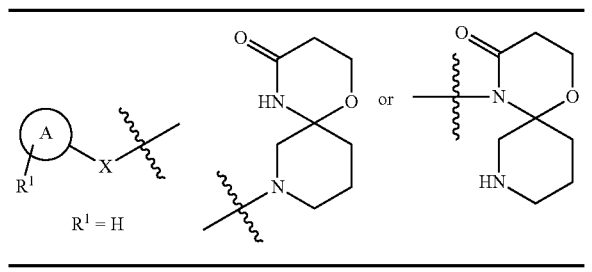
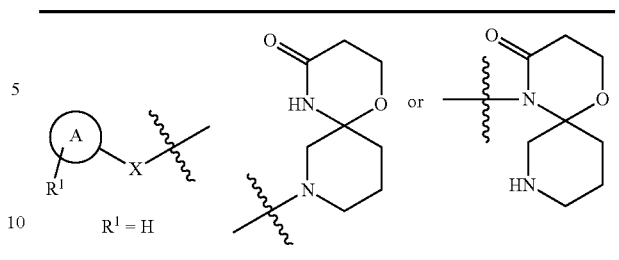
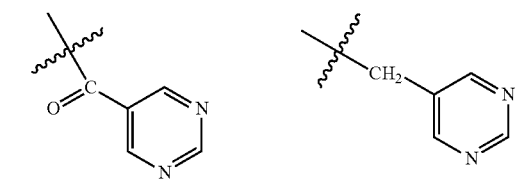
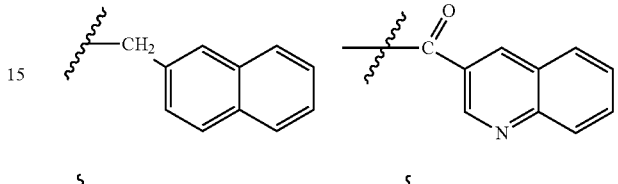
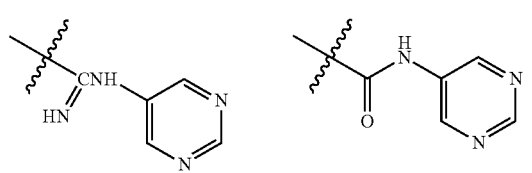
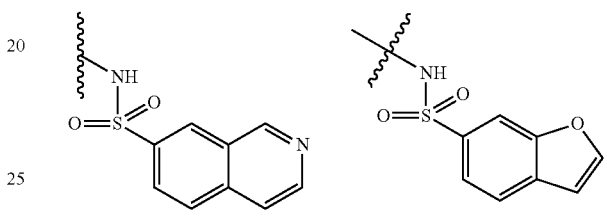
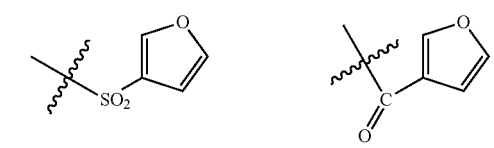
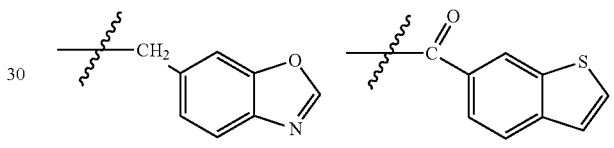
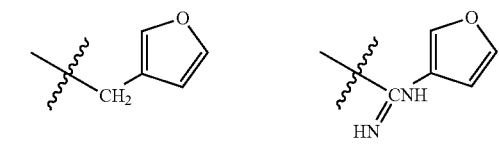
TABLE T
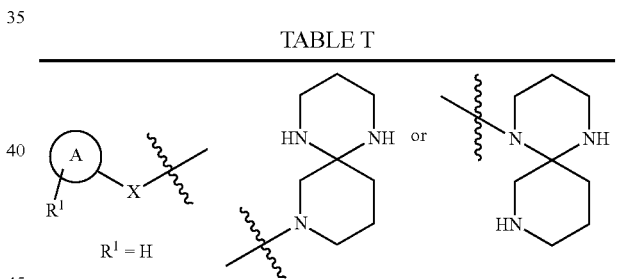
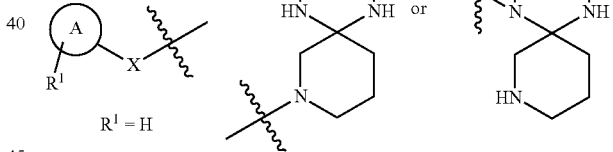
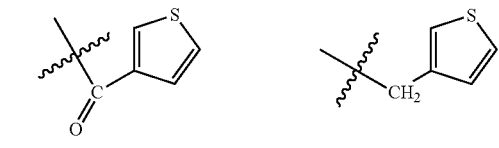
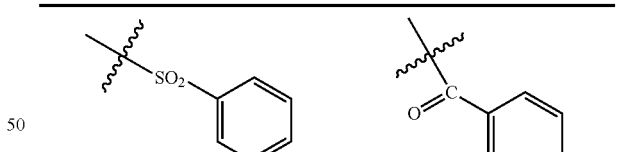
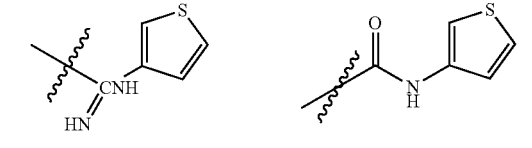
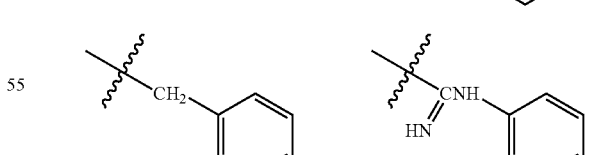
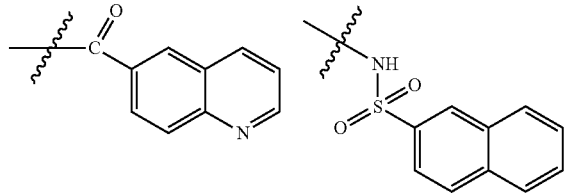
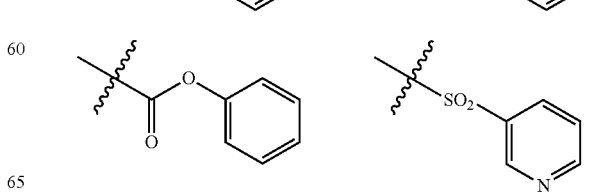

TABLE T-continued
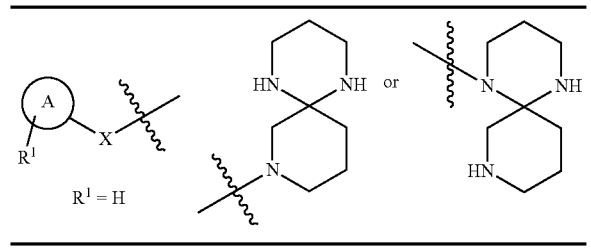
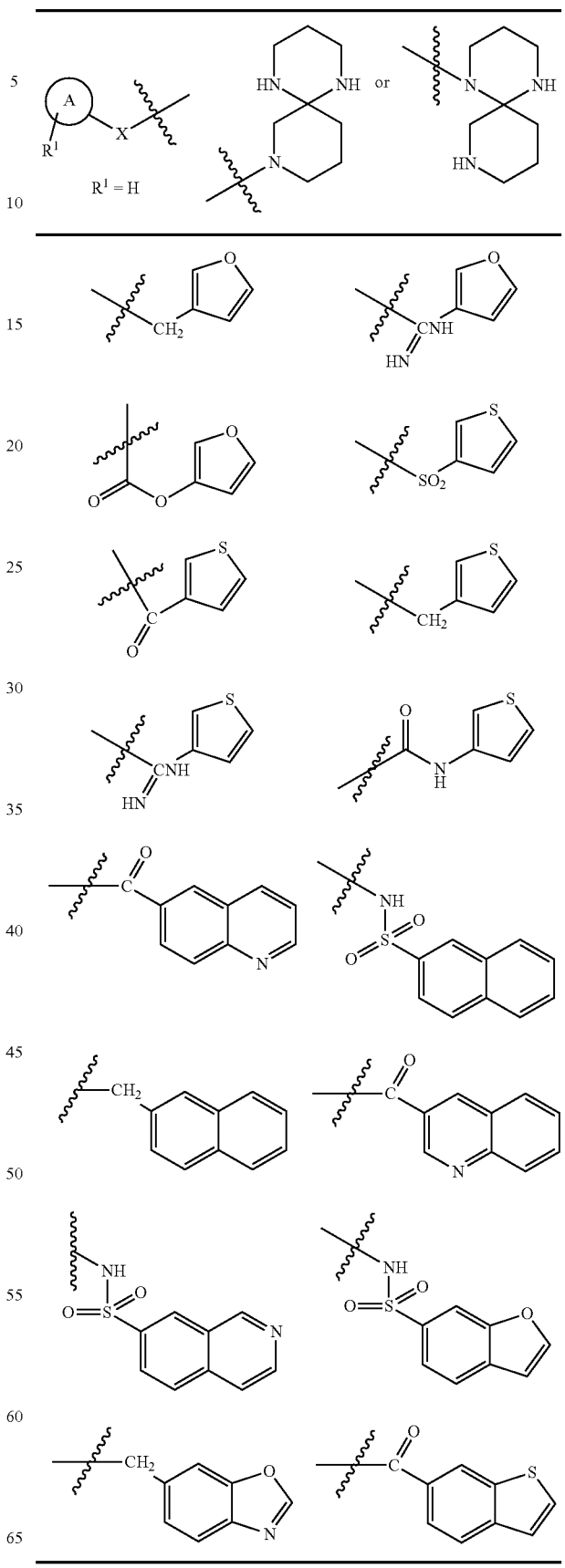

TABLE U
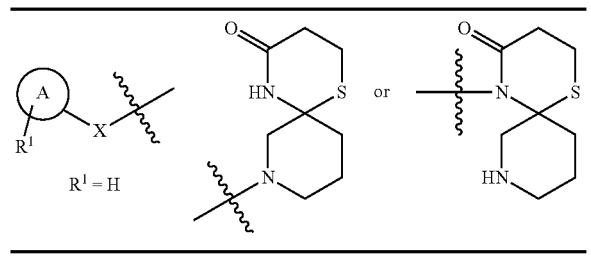
R¹ = H
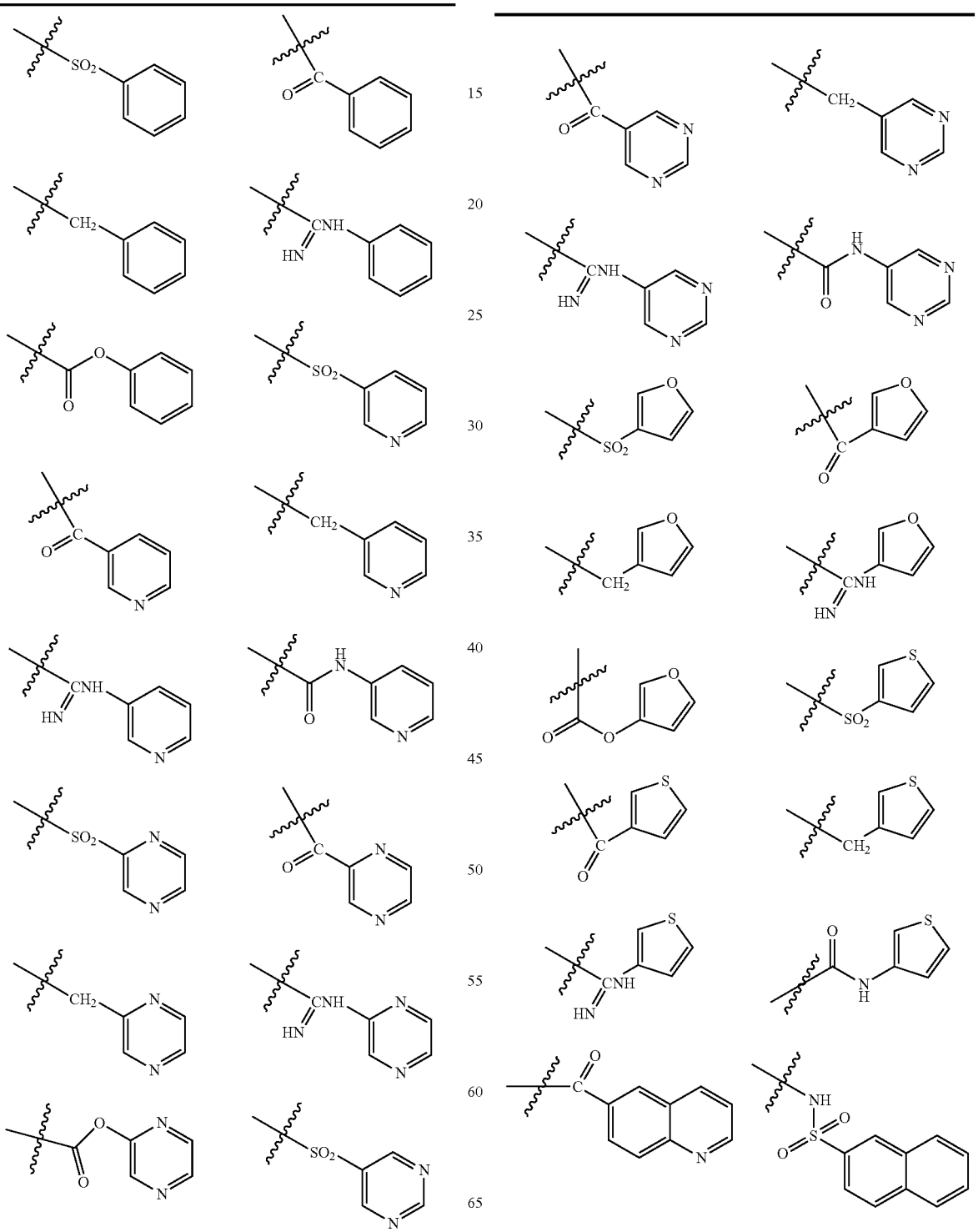
TABLE U-continued
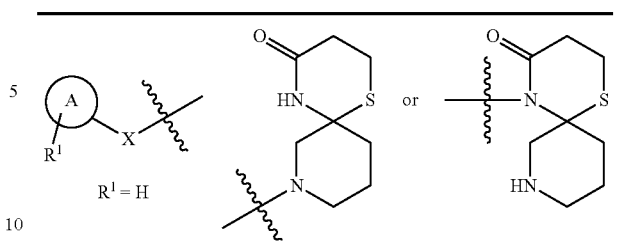
R¹ = H TABLE U-continued
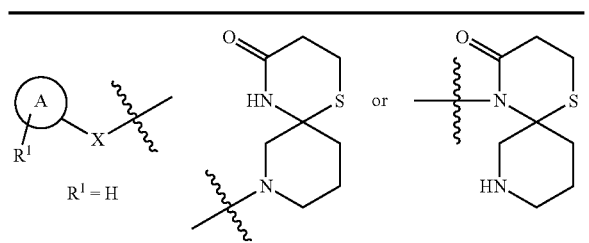
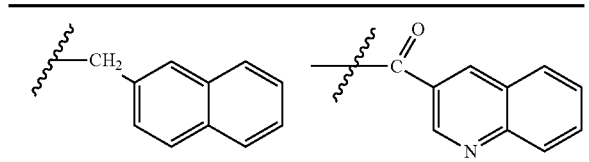
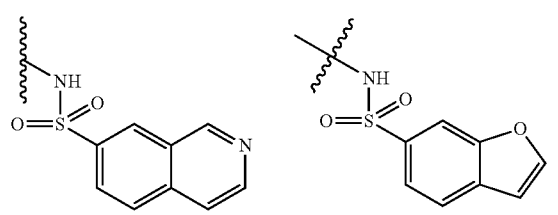
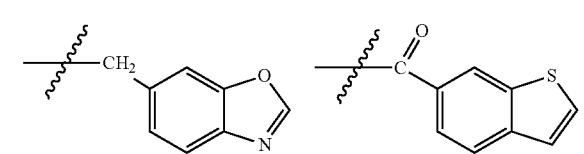
TABLE V
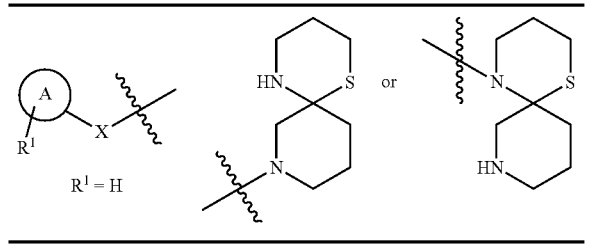
TABLE V-continued
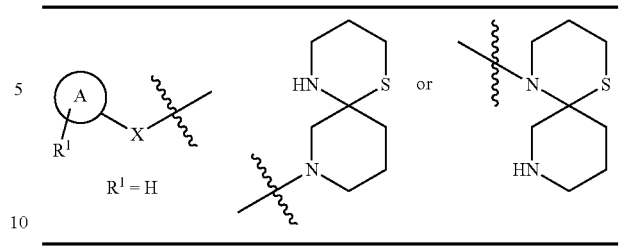
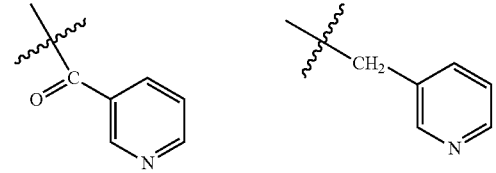
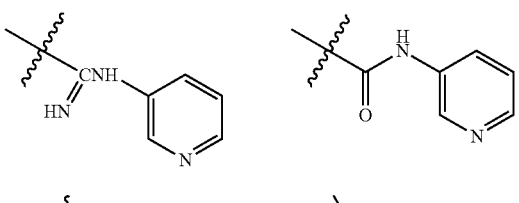
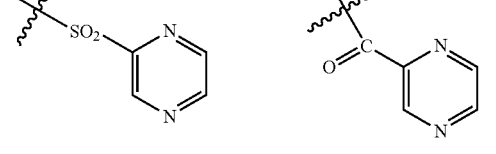
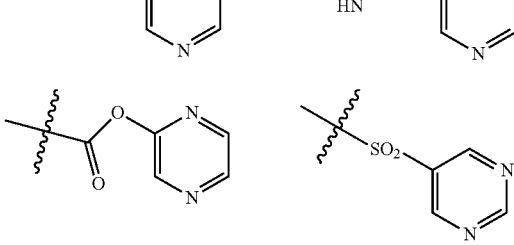
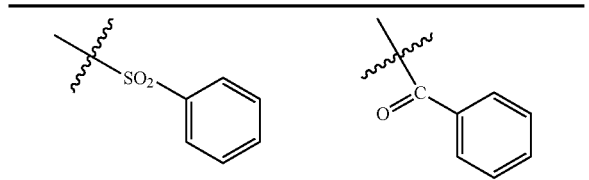
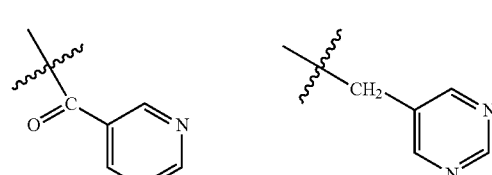
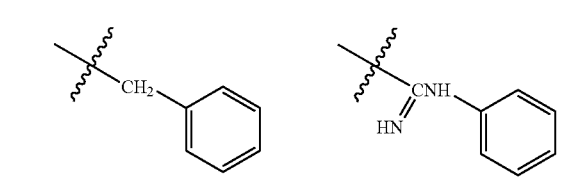
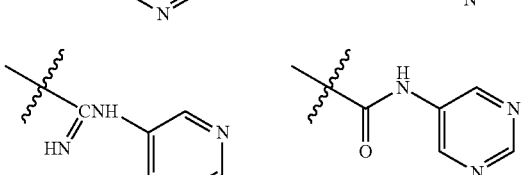
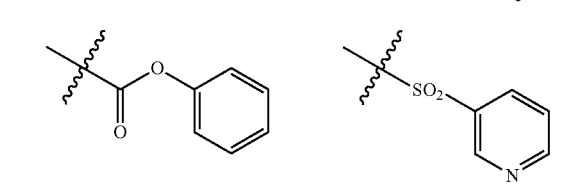
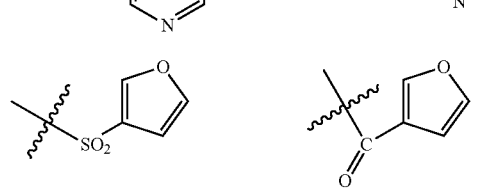

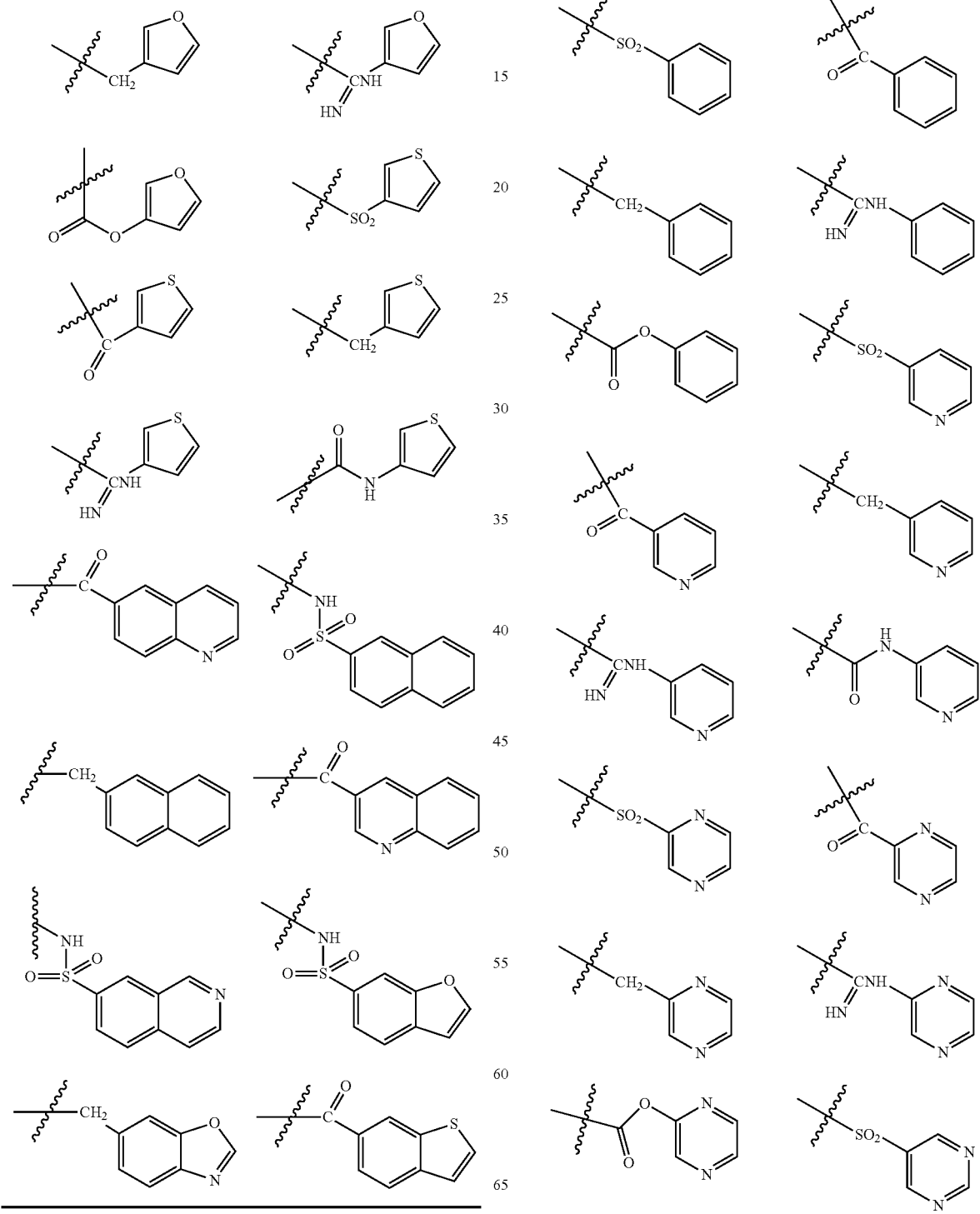

TABLE W-continued
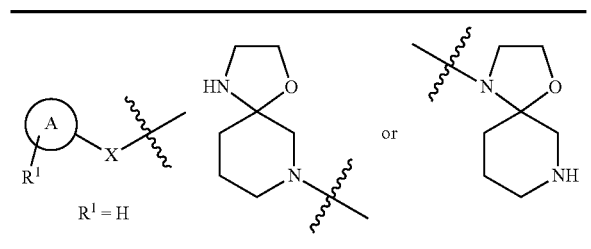
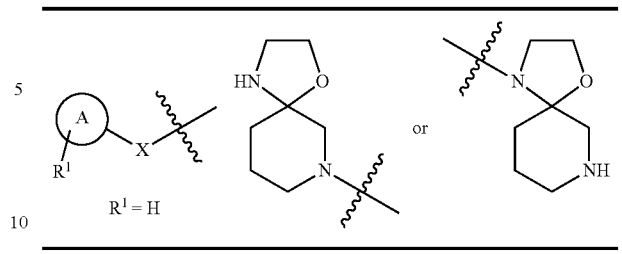
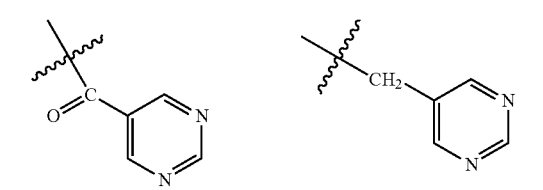
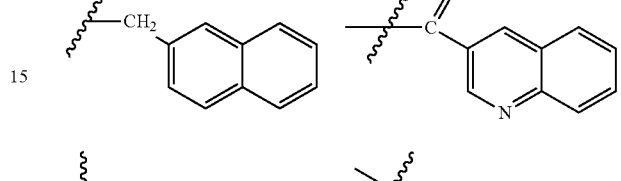
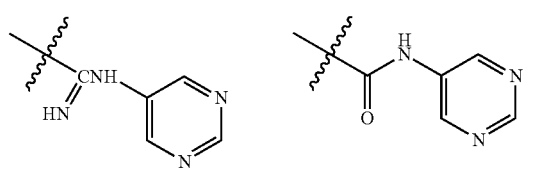
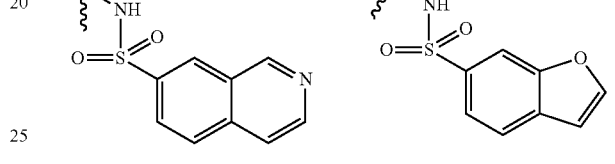
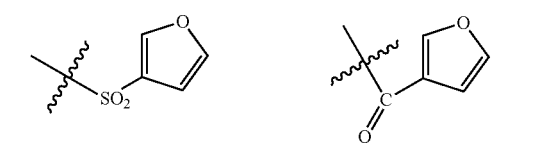
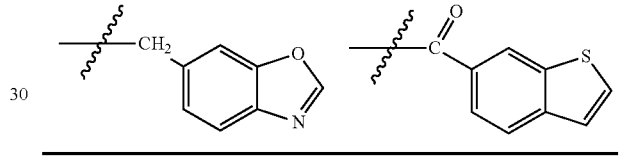
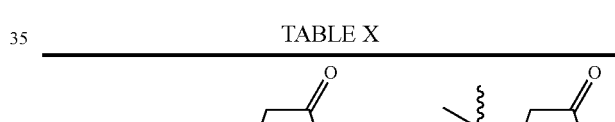
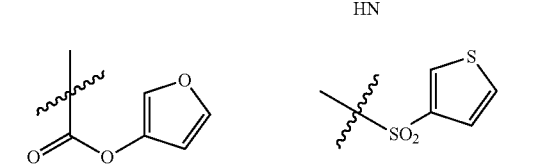
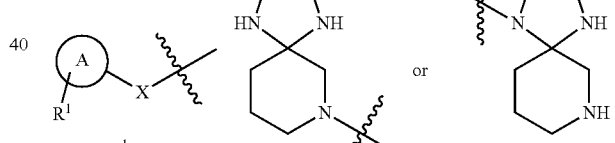
TABLE X
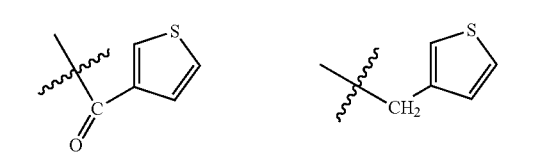
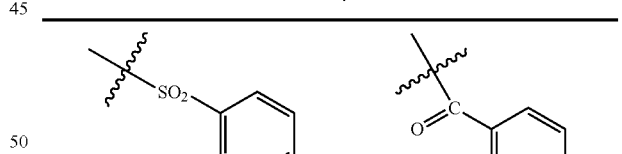
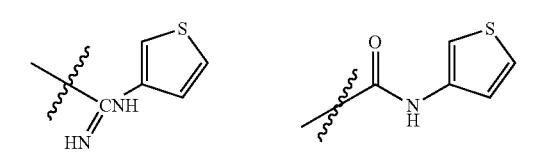
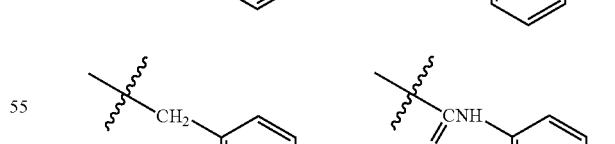
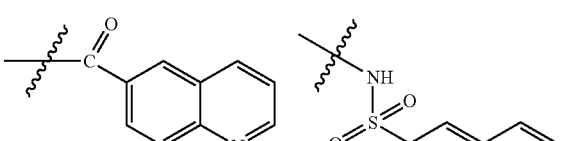
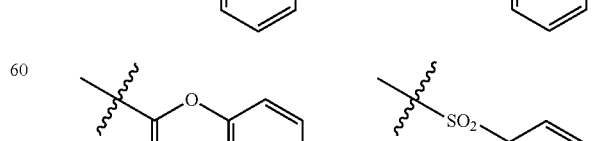
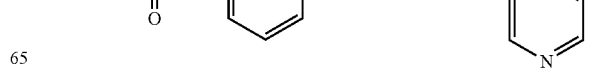

TABLE X-continued
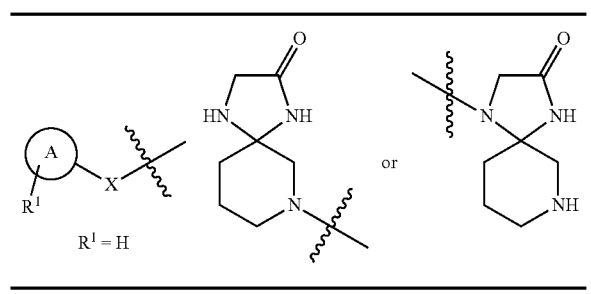
R¹ = H
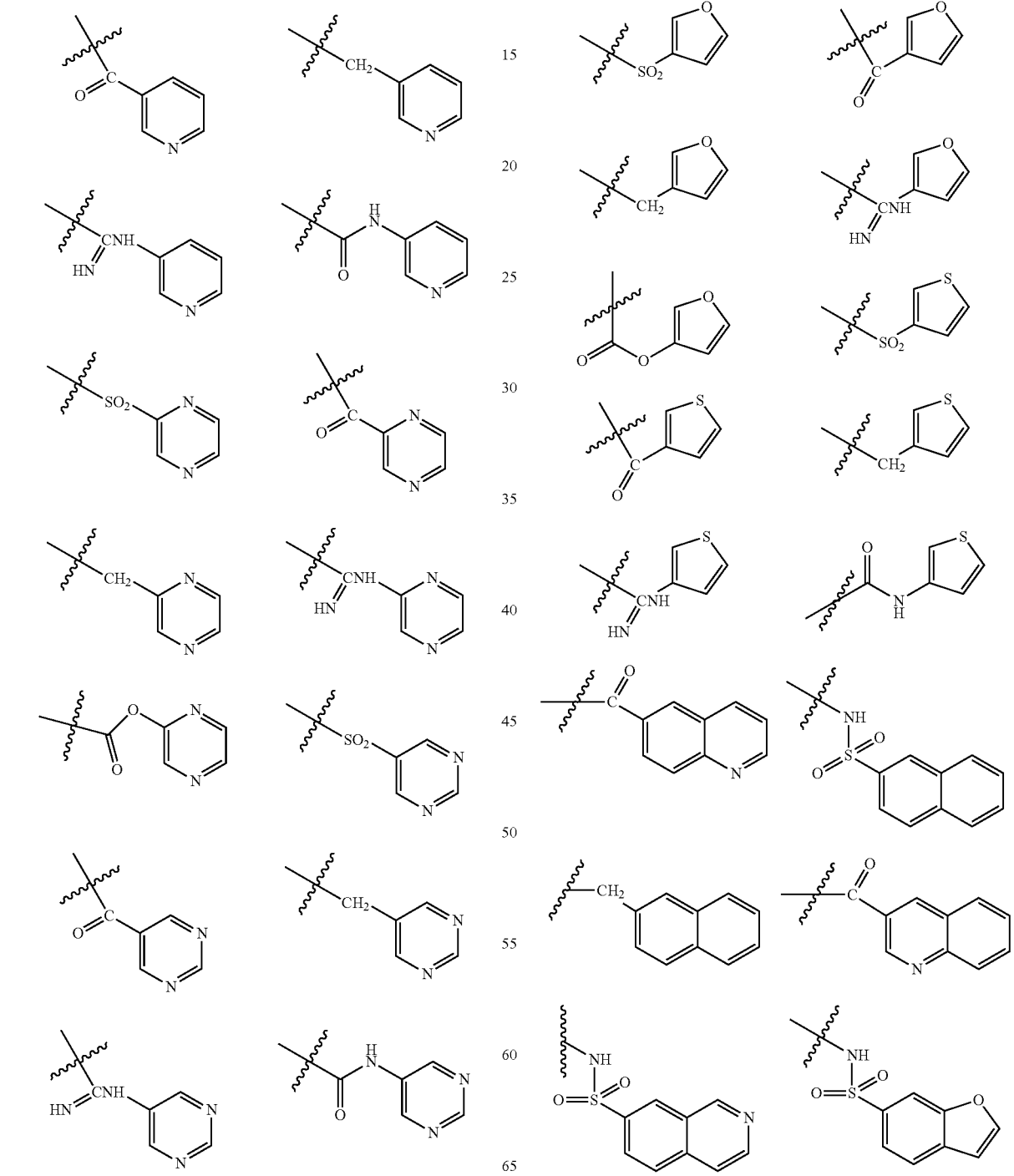

TABLE X-continued
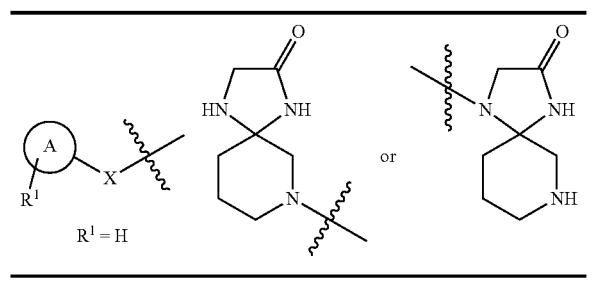
TABLE Y
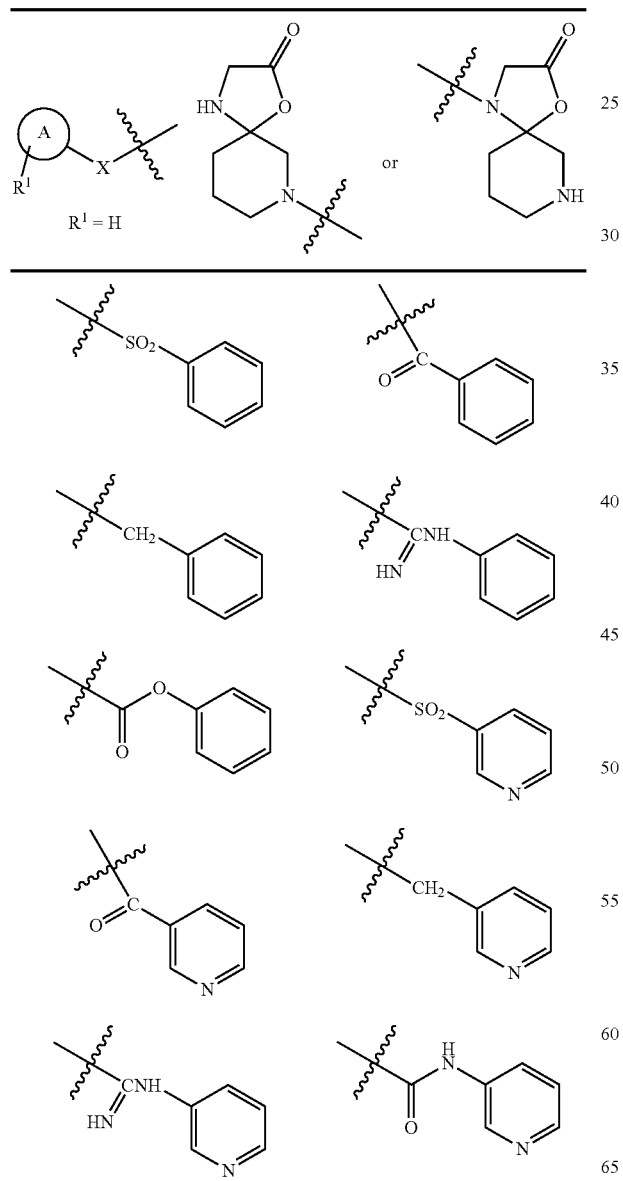
TABLE Y-continued
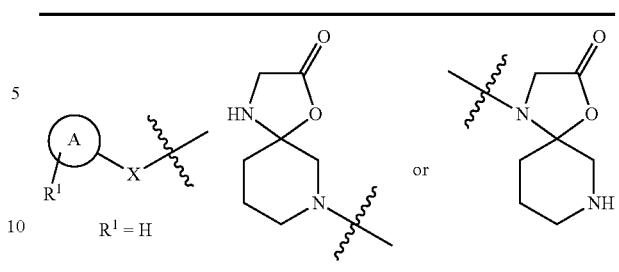
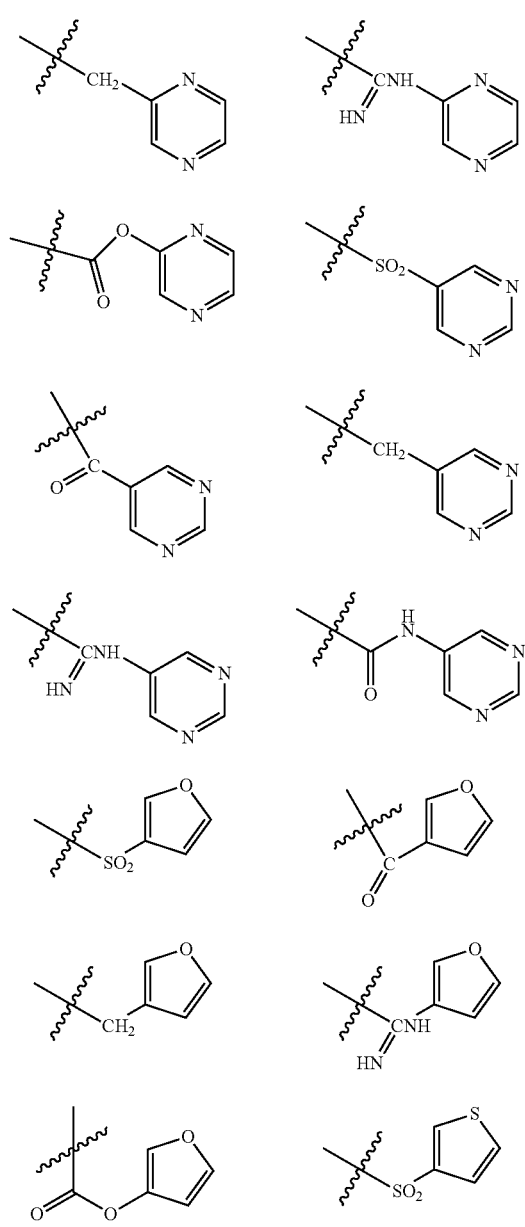

TABLE Y-continued
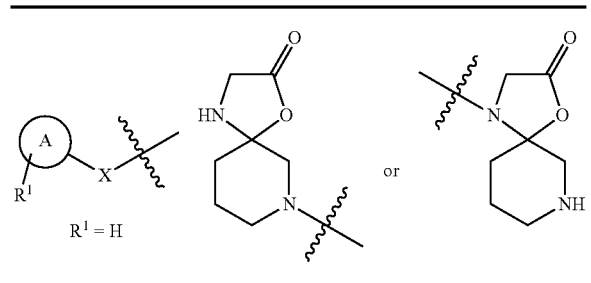
TABLE Z
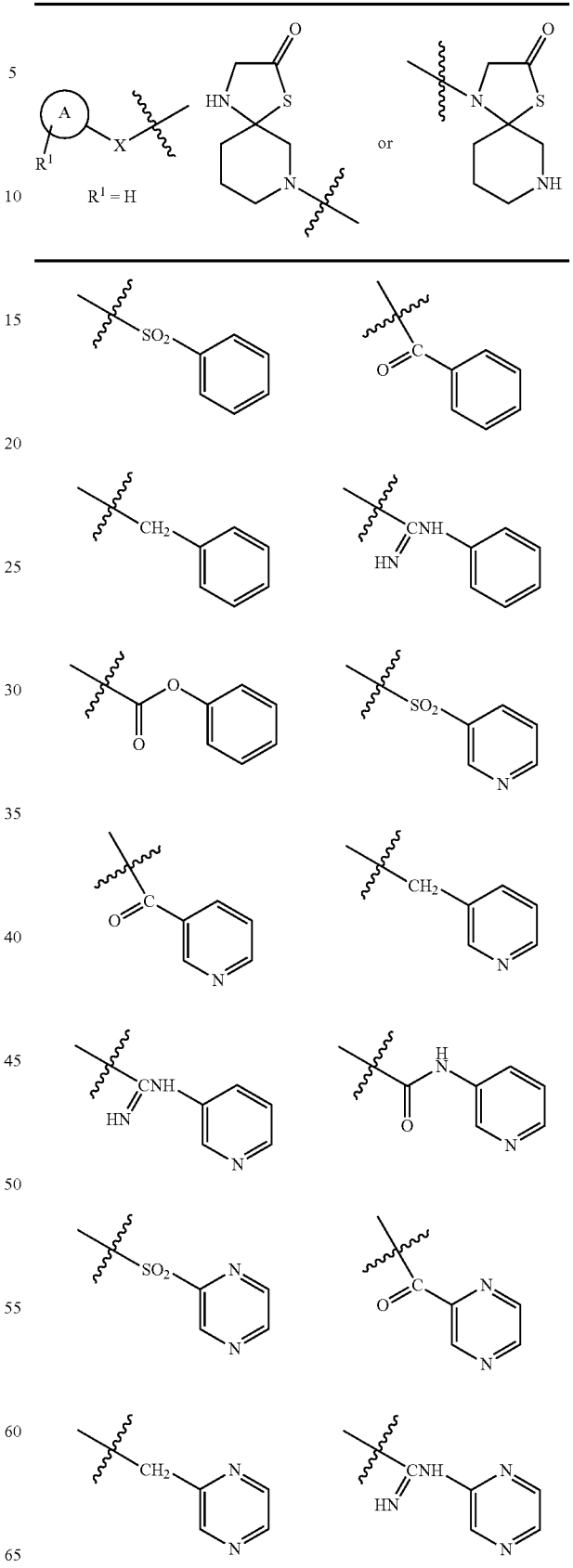

TABLE Z-continued
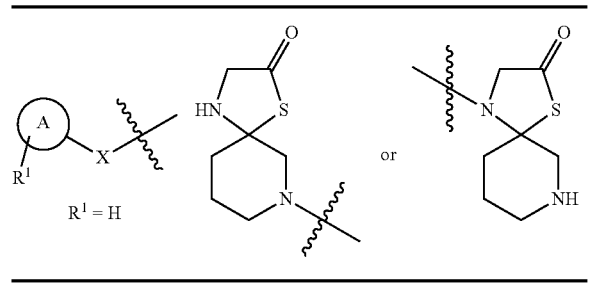
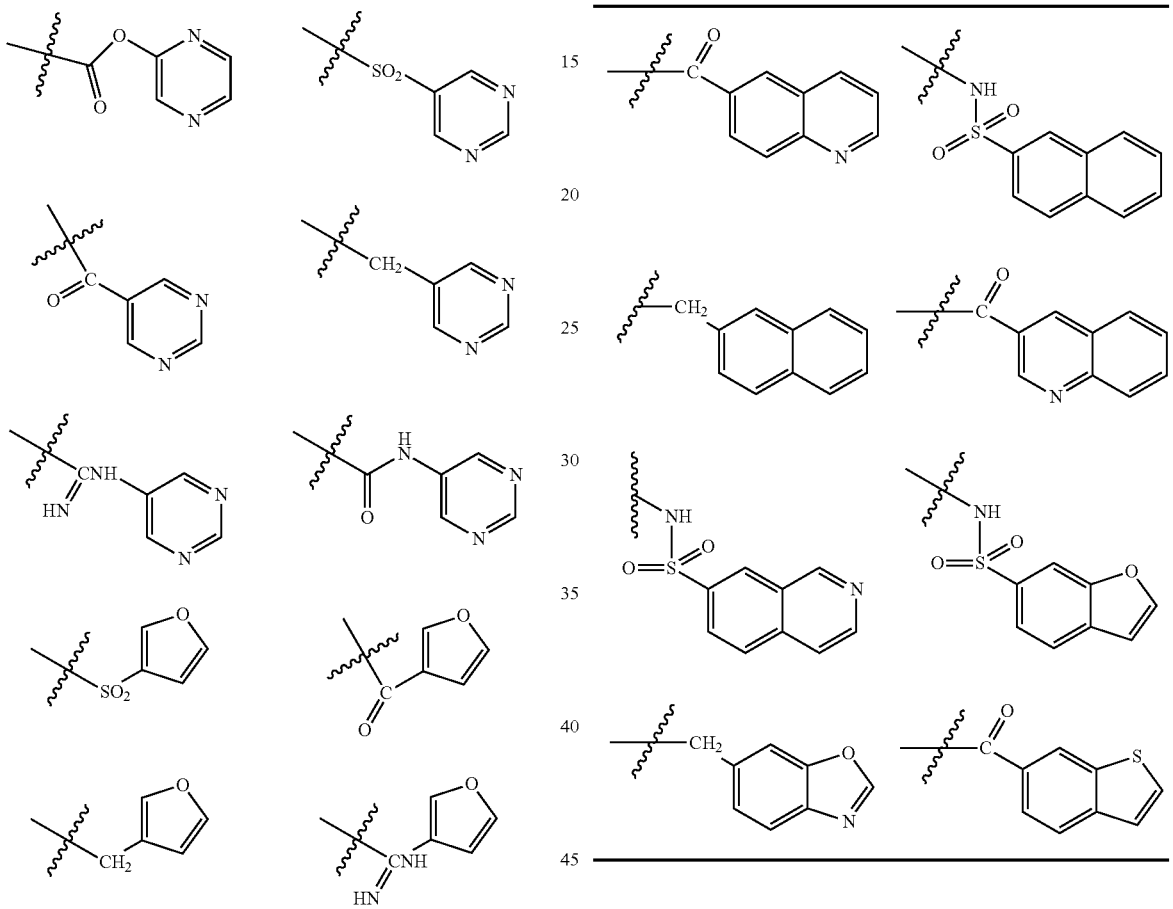
TABLE AA
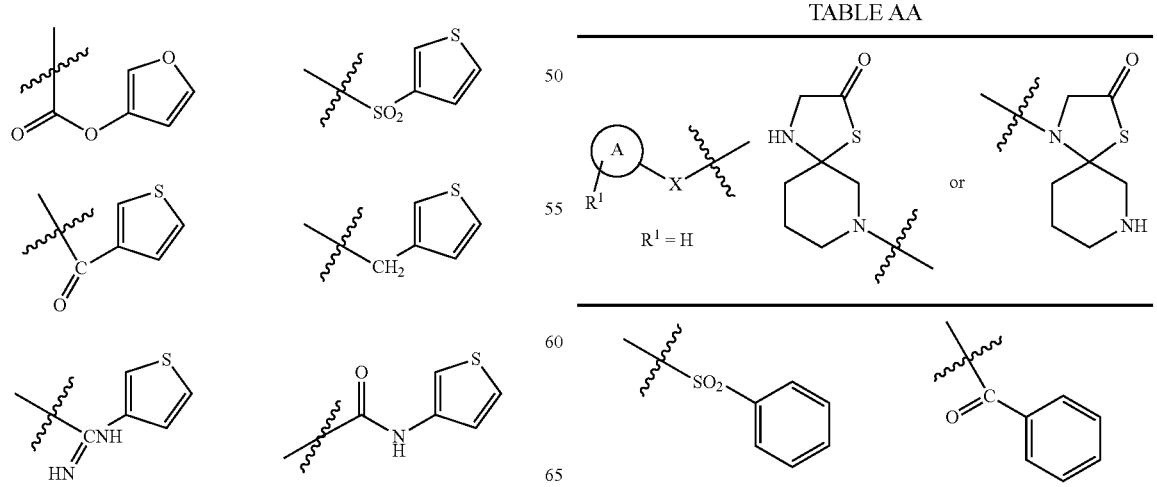

TABLE AA-continued
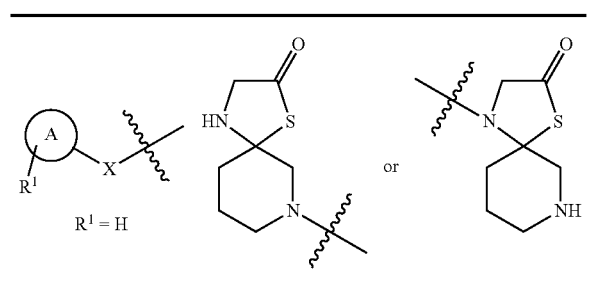
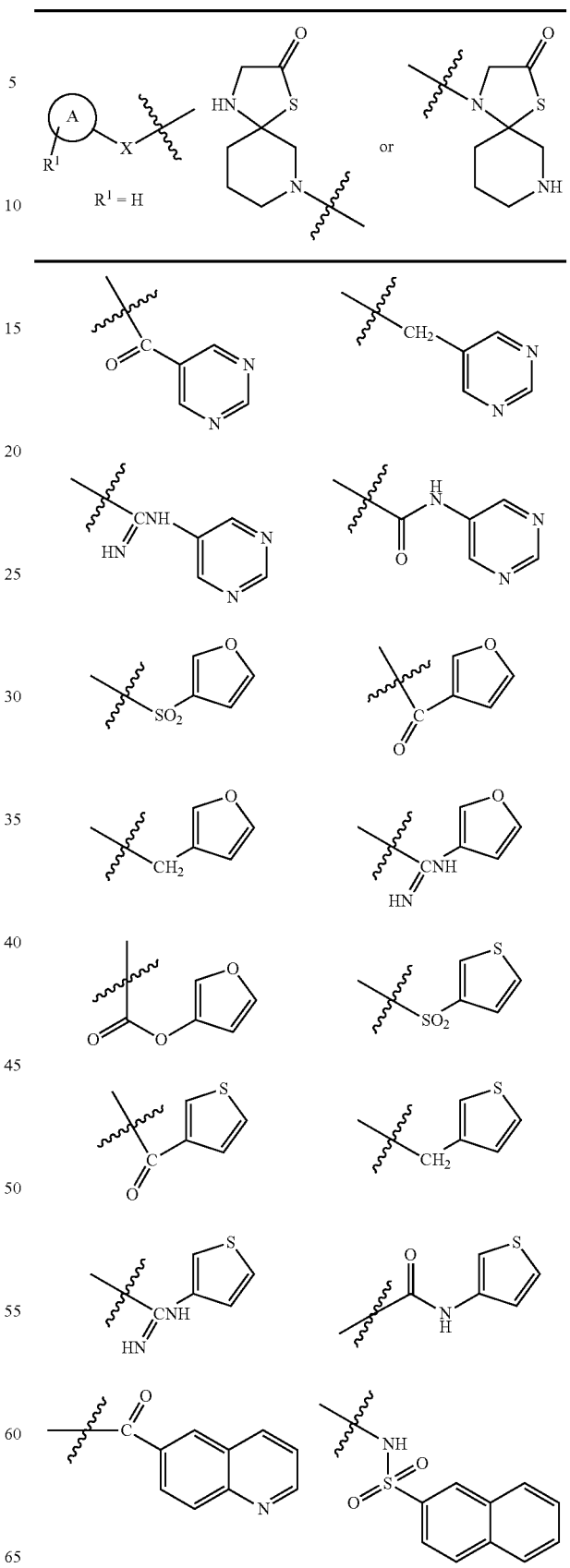

TABLE AA-continued
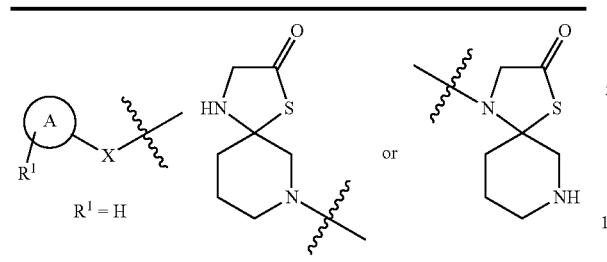
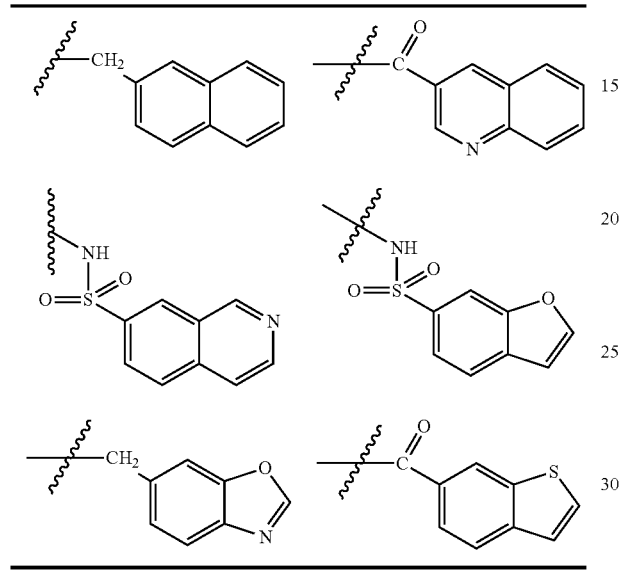
TABLE AB
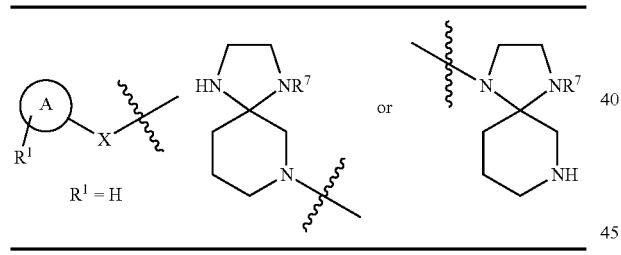
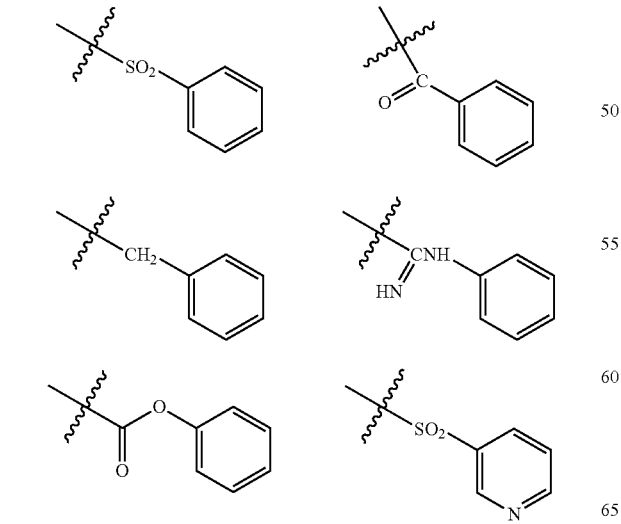
TABLE AB-continued
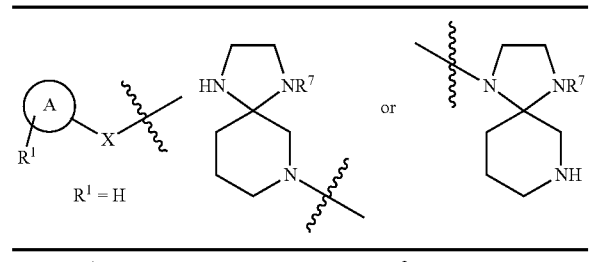
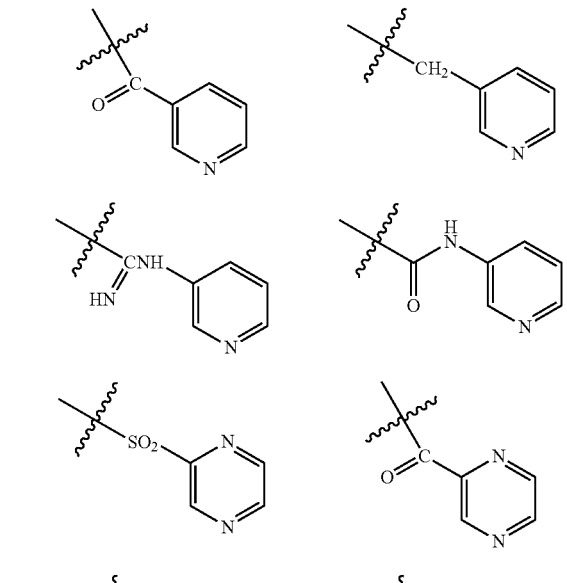
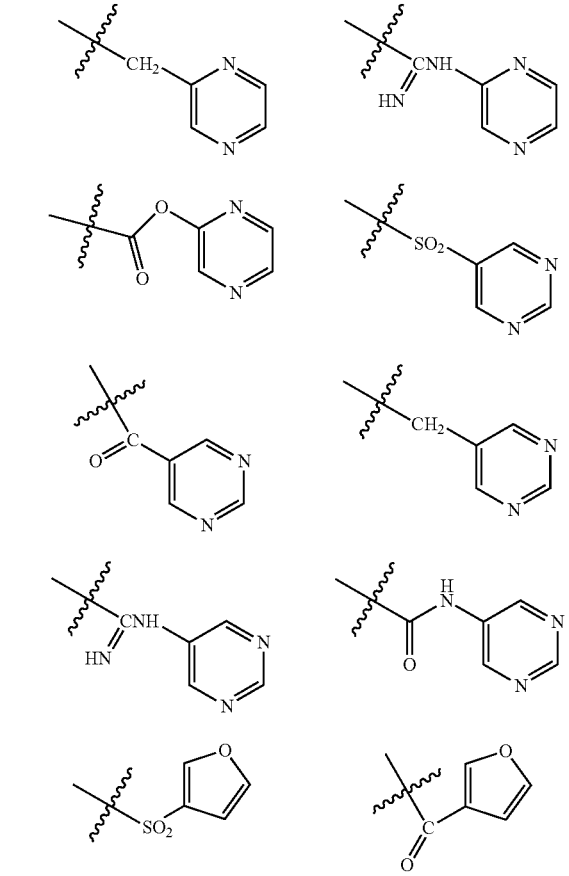

TABLE AB-continued
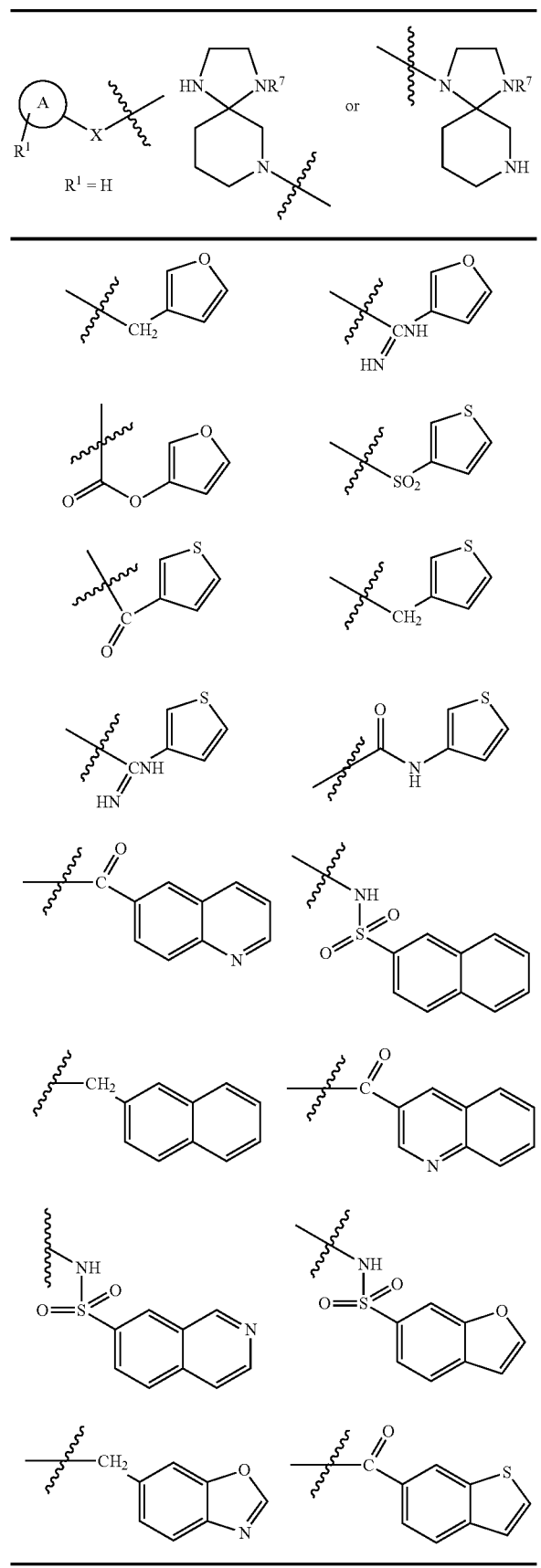
TABLE AC
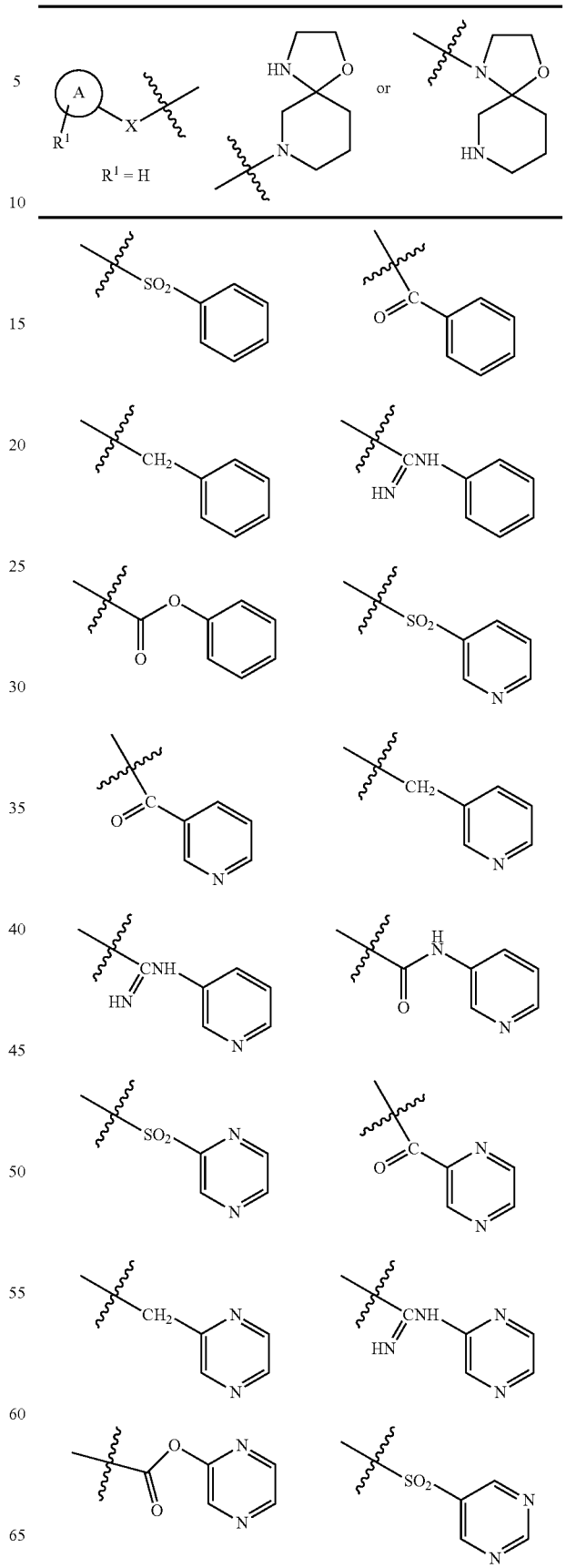

TABLE AC-continued
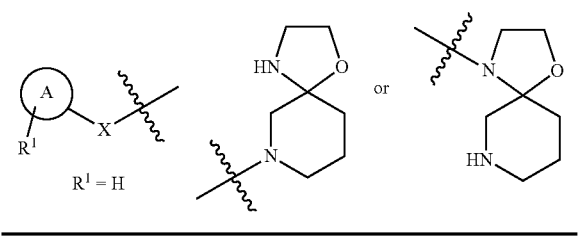
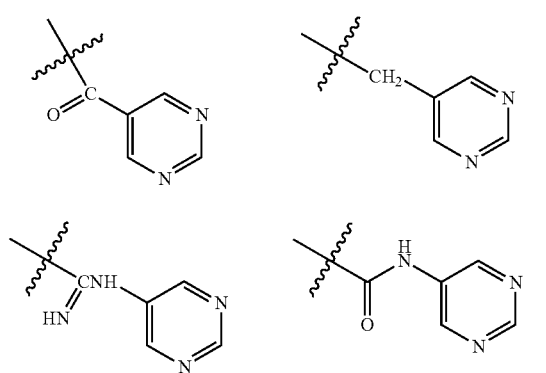
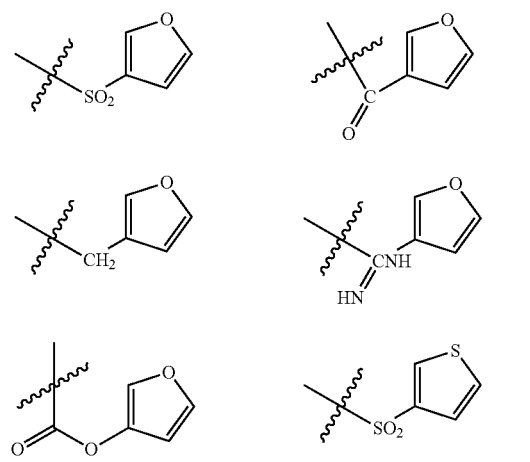
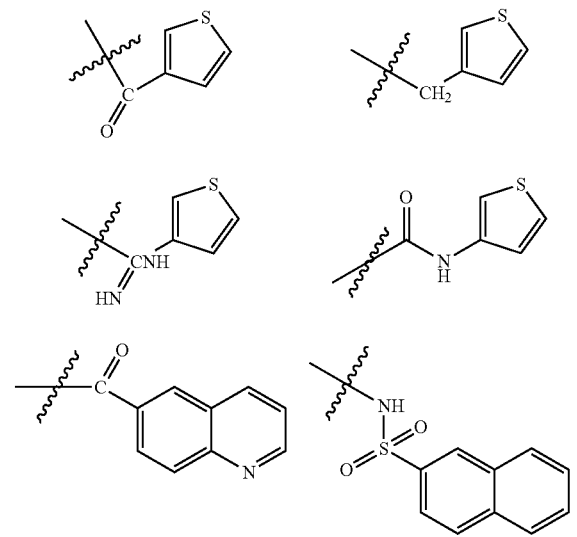
TABLE AC-continued
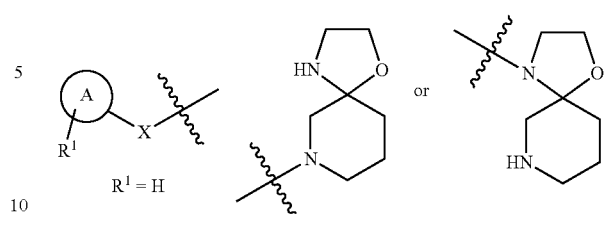
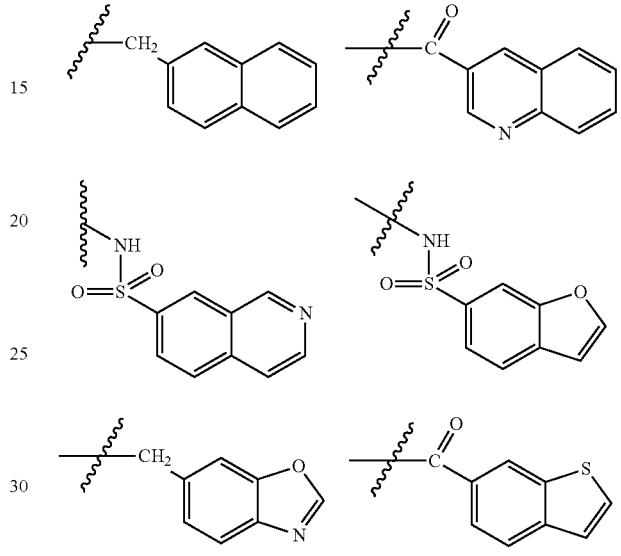
TABLE AD
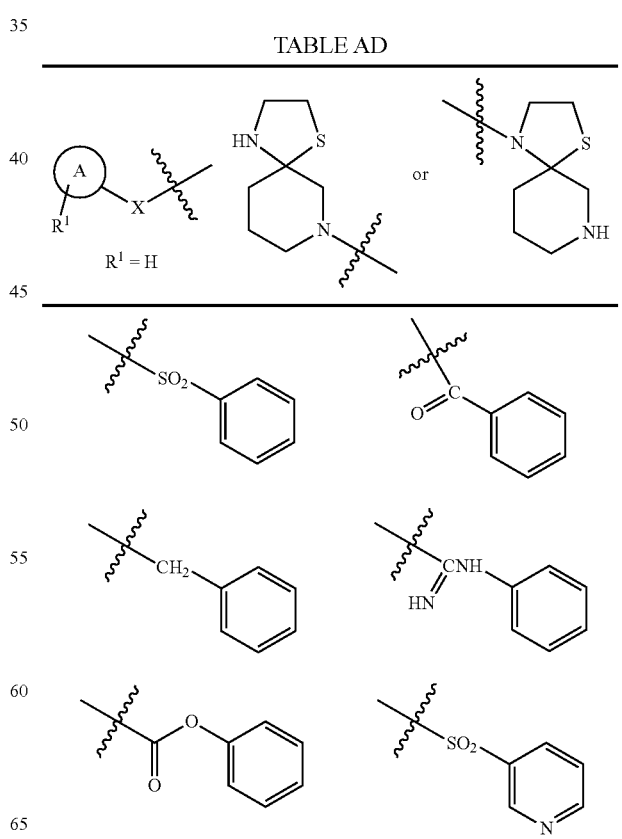

TABLE AD-continued
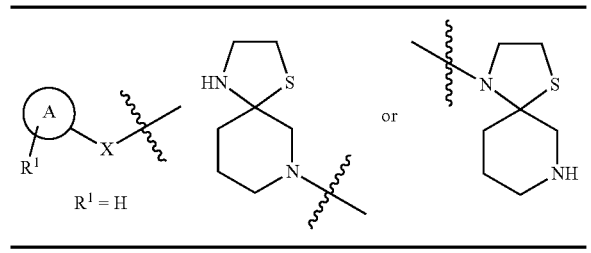
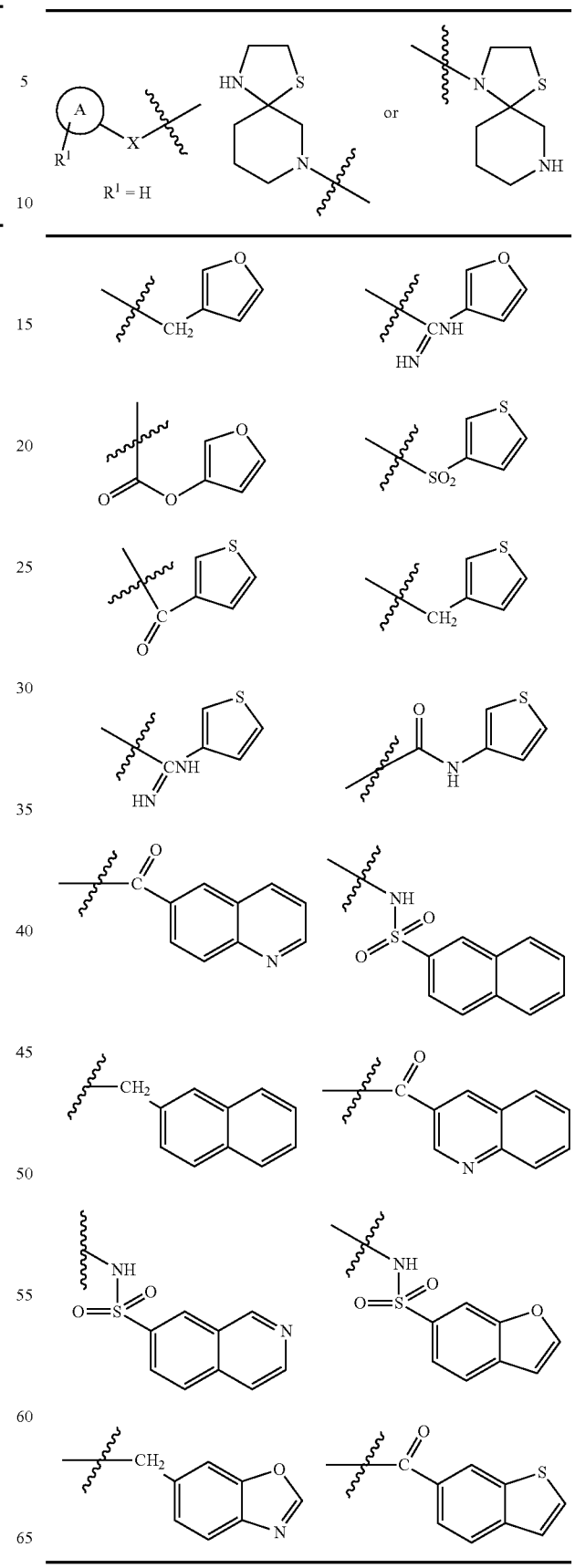

TABLE AE
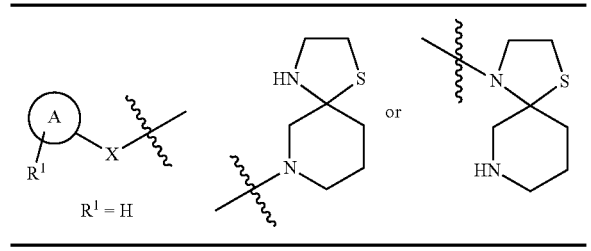
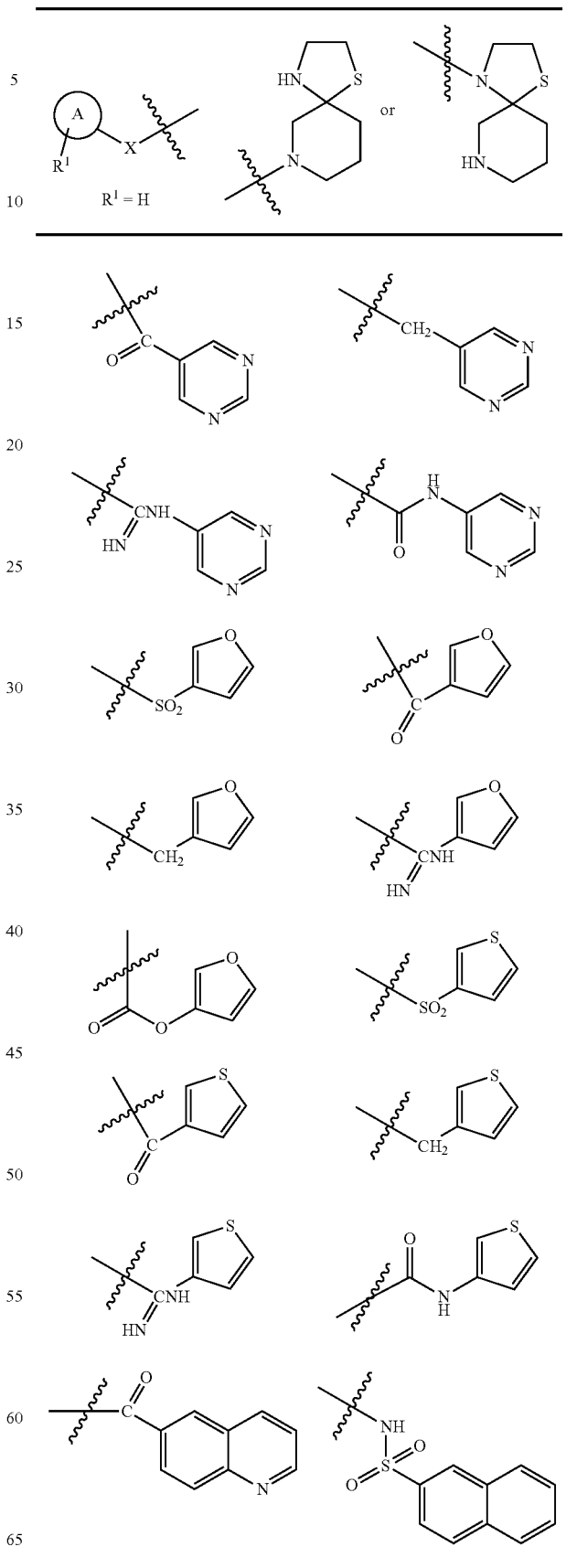

TABLE AE-continued

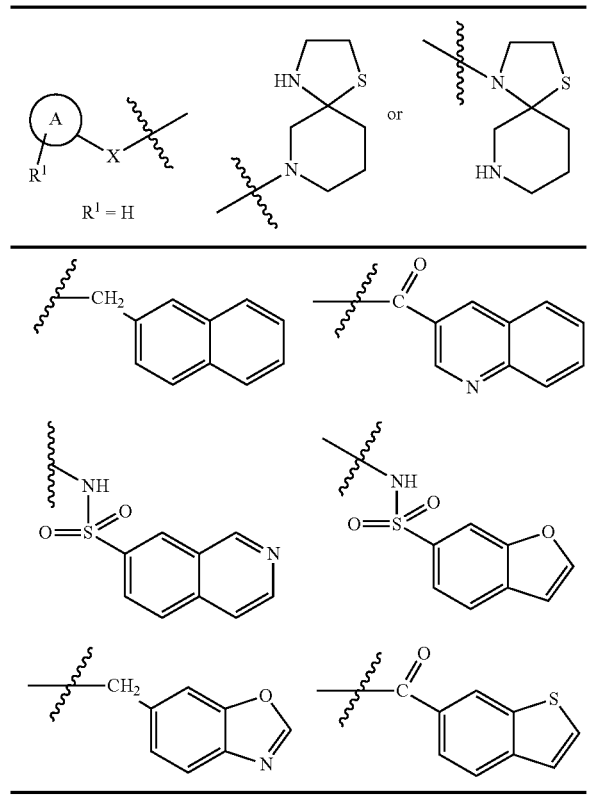

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

Example 1

MOR Agonist Activity

Using GTPγS Binding Assay

To assess the mu opiate receptor (MOR) agonist activity of positive compounds from the FLNA screening, compounds were tested in a [$^{35}$S]GTPγS binding assay using striatal membranes. Our previous study has shown that in striatal membranes, activation of MOR leads to an increase in [$^{35}$S] GTPγS binding to Gαo (Wang et al., 2005 Neuroscience 135:247-261).

Striatal tissue was homogenized in 10 volumes of ice cold 25 mM HEPES buffer, pH 7.4, which contained 1 mM EGTA, 100 mM sucrose, 50 µg/ml leupeptin, 0.04 mM PMSF, 2 µg/ml soybean trypsin inhibitor and 0.2% 2-mercaptoethanol. The homogenates were centrifuged at 800×g for 5 minutes and the supernatants were centrifuged at 49,000×g for 20 minutes. The resulting pellets were suspended in 10 volume of reaction buffer, which contained 25 mM HEPES, pH 7.5, 100 mM NaCl, 50 µg/ml leupeptin, 2 µg/ml soybean trypsin inhibitor, 0.04 mM PMSF and 0.02% 2-mercaptomethanol.

The resultant striatal membrane preparation (200 µg) was admixed and maintained (incubated) at 30° C. for 5 minutes in reaction buffer as above that additionally contained 1 mM MgCl$_2$ and 0.5 nM [$^{35}$S]GTPγS (0.1 µCi/assay, PerkinElmer Life and Analytical Sciences) in a total volume of 250 µl and continued for 5 minutes in the absence or presence of 0.1-10 µM of an assayed compound of interest. The reaction was terminated by dilution with 750 µl of ice-cold reaction buffer that contained 20 mM MgCl$_2$ and 1 mM EGTA and immediate centrifugation at 16,000×g for 5 minutes.

The resulting pellet was solubilized by sonicating for 10 seconds in 0.5 ml of immunoprecipitation buffer containing 0.5% digitonin, 0.2% sodium cholate and 0.5% NP-40. Normal rabbit serum (1 µl) was added to 1 ml of lysate and incubated at 25° C. for 30 minutes. Nonspecific immune complexes were removed by incubation with 25 µl of protein A/G-conjugated agarose beads at 25° C. for 30 minutes followed by centrifugation at 5,000×g at 4° C. for 5 minutes. The supernatant was divided and separately incubated at 25° C. for 30 minutes with antibodies raised against Gαo proteins (1:1,000 dilutions).

The immunocomplexes so formed were collected by incubation at 25° C. for 30 minutes with 40 µl of agarose-conjugated protein A/G beads and centrifugation at 5,000×g at 4° C. for 5 minutes. The pellet was washed and suspended in buffer containing 50 mM Tris-HCl, pH 8.0, and 1% NP-40. The radioactivity in the suspension was determined by liquid scintillation spectrometry. The specificity of MOR activation of [$^{35}$S]GTPγS binding to Gαo induced by a selective compound was defined by inclusion of 1 µM β-funaltrexamine (β-FNA; an alkylating derivative of naltrexone that is a selective MOR antagonist). DAMGO (H-Tyr-D-Ala-Gly-N-Me-Phe-Gly-OH; 1 or 10 µM) was used as a positive control.

The results of this study are shown in the Table below.

| FLNA-Binding Compound MOR Agonist Activity | | | | | | |
|---|---|---|---|---|---|---|
| FLNA-Binding Compound | Concentration of FLNA-Binding Compound as Agonist | | | | | |
| | 0.1 µM | 1 µM | 1 µM + BFNA | % DAMGO (0.1 µM) | % DAMGO (1 µM) | % DAMGO + BFNA |
| C0011 | 217.0% | 305.0% | 19.0% | 126.8% | 114.3% | 36.5% |
| C0026 | 207.2% | 288.4% | 21.2% | 107.7% | 105.6% | 48.3% |
| C0027 | 233.2% | 313.9% | 72.2% | 121.3% | 115.0% | 164.5% |
| C0040 | 145.8% | 308.3% | 90.4% | 93.1% | 133.2% | 277.3% |
| C0043 | 175.4% | 242.6% | 83.3% | 103.8% | 110.9% | 501.8% |
| C0044 | 173.7% | 280.1% | 59.1% | 102.8% | 128.0% | 356.0% |
| C0045 | 149.2% | 238.8% | 105.3% | 88.3% | 109.1% | 634.3% |
| C0046 | 286.2% | 492.9% | 156.8% | 197.4% | 211.5% | 356.4% |
| C0050 | 110.3% | 127.6% | 59.0% | 76.1% | 54.8% | 134.1% |
| C0055 | — | — | — | — | — | — |
| C0056 | 98.6% | 193.4% | 86.3% | 68.0% | 83.0% | 196.1% |
| C0060 | 166.5% | 218.9% | 143.9% | 114.8% | 93.9% | 327.0% |

-continued

| FLNA-Binding Compound MOR Agonist Activity | | | | | |
|---|---|---|---|---|---|
| FLNA- | Concentration of FLNA-Binding Compound as Agonist | | | | |
| Binding Compound | 0.1 μM | 1 μM | 1 μM + BFNA | % DAMGO (0.1 μM) | % DAMGO (1 μM) | % DAMGO + BFNA |
| C0066 | 162.4% | 316.7% | 42.3% | 104.0% | 137.4% | 106.0% |
| C0086M | 206.8% | 265.3% | 152.3% | 117.5% | 104.9% | 692.3% |
| C0087M | 262.8% | 329.6% | 142.5% | 138.9% | 132.8% | 293.8% |
| C0088M | 276.3% | 355.3% | 177.1% | 160.5% | 161.7% | 513.3% |
| C0089M | 234.5% | 295.3% | 81.9% | 136.3% | 134.4% | 237.4% |
| C0090M | 237.0% | 341.0% | 41.0% | 137.7% | 155.2% | 118.8% |
| C0091M | 207.9% | 274.4% | 80.8% | 118.1% | 108.5% | 367.3% |
| C0093M | 140.0% | 211.8% | 44.0% | 81.3% | 96.4% | 127.5% |
| C0094M | 172.5% | 263.5% | 115.3% | 100.2% | 119.9% | 334.2% |
| C0095M | 189.1% | 224.6% | 107.7% | 107.4% | 88.8% | 489.5% |
| C0096M | 186.4% | 328.9% | 127.1% | 105.9% | 130.0% | 577.7% |
| C0098M | 125.8% | 256.9% | 61.9% | 71.5% | 101.5% | 281.4% |
| C0099M | 157.2% | 195.7% | 114.7% | 93.8% | 88.0% | 241.5% |
| C0100M | 173.6% | 245.9% | 195.6% | 103.6% | 110.6% | 411.8% |
| C0101M | 138.2% | 274.3% | 174.8% | 82.5% | 123.4% | 368.0% |
| C0102M | 131.8% | 272.0% | 150.4% | 78.6% | 122.4% | 316.6% |
| C0104M | 188.2% | 238.9% | 143.8% | 99.5% | 96.3% | 296.5% |
| C0105M | 198.1% | 220.3% | 73.1% | 104.7% | 88.8% | 150.7% |
| C0106M | 171.8% | 240.7% | 117.2% | 102.5% | 108.3% | 246.7% |
| C0108M | 205.6% | 258.5% | 76.9% | 108.7% | 104.1% | 158.6% |
| C0114M | 114.0% | 144.3% | 35.9% | 77.6% | 71.4% | 91.3% |
| C0115M | 177.2% | 226.8% | 118.4% | 105.7% | 102.0% | 249.3% |
| C0116M | 258.4% | 302.8% | 152.0% | 136.6% | 122.0% | 313.4% |
| C0118M | 166.2% | 261.5% | 79.2% | 87.8% | 105.4% | 163.3% |
| C0119M | 105.7% | 167.8% | 35.1% | 71.9% | 83.0% | 89.3% |
| C0124M | 252.0% | 305.1% | 61.4% | 133.2% | 122.9% | 126.6% |
| C0125M | 168.6% | 195.2% | 159.7% | 89.1% | 78.6% | 329.3% |
| C0126M | 181.8% | 265.3% | 108.5% | 108.5% | 119.3% | 228.4% |
| C0128M | 197.8% | 286.0% | 63.9% | 104.5% | 115.2% | 131.8% |
| C0133M | 139.4% | 214.8% | 72.4% | 83.2% | 96.6% | 152.4% |
| C0134M | 158.5% | 207.3% | 46.6% | 94.6% | 93.3% | 98.1% |
| C0135M | 161.3% | 310.1% | 113.3% | 85.3% | 124.9% | 233.6% |
| C0136M (P5) | 176.8% | 237.3% | 74.5% | 93.4% | 95.6% | 153.6% |
| 0137M (P7) | 180.8% | 193.8% | 55.8% | 95.6% | 78.1% | 115.1% |
| C0142M | 143.7% | 192.5% | 98.7% | 97.8% | 95.2% | 251.1% |
| C0143M | — | — | — | — | — | — |
| C0144M-2 | — | — | — | — | — | — |
| C0145M-3 | — | — | — | — | — | — |
| C0149M-2 | — | — | — | — | — | — |
| C0150M-2 | — | — | — | — | — | — |
| C0151M-2 | — | — | — | — | — | — |
| C0152M-2 | — | — | — | — | — | — |
| C0153M-3 | — | — | — | — | — | — |
| DAMGO Average | 168.5% | 266.1% | 53.2% | — | — | — |

Example 2

FITC-NLX-Based FLNA Screening Assay

A. Streptavidin-Coated 96-Well Plates

Streptavidin-coated 96-well plates (Reacti-Bind™ NeutrAvidin™ High binding capacity coated 96-well plate, Pierce-ENDOGEN) are washed three times with 200 μl of 50 mM Tris HCl, pH 7.4 according to the manufacturer's recommendation.

B. N-Biotinylated VAKGL Pentapeptide (Bn-VAKGL) (SEQ ID NO: 1)

Bn-VAKGL peptide (0.5 mg/plate) is dissolved in 50 μl DMSO and then added to 4450 μl of 50 mM Tris HCl, pH 7.4, containing 100 mM NaCl and protease inhibitors (binding medium) as well as 500 μl superblock in PBS (Pierce-ENDOGEN) [final concentration for DMSO: 1%].

C. Coupling of Bn-VAKGL Peptides to Streptavidin-Coated Plate

The washed streptavidin-coated plates are contacted with 5 μg/well of Bn-VAKGL (100 μl) for 1 hour (incubated) with constant shaking at 25° C. [50 μl of Bn-VAKGL peptide solution from B+50 μl binding medium, final concentration for DMSO: 0.5%]. At the end of the incubation, the plate is washed three times with 200 μl of ice-cold 50 mM Tris HCl, pH 7.4.

D. Binding of FITC-Tagged Naloxone [FITC-NLX] to VAKGL

Bn-VAKGL coated streptavidin plates are incubated with 10 nM fluorescein isothiocyanate-labeled naloxone (FITC- NLX; Invitrogen) in binding medium (50 mM Tris HCl, pH 7.4 containing 100 mM NaCl and protease inhibitors) for 30 minutes at 30° C. with constant shaking. The final assay volume is 100 µl. At the end of incubation, the plate is washed twice with 100 µl of ice-cold 50 mM Tris, pH 7.4. The signal, bound-FITC-NLX is detected using a DTX-880 multi-mode plate reader (Beckman).

E. Screening of Medicinal Chemistry Analogs

The compounds are first individually dissolved in 25% DMSO containing 50 mM Tris HCl, pH 7.4, to a final concentration of 1 mM (assisted by sonication when necessary) and then plated into 96-well compound plates. To screen new compounds, each compound solution (1 µl) is added to the Bn-VAKGL coated streptavidin plate with 50 µl/well of binding medium followed immediately with addition of 50 µl of FITC-NLX (total assay volume/well is 100 µl). The final screening concentration for each compound is 10 µM.

Each screening plate includes vehicle control (total binding) as well as naloxone (NLX) and/or naltrexone (NTX) as positive controls. Compounds are tested in triplicate or quadruplicate. Percent inhibition of FITC-NLX binding for each compound is calculated [(Total FITC-NLX bound in vehicle−FITC-NLX bound in compound)/Total FITC-NLX bound in vehicle]×100%]. To assess the efficacies and potencies of the selected compounds, compounds that achieve approximately 60-70% inhibition at 10 µM are screened further at 1 and 0.1 µM concentrations.

The results of this screening assay are shown in the table below.

| FLNA Peptide Binding Assay | | | |
|---|---|---|---|
| FLNA-binding | Concentration of FLNA-binding Compound | | |
| Compound | 0.01 µM | 0.1 µM | 1 µM |
| C0011 | 37.6% | 41.4% | 46.0% |
| C0026 | 42.3% | 44.8% | 49.0% |
| C0027 | 50.8% | 61.2% | 63.8% |
| C0040 | 38.4% | 46.3% | 55.9% |
| C0043 | 43.9% | 51.3% | 58.0% |
| C0044 | 37.3% | 43.9% | 50.6% |
| C0045 | 39.1% | 48.9% | 53.7% |
| C0046 | 30.8% | 35.7% | 42.2% |
| C0050 | 26.7% | 34.5% | 36.4% |
| C0055 | 29.0% | 34.9% | 39.5% |
| C0056 | 33.7% | 38.9% | 41.4% |
| C0060 | 60.3% | 64.0% | 68.0% |
| C0066 | 39.2% | 46.2% | 50.9% |
| C0086M | 37.9% | 48.1% | 53.4% |
| C0087M | 51.6% | 57.9% | 61.5% |
| C0088M | 40.1% | 52.4% | 56.1% |
| C0089M | 40.7% | 46.1% | 51.2% |
| C0090M | 42.5% | 52.5% | 55.8% |
| C0091M | 38.1% | 39.8% | 46.3% |
| C0093M | 44.8% | 49.9% | 53.5% |
| C0094M | 43.0% | 52.8% | 57.5% |
| C0095M | 40.1% | 46.6% | 50.5% |
| C0096M | 43.0% | 48.3% | 55.0% |
| C0098M | 52.4% | 55.6% | 62.6% |
| C0099M | 46.9% | 53.3% | 56.0% |
| C0100M | 52.2% | 58.2% | 64.5% |
| C0101M | 50.5% | 56.4% | 59.0% |
| C0102M | 52.3% | 53.1% | 56.6% |
| C0104M | 51.4% | 54.1% | 55.2% |
| C0105M | 55.7% | 62.0% | 68.8% |
| C0106M | 45.8% | 55.6% | 58.9% |
| C0108M | 54.6% | 61.4% | 68.7% |
| C0114M | 57.1% | 63.2% | 66.7% |
| C0115M | 47.8% | 57.8% | 59.9% |
| C0116M | 53.9% | 60.0% | 62.9% |
| C0118M | 56.6% | 61.4% | 62.4% |
| C0119M | 41.6% | 55.5% | 60.0% |
| C0124M | 47.7% | 52.2% | 58.7% |
| C0125M | 54.2% | 59.7% | 63.3% |
| C0126M | 50.7% | 55.4% | 67.3% |
| C0128M | 46.5% | 54.4% | 58.2% |
| C0133M | 47.8% | 54.9% | 58.5% |
| C0134M | 55.7% | 60.5% | 61.9% |
| C0135M | 53.9% | 55.1% | 62.3% |
| C0136M (P5) | 46.7% | 55.2% | 58.2% |
| C0137M (P7) | 42.4% | 49.9% | 61.2% |
| C0142M | 35.1% | 39.4% | 56.0% |
| C0143M | — | — | — |
| C0144M-2 | — | — | — |
| C0145M-3 | — | — | — |
| C0149M-2 | — | — | — |
| C0150M-2 | — | — | — |
| C0151M-2 | — | — | — |
| C0152M-4 | — | — | — |
| C0153M-3 | — | — | — |
| Naloxone Average | 40.61% | 47.75% | 51.54% |

Example 3

Tail-Flick Test

The mouse "tail flick" test was used to assay the relative antinociceptive activity of compositions containing a compound to be assayed. This assay was substantially that disclosed by Xie et al., 2005 *J. Neurosci* 25:409-416.

The mouse hot-water tail-flick test was performed by placing the distal third of the tail in a water bath maintained at 52° C. The latency until tail withdrawal from the bath was determined and compared among the treatments. A 10 second cutoff was used to avoid tissue damage. Data are converted to percentage of antinociception by the following formula: (response latency−baseline latency)/(cutoff−baseline latency)×100 to generate dose-response curves. Linear regression analysis of the log dose-response curves was used to calculate the $A_{50}$ (dose that resulted in a 50% antinociceptive effect) doses and the 95% confidence intervals (CIs). Relative potency was determined as a ratio of the $A_{50}$ values. The significance of the relative potency and the confidence intervals are determined by applying the t test at $p<0.05$.

To assess tolerance to the antinociceptive effect, the compound was administered twice daily for 7 days at an $A_{90}$ dose (dose that results in a 90% antinociceptive effect in the 52° C. warm-water tail-flick test), and the tail-flick test was performed daily after the a.m. dose. A significant reduction in tail-flick latency on subsequent days compared to the Day 1 administration of the $A_{90}$ dose indicates antinociceptive tolerance. Assays were typically carried out separately using at least 32 and 56 mg/kg dosages, with some assays also separately carried out at 18 and 100 mg/kg.

Orally administered morphine exhibited an $A_{50}$ value of 61.8 (52.4-72.9) mg/kg, and a mean maximum antinociception amount of about 43% at 56 mg/kg at about 20 minutes. Orally administered compound C0027 exhibited a mean maximum antinociception amount of about 70% at 56 mg/kg at about 20 minutes, whereas orally administered compound C0134M exhibited a mean maximum antinociception amount of about 50% at 56 mg/kg at about 30 minutes, compound C0066 exhibited a mean maximum antinociception amount of about 55% at 56 mg/kg at about 20 minutes, compound C0108M exhibited a mean maximum antinociception amount of about 50% at 56 mg/kg at about 20 minutes, compound C0090 exhibited a mean maximum antinociception amount of about 35% at 56 mg/kg at about 20 minutes, and compound C0089 exhibited a mean maximum antinociception amount of about 30% at 56 mg/kg at about 20 minutes.

Example 4

Dependence Test

On day 8, 16-20 hours after the last administration of an assay composition, animals were given naloxone to precipitate withdrawal (10 mg/kg, s.c.) before being placed in an observation chamber for 1 hour. A scale adapted from MacRae et al., 1997 *Psychobiology* 25:77-82 was used to quantify four categories of withdrawal behaviors: "wet dog" shakes, paw tremors, mouth movements, and ear wipes. Scores are summed to yield a total withdrawal score across the 1-hour test.

Example 5

Relative Gs/Go Switching

In this set of studies, the rat brain slice organotypic culture methods were modified from those published previously (Adamchik et al., 2000 *Brain Res Protoc* 5:153-158; Stoppini et al., 1991 *J Neurosci Methods* 37:173-182). Striatal slices (200 μM thickness) were prepared using a McIlwain tissue chopper (Mickle Laboratory Engineering Co., Surrey, UK). Slices were carefully transferred to sterile, porous culture inserts (0.4 μm, Millicell-CM) using the rear end of a glass Pasteur pipette. Each culture insert unit contained 2 slices and was placed into one well of the 12-well culture tray. Each well contain 1.5 ml of culture medium composed of 50% MEM with Earl's salts, 2 mM L-glutamine, 25% Earl's balanced salt solution, 6.5 g/l D-glucose, 20% fetal bovine serum, 5% horse serum, 25 mM HEPES buffer, 50 mg/ml streptomycin and 50 mg/ml penicillin. The pH value was adjusted to 7.2 with HEPES buffer.

Cultures were first incubated for 2 days to minimize the impact of injury from slice preparation. Incubator settings throughout the experiment were 36° C. with 5% $CO_2$. To induce tolerance, culture medium was removed and the culture insert containing the slices was gently rinsed twice with warm (37° C.) phosphate-buffered saline (pH 7.2) before incubation in 0.1% fetal bovine serum-containing culture medium with 100 μM morphine for 1 hour twice daily (at 9-10 AM and 3-4 PM) for 7 days.

Slices were returned to culture medium with normal serum after each drug exposure. Tissues were harvested 16 hours after the last drug exposure by centrifugation.

For determination of MOR-G protein coupling, slices were homogenated to generate synaptic membranes. Synaptic membranes (400 μg) were incubated with either 10 μM oxycodone or Kreb's-Ringer solution for 10 minutes before solubilization in 250 μl of immunoprecipitation buffer (25 mM HEPES, pH 7.5; 200 mM NaCl, 1 mM EDTA, 50 μg/ml leupeptin, 10 μg/ml aprotinin, 2 μg/ml soybean trypsin inhibitor, 0.04 mM PMSF and mixture of protein phosphatase inhibitors). Following centrifugation, striatal membrane lysates were immunoprecipitated with immobilized anti-Gαs/olf or -Gαo conjugated with immobilized protein G-agarose beads. The level of MOR in anti-Gαs/olf or -Gαo immunoprecipitates was determined by Western blotting using specific anti-MOR antibodies.

To measure the magnitude of MOR-mediated inhibition of cAMP production, brain slices were incubated with Kreb's-Ringer (basal), 1 μM DAMGO, 1 μM forskolin or 1 μM DAMGO+1 μM forskolin for 10 minutes at 37° C. in the presence of 100 μM of the phosphodiesterase inhibitor IBMX. Tissues were homogenized by sonication and protein precipitated with 1M TCA. The supernatant obtained after centrifugation was neutralized using 50 mM Tris, pH 9.0. The level of cAMP in the brain lysate was measured by a cAMP assay kit (PerkinElmer Life Science, Boston) according to manufacturer's instructions.

| Condition | Gs/olf | Go | Gs/Go-Coupled Ratio |
|---|---|---|---|
| Vehicle | | | |
| Average | 330.7 | 1996.4 | 0.173 |
| SEM | 34.6 | 192.0 | 0.34 |
| Oxycodone, 10 μM | | | |
| Average | 1425.2 | 900.4 | 1.588 |
| SEM | 77.8 | 26.2 | 0.103 |
| C0011, 10 μM | | | |
| Average | 534.3 | 1603.3 | 0.332 |
| SEM | 51.8 | 68.5 | 0.023 |
| C0011, 100 μM | | | |
| Average | 658.2 | 1598.8 | 0.420 |
| SEM | 34.2 | 114.9 | 0.030 |

Example 6

Carrageenan-Induced

Acute Inflammatory Pain

To test the antinociceptive activity of the compounds under acute inflammatory conditions, the latency to paw withdrawal from a noxious thermal stimulus is determined before and 3 hours after injection of a 50 μl solution of 20 carrageenan into the plantar surface of the hindpaw (Mogil et al. 1999 *Pain* 80:67-82). Animals are placed in plexiglas boxes on top of a glass plate maintained at 30° C. and allowed to habituate for two sessions (−24 hours and −1 hour). Each habituation session lasts approximately 45-60 minutes.

For baseline paw withdrawal latencies, an infrared heat source (Ugo Basile model 37370) is applied from under the glass plate onto the plantar surface of the right hind paw with the focus of the light beam no larger than a 3- to 5-mm diameter. The time to withdrawal of the hind paw from the heat source is recorded. A maximum cutoff of 30 seconds is used to prevent tissue damage. The intensity of the beam is set so that baseline latencies are approximately 15 seconds. The post-carrageenan baseline is reestablished 3 hours after the carrageenan injections and only animals with a significant decrease in the latency of hind paw withdrawal from the thermal stimulus (thermal hypersensitivity) are tested. Animals are administered compounds, and hind paw withdrawal latencies are tested at various intervals after injection until the drug response falls below ~200 MPE.

Antihyperalgesia (thermal hypersensitivity) and antinociception are calculated as follows: percentage activity=100 in the opposite configurations from those shown. More detailed syntheses are set out hereinafter.

General Reaction Scheme

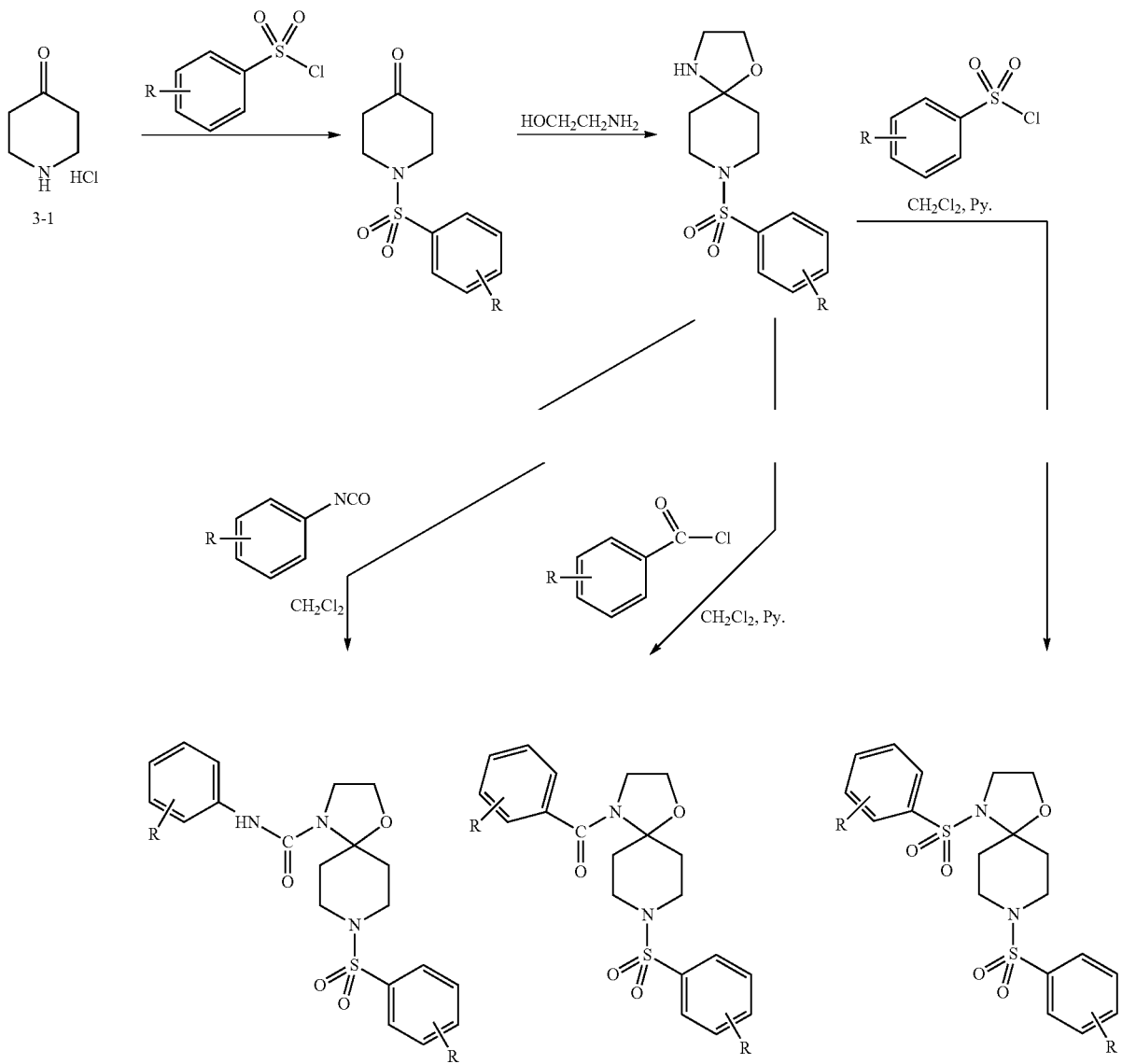

[(test paw withdrawal latency−post-carrageenan baseline paw withdrawal latency)/(pre-carrageenan baseline paw withdrawal latency−post-carrageenan baseline paw withdrawal latency)].

Paw edema is determined by use of a plethysmometer (Ugo Basile) in the mice undergoing the thermal latency testing. Paw volumes for the left and right hind paw are measured at the conclusion of the thermal latency testing (120 minutes after drug administration).

Compound Syntheses

A compound useful herein can be readily synthesized. An illustrative synthetic scheme is shown below that preparation of compounds containing two sulfonyl linkages and one sulfonyl and one carbonyl linkage. That scheme can be readily adapted for the preparation of compounds containing two carbonyl linkages and one carbonyl and one sulfonyl linkage Preparation of Compound 3-3

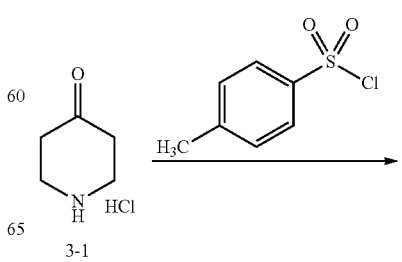

-continued

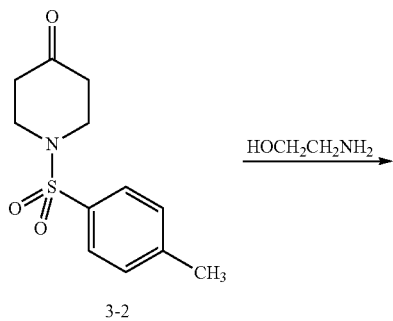

3-2

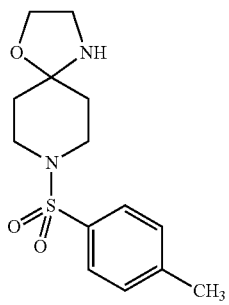

3-3 a. Preparation of Compound 3-2

4-Methylbenzene-1-sulfonyl chloride (1.04 g, 5.49 mmol) was added to a solution of compound 3-1 (0.8 g, 5.23 mmol) in pyridine (20 mL) in an atmosphere of $N_2$ and the mixture was allowed to react overnight (about 18 hours) at room temperature. Water was added and the resulting reaction mixture was extracted with $CH_2Cl_2$ 3 times. The combined organic layers were washed with 3M HCl and brine and concentrated to give compound 3-2 (0.78 g, yield: 59%, NMR confirmed).

b. Preparation of Compound 3-3

A solution of compound 3-2 (250 mg, 0.99 mmol), p-toluenesulfonic acid monohydrate (20 mg) and 2-aminoethanol (5 mL) in ethanol (20 mL) was stirred overnight (about 18 hours) at room temperature. The solvent was removed under reduced pressure and the residue was partitioned between ethyl acetate and water. The organic layer was washed with water and brine, dried with $Na_2SO_4$ and concentrated to give compound 3-3 (230 mg, yield: 80%, NMR confirmed) as a white solid.

Preparation of Compound 3-5

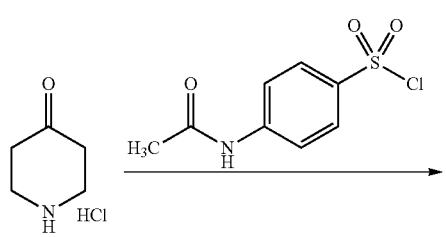

-continued

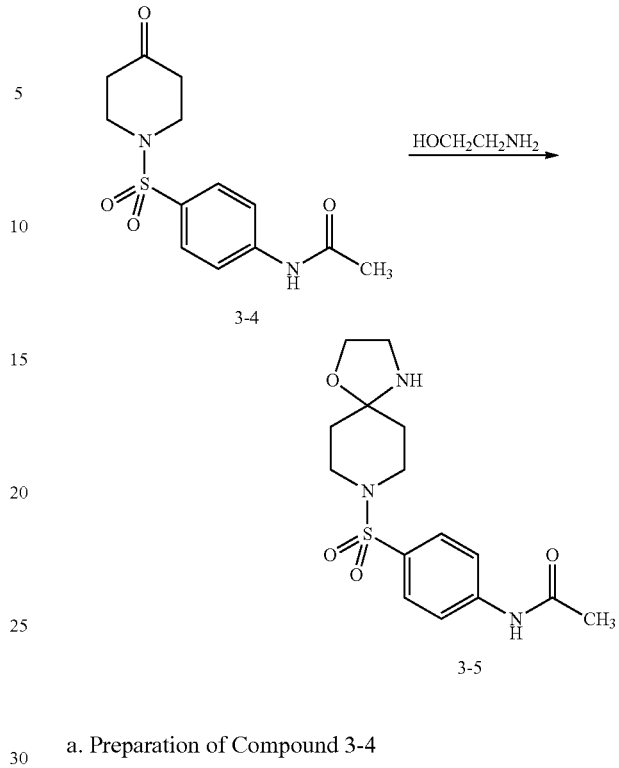

a. Preparation of Compound 3-4

To a solution of piperidin-4-one (0.47 g, 3.08 mmol) in pyridine (20 mL) was added 4-acetylaminobenzene sulfonyl chloride (0.6 g, 2.57 mmol). The mixture was stirred overnight (about 18 hours) at room temperature. Then the solvent was removed under reduced pressure. To the residue was added $CH_2Cl_2$ (100 mL) and 2N HCl (50 mL). The organic layer was separated and washed with 2N HCl (30 mL×2), then dried over $Na_2SO_4$ and concentrated to give the title compound as yellow solid. (0.4 g, yield: 52.6%).

b. Preparation of Compound 3-5

To a solution of compound 3-4 (0.55 g, 1.86 mmol) in ethanol (50 mL) was added p-toluenesulfonic acid monohydrate (50 mg) and 2-aminoethanol (0.5 g, 8.2 mmol). The mixture was stirred overnight (about 18 hours) at 26° C. Then the solvent was removed under reduced pressure. To the residue was added $CH_2Cl_2$ (100 mL) and saturated $Na_2CO_3$ (100 mL). The organic layer was separated and washed with saturated $Na_2CO_3$ (50 mL×3), then dried over $Na_2SO_4$ and concentrated to give the crude product as white powder. (0.59 g, yield: 92.1%).

Preparation of Compound 3-7

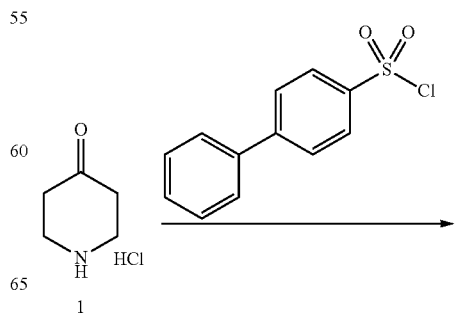

1

-continued

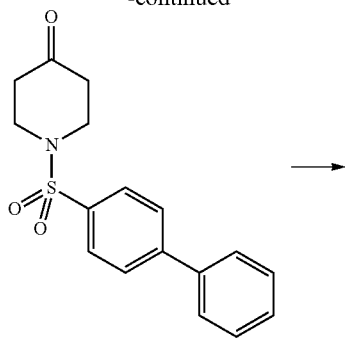

3-6

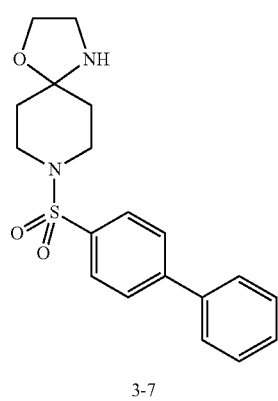

3-7 a. Preparation of Compound 3-6

To a solution of compound I (150 mg, 1.11 mmol) in pyridine (4 mL) was treated with 4-phenylnezenesulfonyl chloride (279.2 mg, 1.11 mmol). The mixture was stirred at room temperature overnight (about 18 hours). To the solution was added water and then extracted with dichloromethane (3 times). The combined organic phase was washed with 3M HCl and concentrated to give 205 mg of desired product as solid ($^1$H NMR confirmed, 58.6% yield).

b. Preparation of Compound 3-7

To a solution of compound 3-6 (205 mg, 0.65 mmol) in ethanol (EtOH) (6 mL) was treated with p-toluenesulfonic acid monohydrate (20 mg) and HOCH$_2$CH$_2$NH$_2$ (2 mL). The mixture was stirred at room temperature overnight (about 18 hours). Then EtOH was removed under reduced pressure. The residue was partitioned between dichloromethane and water. The organic phase was washed by saturated aqueous NaHCO$_3$ and brine. Then organic layer was concentrated to give 202 mg of crude as white liquid (yield 87%).

Preparation of Compound 3-11

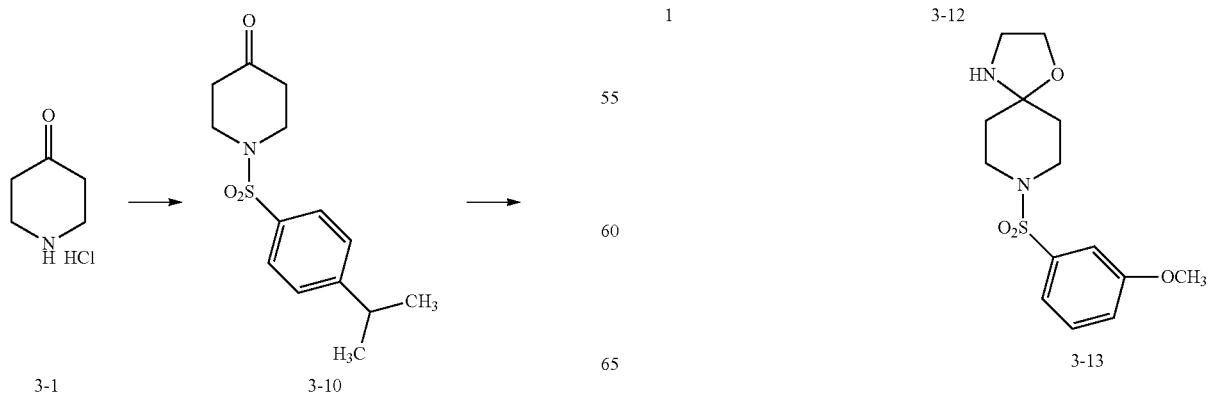

3-1                   3-10

-continued

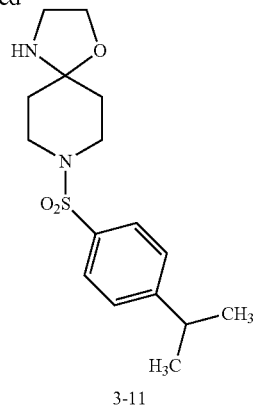

3-11 a. Preparation of Compound 3-10

4-Isopropylbenzene-1-sulfonyl chloride (0.13 mL, 0.7375 mmol) was added to a solution of piperidin-4-one hydrochloride hydrate (100 mg, 0.7375 mmol) in pyridine (3 mL) and the reaction mixture was stirred at room temperature for 3 hours. Water was added and the resulting reaction mixture was extracted with CH$_2$Cl$_2$ 3 times. The combined organic layers were washed with 3M HCl and concentrated to give compound 3-10 (105 mg, yield: 50.7%, NMR confirmed) as a white solid.

b. Preparation of Compound 3-11

To a solution of compound 3-10 (200 mg, 0.71 mmol) in ethanol (EtOH) (6 mL) was added p-toluenesulfonic acid monohydrate (15 mg) and 2-aminoethanol (1.5 mL) and the reaction mixture was stirred overnight (about 18 hours) at room temperature. EtOH was removed under reduced pressure and the residue was partitioned between CH$_2$Cl$_2$ and water. The organic phase was washed with saturated aqueous NaHCO$_3$ and brine and concentrated to give compound 3-11 (231 mg, yield: 100%) as a white foam.

Preparation of Compound 3-13

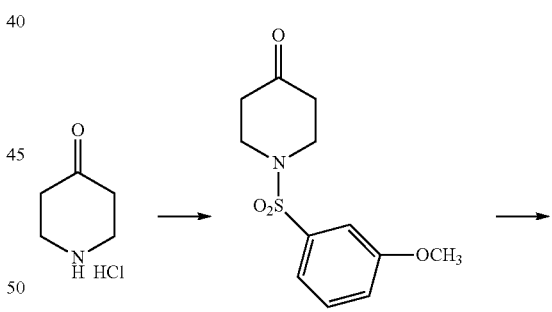

1                   3-12

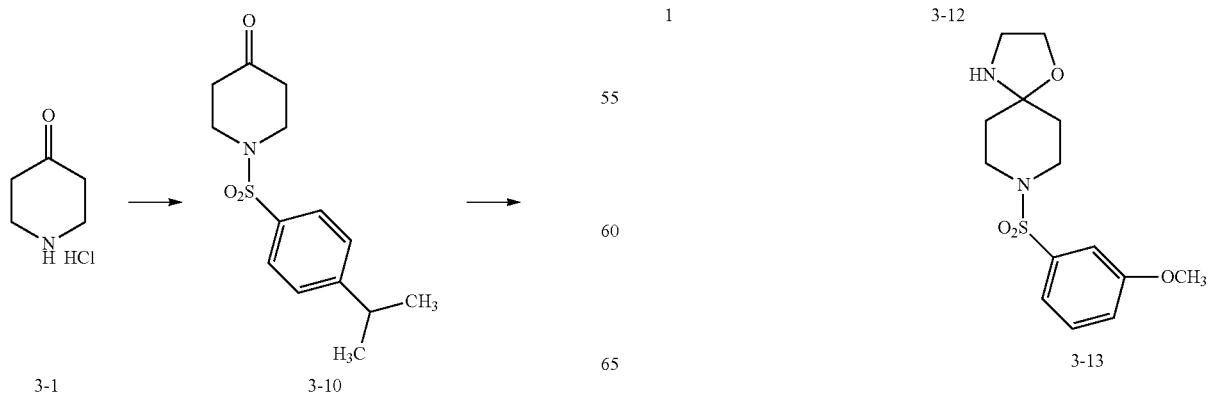

3-13 a. Preparation of Compound 3-12

A solution of compound 1 (300 mg, 2.21 mmol) in pyridine (8 mL) was admixed with 4-methoxy-sulfonylbenzene-1-sulfonyl chloride (0.34 mL, 2.21 mmol). The mixture was stirred at room temperature for 3 hours. To the solution was added water and that composition was extracted with dichloromethane 3 times. The combined organic phase was washed with 3 M HCl and concentrated to give 335 mg of white solid ($^1$H NMR confirmed, 56% yield).

a. Preparation of Compound 3-12

A solution of compound 3-12 (335 mg, 1.244 mmol) in ethanol (10 mL) was treated with p-toluenesulfonic acid monohydrate (25 mg) and $HOCH_2CH_2NH_2$ (2 mL). The mixture was stirred at room temperature overnight (about 18 hours). The ethanol was removed under reduced pressure. The residue was partitioned between dichloromethane and water. The organic phase was washed by saturated $NaHCO_3$ and brine then concentrated to provide 380 mg of colorless oil (yield 97.7%).

b. Preparation of Compound 3-13

To a solution of compound 3-12 (335 mg, 1.244 mmol) in ethanol (10 mL) was added p-toluenesulfonic acid monohydrate (25 mg) and 2-aminoethanol (2 mL) and the reaction mixture was stirred overnight (about 18 hours) at room temperature. Ethanol was removed under reduced pressure and the residue was partitioned between $CH_2Cl_2$ and water. The organic phase was washed with saturated $NaHCO_3$ and brine and concentrated to give compound 3-13 (380 mg, yield: 97.7%) as a colorless oil.

Preparation of Compound 3-15

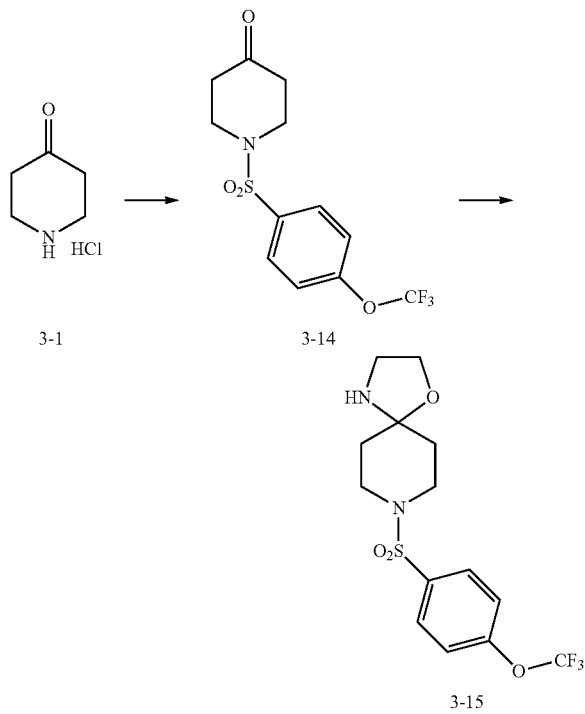

a. Preparation of Compound 3-14

To a solution of compound 3-1 (100 mg, 0.7375 mmol) in pyridine (3 mL) was added 4-trifluoromethoxy-benzene-1-sulfonyl chloride (192.38 mg, 0.7375 mmol) and the reaction mixture was stirred at room temperature for 3 hours. Water was added and the resulting reaction mixture was extracted with $CH_2Cl_2$ 3 times. The combined organic layers were washed with 3M HCl and concentrated to give compound 3-14 (111 mg, yield: 46.6%, $^1$H-NMR confirmed) as a white solid.

b. Preparation of Compound 3-15 p-Toluenesulfonic acid monohydrate (10 mg) and 2-aminoethanol (1 mL) were added to a solution of compound 3-14 (111 mg, 0.343 mmol) in ethanol (EtOH) (4 mL) and the reaction mixture was stirred at room temperature for 4 hours. EtOH was removed under reduced pressure and the residue was partitioned between $CH_2Cl_2$ and water. The organic layer was washed with saturated aqueous $NaHCO_3$ and brine and concentrated to give compound 3-15 (128 mg of crude compound, NMR confirmed) as a light yellow liquid.

Preparation of Compound 3-17

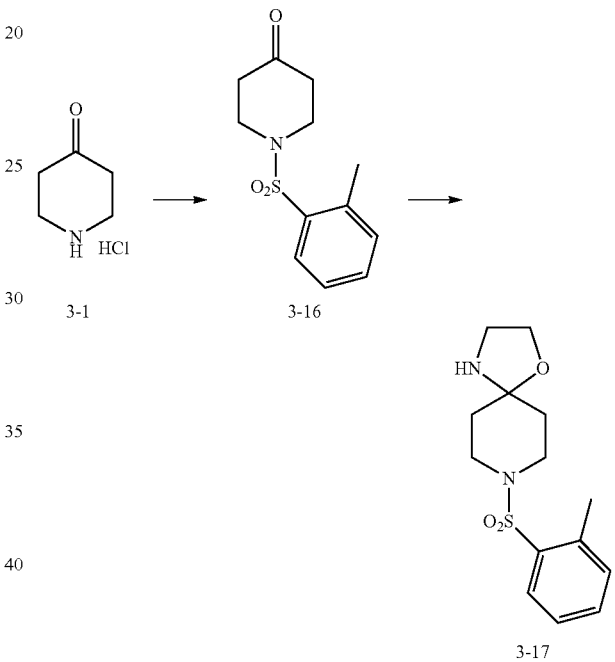

a. Preparation of Compound 3-16

2-Methyl-benzene-1-sulfonyl chloride (140.6 mg, 0.7375 mmol) was added to a solution of compound 3-1 (100 mg, 0.7375 mmol) in pyridine (3 mL) and the reaction mixture was stirred overnight (about 18 hours) at room temperature. Water was added and the resulting reaction mixture was extracted with $CH_2Cl_2$ 3 times. The combined organic layers were washed with 3M HCl and concentrated to give compound 3-16 (104 mg, yield: 56%, $^1$H NMR confirmed) as a white solid.

b. Preparation of Compound 3-17

To a solution of compound 3-16 (104 mg, 0.41 mmol) in ethanol (EtOH) (4 mL) was added p-toluenesulfonic acid monohydrate (10 mg) and 2-aminoethanol (1 mL) and the reaction mixture was stirred overnight (about 18 hours) at room temperature. EtOH was removed under reduced pressure and the residue was partitioned between $CH_2Cl_2$ and water. The organic phase was washed with saturated aqueous $NaHCO_3$ and brine and concentrated to give the crude compound 3-17 (120 mg, yield: 100%) as a light yellow liquid.

Preparation of Compound 3-25

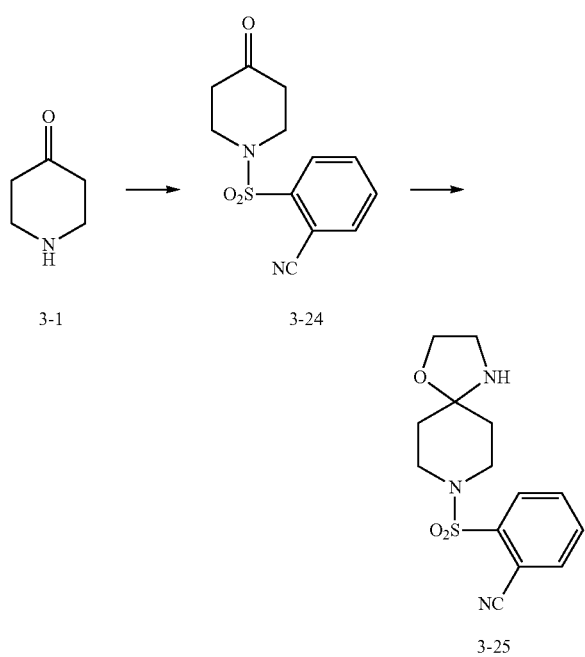

3-1 → 3-24 → 3-25 a. Preparation of Compound 3-24

2-Cyanobenzenesulfonyl chloride (100 mg, 0.50 mmol) was added to a solution of piperidin-4-one (92 mg, 0.60 mmol) in pyridine (10 mL). The mixture was stirred at room temperature overnight (about 18 hours). Pyridine was removed by reduced pressure evaporation. The residue was dissolved in $CH_2Cl_2$ (50 mL), and water (30 mL) was added. The $CH_2Cl_2$ layer was separated and the water phase was extracted with $CH_2Cl_2$ (2×20 mL). The organic layers were combined and washed with 3M HCl (20 mL×2). The organic layer was dried over anhydrous $Na_2SO_4$ and concentrated to give the title product as light-yellow oil (70 mg, yield: 53.4%, confirmed by MS).

b. Preparation of Compound 3-25

To a solution of compound 3-24 (35 mg, 0.13 mmol) in ethanol (10 mL) was added 2-aminoethanol (0.5 mL) and p-toluenesulfonic acid monohydrate (5 mg). The mixture was stirred at 30° C. overnight (about 18 hours). The solvent was removed by evaporation under vacuum. To the residue was added $CH_2Cl_2$ (30 mL), then the $CH_2Cl_2$ layer was washed with saturated $Na_2CO_3$ (15 mL×2) and water (20 mL×3), dried over $Na_2SO_4$ and concentrated to give the crude product as yellow oil (33 mg, yield: 80.5%, $^1$H-NMR confirmed).

Preparation of Compound 3-29

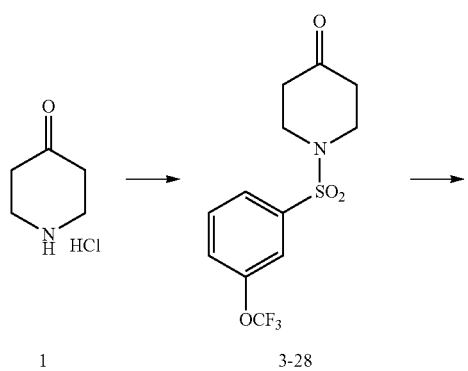

1 → 3-28

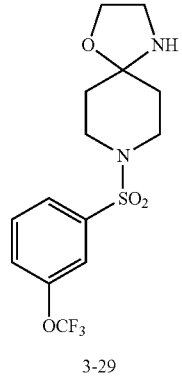

3-29 a. Preparation of Compound 3-28

3-Trifluoro-methoxybenzenesulfonyl chloride (287 mg, 1.1 mmol) was added to a solution of compound I (150 mg, 1.1 mmol) in pyridine (7 mL). The mixture was stirred at room temperature overnight (about 18 hours). Water was added to the solution and then the solution was extracted with dichloromethane (3 times). The combined organic phase was washed with 3 M HCl and concentrated to give 150 mg of the desired product as light yellow solid ($^1$H NMR confirmed, 42% yield).

b. Preparation of Compound 3-29

A solution of compound 3-28 (140 mg, 0.46 mmol) in ethanol (EtOH) (6 mL) was treated with p-toluenesulfonic acid (15 mg) and $HOCH_2CH_2NH_2$ (1.5 mL). The mixture was stirred at room temperature overnight (about 18 hours). The EtOH was removed under reduced pressure. The residue was partitioned between dichloromethane and water. The organic phase was washed by saturated aqueous $NaHCO_3$ and brine. The organic layer was concentrated to give 145 mg of compound 3-29 as white liquid ($^1$H-NMR confirmed, yield 85%).

Preparation of Compound 3-31

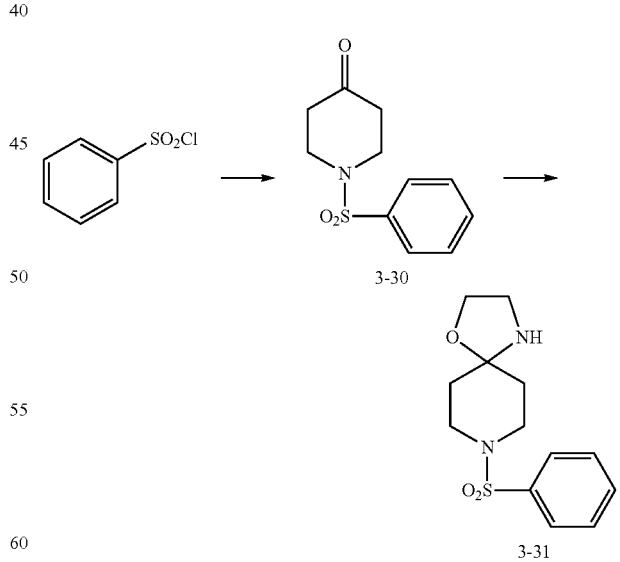

3-30 → 3-31 a. Preparation of Compound 3-30

Benzenesulfonyl chloride (200 mg, 1.13 mmol) was added to a solution of piperidin-4-one (208 mg, 1.36 mmol) in 20 mL of pyridine was added benzenesulfonyl chloride (200 mg, 1.13 mmol). The mixture was stirred at room temperature overnight (about 18 hours). The pyridine was then removed by evaporation under vacuum. To the residue was added CH₂Cl₂ (50 mL), then the CH₂Cl₂ layer was washed with 3M HCl (30 mL×3), dried over Na₂SO₄ and concentrated to give the crude product as a light yellow solid (138 mg, yield: 51%).

b. Preparation of Compound 3-31

A solution of compound 3-30 (136 mg, 0.57 mmol), p-toluenesulfonic acid monohydrate (15 mg) and 2-aminoethanol (2 mL) in ethanol (EtOH) (20 mL) was stirred overnight (about 18 hours) at room temperature. The solvent was removed by evaporation under vacuum. To the residue was added ethyl acetate (50 mL) and water (50 mL). The ethyl acetate layer was washed with water (30 mL×3). The water phase was washed with ethyl acetate (20 mL). The combined organic layers were dried over Na₂SO₄, filtered and concentrated to give the crude product (151 mg, yield: 92.5%). The crude product was directly used in the next step.

Preparation of Compound 3-33

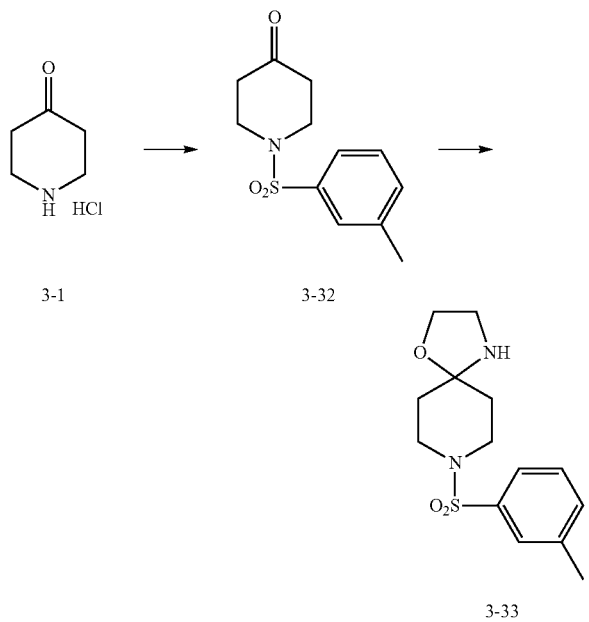

a. Preparation of Compound 3-32

3-Methyl-benzenesulfonyl chloride was added to a solution of piperidin-4-one hydrochloride monohydrate (159 mg, 1.03 mmol) in 10 mL pyridine (130 mg, 0.69 mmol). The mixture was stirred overnight (about 18 hours) at room temperature. The pyridine was removed by evaporation under vacuum. To the residue was added CH₂Cl₂ (50 mL), the CH₂Cl₂ layer was washed with 3 M HCl (30 mL×3), dried over Na₂SO₄ and concentrated to give the crude product as light yellow solid (140 mg, yield: 80.5%).

b. Preparation of Compound 3-33

A solution of compound 3-32 (140 mg, 0.55 mmol), p-toluenesulfonic acid (15 mg) and 2-aminoethanol (2 mL) in ethanol (20 mL) was stirred overnight (about 18 hours) at room temperature. The solvent was removed by evaporation under vacuum. To the residue was added ethyl acetate (50 mL) and water (50 mL). The ethyl acetate layer was washed with water (30 mL×3), dried over Na₂SO₄ and concentrated to give the crude product as a yellow oil (170 mg).

Preparation of Compounds 3-35

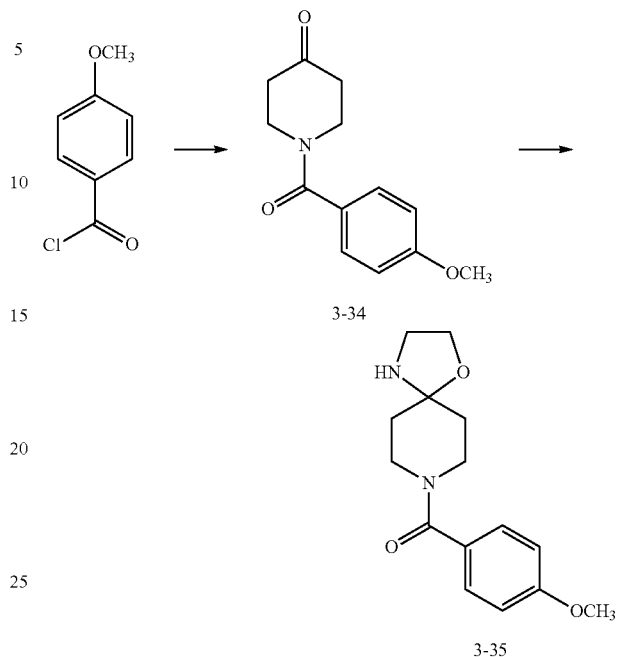

a. Preparation of Compound 3-34

4-Methoxybenzoyl chloride (0.5 g, 2.93 mmol) was added to a solution of piperidin-4-one hydrochloride monohydrate (0.30 g, 1.95 mmol) in pyridine (20 mL). The reaction mixture was stirred at room temperature overnight (about 18 hours). The reaction solvent was then removed under reduced pressure. The residue was dissolved in CH₂Cl₂ (50 mL), then washed with 3M HCl (50 mL×3). The organic layer was dried over Na₂SO₄ and evaporated to give the title compound as a brown oil (330 mg, yield: 61.5%, LC-MS confirmed).

b. Preparation of Compound 3-35

A solution of compound 3-34 (330 mg, 1.42 mmol), 2-aminoethanol (2 mL) and p-toluenesulfonic acid monohydrate (33 mg) in ethanol (20 mL) was stirred at room temperature overnight (about 18 hours). The solvent was then removed by evaporation under reduced pressure. The residue was diluted with CH₂Cl₂ (50 mL), then washed with water (50 mL×3). The organic layer was dried over Na₂SO₄ and evaporated to give the crude product as a yellow oil (360 mg, yield: 92.1%, ¹H-NMR and MS confirmed).

Preparation of Compound 3-37

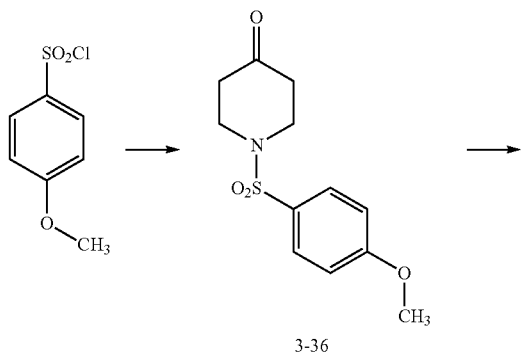

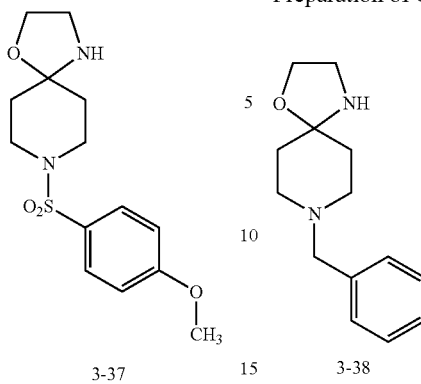

3-37

Preparation of Compound 3-40

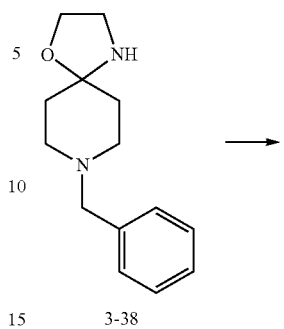

3-38

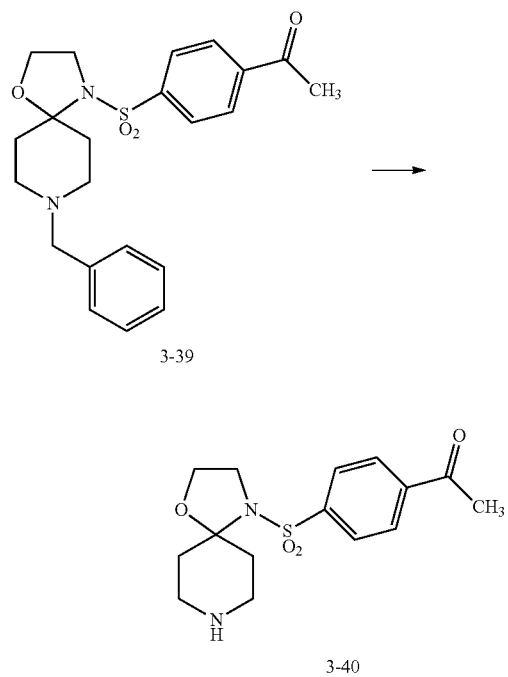

a. Preparation of Compound 3-36

A solution of piperidine-4-one hydrochloride monohydrate (178 mg, 1.16 mmol) in pyridine (20 ml) was treated with 4-methoxybenzenesulfonyl chloride (200 mg, 0.97 mmol). The mixture was stirred at room temperature overnight (about 18 hours). The pyridine was then removed under reduced pressure. The residue was diluted with $CH_2Cl_2$ (50 mL), then washed with 3M HCl (30 mL×3). The organic layer was dried over anhydrous $Na_2SO_4$ and concentrated to give the product as a yellow solid (260 mg, yield: 100%, LC-MS confirmed).

b. Preparation of Compound 3-37

A solution of compound 3-36 (130 mg, 0.48 mmol), 2-aminoethanol (2 mL) and p-toluenesulfonic acid monohydrate (13 mg) in ethanol (20 mL) was stirred at room temperature overnight (about 18 hours). The solvent was removed under reduced pressure. The residue was dissolved in $CH_2Cl_2$ (50 mL), then washed with saturated $Na_2CO_3$ (50 mL×2) and water (50 mL×2). The organic layer was then dried over $Na_2SO_4$ and concentrated to give the product as a white colloid (118 mg, yield: 78.1%, LC-MS confirmed)

Preparation of Compound 3-38

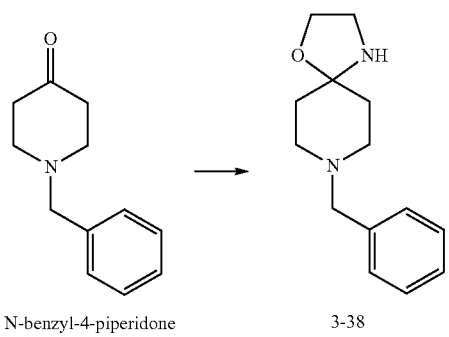 [SMILES: O=C1CCN(Cc2ccccc2)CC1 ; c1ccc(CN2CCC3(CC2)NCCO3)cc1]

N-benzyl-4-piperidone     3-38 p-Toluenesulfonic acid monohydrate (0.1 g) and 2-aminoethanol (2.45 g, 40.2 mmol) were added to a solution of N-benzyl-4-piperidone (3.8 g, 20.1 mmol) in ethanol (30 mL). The mixture was stirred at 30° C. overnight (about 18 hours). The solvent was removed under reduced pressure. To the residue was added $CH_2Cl_2$ (100 mL) and saturated $Na_2CO_3$ (60 mL). The $CH_2Cl_2$ layer was separated and washed with saturated $Na_2CO_3$ (50 mL×4). The organic layer was dried over $Na_2SO_4$ and concentrated to give the crude product as a brown oil (3 g, yield: 63.8%, $^1H$ NMR confirmed).

a. Preparation of Compound 3-39

To a solution of compound 3-38 (382 mg, 1.65 mmol) in pyridine (10 mL) was added p-acetylbenzenesulfonyl chloride (300 mg, 1.37 mmol). The mixture was stirred at room temperature overnight (about 18 hours). The solvent was removed under reduced pressure. To the residue was added $CH_2Cl_2$ (50 mL), then the solution was washed with saturated $Na_2CO_3$ aqueous (30 mL×3), dried over $Na_2SO_4$ and concentrated to give the crude product as brown oil.

b. Preparation of Compound 3-40

To a solution of compound 3-39 (1.33 g, 3.2 mmol) in $CH_3OH/CH_2Cl_2$ (40/20 mL) was added 10% Pd/C (270 mg). The mixture was stirred under $H_2$ at room temperature for 24 hours. Thin-layer chromatography (TLC) indicated that no reaction had taken place. Then the Pd/C was replaced with Pd(OH)$_2$/C, and the reaction was stirred under $H_2$ at room temperature and atmosphere pressure overnight (about 18 hours). TLC indicated that the reaction completed. The reaction mixture was filtrated and evaporated to give the crude product as light yellow solid, (0.98 g, yield: 93.6%, LC-MS confirmed).

Preparation of Compound 3-44

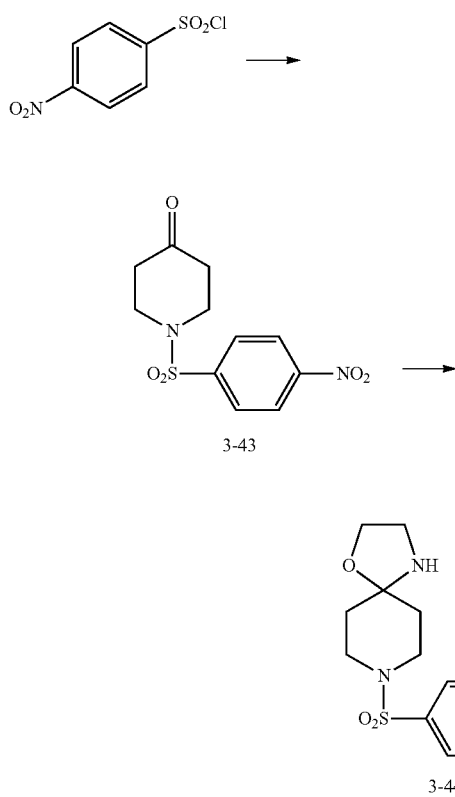

a. Preparation of Compound 3-43

To a solution of piperidine-4-one hydrochloride monohydrate (0.52 g, 3.38 mmol) in pyridine (10 mL), p-nitro-benzenesulfonyl chloride (0.5 g, 2.26 mmol) was added. The reaction mixture was stirred overnight (about 18 hours) at 30° C. and the solvent was removed under the reduced pressure. The residue was diluted with $CH_2Cl_2$ (30 mL), washed with 3N HCl (15 mL×3), the organic layer was dried, and evaporated to give the crude compound as light yellow solid (200 mg, yield: 31%, LC-MS confirmed).

b. Preparation of Compound 3-44

To a solution compound 3-43 (0.58 g, 2.04 mmol) in 20 mL of ethanol was added 2-aminoethanol (2 mL) and 4-methylbenzenesulfonic acid monohydrate (60 mg). The mixture was stirred at 25° C. overnight (about 18 hours). The solvent was removed under reduced pressure. The residue was diluted with $CH_2Cl_2$ (100 mL), washed with saturated $Na_2CO_3$ (100 mL×3) and saturated $NaHCO_3$ (50 mL×3). The organic phase was dried over anhydrous $Na_2SO_4$ and concentrated to give the title compound as yellow solid (0.58 g, yield: 90.6%)

Preparation of Compound C0008-2

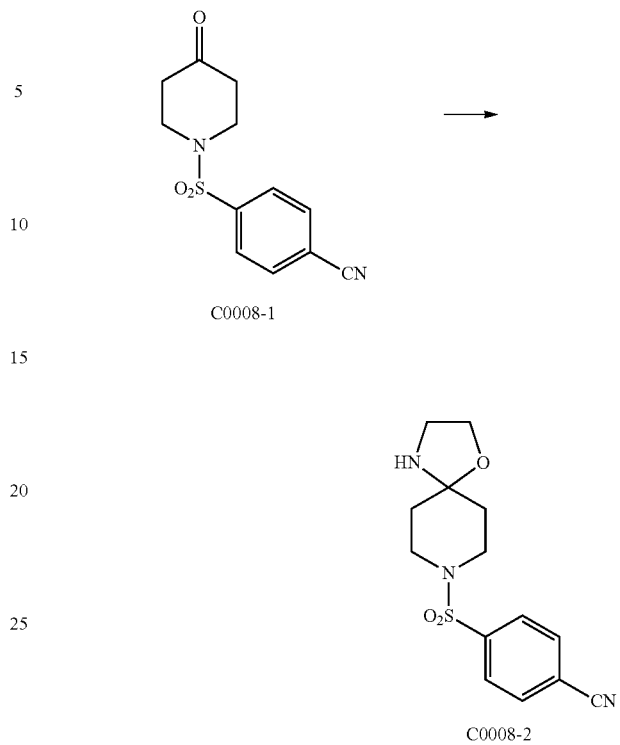

a. Preparation of Compound C0008-1

To a solution of piperidin-4-one hydrochloride hydrate (343 mg, 2.23 mmol) in pyridine (6 mL) was added 4-cyanobenzene-1-sulfonyl chloride (400 mg, 1.98 mmol). The mixture was stirred at room temperature overnight (about 18 hours). The solvent was removed under reduced pressure. The residue was diluted with $CH_2Cl_2$ (50 mL) and washed with 1 N HCl (50 mL×3). The organic phase was dried over anhydrous $Na_2SO_4$, and concentrated to give the crude product as white solid (168 mg; yield: 50%).

b. Preparation of Compound C0008-2

To the solution of compound C0008-1 (268 mg, 1.015 mmol) in ethanol (10 mL) was added 2-aminoethanol (1.23 mL) and toluene-4-sulfonic acid monohydrate (6 mg, 0.03 mmol). The mixture was stirred at room temperature overnight (about 18 hours). The solvent was removed under reduced pressure. The residue was diluted with $CH_2Cl_2$ (50 mL) and washed with saturated aqueous $NaHCO_3$ (50 mL×6). The organic phase was dried over anhydrous $Na_2SO_4$ and concentrated to give compound C0008-2 as yellow oil (295 mg; yield: 94.7%).

Preparation of Compound C0009-2

-continued

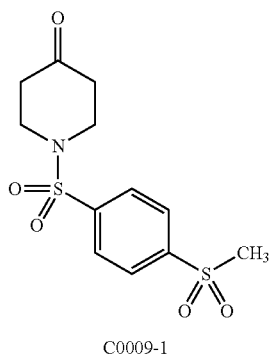
C0009-1

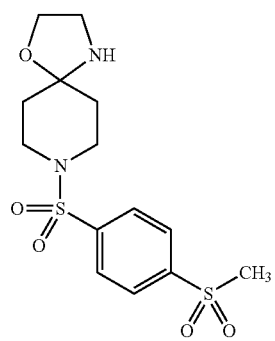
C0009-2 a. Preparation of Compound C0009-1

4-(Methylsulfonyl)benzene-1-sulfonyl chloride (410 mg, 1.6 mmol) was added to a solution of piperidin-4-one hydrochloride hydrate (247 mg, 1.6 mmol) in pyridine (10 mL). The mixture was stirred at room temperature overnight (about 18 hours). The solvent was removed under reduced pressure. To the residue was added CH$_2$Cl$_2$ (50 mL), then the solution was washed with 1N HCl (20 mL×3), dried over Na$_2$SO$_4$ and concentrated to give the title product 225 mg as yellow solid (yield: 44%).

b. Preparation of Compound C0009-2 p-Toluenesulfonic acid monohydrate (4 mg) and 2-aminoethanol (0.8 mL, 13.3 mmol) were added to a solution of compound C0009-1 (225 mg, 0.7 mmol) in ethanol (6 mL). The mixture was stirred at room temperature overnight (about 18 hours). The solvent was removed under reduced pressure. To the residue was added CH$_2$Cl$_2$ (70 mL) and washed with saturated NaHCO$_3$ (25 mL×4), then dried over Na$_2$SO$_4$ and concentrated to give the product 205 mg as white solid (yield: 81%).

Preparation of Compound C0011-3

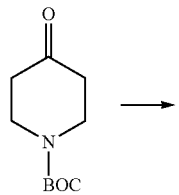

-continued

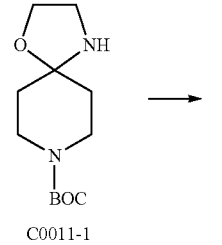
C0011-1

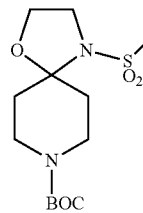

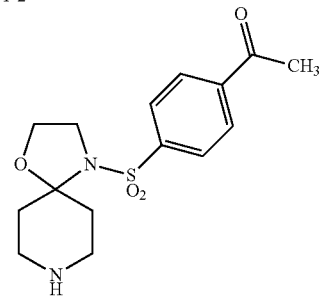
C0011-2

C0011-3 a. Preparation of Compound C0011-1

To a solution of N—BOC-piperidin-4-one (5 g, 23.2 mmol) and p-toluenesulfonic acid monohydrate (100 mg) in 50 mL of ethanol was added 2-aminoethanol (6 mL). The mixture was stirred at 25° C. overnight (about 18 hours). The solvent was removed under reduced pressure and the residue was separated between 100 mL of dichloromethane and 100 mL of saturated Na$_2$CO$_3$, the organic layer was separated and washed with water (100 mL×3). Then the organic layer was dried over anhydrous Na$_2$SO$_4$ and concentrated to give the crude product as yellow oil (5.9 g, yield: 100%). $^1$H NMR indicated that the crude product was a mixture containing the title product, which was used directly in the next step without further purification.

b. Preparation of Compound C0011-2

4-Acetylbenzene-1-sulfonyl chloride (3 g, 13.7 mmol) was added to a solution of compound C0011-1 (5.3 g, 20.6 mmol) in 40 mL of pyridine. The mixture was stirred at room temperature overnight (about 18 hours). Then the solvent was removed under reduced pressure. The residue was diluted with CH$_2$Cl$_2$ (100 mL) and saturated Na$_2$CO$_3$ (100 mL), the organic layer was separated and washed with saturated Na$_2$CO$_3$ (100 mL×3), and concentrated to give the yellow oil, which was purified with silica gel column to give the pure title compound (0.3 g, yield: 3.4%, $^1$H NMR and LC-MS confirmed)

c. Preparation of Compound C0011-3

To a solution of compound C0011-2 (0.3 g, 0.71 mmol) in CH$_2$Cl$_2$ (10 mL) was added trifluoroacetic acid (2 mL). The mixture was stirred for 1 hour at room temperature. CH$_2$Cl$_2$ (20 mL) was added, and saturated Na$_2$CO$_3$ (30 mL) was added slowly with an ice-bath. The organic phase was separated, dried over anhydrous Na$_2$SO$_4$ and then concentrated to give the crude product as yellow oil (160 mg, yield: 42%, LC-MS confirmed).

Preparation of Compound C0025-2

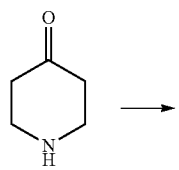

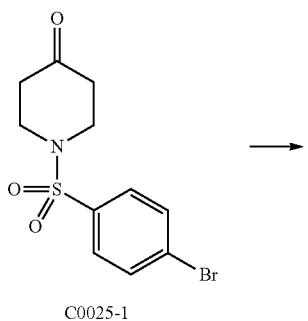

C0025-1

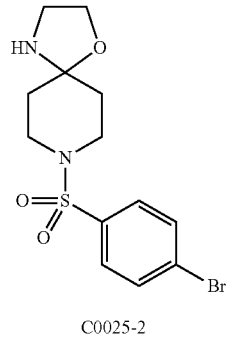

C0025-2 a. Preparation of Compound C0025-1

To a solution of piperidin-4-one hydrochloride monohydrate (1.8 g, 11.74 mmol) in pyridine (30 mL) was added 4-bromobenzene-1-sulfonyl chloride (2 g, 7.83 mmol). The mixture was stirred overnight (about 18 hours) at room temperature. The solvent was removed under reduced pressure. The residue was diluted with CH$_2$Cl$_2$ (100 mL), washed with 3N HCl (100 mL×2), dried over anhydrous Na$_2$SO$_4$ and concentrated to give the title compound as a pale solid (1.3 g, yield: 52%, TLC confirmed).

b. Preparation of Compound C0025-2

A solution of C0025-1 (1.3 g, 4.09 mmol), 2-aminoethanol (5 mL) and p-toluenesulfonic acid monohydrate (130 mg) was stirred overnight (about 18 hours) at 25° C. in 60 mL ethanol. The solvent was removed by reduced pressure evaporation. The residue was diluted with 200 mL dichloromethane, washed with water (100 mL×3) and saturated sodium bicarbonate solutions (100 mL×3). Next, the organic layer was dried and concentrated to get the product as a white solid. (1.44 g, yield: 97%, TLC confirmed).

Preparation of Compound C0026

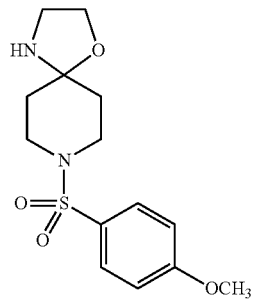

Prepared using procedures illustrated elsewhere herein.

Preparation of Compound C0027

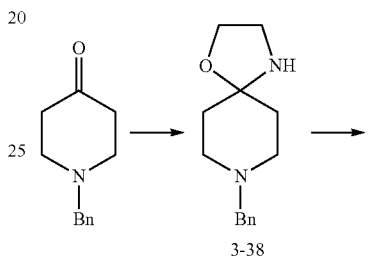

3-38

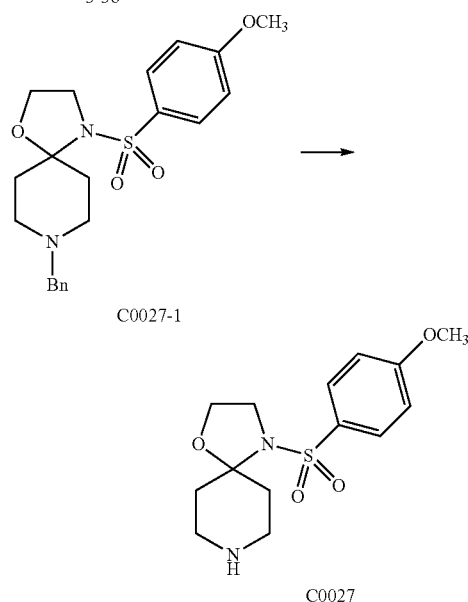

C0027-1

C0027 a. Preparation of Compound 3-38 p-Toluenesulfonic acid monohydrate (100 mg) and 2-aminoethanol (5 mL) were added to a solution of N-benzyl-piperidin-4-one (10 g 52.8 mmol) in 80 mL of ethanol. The mixture was stirred at 25° C. overnight (about 18 hours). The solvent was removed under reduced pressure, the residue was diluted with 50 mL dichloromethane, and washed with saturated sodium bicarbonate solutions (30 mL×3), saturated sodium carbonate (30 mL×3). The organic layer was dried and concentrated to get the product as yellow oil (11.5 g, yield: 93.8).

b. Preparation of Compound C0027-1

4-Methoxybenzene-1-sulfonyl chloride was added to the solution of compound 3-38 (1.37 g, 5.91 mmol) in pyridine (20 mL) (1.83 g, 8.85 mmol). The reaction mixture was stirred overnight (about 18 hours) at room temperature. The solvent was removed under reduced pressure. The residue (brown oil) was purified with silica gel column to give yellow foam (410 mg, yield: 17%, confirmed by LC-MS).

c. Preparation of Compound C0027

To the solution of C0027-1 (410 mg, 1.02 mmol) in MeOH: $CH_2Cl_2$=2:1 (30 mL), 10% Pd/C (0.2 g) was added and the reaction mixture was stirred at room temperature overnight (about 18 hours) under $H_2$. The solvent was filtered to remove Pd/C. The solvent was removed under the reduced pressure to give the white foam as product (310 mg, yield: 98%, confirmed by LCMS).

$^1$H NMR (400 MHz, DMSO-d$^6$) δ:7.79 (d, J=9.2 Hz, 2H), 7.15 (d, J=8.4 Hz, 2H), 3.96 (t, J=6.4 Hz, 2H), 3.85 (s, 3H), 3.47 (t, J=6.4 Hz, 2H), 3.28-3.24 (m, 2H), 2.86 (t, J=12 Hz, 2H), 2.46 (dt, J=13.6 Hz, 2H), 1.74 (d, J=12.8 Hz, 2H); MS (ESI) calcd for $C_{14}H_{20}N_2O_4S$ (m/z):312.11. found: 313.0 $[M+1]^+$ Preparation of Compound C0029-2

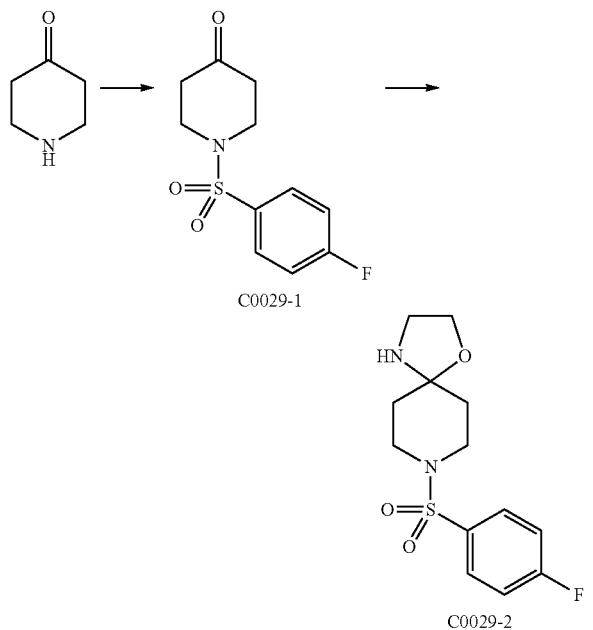

a. Preparation of Compound C0029-1

4-Fluorobenzene-sulfonyl chloride (1 g, 5.14 mmol) was added to a solution of piperidine-4-one hydrochloride monohydrate (1.47 g, 9.57 mmol) in pyridine (20 mL). The reaction mixture was stirred at room temperature overnight (about 18 hours). Next, the solvent was removed under the reduced pressure and the residue was diluted with $CH_2Cl_2$ (20 mL) and washed with 3 N HCl (15 mL×3). The organic layer was dried over anhydrous $Na_2SO_4$, filtered, and evaporated to give the crude compound as white solid (0.72 g, yield: 54.5%, $^1$H-NMR confirmed).

b. Preparation of Compound C0029-2

A solution of compound C0029-1 (0.72 g, 2.8 mmol), 2-aminoethanol (0.26 g, 4.2 mmol) and p-toluenesulfonic acid monohydrate (100 mg) in ethanol (20 mL) was stirred at 25° C. overnight (about 18 hours). The solvent was removed under the reduced pressure. The residue was diluted with $CH_2Cl_2$ (20 mL) and washed with $NaHCO_3$ solution (20 mL×3). The organic layer was dried over anhydrous $Na_2SO_4$, filtered, and evaporated to give the crude compound as white solid (0.81 g, yield: 96%, $^1$H NMR confirmed).

$^1$H-NMR (400 MHz, CDCl$_3$) δ: 7.81~7.75 (m, 2H), 7.20~7.14 (m, 2H), 3.67 (t, J=6.4 Hz, 2H), 3.31~3.26 (m, 2H), 3.12 (t, J=6.4 Hz, 2H), 2.97~2.94 (m, 2H), 1.76~1.74 (m, 4H).

Preparation of Compound C0030

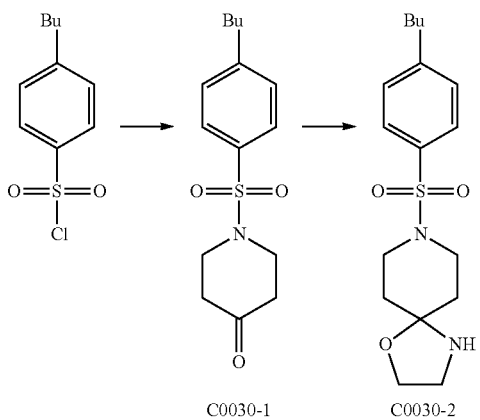

a. Preparation of Compound C0030-1

To a solution of piperidin-4-one hydrochloride monohydrate (594 mg, 3.9 mmol) in 20 mL of pyridine was added 4-n-butylbenzenesulfonyl chloride (600 mg, 2.6 mmol). The mixture was stirred overnight (about 18 hours) at room temperature. The solvent was removed under reduced pressure. The residue was then diluted with 50 mL of dichloromethane, washed with 1N hydrochloric acid (30 mL×3). Next, the organic layer was dried and concentrated to give the crude product as a white solid (501 mg, yield: 66%, $^1$H NMR confirmed).

b. Preparation of Compound C0030-2

A solution of C0030-1 (500 mg, 1.7 mmol), 2-aminoethanol (5 mL) and p-toluenesulfonic acid monohydrate (100 mg) in 30 mL of ethanol was stirred at 25° C. overnight (about 18 hours). The solvent was removed by reduced pressure evaporation. The residue was diluted with 50 mL dichloromethane, washed with water (50 mL×3) and saturated sodium bicarbonate aqueous (50 mL×3). The organic layer was dried and concentrated to give the product as a yellow solid (200 mg, yield: 89%, $^1$H NMR confirmed).

Preparation of Compound C0032-2

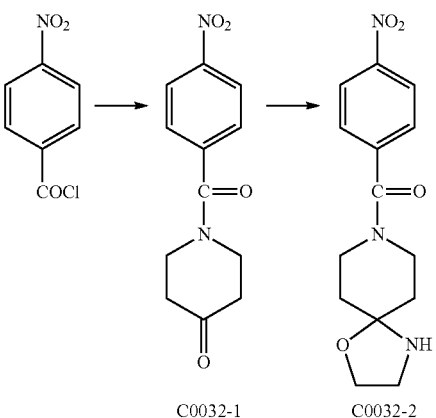 [SMILES: O=C(Cl)c1ccc([N+](=O)[O-])cc1 ; O=C1CCN(C(=O)c2ccc([N+](=O)[O-])cc2)CC1 ; O=C(c1ccc([N+](=O)[O-])cc1)N1CCC2(CC1)NCCO2 ; "C0032-1" ; "C0032-2"]

a. Preparation of Compound C0032-1

To a solution of piperidine-4-one hydrochloride monohydrate (3.15 g, 20.51 mmol) in pyridine (30 mL), p-nitrobenzoyl chloride (2 g, 10.87 mmol) was added. The reaction mixture was stirred at room temperature overnight (about 18 hours). The solvent was removed under reduced pressure. The residue was diluted with $CH_2Cl_2$ (30 mL) and washed with 3N HCl (20 mL×3). The organic layer was dried over anhydrous $Na_2SO_4$, filtered, and evaporated to give the crude compound as a yellow solid (1.49 g, yield: 55.9%, confirmed by $^1$H-NMR and LCMS).

b. Preparation of Compound C0032-2

A solution of compound C0032-1 (2 g, 8.06 mmol), 2-aminoethanol (0.73 g) and p-toluenesulfonic acid monohydrate (200 mg) in ethanol (40 mL) was stirred at 25° C. overnight (about 18 hours). The solvent was removed under reduced pressure. The residue was diluted with $CH_2Cl_2$ (30 mL) and washed with $NaHCO_3$ (30 mL×3). Next, the organic layer was dried over anhydrous $Na_2SO_4$, filtered, and evaporated to give the crude compound as an orange solid. (2.2 g, yield: 93.7%, confirmed by $^1$H-NMR and LCMS).

Preparation of Compound C0034-3

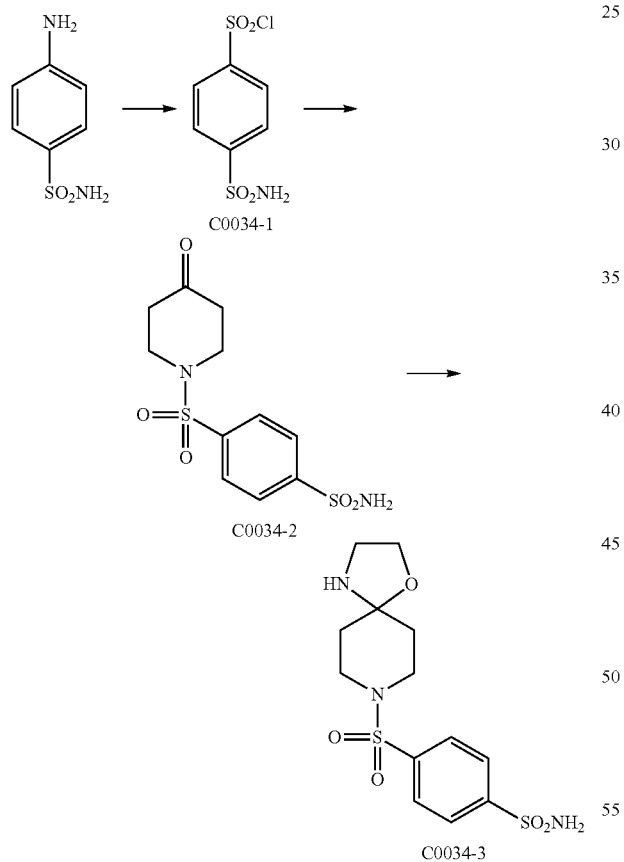

a. Preparation of Compound C0034-1

Cupric chloride (5 g) was added to a saturated solution of sulfur dioxide in $CH_3COOH$ (200 mL) and sulfur dioxide gas (from the reaction of $NaHSO_4$ and $H_2SO_4$). The gas was slowly bubbled into the solution for 4 hours until the solution became blue-green. Next, 4-amino-benzene-1-sulfonamide (20 g, 116 mmol) was added to a solution of concentrated HCl (40 mL) and $H_2O$ (50 mL) with stirring for 1 hour at 0° C. To this mixture was added a solution of sodium nitrate (8 g, 116 mmol) at such a rate of addition that the temperature did not rise above 0° C. The mixture was stirred for 0.5 hours then quenched with the $SO_2/CuCl_2$ solution made earlier. The mixture was then stirred for 1 hour at room temperature. Next, $H_2O$ (500 mL) was added, and stirring continued for an additional 30 minutes. The product was collected by suction filtration, washed with $H_2O$, dried in vacuo at 60° C. to give the title product as a light yellow solid (LC-MS confirmed). After drying, about 10 g crude product as a light yellow solid was obtained (10 g, yield: 33%, confirmed by LC-MS).

b. Preparation of Compound C0034-2

Compound C0034-1 (2.00 g, 7.8 mmol) was added to a solution of piperidine-4-one hydrochloride monohydrate (1.4 g, 9.4 mmol) in 30 mL pyridine. The mixture was stirred overnight (about 18 hours) at room temperature. The solvent was removed under reduced pressure and the residue was diluted with $CH_2Cl_2$. The crude product was washed with 2N HCl (50 mL×3). The aqueous layer was extracted with $CH_2Cl_2$. The organic phase was combined and concentrated to give the crude product as a light yellow solid (0.65 g, yield: 37%, TLC confirmed).

c. Preparation of C0034-3

To a solution of compound C0034-2 (0.5 g, 1.58 mmol) in 10 mL ethanol was added ethanolamine (5 mL) and 4-methylbenzenesulfonic acid monohydrate (0.1 g). The mixture was stirred overnight (about 18 hours) at 25° C. Then the solvent was removed under reduced pressure. The residue was diluted with $CH_2Cl_2$ (100 mL), and washed with saturated $NaHCO_3$ (50 mL×6), there was much dissolved solid. Then the organic phase was dried over anhydrous $Na_2SO_4$ and concentrated to give few yellow solid. The aqueous layer was filtered to provide a white solid. The white solid was confirmed to be the product, which was purified with silica gel column to give the pure product as white solid (0.25 g, yield: 43.9%, $^1$H NMR confirmed).

Preparation of Compound C0037-2

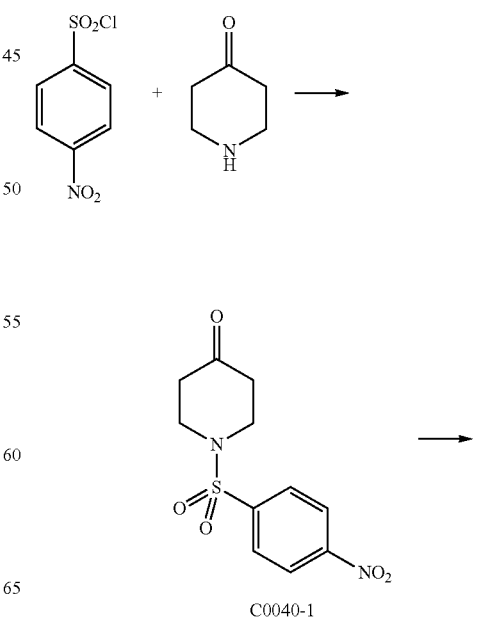

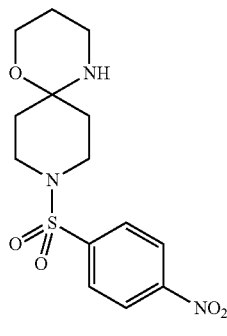

C0037-2

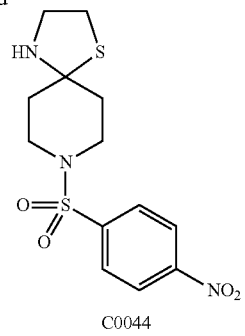

C0044 a. Preparation of Compound C0040-1

To the solution of piperidin-4-one hydrochloride monohydrate (200 mg, 1.3 mmol) in pyridine (20 mL) was added 4-nitrobenzene-1-sulfonyl chloride (262 mg, 1.18 mmol). The mixture was stirred overnight (about 18 hours) at room temperature. The solvent was removed under reduced pressure. The residue was diluted with 50 mL dichloromethane and washed with 0.5 M HCl (50 mL×3). The organic layer was dried and evaporated to give the product as white solid. (180 mg, yield: 41.2%, confirmed by $^1$H-NMR.

b. Preparation of Compound C0037-2

3-Aminopropanol (0.5 mL, 6.54 mmol) and p-toluenesulfonic acid monohydrate (30 mg) were added to the solution of compound C0040-1 (200 mg, 0.7 mmol) in 8 mL ethanol. The mixture was stirred at 25° C. overnight (about 18 hours). Then the solvent was removed by evaporation under reduced pressure. The residue was diluted with $CH_2Cl_2$ (20 mL), washed with saturated $Na_2CO_3$ (20 mL×3) and saturated $NaHCO_3$ (20 mL×3). Then the organic phase was dried over anhydrous $Na_2SO_4$ and concentrated to give the title compound as yellow solid (0.21 g; yield: 90.4%; LC-MS& $^1$H NMR confirmed, HPLC 96.7%).

Preparation of Compound C0040

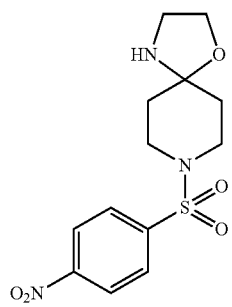 [SMILES: O=[N+]([O-])c1ccc(S(=O)(=O)N2CCC3(CC2)NCCO3)cc1]

Prepared using procedures illustrated elsewhere herein.

Preparation of Compound C0044

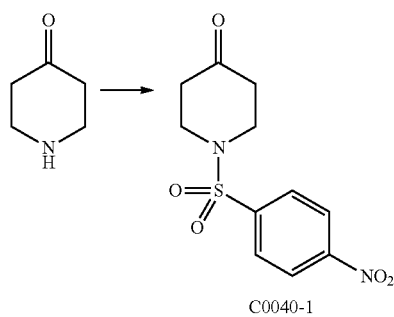

C0040-1 a. Preparation of Compound C0040-1

To the solution of piperidin-4-one hydrochloride monohydrate (200 mg, 1.3 mmol) in pyridine (20 mL) was added 4-nitrobenzene-1-sulfonyl chloride (262 mg, 1.18 mmol). The mixture was stirred overnight (about 18 hours) at room temperature. The solvent was removed under reduced pressure. The residue was diluted with 50 mL dichloromethane and washed with 0.5 M HCl (50 mL×3). The organic layer was dried and evaporated to give the product as white solid. (180 mg, yield: 41.2%, confirmed by $^1$H-NMR).

b. Preparation of Compound C0044

To the solution of C0040-1 (170 mg, 0.5 mmol) and p-toluenesulfonic acid monohydrate (1.7 mg) in ethanol (10 mL) was added cysteamine (46 mg, 0.6 mmol). The mixture was stirred overnight (about 18 hours) at 25° C. The solvent was removed under reduced pressure. The residue was diluted with dichloromethane (50 mL) and washed with saturated $Na_2CO_3$ solution (40 mL×3). The organic layer was dried and evaporated to give the crude product as yellow solid. The solid was washed with 1M HCl. The mixture was filtered to get the filtration as white solid. The solid was washed with saturated $Na_2CO_3$ solution and extracted with dichloromethane. The organic layer was dried and evaporated to give the product as white solid. (120 mg, yield: 57.9%, confirmed by LCMS).

Preparation of Compound C0046

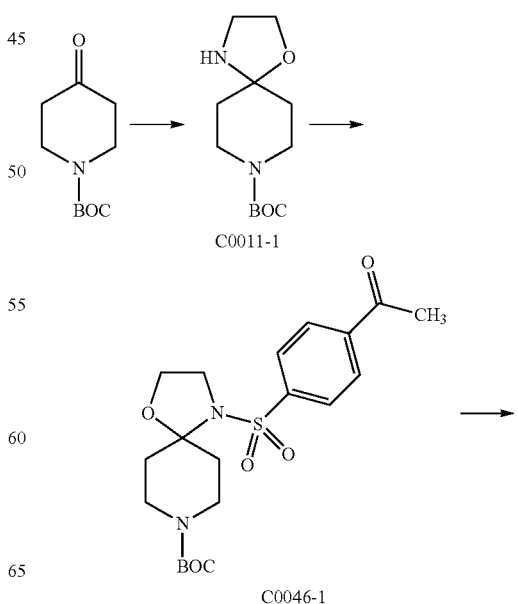

C0011-1

C0046-1

-continued

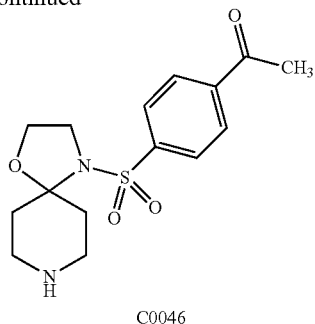

C0046 a. Preparation of Compound C0046-1

4-Acetylbenzene-1-sulfonyl chloride (2 g, 9.1 mmol) was added to a solution of C0011-1 (2.63 g, 10.9 mmol) in pyridine (20 mL). The mixture was stirred at room temperature overnight (about 18 hours). The solvent was removed under reduced pressure. The residue was diluted with $CH_2Cl_2$ (100 mL) and washed with saturated $NaHCO_3$ (100 mL×3). The organic phase was dried over anhydrous $Na_2SO_4$ and concentrated to give the crude product as yellow solid, which was purified with silica gel column (eluted with $CH_2Cl_2$: $CH_3OH$=80:1) to give the title compound as a white solid (3.3 g, yield: 71.7%, $^1H$ NMR confirmed).

b. Preparation of Compound C0046

To the solution of C0046-1 (3.26 g, 11.48 mmol) in dichloromethane (DCM) (20 mL) was add $CF_3COOH$ (5 mL). The mixture was stirred overnight (about 18 hours) at room temperature. Thin-layer chromatography indicated that the material reacted completely. DCM (30 mL) was added and the organic layer was washed with saturated sodium carbonate solution (50 mL×3). Then the organic layer was dried and evaporated to get yellow oil, which was purified with silica gel column to give the product as yellow oil (1.1 g, yield: 44%, confirmed by LCMS, MS and $^1H$ NMR, HPLC: 98.2%).

Preparation of Compound C0049-2

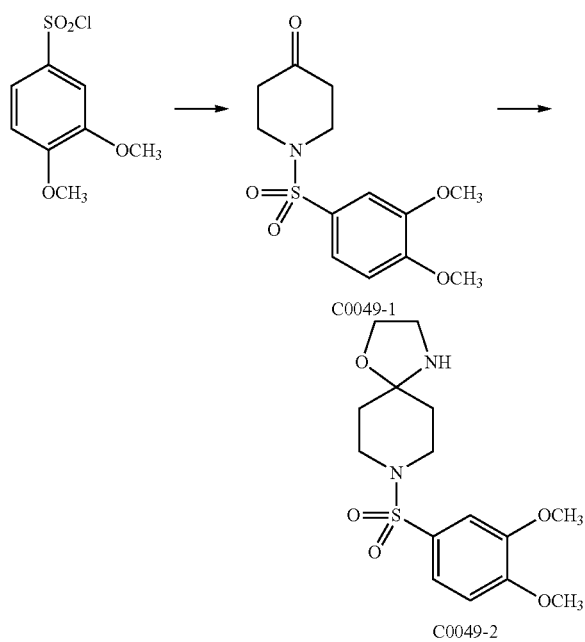

a. Preparation of Compound C0049-1

3,4-Dimethoxy-benzene-1-sulfonyl chloride (500 mg, 2.1 mmol) was added to a solution of piperidin-4-one hydrochloride monohydrate (486 mg, 3.2 mmol) in 20 mL pyridine. The mixture was stirred overnight (about 18 hours) at room temperature. Then the solvent was removed under reduced pressure. The residue was diluted with dichloromethane (50 mL) and washed with 1 N HCl (30 mL×3). The organic layer was dried and concentrated to give the product as yellow solid (260 mg, yield: 41.2%, confirmed by LCMS).

b. Preparation of Compound C0049-2 p-Toluenesulfonic acid monohydrate (26 mg) and 2-aminoethanol (5 mL) were added to a solution of compound C0049-1 (260 mg, 0.87 mmol) in 10 mL of ethanol and stirred at 25° C. overnight (about 18 hours). The solvent was removed by reduced pressure evaporation. The residue was diluted with 50 mL of dichloromethane, and then washed with saturated sodium bicarbonate solutions (20 mL×3). The organic layer was dried and concentrated to give the product as yellow solid (297 mg, yield: 100%, confirmed by $^1H$ NMR).

Preparation of Compound C0050

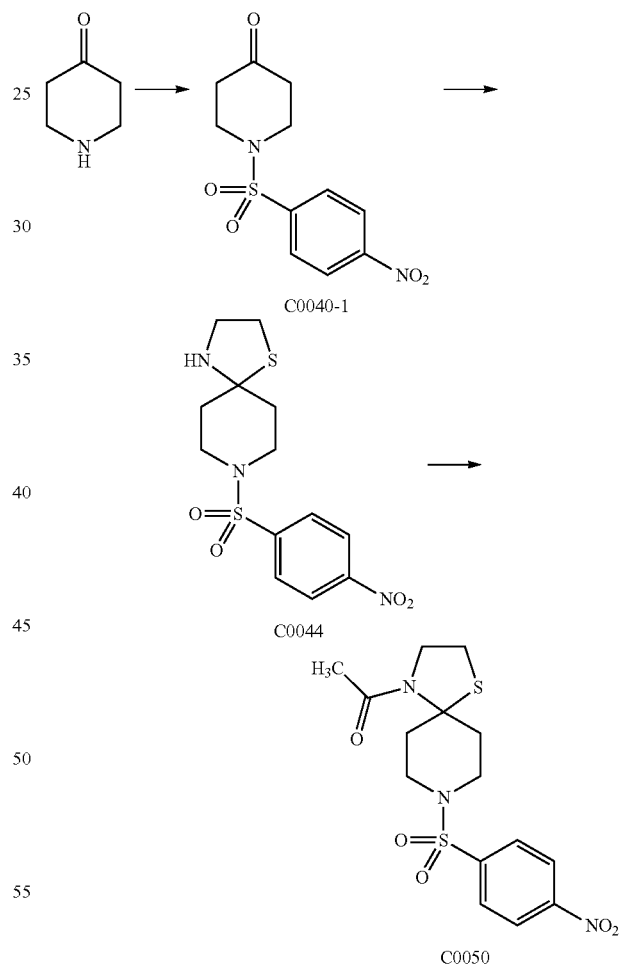

a. Preparation of Compound C0040-1

To a solution of piperidin-4-one (200 mg, 1.2 mmol) in pyridine (20 mL) was added 4-nitrobenzene-1-sulfonyl chloride (262 mg, 1.18 mmol). The mixture was stirred overnight (about 18 hours) at room temperature. The solvent was removed under reduced pressure. The residue was diluted with 50 mL dichloromethane and washed with 0.5 M HCl (50 mL×3). The organic layer was dried and evaporated to give the product as white solid. (180 mg, yield: 41.2%, confirmed by $^1H$ NMR).

b. Preparation of Compound C0044

To a solution of 4-nitrobenzene-1-sulfonyl chloride (170 mg, 0.6 mmol) in 20 mL ethanol was added 2-mercaptoethylamine (70 mg, 0.9 mmol) and p-toluenesulfonic acid (1.7 mg). The mixture was stirred overnight (about 18 hours) at 25° C. The solvent was removed and the residue was diluted with 50 mL dichloromethane, washed with saturated $Na_2CO_3$ solutions (30 mL×3). The organic layer was separated, dried, and concentrated to give the crude product as yellow solid, which was purified with silica gel column to give the title product as white solid (100 mg, yield: 48.7%)

c. Preparation of Compound C0050

To the solution of C0044 (120 mg, 0.35 mmol) and triethylamine (106 mg, 1.05 mmol) in dry dichloromethane (DCM) (20 mL) was added dropwise acetyl chloride (55 mg, 0.7 mmol). The mixture was stirred overnight (about 18 hours) at room temperature. The mixture was washed with water, purified by silica gel column chromatography and then purified by preparative thin-layer chromatography to give a white solid, but HPLC showed it was not pure enough. The partially purified product was further purified by silica gel column chromatography (ethyl acetate:petroleum ether=3:1) to give the pure product as white solid (13 mg, yield: 9.7%, confirmed by LCMS, $^1$H-NMR and MS, HPLC: 97.3%).

Preparation of Compound C0053-3 a. Preparation of Compound C0053-1

To a solution of 4-acetylbenzoic acid (250 mg, 1.52 mmol) in dry dichloromethane (20 mL) and dimethylformamide (0.1 mL) was added dropwise oxalyl chloride (570 mg, 4.5 mmol) at 0° C. After addition, the mixture was stirred for 2 hours at room temperature. The solvent and excess oxalyl chloride was removed by reduced pressure evaporation to give the product as a yellow solid (270 mg, yield: 97%, confirmed by LCMS dissolved with methanol.

b. Preparation of Compound C0053-2

To a solution of C0011-1 (727 mg, 23 mmol) and diisopropyl ethyl amine (1 mL) in dry dichloromethane (DCM) (20 mL) was added C0053-1 (500 mg, 2.74 mmol solution in 20 mL dry DCM) dropwise at 0° C. The mixture was stirred at room temperature for 3 days. The mixture was then washed three times with water (50 mL), the organic layer was dried then evaporated to get the product as brown oil (1.28 g, yield: 100%, confirmed by LCMS).

c. Preparation Compound C0053-3

A solution of C0053-2 (1 g, 2.58 mmol) and $CF_3COOH$ (5 mL) in dichloromethane (20 mL) was stirred overnight (about 18 hours) at room temperature. The mixture was washed with a saturated $Na_2CO_3$ solution, the organic layer was dried and evaporated to give the crude product as a brown oil. The crude product was purified on a silica gel column chromatography to provide the purified product as a brown oil (360 mg, yield: 48.3%, confirmed by LCMS.)

Preparation of Compound C0055

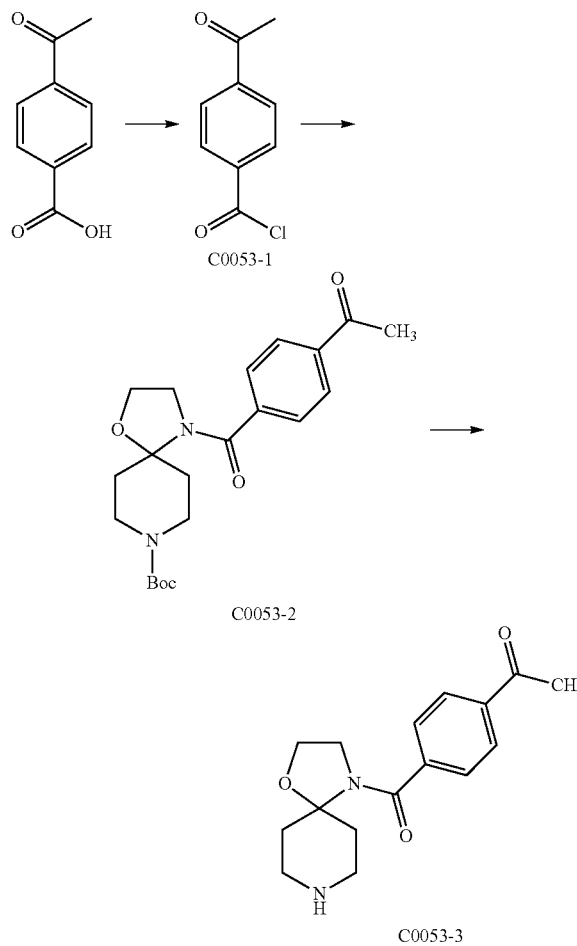

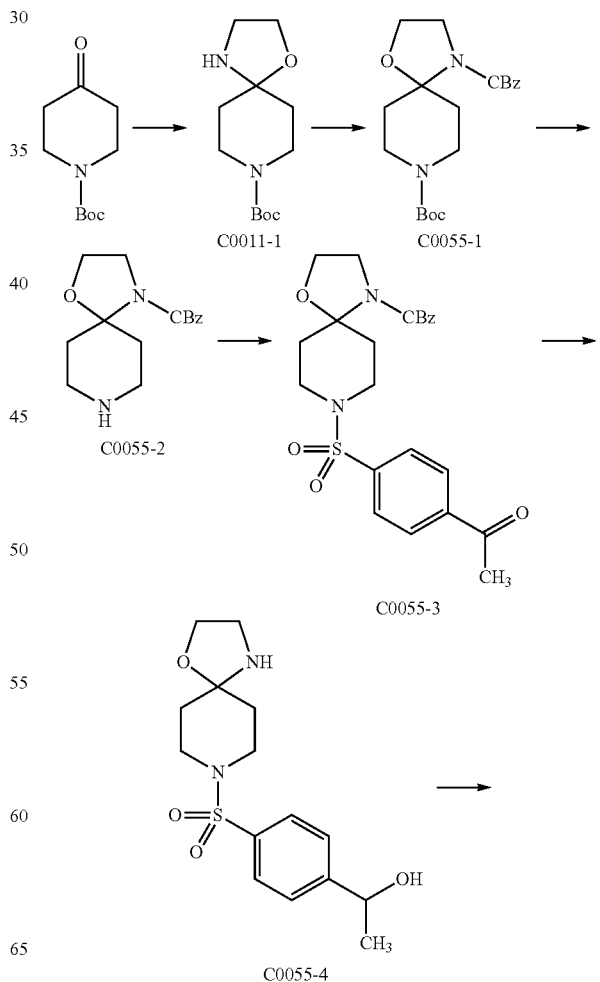

Preparation of C0056

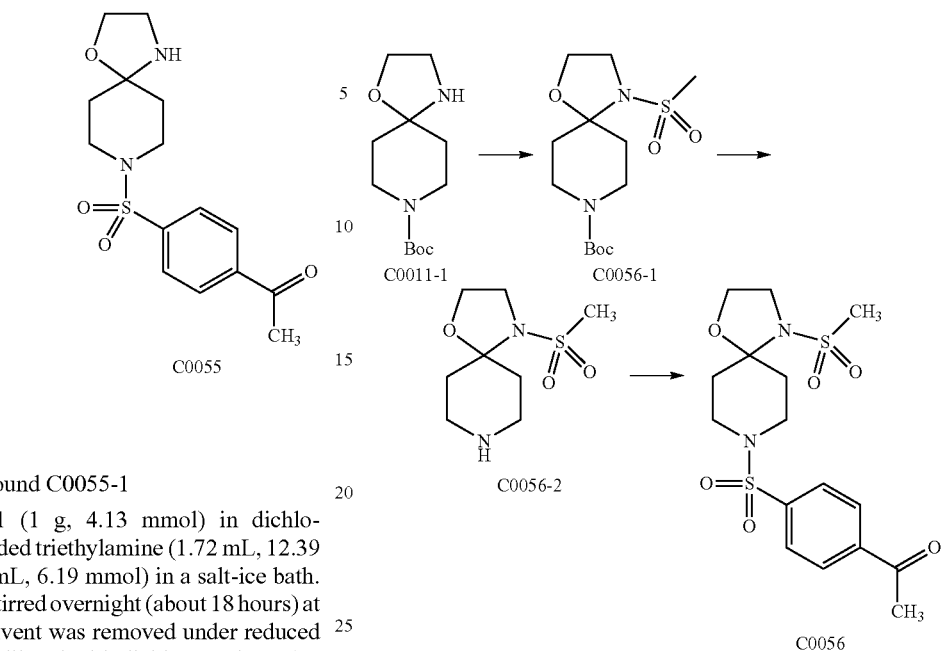

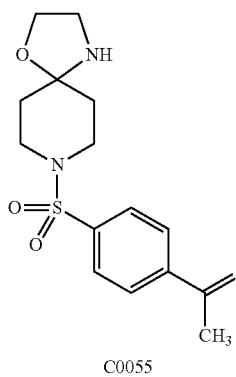

C0055 a. Preparation of Compound C0055-1

To compound C0011-1 (1 g, 4.13 mmol) in dichloromethane (15 mL) was added triethylamine (1.72 mL, 12.39 mmol) and CBz-Cl (0.88 mL, 6.19 mmol) in a salt-ice bath. The reaction mixture was stirred overnight (about 18 hours) at room temperature. The solvent was removed under reduced pressure. The residue was diluted with dichloromethane (30 mL), and washed with water (20 mL×2). The organic layer was dried and evaporated to give the crude product as light yellow oil (1.4 g, yield: 91%, confirmed by $^1$H NMR.)

b. Preparation of Compound C0055-2

A solution of C0055-1 (1.4 g, 3.72 mmol) and trifluoroacetic acid (3 mL) in dichloromethane (15 mL) was stirred overnight (about 18 hours) at room temperature. The mixture was quenched with saturated $Na_2CO_3$ solution, diluted with $CH_2Cl_2$ (20 mL) and washed with saturated $Na_2CO_3$ solution (15 mL×2). The aqueous layer was extracted with $CH_2Cl_2$ (20 mL×3). The organic layer was combined, dried over anhydrous $Na_2SO_4$ and evaporated to give the crude product as orange oil (0.88 g, yield: 86%, confirmed by LCMS and $^1$H NMR).

c. Preparation of Compound C0055-3

To the solution of C0055-2 (0.34 g, 1.25 mmol) and diisopropylethylamine (0.46 mL, 2.81 mmol) in dichloromethane (10 mL), was added 4-acetylbenzene-1-sulfonyl chloride (0.41 g, 1.87 mmol). The mixture was stirred overnight (about 18 hours) at room temperature. The solvent was removed under reduced pressure. The mixture was diluted with $CH_2Cl_2$ (20 mL) and washed with $NaHCO_3$ (15 mL×2) and water (15 mL). The organic layer was dried and evaporated to give the crude compound as yellow solid, which was purified with silica gel column to give the pure product as white solid (290 mg, yield: 52%, $^1$H NMR and LCMS confirmed).

d. Preparation of Compound C0055-4

To the solution of C0055-3 (100 mg, 0.22 mmol) in methanol (10 mL), was added Pd(OH)$_2$/C (20 mg). The mixture was stirred overnight (about 18 hours) at room temperature under H$_2$. Thin-layer chromatography showed that the reaction was not completed, so a little more Pd(OH)$_2$/C was added, then stirred overnight (about 18 hours) under H$_2$. The mixture was filtered; the solution was evaporated to give the crude product as white solid (65 mg, yield: 91%, confirmed by LCMS, $^1$H NMR.

a. Preparation of C0056-1

To a solution of C0011-1 (500 mg, 2.06 mmol) in dry $CH_2Cl_2$ (10 mL) was added diisopropyl ethyl amine (0.68 mL, 4.12 mmol) and methane sulfonyl chloride (0.24 mL, 3.1 mmol). The reaction mixture was stirred overnight (about 18 hours) at room temperature. The mixture was washed with saturated $NaHCO_3$ (2×20 mL) and water (1×20 mL). The organic layer was dried and concentrated to give the crude compound as orange oil (yield: 650 mg, 99%, confirmed by $^1$H NMR).

b. Preparation of C0056-2

To the solution of C0056-1 (650 mg, 2.04 mmol) in $CH_2Cl_2$ (8 mL), trifluoroacetic acid (2 mL) was added. The reaction mixture was stirred at room temperature overnight (about 18 hours). The mixture was quenched with sat $Na_2CO_3$ solution, diluted with $CH_2Cl_2$ (20 mL) and washed with $Na_2CO_3$ solution (15 mL×2). The aqueous layer was extracted with $CH_2Cl_2$ (20 mL×4). The organic layer was dried over anhydrous $Na_2SO_4$ and evaporated to give the crude product as brown solid (178 mg, yield: 40%, confirmed by LC/MS).

c. Preparation of C0056

4-Acetylbenzene-sulfonyl chloride (0.26 g, 1.21 mmol) was added to the solution of C0056-2 (178 mg, 0.81 mmol) in pyridine (10 mL). The mixture was stirred overnight (about 18 hours) at room temperature. The solvent was removed under reduced pressure. The residue was diluted with $CH_2Cl_2$ (30 mL) and washed with 1N HCl (20 mL×2) and water (20 The organic layer was dried and evaporated to give the crude compound as yellow solid. Which was purified with silica gel column to give the pure product as white foam (60 mg, yield: 18.5%, $^1$H NMR and MS confirmed, HPLC 98%).

$^1$H-NMR (400 MHz, CDCl$_3$) δ:8.09 (d, J=8.4 Hz, 2H), 7.86 (d, J=8.4 Hz, 2H), 3.93 (t, J=6 Hz, 2H), 3.81 (dd, J=8.8 Hz, 1.6 Hz, 2H), 3.53 (t, J=6 Hz, 2H), 2.94 (s, 3H), 2.81 (s, 3H), 2.66-2.49 (m, 4H), 1.74 (d, J=11.6 Hz, 2H). MS (ESI) calcd for $C_{16}H_{22}N_2O_6S_2$ (m/z):402.09. found: 403.3 [M+1]$^+$, 425.2 [M+23]$^+$.

Preparation of Compound C0058

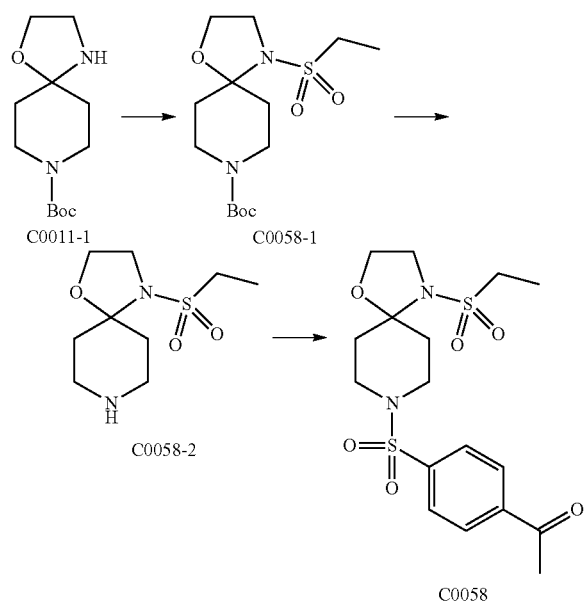

a) Preparation of Compound C0058-1

To the C0011-1 (600 mg, 2.48 mmol) and diisopropylethylamine (0.82 mL, 4.96 mmol) in dichloromethane (DCM) (10 mL), ethylsulfonyl chloride (478 mg, 3.72 mmol) was added. The reaction mixture was stirred overnight (about 18 hours) at room temperature. The reaction mixture was diluted with DCM (50 mL) and washed with saturated with aqueous Na$_2$CO$_3$ (30 mL×3). The organic layer was dried over anhydrous Na$_2$SO$_4$ and concentrated to give the crude product as brown-black oil. LC-MS indicated that there was no the desired product peak. Purification with silica gel could not give the pure product.

Run#2: Pyridine ethyl sulfonyl chloride (0.3 mL, 3.17 mmol) was added dropwise to the solution of N-Boc-piperidin-4-one (500 mg, 2.06 mmol) in 15 mL of pyridine. The mixture was stirred at room temperature overnight (about 18 hours).

Preparation of Compound C0059

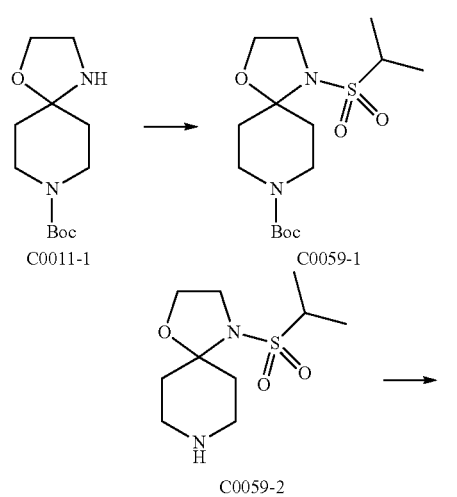

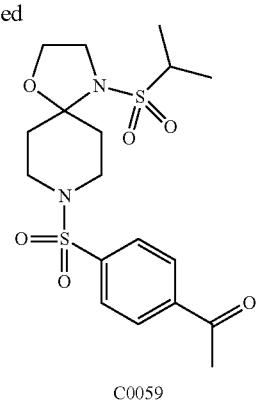

a. Preparation of C0059-1

Run#1: Isopropylsulfonyl chloride (0.35 mL, 3.09 mmol) was added To the C0011-1 (500 mg, 2.06 mmol) and diisopropylethylamine (1.02 mL, 6.18 mmol) in dichloromethane (10 mL). The reaction mixture was stirred overnight at room temperature. The mixture was diluted with dichloromethane and washed with NaHCO$_3$ (20 mL×2). The organic layer was dried and evaporated to give the crude product as dark yellow oil. After checking LC-Ms, the peak of the product could not be observed, and TLC was showed it was complicated Run#2: Isopropyl sulfonyl chloride (0.28 mL, 2.47 mmol) was added dropwise to the solution of C0011-1 (500 mg, 2.06 mmol) in pyridine (20 mL). The mixture was stirred at room temperature overnight. The solvent was removed by reduced pressure evaporation. The residue was diluted with 50 mL of dichloromethane and washed with 0.5N HCl (40 mL×3). The organic layer was dried and evaporated to give the crude product as yellow solid. LCMS showed there was no the desired peak.

Preparation of Compound C0060

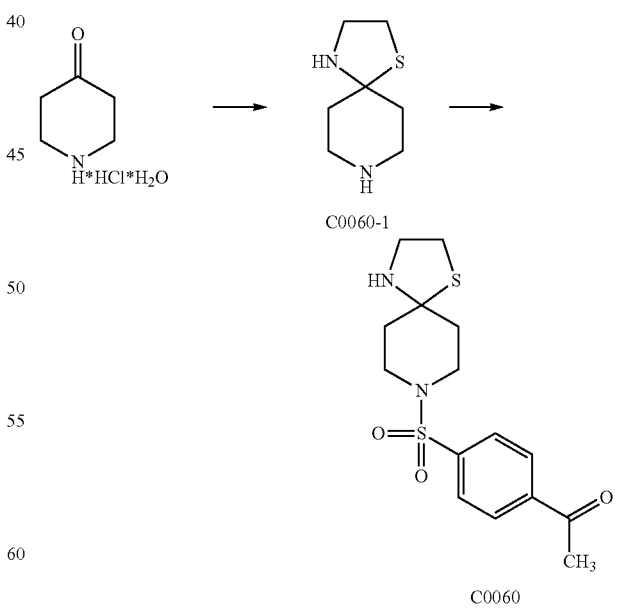

a. Preparation of Compound C0060-1

2-Mercaptoethylamine (100 mg, 1.3 mmol) was added to the solution of piperidin-4-one hydrochloride monohydrate (200 mg, 1.3 mmol) in ethanol (10 mL). The mixture was stirred overnight (about 18 hours) at 25° C. The solvent was removed under reduced pressure to give the product as yellow foam (310 mg, LC-MS showed there was the desired product peak. The crude was used directly in the next step.

b. Preparation of Compound C0060

4-Acetylbenzenesulfonyl chloride (0.348 g, 1.59 mmol) was added to the solution of C0060-1 (0.31 g, 1.59 mmol) in 10 mL of pyridine. The mixture was stirred at room temperature overnight (about 18 hours). The solvent was removed by reduced pressure evaporation, the residue was diluted with 50 mL dichloromethane, and then washed with 1M HCl (30 mL×3), and then the organic layer was dried with anhydrous sodium sulfate and concentrated to give the crude product as yellow oil (0.1 g). The crude product was further purified with silica gel column giving the title compound C0060 as white solid (200 mg, yield: 37%, HPLC: 95.99%, $^1$H NMR and MS confirmed).

$^1$H NMR (400 MHz, CDCl$_3$) δ: 8.11 (d, J=8.4 Hz, 2H), 7.88 (d, J=8.4 Hz, 2H), 3.46~3.41 (m, 2H), 3.28 (t, J=6 Hz, 2H), 3.01~2.93 (m, 4H), 2.68 (s, 3H), 2.04~1.99 (m, 4H), 1.67 (brs, 1H). MS (ESI) calcd for $C_{15}H_{20}N_2O_3S_2$ (m/z): 340.09. found: 341.1 [M+1]$^+$.

Preparation of Compound C0062-3

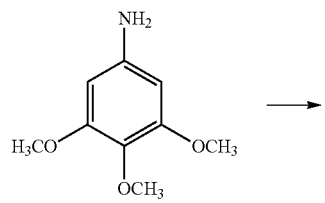

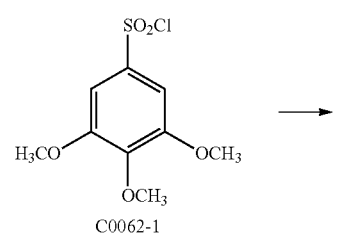

C0062-1

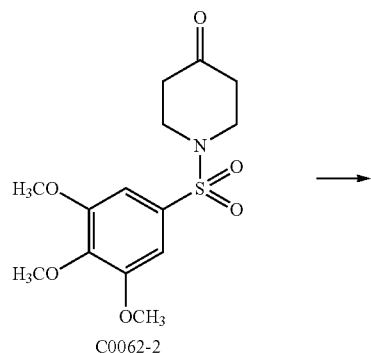

C0062-2

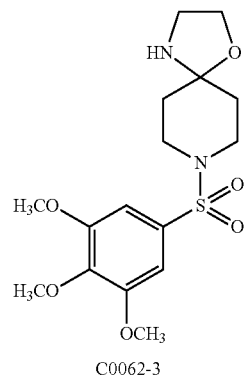

C0062-3 a. Preparation of Compound C0062-1

CuCl$_2$ (2.5 g) was added to the saturated solution of SO$_2$ (get from the reaction of NaHSO$_3$ and H$_2$SO$_4$) in glacial acetic acid (200 mL) and SO$_2$ gas was slowly bubbled into the solution for 2 hours. 3,4,5-Trimethoxyaniline (10 g, 54.6 mmol) was added to the solution of concentrated HCl (40 mL) and H$_2$O (50 mL) and the mixture was stirred for 1 hour at 0° C. To this solution was added a solution of NaNO$_2$ (3.77 g, 54.6 mmol) in H$_2$O (20 mL) at such a rate that the temperature did not rise above 0° C. The mixture was stirred for 0.5 hours and then added dropwise to the SO$_2$ and CuCl$_2$ saturated solution before. The reaction was then stirred for 1 hour. H$_2$O (1000 mL) was added and continued stirring for 0.5 hours. Then the product was collected by suction filtration, washed with H$_2$O, and dried in vacuum at 50° C.

b. Preparation of Compound C0062-2

To a solution of piperidin-4-one hydrochloride (229 mg, 1.68 mmol) in pyridine (10 mL) was added compound C0062-1 (300 mg, 1.12 mmol). The reaction mixture was stirred overnight (about 18 hours) at room temperature. To the reaction mixture 20 mL water was added, and the reaction mixture was extracted with dichloromethane three times. The organic layers was combined and was washed with 1N HCl two times and brine one times, dried, concentrated under vacuum to afford 279 mg of crude product (yield: 75.7)

c. Preparation of Compound C0062-3

To a solution of C0062-2 (279 mg, 0.848 mmol) in ethanol (5 mL) was added compound p-toluenesulfonic acid monohydrate (4.51 mg, 0.024 mmol) and 2-aminoethanol (0.9 mL). The reaction mixture was stirred overnight (about 18 hours) at room temperature. The reaction mixture was dissolved in CH$_2$Cl$_2$ (30 mL) and washed with aqueous of NaHCO$_3$ and brine, dried, concentrated under vacuum to afford 226 mg of crude product. (yield: 71.6%).

Preparation of Compound C0065-9

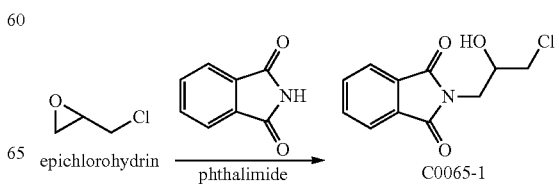

epichlorohydrin → phthalimide → C0065-1

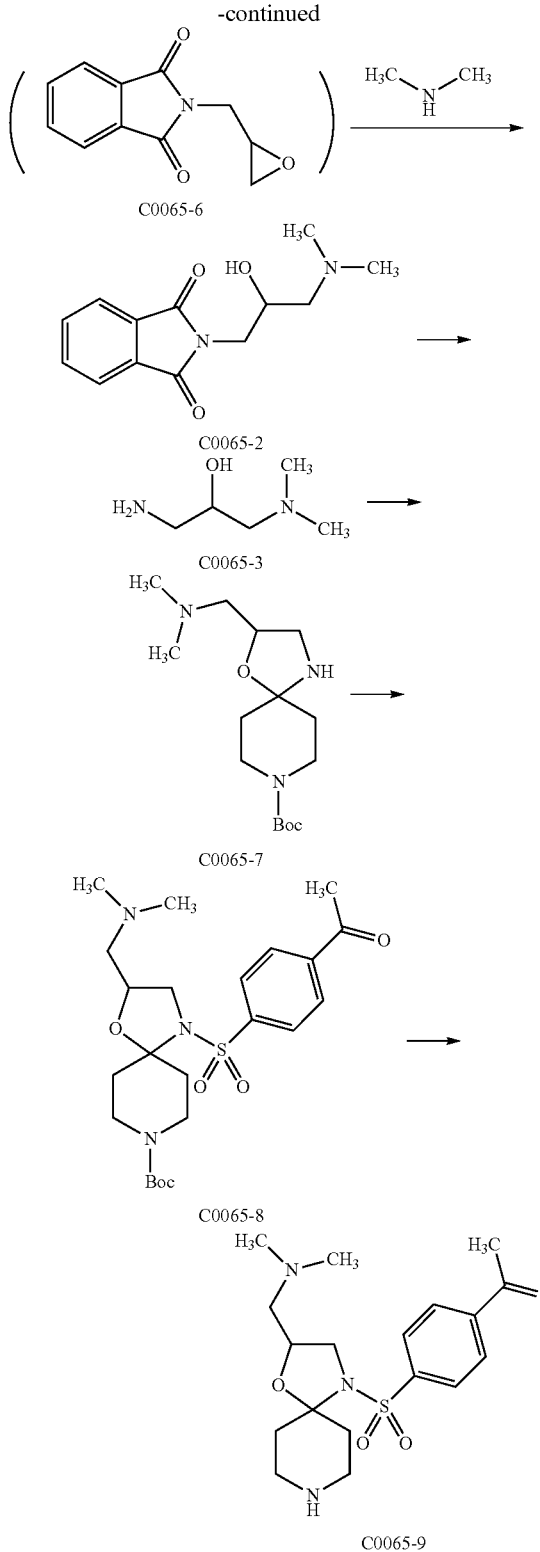

a. Preparation of Mixture C0065-1 and C0065-6

A suspension of phthalimide (7.35 g, 50 mmol) in epichlorohydrin (15.7 mL, 200 mmol) was boiled under reflux for 10 hours. The mixture was allowed to cool and was concentrated producing a brown oil. The crude product was purified by silica gel chromatography to obtain 4.7 g of C0065-6 as white solid (yield: 46%) and 4.1 g of C0065-1 as white solid.

b. Preparation of Compound C0065-2

The mixture of compound C0065-1 and C0065-6 (3.1 g, 15 mmol) and aqueous dimethylamine (10.3 g) was stirred overnight (about 18 hours) at room temperature. Thin-layer chromatography suggested the reaction complete. The reaction mixture was washed with $CH_2Cl_2$ for 3 times, and the water was removed under reduced pressure to obtain the crude product of C0065-2.

c. Preparation of Compound C0065-3

The compound C0065-2 was added into 20% hydrochloric acid (20 mL) and refluxed for 4 hours. Then the mixture was cooled to room temperature, phthalic acid was separated. The aqueous solution was washed by ether and concentrated. The residue was dissolved in NaOH (20%) and extracted with $CH_2Cl_2$ for 3 times. The combined organic layers were dried over $Na_2SO_4$ and concentrated to obtain 1.1 g of the product as yellow oil (yield: 62%).

d. Preparation of Compound C0065-7

To a solution of N-Boc-piperidin-4-one (420 mg, 2.1 mmol) in ethanol (4 mL) was added compound C0065-3 (500 mg, 4.2 mmol). The mixture was stirred overnight (about 18 hours) at room temperature. The solvent was removed under reduced pressure. The residue was diluted with $CH_2Cl_2$ (30 mL) and washed with saturated aqueous $Na_2CO_3$ (30 mL×6). The organic phase was dried over anhydrous $Na_2SO_4$, then concentrated to give 600 mg of compound C0065-4 as a yellow oil (yield: 95%)

e. Preparation of Compound C0065-8

4-Acetylbenzene-1-sulfonyl chloride (200 mg, 0.9 mmol) was added to a solution of compound C0065-7 (600 mg, 2.0 mmol) in pyridine (4 mL). The mixture was stirred at room temperature for 4 hours. The solvent was removed under reduced pressure. The residue was purified with silica gel to obtain 220 mg of the title compound as a white solid (yield: 50%)

f. Preparation of Compound C0065-9

To the solution of compound C0065-8 (220 mg, 0.45 mmol) in 3 mL $CH_2Cl_2$ was add 0.5 mL $CF_3COOH$ and the mixture was kept stirring for 1 hour at room temperature. To the mixture was added 30 mL of $CH_2Cl_2$ and washed with saturated sodium carbonate solution (30 mL×3). The organic layer was dried and concentrated to get the crude product 150 mg as white solid.

Preparation of Compound C0066

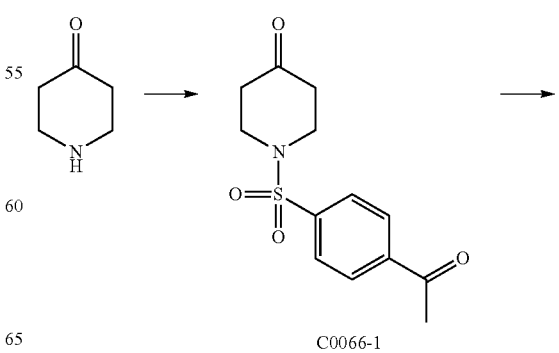

C0066-1

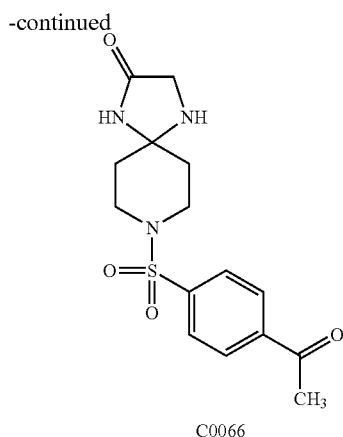

C0066 a. Preparation of Compound C0066-1

Triethylamine (606 mg, 6.0 mmol) and piperidin-4-one (297 mg, 3.0 mmol) were added to a solution of 4-acetylbenzene-1-sulfonyl chloride (656 mg, 3.0 mmol) in $CH_2Cl_2$ (10 mL). The mixture was stirred at room temperature overnight (about 18 hours). The solution was washed with water, dried over anhydrous $Na_2SO_4$ and concentrated to obtain the title product as yellow solid (643 mg, Yield: 76%).

b. Preparation of Compound C0066

To a solution of 2-aminoacetamide hydrochloride (252 mg, 2.28 mmol) in $CH_3OH$ (20 mL) was added triethylamine (230 mg, 2.28 mmol) and C0066-1 (643 mg, 2.28 mmol). The mixture was heated to reflux overnight (about 18 hours). The solution was cooled and filtered to obtain C0066 as white solid (550 mg, Yield: 72%).

$^1$H NMR (400 MHz, DMSO): 8.53 (s, 1H); 8.30 (d, J=8.8 Hz, 2H); 8.00 (d, J=8.8 Hz, 2H); 3.51-3.37 (m, 2H); 3.19 (s, 2H); 3.11 (s, 1H); 2.95-2.91 (m, 2H); 2.78 (s, 3H); 2.63-2.61 (m, 4H); MS (ESI) calcd for $C_{15}H_{19}N_3O_4S$ (m/z): 337.39. found: 338.3 [M+1]$^+$.

Preparation of Compound C0068-2

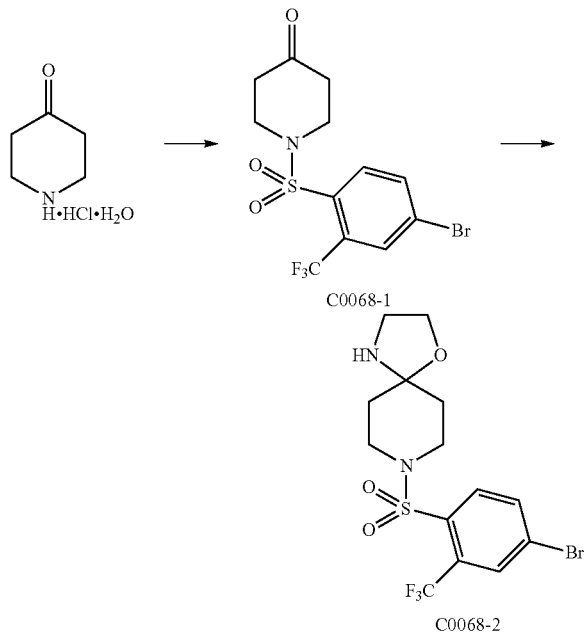

a. Preparation of Compound C0068-1

Piperidin-4-one hydrochloride hydrate (92 mg, 0.6 mmol) in pyridine (2 mL) was treated with 4-bromo-2-(trifluoromethyl)benzene-1-sulfonyl chloride (194 mg, 0.6 mmol). The mixture was stirred at room temperature overnight (about 18 hours). The solvent was removed under reduced pressure. To the residue was added $CH_2Cl_2$ (50 mL), the solution was washed with 1N HCl (20 mL×3), dried over $Na_2SO_4$, and concentrated to give the title product as yellow solid (117 mg; yield: 50.5%).

b. Preparation of Compound C0068-2 p-Toluenesulfonic acid monohydrate (1.59 mg) and 2-aminoethanol (0.32 mL, 5.54 mmol) were added to a solution of compound C0068-1 (107 mg, 0.28 mmol) in ethanol (4 mL). The mixture was stirred at room temperature overnight (about 18 hours). Then the solvent was removed under reduced pressure. To the residue was added $CH_2Cl_2$ (70 mL) and washed with saturated $NaHCO_3$ (25 mL×4), then dried over $Na_2SO_4$ and concentrated to give the product as yellow oil (110 mg, yield: 91.6%).

Preparation of Compound C0071-2

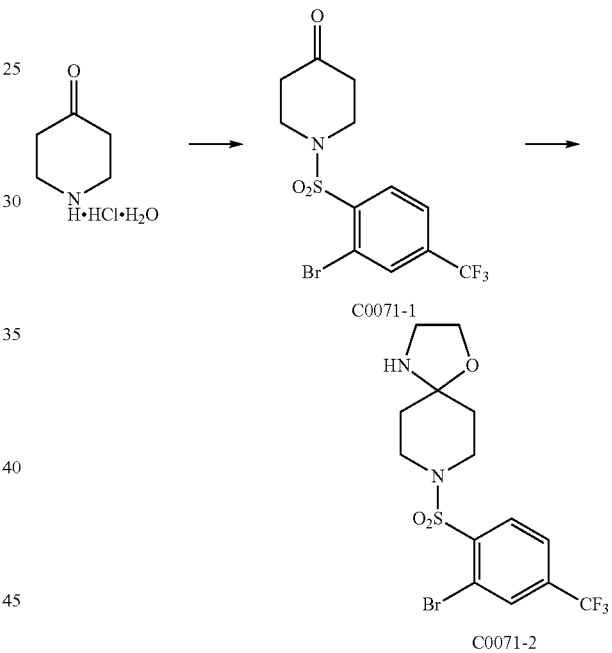

a. Preparation of Compound C0071-1

Piperidin-4-one hydrochloride hydrate (95 mg, 0.62 mmol) in pyridine (3 mL) was treated with 2-bromo-4-(trifluoromethyl)benzene-1-sulfonyl chloride (200 mg, 0.62 mmol). The mixture was stirred at room temperature overnight (about 18 hours). The solvent was removed under reduced pressure. The residue was diluted with $CH_2Cl_2$ (30 mL) and washed with 1 N HCl (30 mL×3). The organic phase was dried over anhydrous $Na_2SO_4$, and concentrated to give the crude product as yellow solid (150 mg; yield: 62.6%). The structure was confirmed by $^1$H-NMR & LC-MS.

b. Preparation of Compound C0071-2

To the solution of compound C0071-1 (145 mg, 0.376 mmol) in ethanol (3 mL) was added 2-aminoethanol (0.44 mL) and p-toluenesulfonic acid monohydrate (2 mg, 0.01 mmol). The mixture was stirred overnight (about 18 hours) at room temperature. The solvent was removed under reduced pressure. The residue was diluted with $CH_2Cl_2$ (30 mL) and washed with saturated aqueous $NaHCO_3$ (30 mL×6). The organic phase was dried over anhydrous Na₂SO₄, then concentrated to give compound C0071-2 as yellow oil (140 mg; yield: 86%). The structure was confirmed by ¹H NMR & LC-MS.

Preparation of Compound C0077

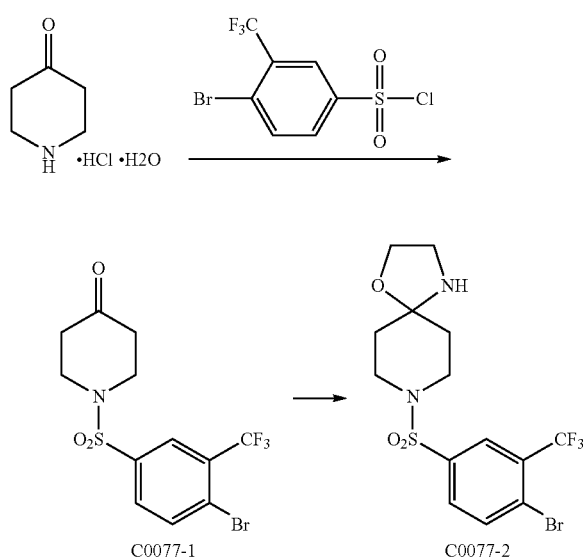 [SMILES: O=C1CCNCC1 ; O=S(=O)(Cl)c1ccc(Br)c(C(F)(F)F)c1 ; O=C1CCN(S(=O)(=O)c2ccc(Br)c(C(F)(F)F)c2)CC1 ; O=S(=O)(c1ccc(Br)c(C(F)(F)F)c1)N1CCC2(CC1)NCCO2 ; "C0077-1" ; "C0077-2"]

a. Preparation of Compound C0077-1

Piperidin-4-one hydrochloride hydrate (153.5 mg, 1 mmol) in pyridine (2 mL) was treated with 4-bromo-3-(trifluoromethyl)benzene-1-sulfonyl chloride (323.5 mg, 1 mmol). The mixture was stirred at room temperature overnight (about 18 hours). The solvent was removed under reduced pressure. To the residue was added CH₂Cl₂ (50 mL), then the solution was washed with 1N HCl (20 mL×3), dried over Na₂SO₄ and concentrated to give the title product as white solid (216 mg; yield: 56%).

b. Preparation of Compound C0077-2 p-Toluenesulfonic acid monohydrate (3.1 mg) and 2-aminoethanol (0.62 mL, 10.7 mmol) were added to a solution of compound C0077-1 (207 mg, 0.54 mmol) in ethanol (5 mL). The mixture was stirred at room temperature overnight (about 18 hours). The solvent was removed under reduced pressure. To the residue was added CH₂Cl₂ (70 mL) and washed with saturated NaHCO₃ (25 mL×4), then dried over Na₂SO₄ and concentrated to give the product as yellow oil (210 mg, yield: 90.7%).

Preparation of Compound C0078

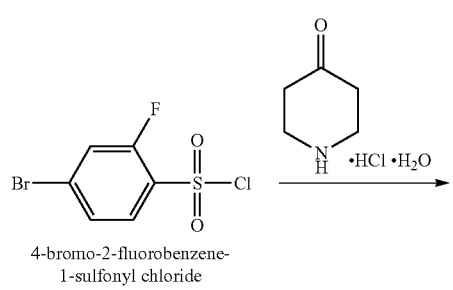

4-bromo-2-fluorobenzene-
1-sulfonyl chloride

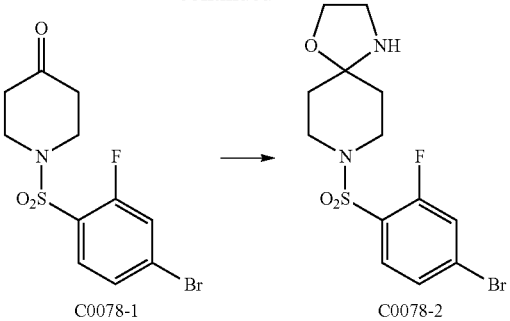

a. Preparation of Compound C0078-1

To a solution of piperidin-4-one hydrochloride hydrate (169 mg, 1.1 mmol) in pyridine (2 mL) was added 4-bromo-2-fluorobenzene-1-sulfonyl chloride (300 mg, 1.1 mmol). The mixture was stirred at room temperature overnight (about 18 hours). The solvent was removed under reduced pressure. The residue was diluted with CH₂Cl₂ (30 mL) and washed with 1N HCl (30 mL×3). The organic phase was dried over anhydrous Na₂SO₄, and concentrated to give the crude product as white solid (230 mg, yield: 62.4%).

b. Preparation of Compound C0078-2

2-Aminoethanol (0.78 mL, 13.39 mmol) and p-toluenesulfonic acid monohydrate (3.8 mg, 0.02 mmol) was added to the solution of compound C0078-1 (225 mg, 0.67 mmol) in ethanol (7 mL). The mixture was stirred overnight (about 18 hours) at room temperature. Then the solvent was removed under reduced pressure. The residue was diluted with CH₂Cl₂ (30 mL) and washed with saturated aqueous NaHCO₃ (30 mL×6). The organic phase was dried over anhydrous Na₂SO₄, and concentrated to give compound C0078-2 as yellow oil (260 mg)

Preparation of Compound C0079M-7

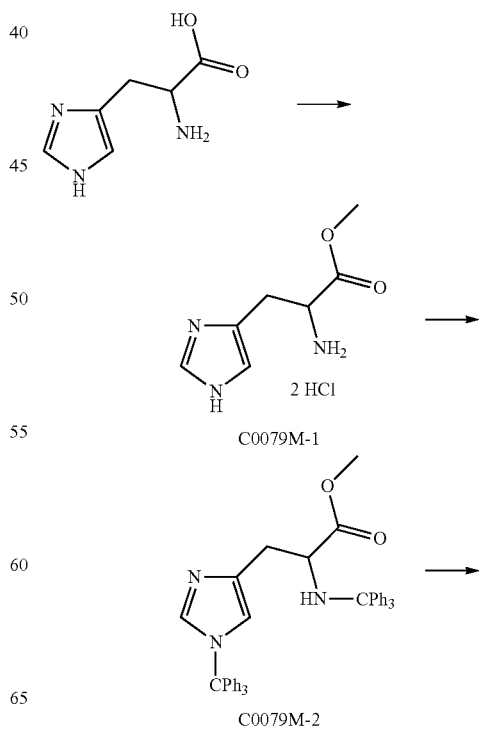

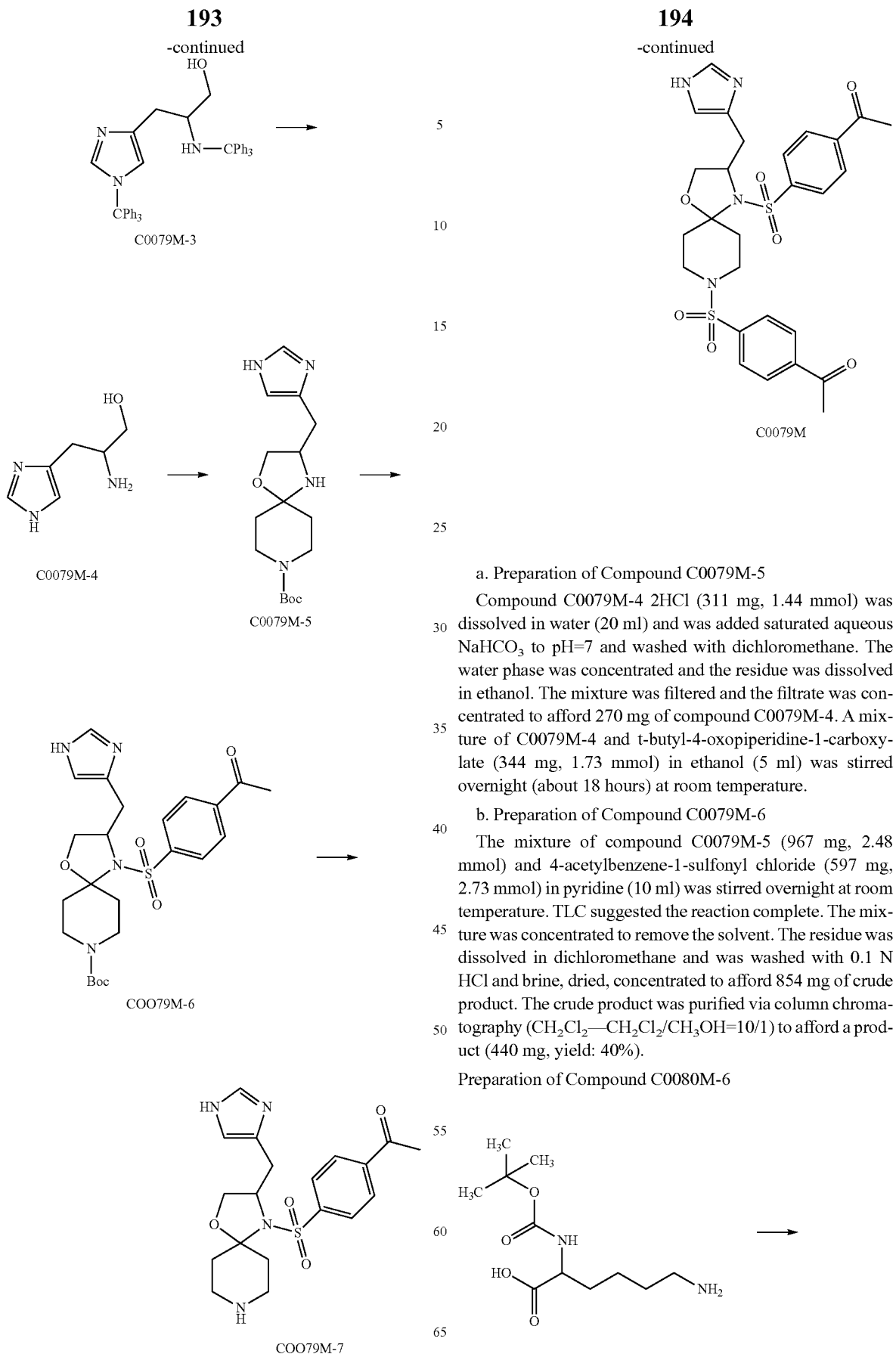

a. Preparation of Compound C0079M-5

Compound C0079M-4 2HCl (311 mg, 1.44 mmol) was dissolved in water (20 ml) and was added saturated aqueous NaHCO₃ to pH=7 and washed with dichloromethane. The water phase was concentrated and the residue was dissolved in ethanol. The mixture was filtered and the filtrate was concentrated to afford 270 mg of compound C0079M-4. A mixture of C0079M-4 and t-butyl-4-oxopiperidine-1-carboxylate (344 mg, 1.73 mmol) in ethanol (5 ml) was stirred overnight (about 18 hours) at room temperature.

b. Preparation of Compound C0079M-6

The mixture of compound C0079M-5 (967 mg, 2.48 mmol) and 4-acetylbenzene-1-sulfonyl chloride (597 mg, 2.73 mmol) in pyridine (10 ml) was stirred overnight at room temperature. TLC suggested the reaction complete. The mixture was concentrated to remove the solvent. The residue was dissolved in dichloromethane and was washed with 0.1 N HCl and brine, dried, concentrated to afford 854 mg of crude product. The crude product was purified via column chromatography (CH₂Cl₂—CH₂Cl₂/CH₃OH=10/1) to afford a product (440 mg, yield: 40%).

Preparation of Compound C0080M-6

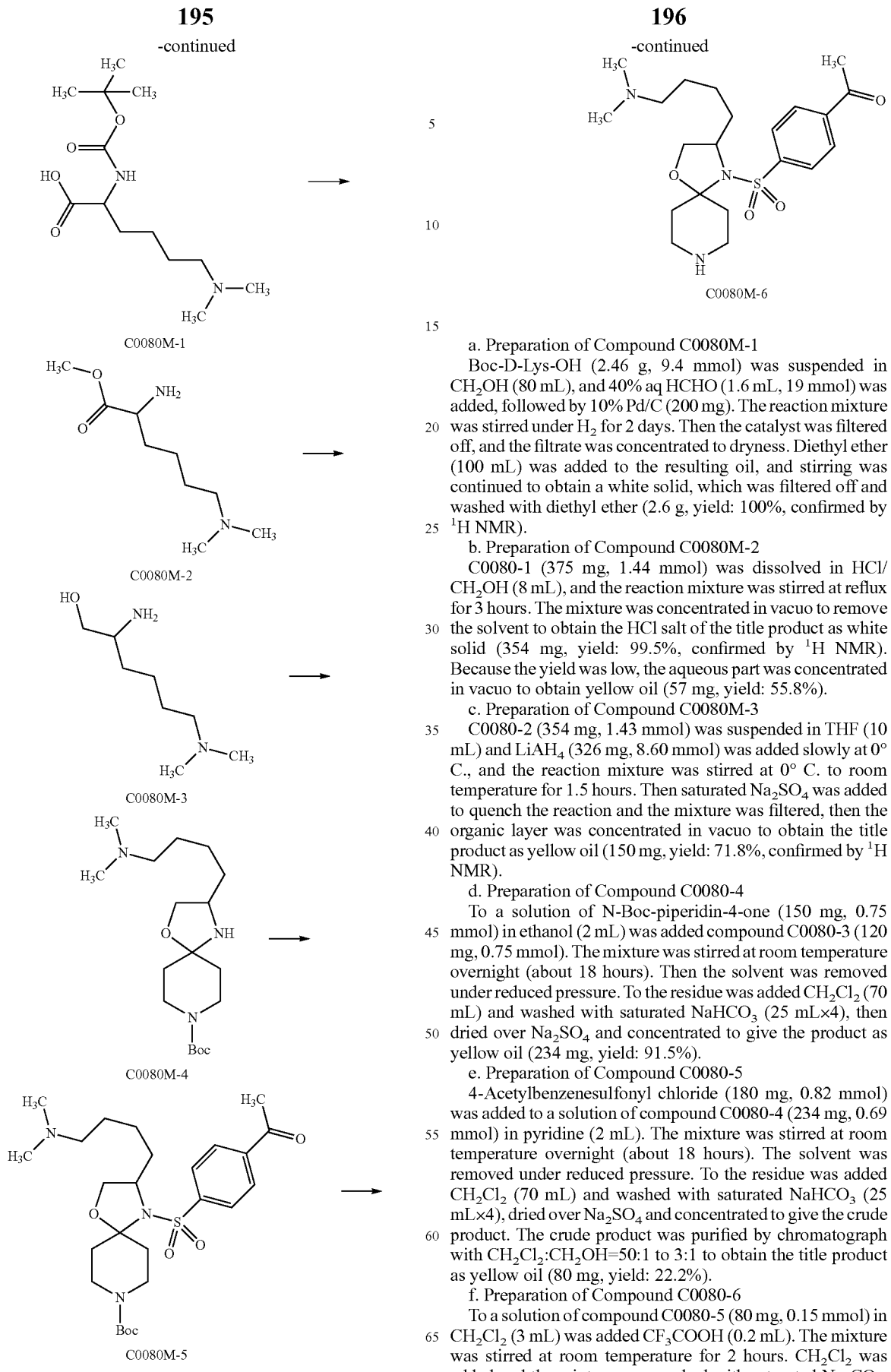

a. Preparation of Compound C0080M-1

Boc-D-Lys-OH (2.46 g, 9.4 mmol) was suspended in $CH_2OH$ (80 mL), and 40% aq HCHO (1.6 mL, 19 mmol) was added, followed by 10% Pd/C (200 mg). The reaction mixture was stirred under $H_2$ for 2 days. Then the catalyst was filtered off, and the filtrate was concentrated to dryness. Diethyl ether (100 mL) was added to the resulting oil, and stirring was continued to obtain a white solid, which was filtered off and washed with diethyl ether (2.6 g, yield: 100%, confirmed by $^1H$ NMR).

b. Preparation of Compound C0080M-2

C0080-1 (375 mg, 1.44 mmol) was dissolved in HCl/$CH_2OH$ (8 mL), and the reaction mixture was stirred at reflux for 3 hours. The mixture was concentrated in vacuo to remove the solvent to obtain the HCl salt of the title product as white solid (354 mg, yield: 99.5%, confirmed by $^1H$ NMR). Because the yield was low, the aqueous part was concentrated in vacuo to obtain yellow oil (57 mg, yield: 55.8%).

c. Preparation of Compound C0080M-3

C0080-2 (354 mg, 1.43 mmol) was suspended in THF (10 mL) and $LiAH_4$ (326 mg, 8.60 mmol) was added slowly at 0° C., and the reaction mixture was stirred at 0° C. to room temperature for 1.5 hours. Then saturated $Na_2SO_4$ was added to quench the reaction and the mixture was filtered, then the organic layer was concentrated in vacuo to obtain the title product as yellow oil (150 mg, yield: 71.8%, confirmed by $^1H$ NMR).

d. Preparation of Compound C0080-4

To a solution of N-Boc-piperidin-4-one (150 mg, 0.75 mmol) in ethanol (2 mL) was added compound C0080-3 (120 mg, 0.75 mmol). The mixture was stirred at room temperature overnight (about 18 hours). Then the solvent was removed under reduced pressure. To the residue was added $CH_2Cl_2$ (70 mL) and washed with saturated $NaHCO_3$ (25 mL×4), then dried over $Na_2SO_4$ and concentrated to give the product as yellow oil (234 mg, yield: 91.5%).

e. Preparation of Compound C0080-5

4-Acetylbenzenesulfonyl chloride (180 mg, 0.82 mmol) was added to a solution of compound C0080-4 (234 mg, 0.69 mmol) in pyridine (2 mL). The mixture was stirred at room temperature overnight (about 18 hours). The solvent was removed under reduced pressure. To the residue was added $CH_2Cl_2$ (70 mL) and washed with saturated $NaHCO_3$ (25 mL×4), dried over $Na_2SO_4$ and concentrated to give the crude product. The crude product was purified by chromatograph with $CH_2Cl_2$:$CH_2OH$=50:1 to 3:1 to obtain the title product as yellow oil (80 mg, yield: 22.2%).

f. Preparation of Compound C0080-6

To a solution of compound C0080-5 (80 mg, 0.15 mmol) in $CH_2Cl_2$ (3 mL) was added $CF_3COOH$ (0.2 mL). The mixture was stirred at room temperature for 2 hours. $CH_2Cl_2$ was added and the mixture was washed with saturated $Na_2CO_3$.

The organic layer was dried over Na₂SO₄, concentrated in vacuo to obtain the product as yellow oil (67 mg)

Preparation of Compound C0081M-7

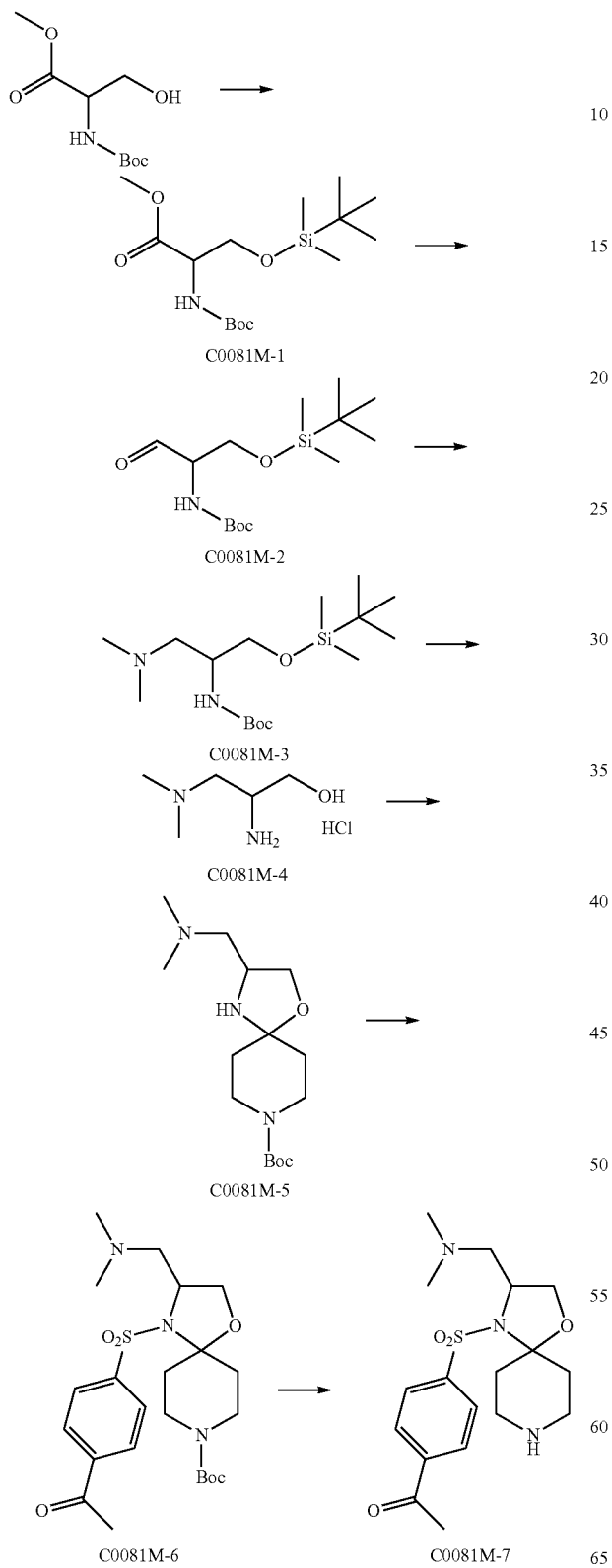

a. Preparation of Compound C0081M-1

To a stirred solution of L-Boc-Ser-OMe (6.85 g, 31.2 mmol) and imidazole (5.3 g, 78 mmol) in dimethylformamide (60 ml) was added dropwise t-butyldimethylsilyl chloride (7.05 g, 46.8 mmol). The reaction was stirred at 50° C. overnight (about 18 hours) after which the solvent was removed in vacuo. The residue was dissolved in dichloromethane and successively washed with a 1 N HCl solution and brine. The organic layer was dried over Na₂SO₄ and the solvent was evaporated in vacuo to give the crude product. The crude reaction product was subjected to column chromatography (petroleum ether:dichloromethane=1:1) to obtain the title product as light yellow oil (7.4 g; yield: 71.2%).

b. Preparation of Compound C0081M-2

DIBAL-H was added to a solution of C0081M-1 (13.8 g, 41.4 mmol) in dry toluene (100 ml) (1.2 M in toluene, 41.4 ml, 50 mmol) in an argon atmosphere at such a rate that the temperature didn't rise above 70° C. After stirring for 2 hours, HCl/CH₃OH solution was added carefully. The reaction mixture was poured into 10% aqueous HCl solution. The organic layer was separated and washed with brine. The organic layer was dried over Na₂SO₄ and concentrated to get the crude product. The crude product was purified with column chromatography (petroleum ether:ethyl acetate=40:1 to 10:1) to obtain the title product as a colorless liquid (8.24 g, yield: 66%).

c. Preparation of Compound C0081M-3

To a solution of C0081M-2 (8.24 g, 27 mmol) in methanol (75 ml) was added NaOAc (2.16 g, 28 mmol) and dimethylamine hydrochloride (2.756 g, 33.8 mmol). The mixture was stirred at room temperature for 1 hour, then NaCNBH₃ (1.7 g, 27 mmol) was added. The mixture was allowed to stir at room temperature overnight (about 18 hours). Water was added and the solution was extracted with CH₂Cl₂. The combined organic layers was dried over Na₂SO₄ and concentrated to get the crude product. The crude product was purified with column chromatography (petroleum ether:ethyl acetate=40:1 to 1:1) to obtain the title product as a colorless liquid (2.512 g, yield: 28%).

Preparation of Compound C0083M

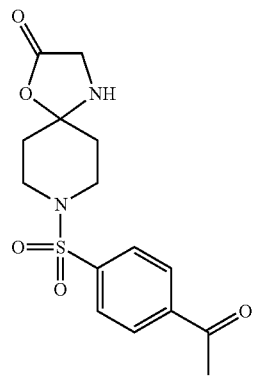 [SMILES: CC(=O)c1ccc(S(=O)(=O)N2CCC3(CC2)NCC(=O)O3)cc1]

This compound is prepared using procedures illustrated elsewhere herein.

Preparation of Compound C0086M

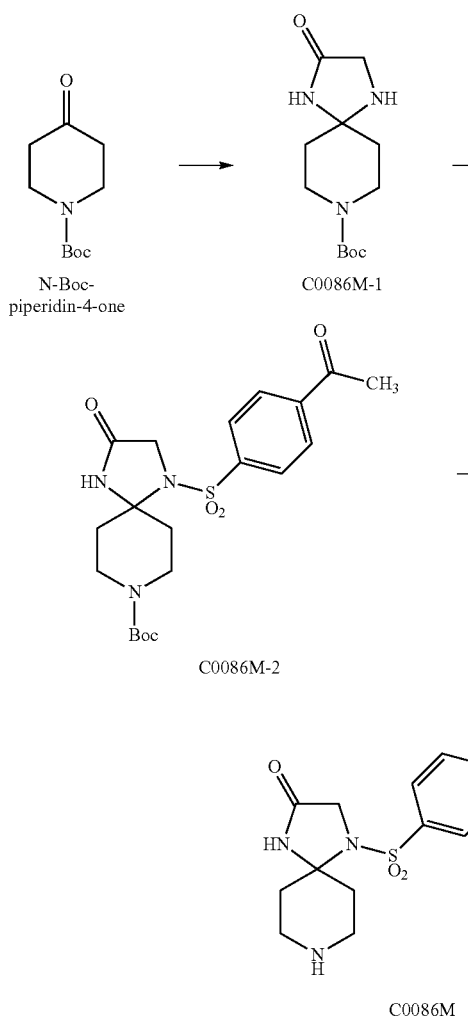

a. Preparation of Compound C0086M-1

To a stirred solution of glycinamide hydrochloride (276 mg, 2.5 mmol) and triethylamine (0.35 mL, 2.5 mmol) in methanol (10 mL) was added N-Boc-piperidin-4-one (500 mg, 2.5 mmol). The reaction was stirred under reflux overnight (about 18 hours) after which the solvent was removed in vacuo. The residue was purified by column chromatography to obtain the title product as white solid (500 mg; yield: 78%).

b. Preparation of Compound C0086M-2

4-Acetylbenzene-1-sulfonyl chloride (258 mg, 1.18 mmol) was added to a solution of compound C0086M-1 (250 mg, 0.98 mmol) in pyridine (10 mL). The mixture was stirred at 60° C. (yield: 46%) overnight (about 18 hours). Then the solvent was removed under reduced pressure. The residue was purified by column chromatography to obtain the title product as yellow solid (250 mg; yield: 58%)

c. Preparation of Compound C0086M

To a solution of compound C0086M-2 (150 mg, 0.343 mmol) in 5 mL dichloromethane was add 0.5 mL $CF_3COOH$, and the mixture was stirred for 2 hours at room temperature. To the mixture was added 30 mL dichloromethane, and the composition formed was washed with saturated sodium carbonate solution (30 mL×3). The organic layer was dried and concentrated to get 90 mg of the crude product as light yellow solid. The crude product was purified by column chromatography to obtain the title product as little yellow solid (50 mg; yield: 43.2%).

$^1$H NMR (400 MHz, DMSO): 9.49 (s, 1H); 8.14 (d, J=8.4 Hz, 2H); 8.04 (d, J=8.4 Hz, 2H); 3.93 (s, 2H); 2.87 (m, 2H); 2.72-2.59 (m, 2H); 2.65 (s, 3H), 2.33 (td, J=12.4, 4.4 Hz, 2H); 1.51 (d, J=12.0 Hz, 2H); LCMS (ESI) calcd for $C_{15}H_{19}N_3O_4S$ (m/z): 337.39. found: 338.4 [M+1]$^+$.

Preparation of Compound C0087M

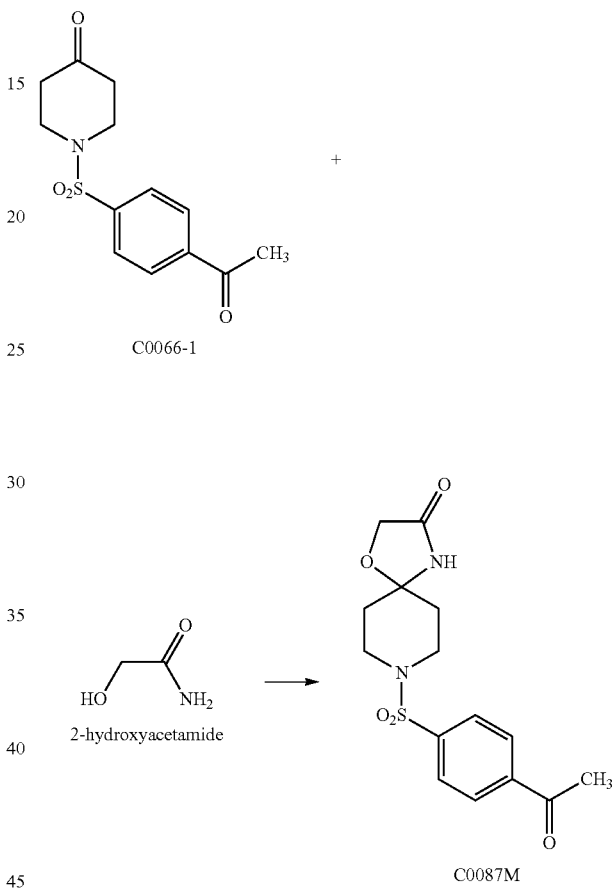

2-Hydroxyacetamide (210 mg, 2.8 mmol) and toluenesulfonic acid monohydrate (3.0 mg) was added to a solution of C0066-1 (200 mg, 0.7 mmol) in dimethylformamide (10 mL). The mixture was stirred at 120° C. overnight (about 18 hours). The solvent was removed under reduced pressure. The residue was diluted with dichloromethane and a yellow solid formed. The mixture was filtered and the filtrate was concentrated and purified by column chromatography (dichloromethane:methanol=100:1 to 30:1) to obtain the impure product as yellow solid (30 mg, yield: 13%). The impure product was recrystallized with chloroform and n-hexane to obtain the title product as yellow solid (20 mg, Yield: 8%).

$^1$H NMR (400 MHz, CDCl$_3$): 8.11 (d, J=9.2 Hz, 2H); 7.87 (d, J=8.4 Hz, 2H); 6.71 (s, 1H); 4.15 (s, 2H); 3.65 (m, 2H); 2.83-2.77 (m, 2H); 2.67 (s, 3H); 1.97-1.88 (m, 4H); MS (ESI) calcd for $C_{15}H_{18}N_2O_5S$ (m/z): 338.38. found: 339.4 [M+1]$^+$.

Preparation of Compound C0088M

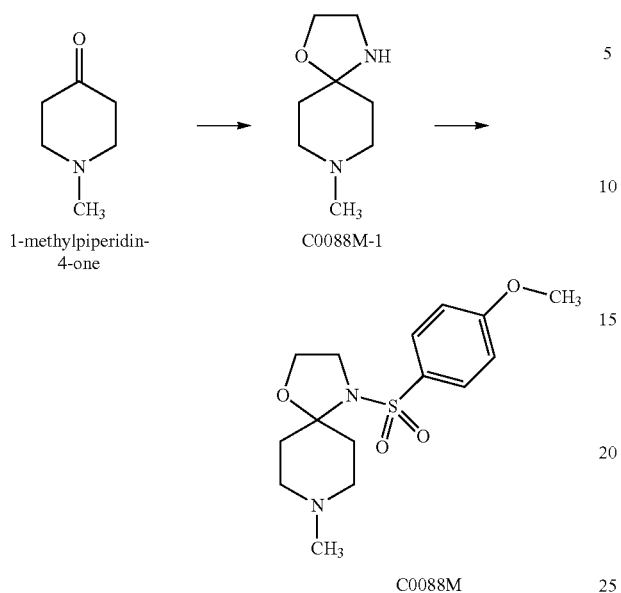

1-methylpiperidin-4-one

C0088M-1

C0088M a. Preparation of Compound C0088M-1

2-aminoethanol (0.13 mL, 2.1 mmol) was added to a solution of 1-methylpiperidin-4-one (227 mg, 2.0 mmol) in ethanol (4 mL). The reaction was stirred under reflux for 2 hours. The solvent was removed in vacuo to obtain the crude product C0088M-1 as yellow oil. The crude product was used for the next step directly with out purification.

b. Preparation of Compound C0088M

To a solution of compound C0088M-1 in pyridine (5 mL) was added 4-methoxybenzene-1-sulfonyl chloride (207 mg, 1.0 mmol). The mixture was stirred at room temperature overnight (about 18 hours). The solvent was removed under reduced pressure. The residue was purified by column chromatography to obtain the crude product. The crude product was purified by preparative HPLC to obtain the title product as yellow oil (35 mg; yield: 10.7%; confirmed by $^1$H NMR and LC-MS, purity: 98.1% by HPLC).

$^1$H NMR (400 MHz, CDCl$_3$): 7.80 (d, J=8.4 Hz, 2H); 6.96 (d, J=8.4 Hz, 2H); 3.94 (t, J=6.0 Hz, 2H); 3.87 (s, 3H); 3.50 (t, J=6.0 Hz, 2H); 2.74 (m, 2H); 2.53 (td, J=12.8, 4.4 Hz, 2H); 2.27 (s, 3H); 2.19 (t, J=11.6 Hz, 2H); 1.57 (d, J=12.4 Hz, 2H); LCMS (ESI) calcd for $C_{15}H_{22}N_2O_4S$ (m/z): 326.41. found: 327.3 [M+1]$^+$.

Preparation of Compound C0089M

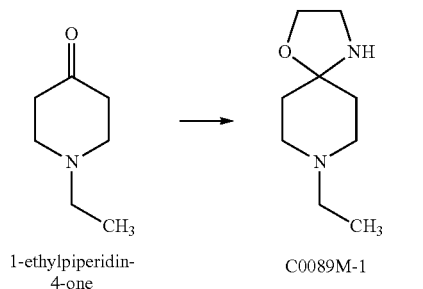

1-ethylpiperidin-4-one

C0089M-1

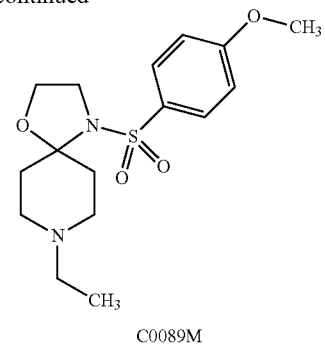

C0089M a. Preparation of Compound C0089M-1

To a solution of 1-ethylpiperidin-4-one (254 mg, 2.0 mmol) in ethanol (4.0 mL) was added 2-aminoethanol (0.13 mL, 2.1 mmol). The reaction was refluxed for 3 hours. The solvent was removed in vacuo to obtain the crude product of C0094M-1 as a red oil. The crude product was used for the next step directly with out purification.

b. Preparation of Compound C0089M

The crude C0089M-1 was dissolved in pyridine (2.5 mL) and added 4-methoxybenzenesulfonyl chloride (207 mg, 1.0 mmol). The mixture was stirred at room temperature overnight (about 18 hours). The solvent was removed under reduced pressure. The residue was purified by column chromatography to give the crude product as yellow solid (80 mg; yield: 24%). The crude product was purified by preparative HPLC to obtain the title product as white solid (40 mg; yield: 11.5%, confirmed by $^1$H-NMR and LC-MS, purity: 99% by HPLC).

$^1$H NMR (400 MHz, CDCl$_3$): 7.80 (d, J=9.2 Hz, 2H); 6.96 (d, J=9.2 Hz, 2H); 3.93 (t, J=6.0 Hz, 2H); 3.86 (s, 3H); 3.50 (t, J=6.0 Hz, 2H); 2.86-2.82 (m, 2H); 2.52-2.49 (m, 2H); 2.42 (q, J=7.2 Hz, 2H); 2.16 (t, J=11.2 Hz, 2H); 1.60-1.56 (m, 2H); 1.07 (t, J=7.2 Hz, 3H); MS (ESI) calcd for $C_{16}H_{24}N_2O_4S$ (m/z): 340.44. found: 341.4 [M+1]$^+$.

Preparation of Compound C0090M

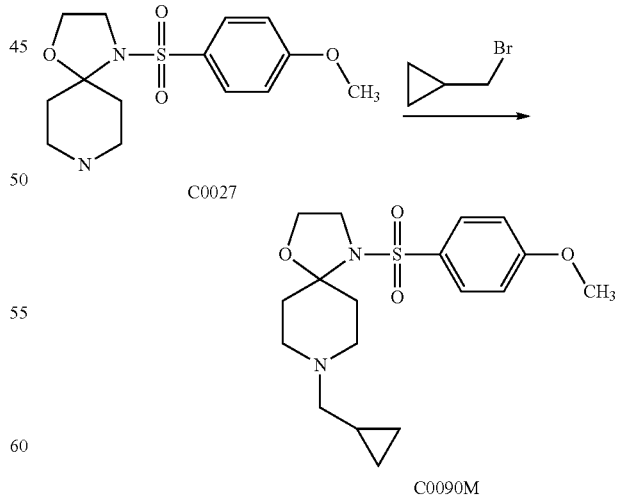

C0027

C0090M

C0027 (200 mg, 0.64 mmol) was dissolved in acetone (20 mL), and (bromomethyl)cyclopropane (86 mg, 0.64 mmol) was added, followed by K$_2$CO$_3$ (265 mg, 1.92 mmol). The reaction mixture was stirred at reflux for 7 hours and then stirred at room temperature overnight (about 18 hours). The mixture was filtered and concentrated in vacuo to obtain the crude product. The crude product was purified by column chromatography eluted with ethyl acetate to obtain 220 mg of the title product as light yellow oil (yield: 93.9%). The structure was confirmed by $^1$H NMR & LC-MS. Purity: 99.6% by HPLC.

$^1$H NMR (400 MHz, CDCl$_3$): 7.81 (d, J=8.4 Hz, 2H); 6.96 (d, J=8.4 Hz, 2H); 3.93 (t, J=6.0 Hz, 2H); 3.87 (s, 3H); 3.50 (t, J=6.0 Hz, 2H); 2.97 (m, 2H); 2.52 (dt, J=4.4, 10.2 Hz, 2H); 2.26-2.17 (m, 4H); 1.58 (m, 2H); 0.92-0.80 (m, 1H); 0.52-0.48 (m, 2H); 0.09-0.05 (m, 2H); MS (ESI) calcd for C$_{18}$H$_{26}$N$_2$O$_4$S (m/z): 366.16. found; 367.2 [M+1]$^+$.

Preparation of Compound C0091M

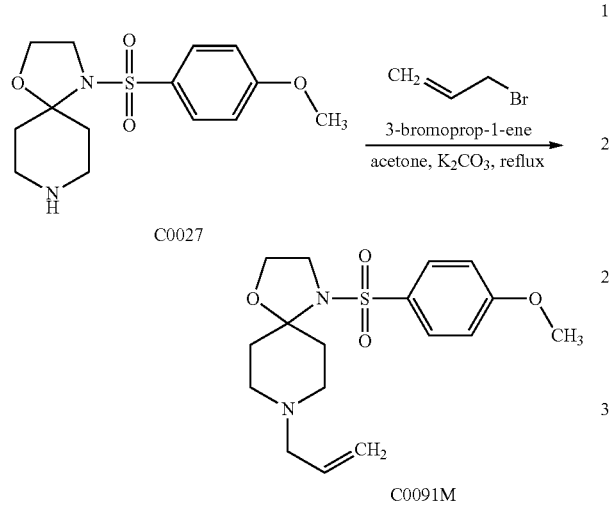

C0027 (50 mg, 0.16 mmol) was dissolved in acetone (5 mL), and 3-bromoprop-1-ene (20 mg, 0.16 mmol) was added, followed by K$_2$CO$_3$ (66 mg, 0.48 mmol). The reaction mixture was stirred at reflux for 7 hours, and then stirred at room temperature overnight (about 18 hours). The mixture was filtered and concentrated in vacuo to obtain the crude product. The crude product was purified by column chromatography with ethyl acetate to obtain 30 mg of the title product as colorless oil (30 mg, yield: 53.3%). The structure was confirmed by $^1$H NMR & LC-MS, purity: 99.9% by HPLC.

$^1$H NMR (400 MHz, CDCl$_3$): 7.79 (d, J=8.4 Hz, 2H); 6.95 (d, J=8.48 Hz, 2H); 5.92-5.84 (m, 1H); 5.18-5.10 (m, 2H); 3.92 (t, J=6.4 Hz, 2H); 3.86 (s, 3H); 3.48 (t, J=6.4 Hz, 2H); 2.99 (d, J=6.0 Hz, 2H); 2.82 (dt, J=2.8, 11.2 Hz, 2H); 2.50 (dt, J=4.8, 12.8 Hz, 2H); 2.16 (dt, J=2.0, 13.6 Hz, 2H); 1.57 (d, J=11.2 Hz, 2H); MS (ESI) calcd for C$_{17}$H$_{24}$N$_2$O$_4$S (m/z): 352.15. found: 353.4 [M+1]$^+$.

Preparation of Compound C0092M

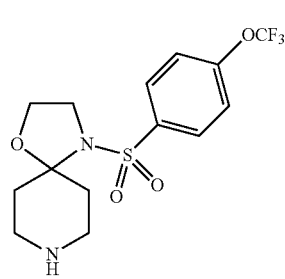

This compound is prepared using procedures illustrated elsewhere herein.

Preparation of Compound C0093M

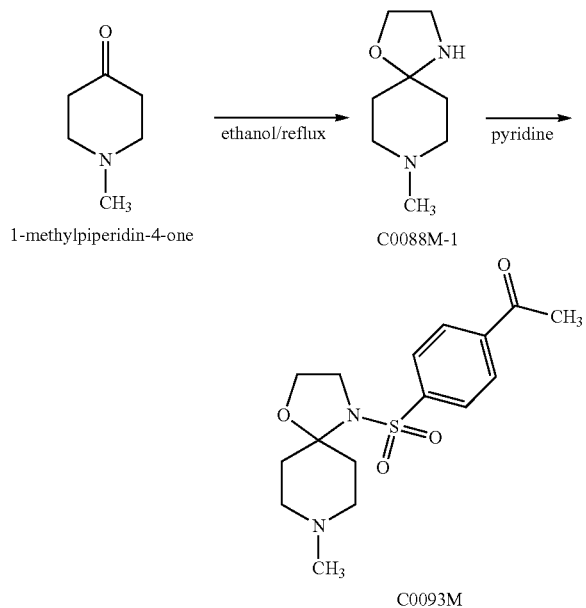

a. Preparation of Compound C0088M-1

2-Aminoethanol (0.13 mL, 2.1 mmol) was added to a solution of 1-methylpiperidin-4-one (227 mg, 2.0 mmol) in ethanol (4 mL). The reaction was stirred under reflux for 2 hours. The solvent was removed in vacuo to obtain the crude product of C0088M-1 as yellow oil. The crude product was used for the next step directly with out purification.

b. Preparation of Compound C0093M

To a solution of compound C0088M-1 in pyridine (5 mL) was added 4-methoxybenzene-1-sulfonyl chloride (219 mg, 1.0 mmol). The mixture was stirred at room temperature overnight (about 18 hours). The solvent was removed under reduced pressure. The residue was purified by column chromatography to obtain the crude product. The crude product was purified by preparative HPLC to obtain the title product as yellow oil (20 mg; yield: 6.0%; confirmed by $^1$H-NMR and LC-MS, purity: 99% by HPLC).

$^1$H NMR (400 MHz, CDCl$_3$): 8.07 (d, J=8.0 Hz, 2H); 7.97 (d, J=8.0 Hz, 2H); 3.97 (t, J=6.0 Hz, 2H); 3.56 (t, J=6.0 Hz, 2H); 2.75 (m, 2H); 2.66 (s, 3H); 2.53 (td, J=12.8, 4.4 Hz, 2H); 2.28 (s, 3H); 2.20 (t, J=11.6 Hz, 2H); 1.56 (d, J=12.4 Hz, 2H); LCMS (ESI) calcd for C$_{16}$H$_{22}$N$_2$O$_4$S (m/z): 338.42. found: 339.5 [M+1]$^+$.

Preparation of Compound C0094M

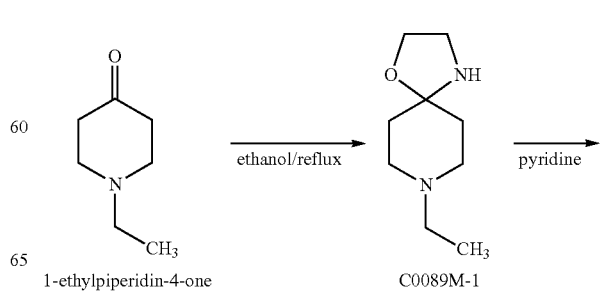

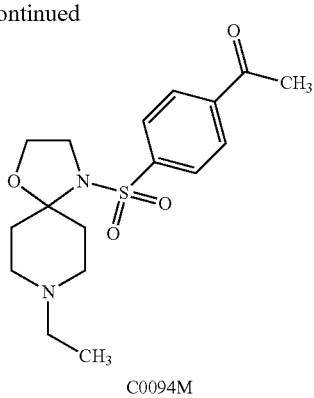

C0094M a. Preparation of Compound C0094M-1

To a solution of 1-ethylpiperidin-4-one (254 mg, 2.0 mmol) in ethanol (4.0 mL) was added 2-aminoethanol (0.13 mL, 2.1 mmol). The reaction was refluxed for 3 hours. Then the solvent was removed in vacuo to obtain the crude product of C0094M-1 as a red oil.

b. Preparation of Compound C0094M

The crude C0094-1 was dissolved in pyridine (2.5 mL) and added 4-acetylbenzene-1-sulfonyl chloride (218 mg, 1.0 mmol). The mixture was stirred at room temperature overnight (about 18 hours). The solvent was removed under reduced pressure. The residue was purified by column chromatography to give the crude product as yellow solid (90 mg; yield: 26%). The crude product was purified by Pre-HPLC to obtain the title product as white solid (50 mg; yield: 14%, confirmed by $^1$H NMR and LC-MS, purity: 99% by HPLC).

$^1$H NMR (400 MHz, CDCl$_3$): 8.07 (d, J=8.4 Hz, 2H); 7.97 (d, J=8.8 Hz, 2H); 3.97 (t, J=6.4 Hz, 2H); 3.57 (t, J=6.0 Hz, 2H); 2.87-2.83 (m, 2H); 2.65 (s, 3H); 2.52-2.48 (m, 2H); 2.44 (q, J=7.2 Hz, 2H); 2.20-2.17 (m, 2H); 1.57 (d, J=10.8 Hz, 2H); 1.08 (t, J=7.2 Hz, 3H); MS (ESI) calcd for C$_{17}$H$_{24}$N$_2$O$_4$S (m/z): 352.45. found: 353.4 [M+1]$^+$.

Preparation of Compound C0095M

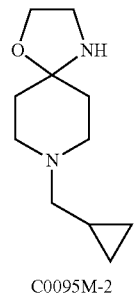

C0095M-2

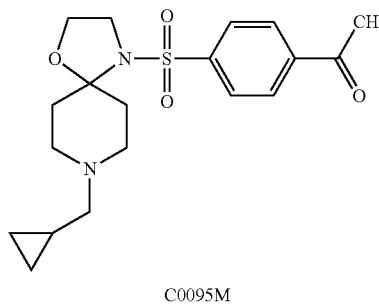

C0095M

To the solution of compound C0095M-2 (260 mg, 1.33 mmol) in pyridine (2.5 mL) was added 4-acetylbenzene-1-sulfonyl chloride (348 mg, 1.59 mmol). The mixture was stirred overnight (about 18 hours) at room temperature. The reaction mixture was concentrated in vacuo to remove the pyridine. The residue was dissolved into dichloromethane and washed with saturated NaHCO$_3$. Then, the organic layer was dried over Na$_2$SO$_4$ and concentrated in vacuo to obtain the crude product. The crude product was purified by column chromatography to obtain 464 mg of C0095M. The product was purified by preparative HPLC to obtain the title product (240 mg, yield: 47.8%).

$^1$H NMR (400 MHz, CDCl$_3$): 8.07 (d, J=8.4 Hz, 2H); 7.97 (d, J=8.4 Hz, 2H); 3.96 (t, J=6.0 Hz, 2H); 3.56 (t, J=6.0 Hz, 2H); 2.97 (dt, J=2.4, 11.2 Hz, 2H); 2.65 (s, 3H); 2.51 (dt, J=4.8, 12.8 Hz, 2H); 2.25 (d, J=6.8 Hz, 2H); 2.22-2.15 (m, 2H); 1.56 (dd, J=2.0, 13.2 Hz, 2H); 0.87-0.83 (m, 1H); 0.52-0.48 (m, 2H); 0.09-0.05 (m, 2H); MS (ESI) calcd for C$_{19}$H$_{26}$N$_2$O$_4$S (m/z): 378.16. found: 379.4 [M+1]$^+$.

Preparation of Compound C0096M

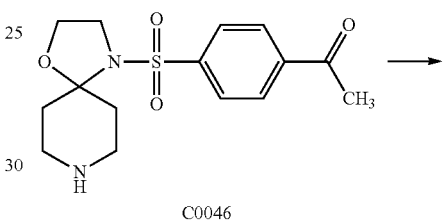

C0046

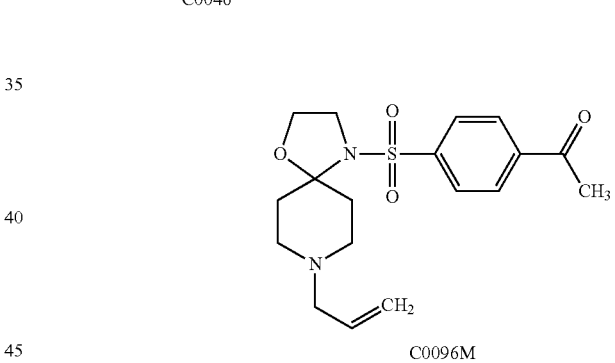

C0096M

C0046 (60 mg, 0.185 mmol) was dissolved in acetone (5 mL), and 3-bromoprop-1-ene (22 mg, 0.185 mmol) was added, followed by K$_2$CO$_3$ (77 mg, 0.556 mmol). The reaction mixture was stirred at reflux for 4 hours, and then stirred at room temperature overnight (about 18 hours). The mixture was filtered and concentrated in vacuo to obtain the crude product. The crude product was purified by column chromatography with ethyl acetate to obtain 43 mg of the title product as white solid (43 mg, yield: 63.9%)

$^1$H NMR (400 MHz, CDCl3): 8.06 (d, J=9.2 Hz, 2H); 7.96 (d, J=9.2 Hz, 2H); 5.90-5.83 (m, 1H); 5.18-5.11 (m, 2H); 3.96 (t, J=6.4 Hz, 2H); 3.55 (t, J=6.4 Hz, 2H); 2.99 (d, J=6.4 Hz, 2H); 2.82 (dt, J=2.0, 11.2 Hz, 2H); 2.65 (s, 3H); 2.50 (dt, J=4.8, 13.6 Hz, 2H); 2.18 (dt, J=2.4, 9.6 Hz, 2H); 1.56 (dd, J=2.4, 10.8 Hz, 2H); MS (ESI) calcd for C$_{18}$H$_{24}$N$_2$O$_4$S (m/z): 364.15. found: 365.3 [M+1]$^+$.

Preparation of Compound C0097M

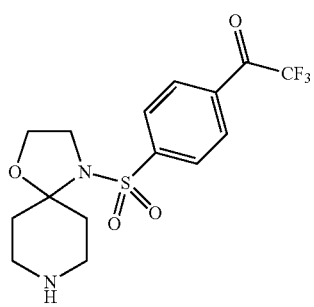

This compound is prepared using procedures illustrated elsewhere herein.

Preparation of Compound C0098M

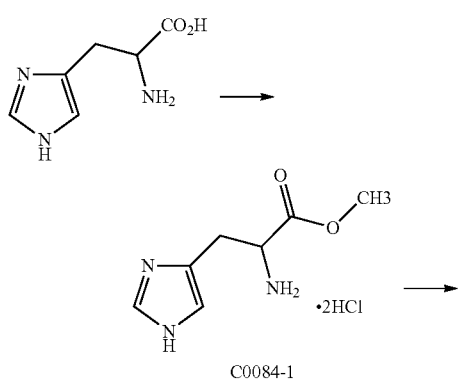

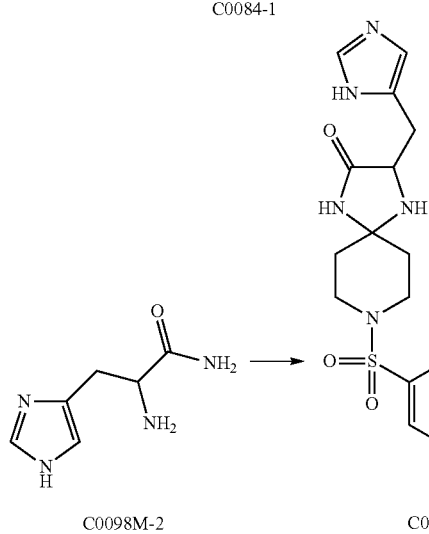

a. Preparation of Compound C0084-1

2-Amino-3-(1H-imidazol-4-yl)propanoic acid (5 g, 32.26 mmol) in HCl/CH$_3$OH (1N, 100 mL) was heated to reflux for 3 hours. The reaction mixture was concentrated to remove the solvent to obtain 7.5 g of the title product as white solid.

b. Preparation of Compound C0098M-2

220 mg of C0084-1 was dissolved in 10 mL of saturated NH$_4$OH (aq). The solution was stirred at room temperature overnight (about 18 hours). The solution was extracted with CHCl$_3$:CH$_2$OH=4:1 (6 times) and the water was evaporated. The residue was washed with acetone and CHCl$_3$ to obtain the crude product (the mixture of the product and NH$_4$Cl) as white solid (210 mg). The structure was confirmed by $^1$H NMR & LC-MS (target M+1=155, material M+1=170).

c. Preparation of Compound C0098M

C0098M-2 (200 mg, 1.3 mmol) was added to 1-(4-acetylphenylsulfonyl)-piperidin-4-one (365 mg, 1.3 mmol) in methanol (10 mL). The reaction was stirred at room temperature overnight (about 18 hours) and heated to reflux for 3 hours after which the solvent was removed in vacuo. The residue was purified by column chromatography to obtain the title product as a white solid (65 mg; yield: 17%). The structure was confirmed by $^1$H-NMR & LC-MS. Purity 98.3% by HPLC, shown as follows:

$^1$H NMR (400 MHz, DMSO): 11.74 (s, 1H); 8.47 (s, 0.8H); 8.18 (d, J=7.6 Hz, 2H); 7.88 (d, J=7.6 Hz, 2H); 7.44 (s, 1H); 7.15 (s, 0.2H); 6.99 (s, 0.2H); 6.72 (s, 0.8H); 3.51 (s, 1H); 3.19 (s, 2H); 2.95-2.56 (m, 7H); 1.61 (m, 3H); 1.46 (s, 1H); MS (ESI) calcd for C$_{19}$H$_{23}$N$_5$O$_4$S (m/z): 417.48. found: 418.3 [M+1]$^+$.

Preparation of Compound C0099M

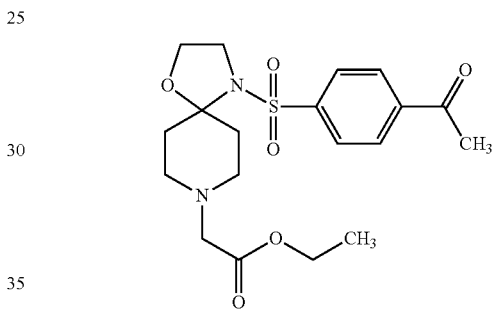

Prepared using procedures illustrated elsewhere herein.

$^1$H NMR (400 MHz, CDCl$_3$): 8.06 (d, J=8.4 Hz, 2H); 7.96 (d, J=8.4 Hz, 2H); 4.18 (q, J=6.8 Hz, 2H); 3.96 (t, J=6.4 Hz, 2H); 3.56 (t, J=6.8 Hz, 2H); 3.21 (s, 2H); 2.85 (dd, J=1.2, 8.8 Hz, 2H); 2.66 (s, 3H); 2.57-2.45 (m, 4H); 1.54 (d, J=11.2 Hz, 2H); 1.27 (t, J=6.8 Hz, 3H); MS (ESI) calcd for C$_{19}$H$_{26}$N$_2$O$_6$S (m/z): 410.15. found: 411.4 [M+1]$^+$.

Preparation of Compound C0100M

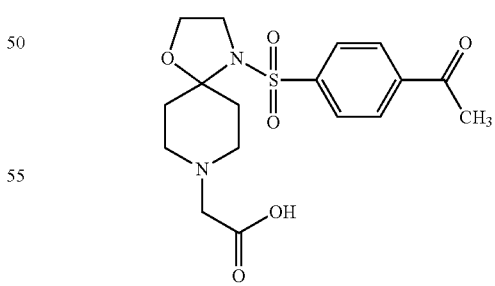

Prepared by hydrolysis of compound C0099M.

$^1$H NMR (400 MHz, CDCl$_3$): 8.07 (d, J=8.4 Hz, 2H); 7.91 (d, J=8.4 Hz, 2H); 3.91 (t, J=6.4 Hz, 2H); 3.47 (t, J=6.4 Hz, 2H); 3.39 (m, 4H); 2.94 (br, m, 2H); 2.63 (dt, J=4.8, 14.4 Hz, 2H); 2.55 (s, 3H); 1.73 (d, J=12.8 Hz, 2H); MS (ESI) calcd for C$_{17}$H$_{22}$N$_2$O$_6$S (m/z): 382.12. found: 383.2 [M+1]$^+$.

Preparation of Compound C0101M

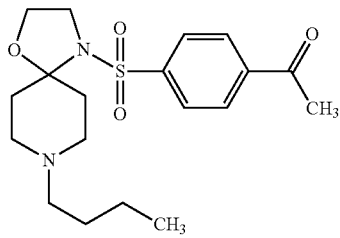 [SMILES: CCCCN1CCC2(CC1)OCCN2S(=O)(=O)c1ccc(C(C)=O)cc1]

Prepared using procedures illustrated elsewhere herein.

$^1$H NMR (400 MHz, CDCl$_3$): 8.06 (d, J=8.0 Hz, 2H); 7.95 (d, J=8.0 Hz, 2H); 3.96 (t, J=6.4 Hz, 2H); 3.56 (t, J=6.4 Hz, 2H); 2.81 (dd, J=2.0, 9.2 Hz, 2H); 2.66 (s, 3H); 2.48 (dt, J=2.0, 8.4 Hz, 2H); 2.32 (d, J=7.2 Hz, 2H); 2.17 (dt, J=1.6, 13.2 Hz, 2H); 1.55 (d, J=11.2 Hz, 2H); 1.47-1.43 (m, 2H); 1.34-1.28 (m, 2H); 0.92 (t, J=7.2 Hz, 3H); MS (ESI) calcd for C$_{19}$H$_{28}$N$_2$O$_4$S (m/z): 380.18. found: 381.4 [M+1]$^+$.

Preparation of Compound C0102M

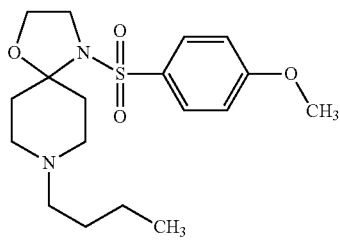 [SMILES: CCCCN1CCC2(CC1)OCCN2S(=O)(=O)c1ccc(OC)cc1]

Prepared using procedures illustrated elsewhere herein.

$^1$H NMR (400 MHz, CDCl$_3$): 7.80 (d, J=8.0 Hz, 2H); 6.96 (d, J=8.0 Hz, 2H); 3.93 (t, J=6.0 Hz, 2H); 3.86 (s, 3H); 3.49 (t, J=6.4 Hz, 2H); 2.81 (dt, J=2.0, 10.8 Hz, 2H); 2.49 (dt, J=4.8, 12.8 Hz, 2H); 2.33-2.29 (m, 2H); 2.16 (dt, J=2.8, 13.2 Hz, 2H); 1.57 (d, J=10.4 Hz, 2H); 1.47-1.42 (m, 2H); 1.34-1.28 (m, 2H); 0.91 (t, J=7.6 Hz, 3H); MS (ESI) calcd for C$_{18}$H$_{28}$N$_2$O$_4$S (m/z): 368.18. found: 369.3 [M+1]$^+$.

Preparation of Compound C0104M

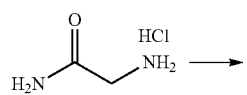

2-aminoacetamide
hydrochloride

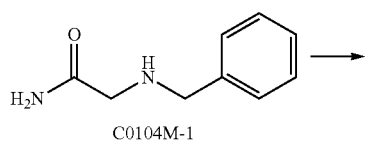

C0104M-1

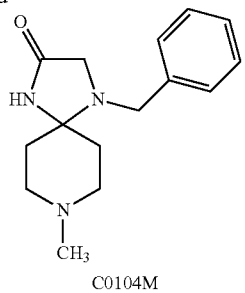

C0104M a. Preparation of Compound C0104M-1

A mixture of 2-aminoacetamide hydrochloride (2.0 g, 18 mmol), triethylamine (3.7 mL) and benzaldehyde (2.3 g, 22 mmol) in methanol (40 mL) was stirred overnight (about 18 hours) at room temperature. To the reaction mixture NaBH$_4$ (1.0 g) was added slowly. The reaction mixture was stirred for 1.5 hours until thin-layer chromatography showed the reaction complete. The solid was filtered. The filtrate was concentrated to remove the solvent. The residue was dissolved in water and ethyl acetate (EA). The mixture was extracted with EA and the organic layers were combined and dried and concentrated. Ether was added to the residue ether when the solid was appeared. The solid was dried to obtain the final product (1.3 g, Yield: 45%).

b. Preparation of Compound C0104M-1

C0104M-1 (100 mg, 0.61 mmol) was dissolved in methanol (5 mL) and 1-methyl-4-piperidone (69 mg, 0.61 mmol) was added, followed by triethylamine 0.085 mL, 0.61 mmol). The reaction mixture was stirred at reflux overnight (about 18 hours). The mixture was concentrated in vacuo to obtain the crude product. The crude product was purified by chromatography with CH$_2$Cl$_2$:CH$_2$OH=50:1 to 10:1 to obtain 75 mg of the title product as white solid (yield: 48%).

Preparation of Compound C0105M

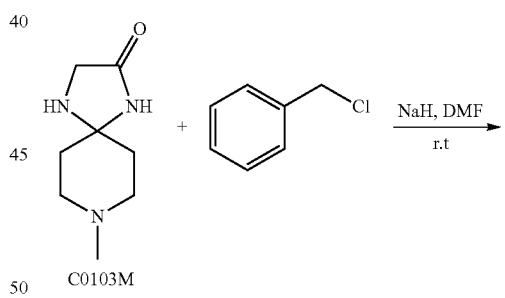

C0103M

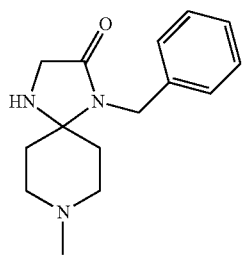

C0105M

C0103M (338 mg, 2.0 mmol) was dissolved in dimethylformamide (10 mL) and NaH (840 mg, 20.0 mmol) was added. The reaction mixture was stirred at room temperature for 1 hour. Then benzylchloride (253 mg, 2.0 mmol) was added, and the mixture was stirred at room temperature overnight (about 18 hours). H₂O was added to quench the reaction and the mixture was extracted with dichloromethane (DCM) (3×). The organic layer was washed with 1M HCl (3×) and the aqueous layer was washed with DCM, alkalized with 1M NaOH to pH 8, and extracted with DCM (3×). The organic layer was washed with saturated NaCl (1×), dried over Na₂SO₄, and then concentrated in vacuo to obtain the crude product. The crude product was purified by chromatography with DCM:actone=4:1 to 2:1 and DCM:CH₃OH=10:1 to 6:1 to obtain 110 mg of the product as colorless oil (110 mg, yield: 21.2%).

Preparation of Compound C0106M-1

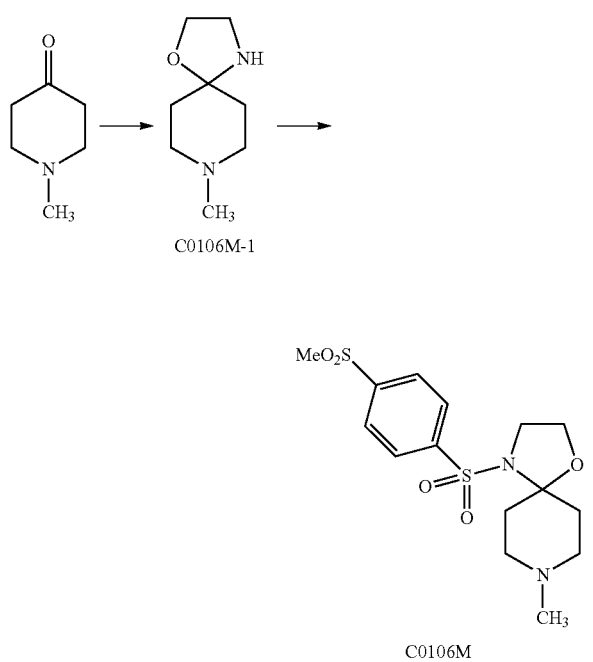

C0106M-1

C0106M a. Preparation of Compound C0106M-1

1-Methyl-4-piperidone (200 mg, 1.77 mmol) was dissolved in ethanol (2 mL), and ethanol amine (97 mg, 1.60 mmol) was added. The reaction mixture was stirred at room temperature overnight (about 18 hours). The reaction mixture was concentrated in vacuo to obtain the crude product. The crude product was used by next step without any purification (184 mg, yield: 66.6%).

a. Preparation of Compound C0106M

To the solution of compound C0106M-1 (184 mg, 1.18 mmol) in pyridine (2.5 mL) was added 4-methylsulfonylbenzenesulfonyl chloride (360 mg, 1.42 mmol). The mixture was stirred overnight (about 18 hours) at room temperature. The precipitated was filtrated to obtain the crude product. The crude product was purified by column chromatography to obtain 170 mg of the title product as light yellow solid (170 mg, yield: 38.5%).

¹H NMR (400 MHz, CD₃OD): 8.09-8.02 (m, 4H); 3.92 (t, J=6.4 Hz, 2H); 3.48 (t, J=6.8 Hz, 2H); 3.19-3.15 (m, 2H); 3.08 (s, 3H); 2.91-2.83 (m, 2H); 2.59 (s, 3H); 2.58-2.51 (m, 2H); 1.75 (d, J=14.8 Hz, 2H); calcd for C₁₅H₂₂N₂O₅S₂ (m/z): 374.1. found: 375.2 [M+1]⁺.

Preparation of Compound C0108M

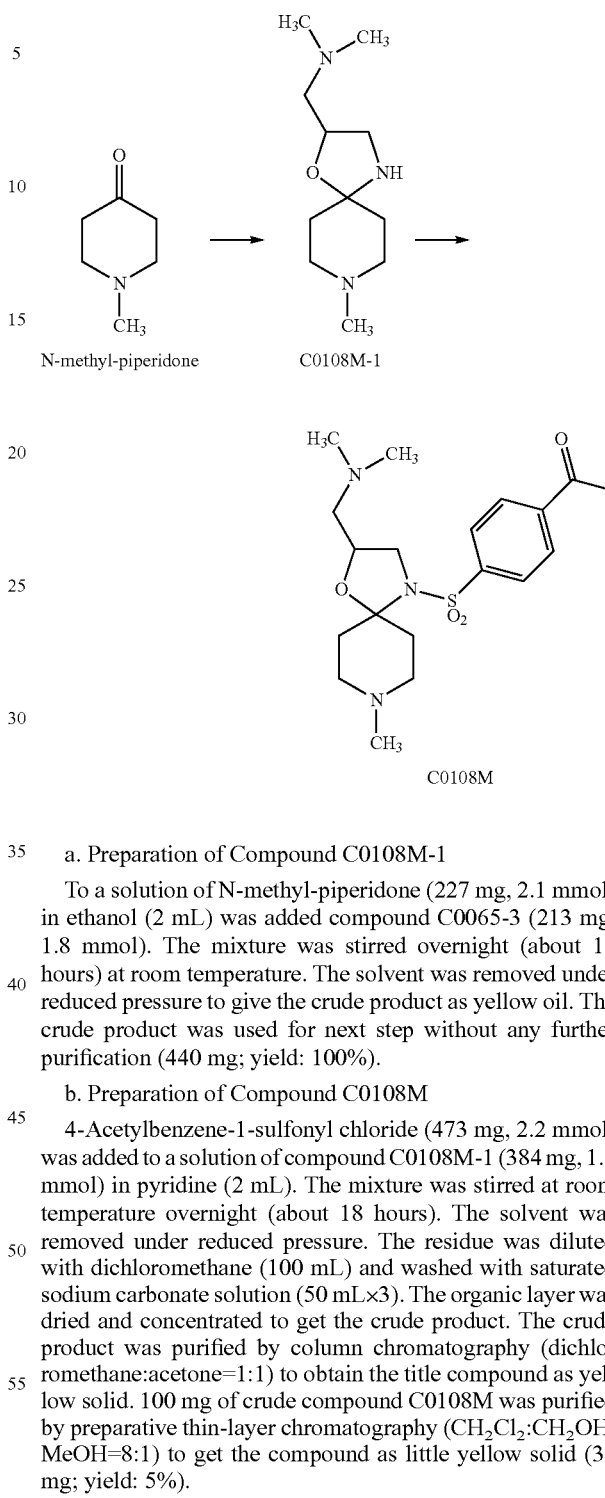

N-methyl-piperidone

C0108M-1

C0108M a. Preparation of Compound C0108M-1

To a solution of N-methyl-piperidone (227 mg, 2.1 mmol) in ethanol (2 mL) was added compound C0065-3 (213 mg, 1.8 mmol). The mixture was stirred overnight (about 18 hours) at room temperature. The solvent was removed under reduced pressure to give the crude product as yellow oil. The crude product was used for next step without any further purification (440 mg; yield: 100%).

b. Preparation of Compound C0108M

4-Acetylbenzene-1-sulfonyl chloride (473 mg, 2.2 mmol) was added to a solution of compound C0108M-1 (384 mg, 1.8 mmol) in pyridine (2 mL). The mixture was stirred at room temperature overnight (about 18 hours). The solvent was removed under reduced pressure. The residue was diluted with dichloromethane (100 mL) and washed with saturated sodium carbonate solution (50 mL×3). The organic layer was dried and concentrated to get the crude product. The crude product was purified by column chromatography (dichloromethane:acetone=1:1) to obtain the title compound as yellow solid. 100 mg of crude compound C0108M was purified by preparative thin-layer chromatography (CH₂Cl₂:CH₂OH:MeOH=8:1) to get the compound as little yellow solid (35 mg; yield: 5%).

¹H NMR (400 MHz, CDCl₃): 8.07 (d, J=8.4 Hz, 2H); 7.96 (d, J=8.4 Hz, 2H); 4.24-4.20 (m, 1H); 3.75 (dd, J=8.4, 5.6 Hz, 1H); 3.11 (t, J=8.8 Hz, 1H); 2.74 (m, 2H); 2.66 (s, 3H); 2.61 (dd, J=12.8, 4.4 Hz, 1H); 2.46 (d, J=5.6 Hz, 2H); 2.40 (dd, J=13.2, 4.4 Hz, 1H); 2.27 (s, 3H), 2.26 (s, 3H), 2.24-2.18 (m, 5H); 1.72 (d, J=10.8 Hz, 1H); 1.41 (d, J=10.8 Hz, 1H); LCMS (ESI) calcd for C₁₉H₂₉N₃O₄S (m/z): 395.52. found: 396.4 [M+1]⁺.

Preparation of Compound C0109M

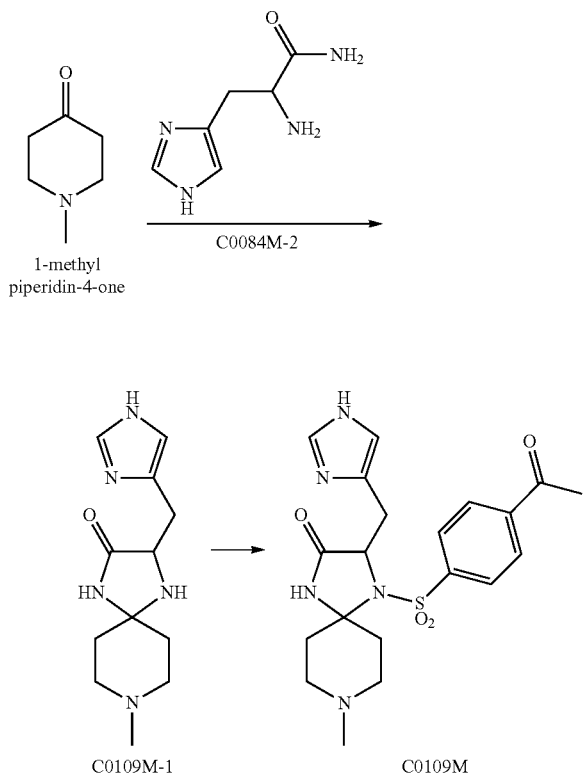

a. Preparation of Compound C0109M-1

To a solution of compound C0084M-2 (617 mg, 4.0 mmol) in methanol (15 mL) was added 1-methylpiperidin-4-one (227 mg, 2.0 mmol). The mixture was stirred at 70° C. overnight (about 18 hours). The solvent was removed under reduced pressure. The residue was purified by column chromatography (dichloromethane:methanol=2:1) to obtain the title compound as yellow solid (130 mg; yield: 26%).

Preparation of Compound C0111M

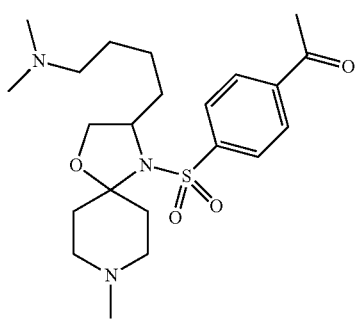

This compound is prepared using procedures illustrated elsewhere herein.

Preparation of Compound C0114M

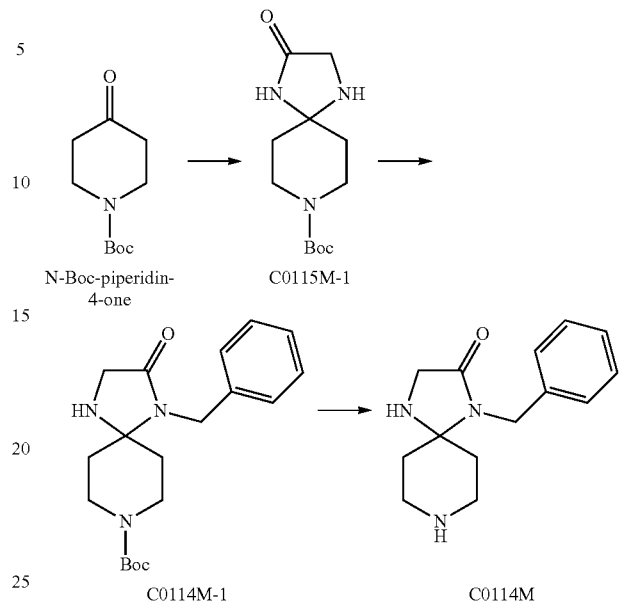

a. Preparation of Compound C0115M-1

A stirred solution of glycinamide hydrochloride (1.65 g, 15 mmol) in triethylamine (2.1 mL) and methanol (50 mL) was treated with N-Boc-piperidin-4-one (3.0 g, 15 mmol). The reaction was stirred under reflux overnight (about 18 hours) after which the solvent was removed in vacuo. The residue was purified by column chromatography ($CH_2Cl_2$ to $CH_2Cl_2$:$CH_2OH$=10:1) to obtain the title product as white solid (3.04 g; yield: 79%). The structure was confirmed by $^1$H NMR.

b. Preparation of Compound C0114M-1

To a solution of C0115M-1 (100 mg, 0.4 mmol) in dimethylformamide (DMF) (2.5 mL), was added 64 mg of NaH as 60% dispersion in mineral oil. The mixture was stirred at room temperature for 1 hour. Then a solution of dichloromethane (55 mg, 0.32 mmol) in 0.5 mL of absolute DMF was added dropwise. The mixture was stirred overnight (about 18 hours). Water was added and the solution was extracted with dichloromethane. The organic layer was washed with water, dried over anhydrous $Na_2SO_4$ and concentrated. The residue was purified by preparative thin-layer chromatography ($CH_2Cl_2$:$CH_2OH$:MeOH=30:1) to obtain the crude product as yellow oil (target M+1=345) (30 mg). Judged by $^1$H NMR & LC-MS, the product was a mixture of the following 2 compounds.

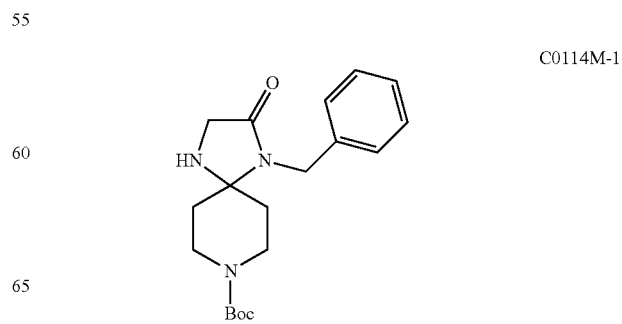

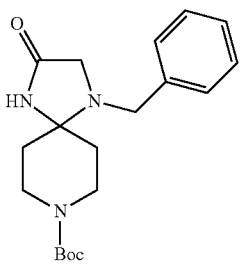

The mixture was purified by preparative thin-layer chromatography (dichloromethane:acetone=4:1) to obtain the title product as yellow oil (9 mg).

c. Preparation of Compound C0114M

To the solution of C0114M (200 mg, 0.58 mmol) in 3.0 mL of dichloromethane was add 0.3 mL of CF$_3$COOH and the mixture was stirred for 1 hour at room temperature. Then CH$_3$CH$_2$OH/NH$_3$ was added and the solvent was removed under reduced pressure. 10 mL of dichloromethane was added and white solid formed. The mixture was filtered and the filtrate was concentrated under reduced pressure. The residue was purified with column chromatography using a stationary phase of aluminum oxide (CH$_2$Cl$_2$:CH$_3$OH=100:1 to 30:1) to obtain the title product as colorless oil (30 mg, yield: 21%).

$^1$H NMR (400 MHz, CDCl$_3$): 7.32-7.23 (m, 5H); 4.46 (s, 2H); 3.54 (s, 2H); 2.99-2.89 (m, 4H); 2.02 (s, 2H); 1.86-1.79 (m, 2H); 1.43-1.40 (m, 2H); MS (ESI) calcd for C$_{14}$H$_{19}$N$_3$O (m/z): 245.32. found: 246.3 [M+1]$^+$.

Preparation of Compound C0115M b. Preparation of Compound C0115M-2

To a solution of C0115M-1 (306 mg, 1.2 mmol) in dimethylformamide (5.0 mL) was added 1-(bromomethyl)benzene (225 mg, 1.32 mmol). The mixture was allowed to stir at room temperature overnight (about 18 hours). Water was added and white solid was formed. The mixture was filtered and the collected solid was washed with water and n-hexane. Then the solid was dried to obtain the title product as white solid (200 mg, Yield: 48%, confirmed by $^1$H NMR).

c. Preparation of Compound C0115M

To the solution of C0115M-2 (200 mg, 0.58 mmol) in 3.0 mL of dichloromethane was add 0.3 mL of CF$_3$COOH and the mixture was kept stirring for 1 hour at room temperature. The solvent was removed under reduced pressure quickly and CH$_2$Cl$_2$OH/NH$_3$ was added. Thin-layer chromatography suggested there was new compound formed. The solvent was removed under reduced pressure and the residue was purified with aluminum oxide chromatography (CH$_2$Cl$_2$: CH$_2$OH=100:1 to 5:1) to obtain the 2 batches of product as white solid (40 mg, yield: 28%, HPLC: 90%; 30 mg, yield: 21%, HPLC: 82%). The 40 mg of sample C0115 was recrystallized with chloroform and n-hexane to obtain the title product as white solid (19 mg, yield 14%). The structure was confirmed by $^1$H NMR and LC-MS (target M+1=246).

$^1$H NMR (400 MHz, CDCl$_3$): 8.18 (s, 1H); 7.34-7.24 (m, 5H); 3.77 (s, 2H); 3.23 (s, 2H); 3.15 (d, J=12.0 Hz, 2H); 2.77 (t, J=12.0 Hz, 2H); 1.98-1.91 (m, 2H); 1.73-1.68 (m, 2H); MS (ESI) calcd for C$_{14}$H$_{19}$N$_3$O (m/z): 245.32. found: 246.3 [M+1]$^+$.

Preparation of Compound C0116M

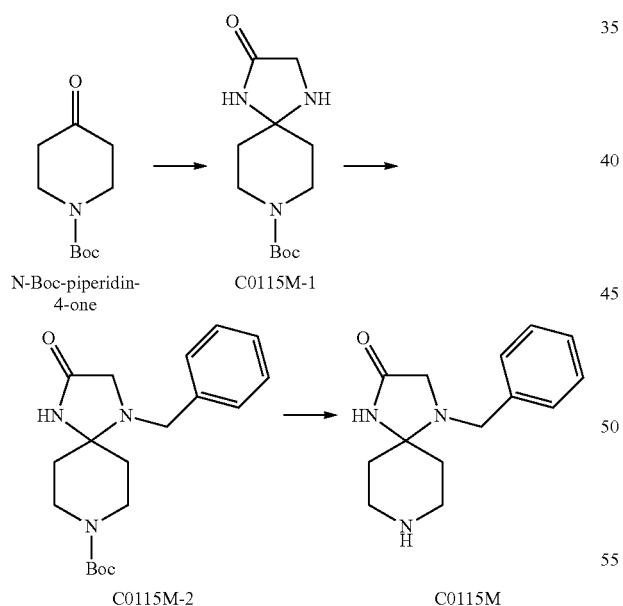

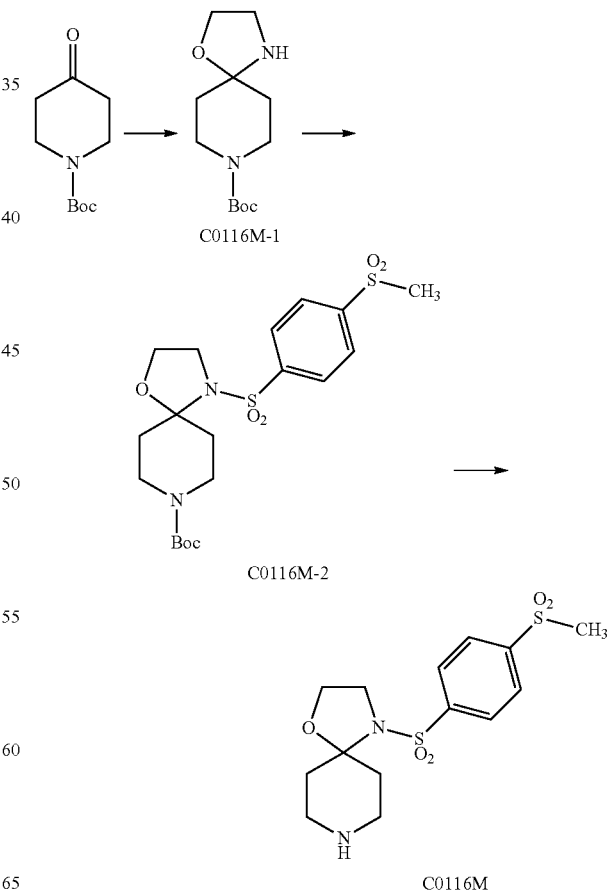

a. Preparation of Compound C0115M-1

N-Boc-piperidin-4-one (3.0 g, 15 mmol) was added to a stirred solution of glycinamide hydrochloride (1.65 g, 15 mmol) in triethylamine (2.1 mL) and methanol (50 mL). The reaction was stirred under reflux overnight (about 18 hours) after which the solvent was removed in vacuo. The residue was purified by column chromatography (CH$_2$Cl$_2$ to CH$_2$Cl$_2$: CH$_2$OH=10:1) to obtain the title product as white solid (3.04 g; yield: 79%).

a. Preparation of Compound C0116M-1

To a solution of N-Boc-piperidin-4-one (0.3 g, 1.5 mmol) in ethanol (3.0 mL) was added ethanolamine (0.3 mL). The mixture was stirred overnight (about 18 hour) at room temperature. The solvent was removed under reduced pressure. The residue was diluted with $CH_2Cl_2$ and washed with saturated aqueous $Na_2CO_3$. The organic phase was dried over anhydrous $Na_2SO_4$, concentrated to obtain the title product as yellow oil (327 mg, yield: 90%)

b. Preparation of Compound C0116M-2

4-(Methylsulfonyl)-benzene-1-sulfonyl chloride (305 mg, 1.2 mmol) was added to a solution of C0116-1 (242 mg, 1.0 mmol) in pyridine (2.0 mL). The mixture was stirred at room temperature overnight (about 18 hours). The solvent was removed under reduced pressure. The residue was diluted with $CH_2Cl_2$ and washed with saturated $NaHCO_3$. The organic phase was dried over anhydrous $Na_2SO_4$ and concentrated to give the crude product as yellow solid, which was purified with column chromatography ($CH_2Cl_2$ to $CH_2Cl_2$:$CH_2OH$=50:1) to give the title compound as a white solid (270 mg, yield: 58%, $^1$H NMR confirmed, confirmed by $^1$H NMR and LC/MS (target M+23=483).

c. Preparation of Compound C0116M

To the solution of C0016M-2 (270 mg, 0.58 mmol) in 3.0 mL dichloromethane (DCM) was add 0.3 mL $CF_3COOH$ and the mixture was kept stirring for 1 hour at room temperature. The mixture was added DCM and washed with saturated sodium carbonate solution. The organic layer was dried and concentrated to get the crude product as yellow gum. The crude product was purified by column chromatography ($CH_2Cl_2$:$CH_2OH$=100:1 to 10:1) to obtain the product as yellow solid (70 mg, yield: 34%).

$^1$H NMR (400 MHz, $CDCl_3$): 8.12-8.07 (m, 4H); 4.01 (t, J=6.0 Hz, 2H); 3.55 (t, J=6.0 Hz, 2H); 3.11 (s, 3H); 3.04-3.00 (m, 2H); 2.86-2.79 (m, 2H); 2.35-2.28 (m, 2H); 1.63-1.60 (m, 2H); calcd for $C_{14}H_{20}N_2O_5S_2$ (m/z): 360.45. found: 361.2 $[M+1]^+$.

Preparation of Compound C0118M

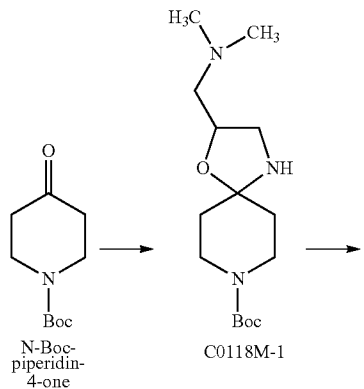

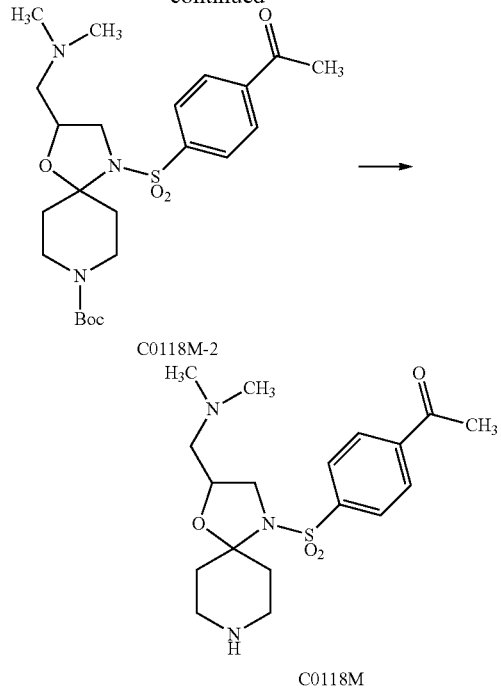

a. Preparation of Compound C0118M-1

To a solution of N-Boc-piperidin-4-one (420 mg, 2.1 mmol) in ethanol (4 mL) was added compound C0065-3 (500 mg, 4.2 mmol). The mixture was stirred overnight (about 18 hours) at room temperature. The solvent was removed under reduced pressure. The residue was diluted with $CH_2Cl_2$ (50 mL) and washed with saturated aqueous $Na_2CO_3$ (30 mL×6). The organic phase was dried over anhydrous $Na_2SO_4$, and concentrated to give compound C0118M-1 as yellow oil (600 mg; yield: 95%).

b. Preparation of Compound C0118M-2

4-Acetylbenzene-1-sulfonyl chloride (525 mg, 2.4 mmol) was added to a solution of compound C0118M-1 (600 mg, 2 mmol) in pyridine (2 mL). The mixture was stirred at room temperature overnight (about 18 hours). The solvent was removed under reduced pressure. The residue was purified by column chromatography (dichloromethane:acetone=3:1) to obtain the title compound as light yellow solid (610 mg; yield: 63.4%).

c. Preparation of Compound C0118M

To the solution of compound C0118M-2 (610 mg, 1.26 mmol) in 10 mL dichloromethane (DCM) was added 0.5 mL $CF_3COOH$ and the mixture was stirred for 1 hour at room temperature. Then DCM (30 mL) was added to the mixture, and the resulting mixture washed with saturated sodium carbonate solution (30 mL×3). The organic layer was dried and concentrated to get the crude product. The crude product was purified by column chromatography ($CH_2Cl_2$:$CH_3CH_2OH$=10:1 to $CH_3OH$) to obtain the title compound as light yellow solid (60 mg; yield: 12.5%).

$^1$H NMR (400 MHz, $CDCl_3$): 8.07 (d, J=8.4 Hz, 2H); 7.96 (d, J=8.4 Hz, 2H); 4.27-4.21 (m, 1H); 3.73 (dd, J=8.4, 5.6 Hz, 1H); 3.08 (t, J=8.8 Hz, 1H); 3.04-2.94 (m, 2H), 2.83 (t, J=11.6 Hz, 2H); 2.66 (s, 3H); 2.46 (d, J=5.6 Hz, 2H); 2.41 (dd, J=12.4, 5.2 Hz, 1H); 2.26 (s, 6H); 2.20 (dd, J=12.8, 4.8 Hz, 1H); 1.78 (d, J=13.2 Hz, 1H); 1.45 (d, J=12.8 Hz, 1H); LCMS (ESI) calcd for $C_{18}H_{27}N_3O_4S$ (m/z): 381.49. found: 382.4 $[M+1]^+$.

Preparation of Compound C0119M

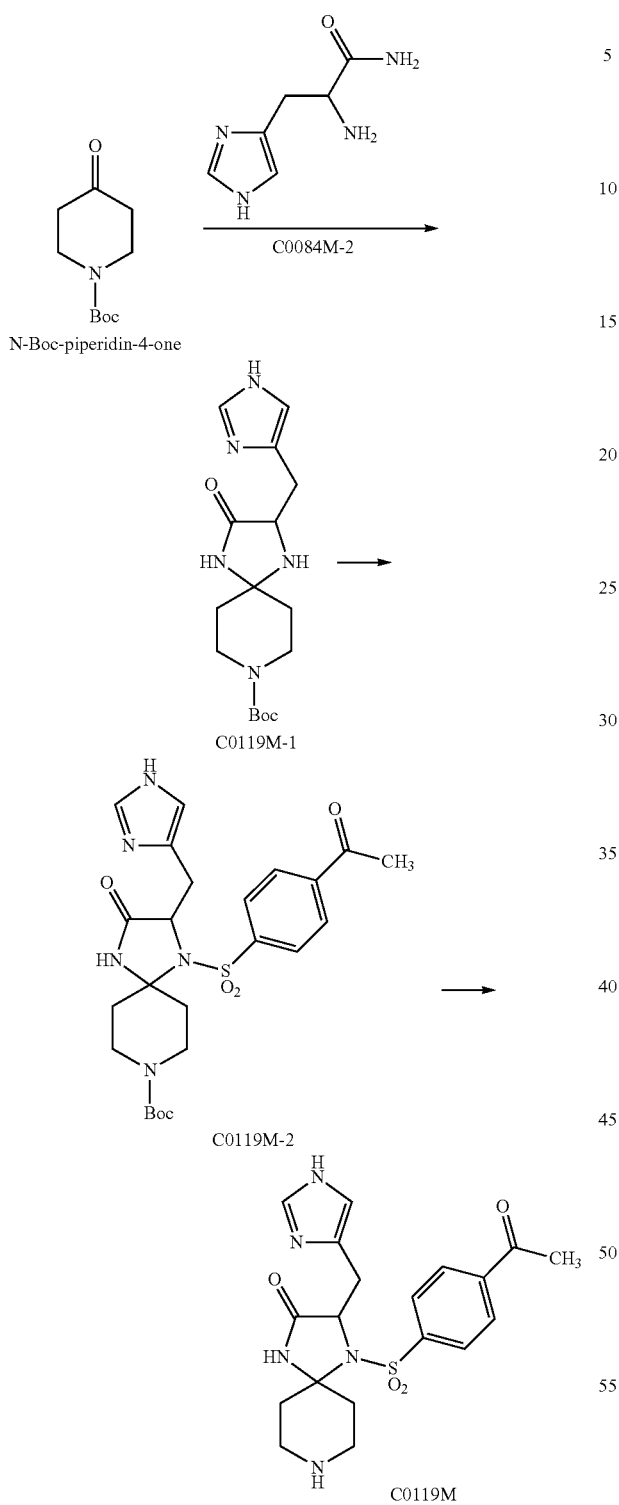

a. Preparation of Compound C0119M-1

N-Boc-piperidin-4-one (797 mg, 4.0 mmol) was added to a solution of compound C0084M-2 (617 mg, 4.0 mmol) in methanol (15 mL). The mixture was stirred at 70° C. overnight (about 18 hours). The solvent was removed under reduced pressure. The residue was purified by column chromatography ($CH_2Cl_2$:$CH_3OH$=8:1) to obtain the title compound as white solid (300 mg; yield: 22.4%).

b. Preparation of Compound C0119M-2

4-Acetyl-benzene-1-sulfonyl chloride (149 mg, 0.68 mmol) and triethylamine (1 mL) was added to a solution of compound C0119M-1 (190 mg, 0.57 mmol) in chloroform (5 mL). The mixture was stirred under reflux overnight (about 18 hours). The solvent was removed under reduced pressure. The residue was purified by column chromatography (dichloromethane:acetone=3:1) to obtain the product as white solid (250 mg; yield: 84%).

c. Preparation of Compound C0119M

To the solution of compound C0119M-2 (330 mg, 0.63 mmol) in 3.5 mL dichloromethane (DCM) was add $CF_3COOH$ (0.35 mL) and the mixture was kept stirring for 1 hour at room temperature. Then $CH_3CH_2OH/NH_3$ (20 mL) was added to the reaction mixture. The solvent was removed under reduced pressure. The residue was diluted with dichloromethane (20 mL) and the white solid was precipitated. TLC showed that the solid was $CF_3COONH_4$. The mixture was filtered and the filtrate was concentrated. The residue was purified by column chromatography ($CH_2Cl_2$:$CH_3OH$=8:1) to obtain the product as white solid (80 mg; yield: 30%).

$^1$H NMR (400 MHz, $CD_3OD$): 8.17 (s, 1H); 8.11 (m, 4H); 7.36 (s, 1H); 3.78 (dd, J=8.0, 4.0 Hz, 1H); 3.22-3.11 (m, 6H); 2.89 (dd, J=15.2, 4.0 Hz, 1H); 2.67 (dd, J=15.2, 8.0 Hz, 1H); 2.56 (s, 3H); 1.89-1.73 (m, 3H); LCMS (ESI) calcd for $C_{19}H_{23}N_5O_4S$ (m/z): 417.48. found: 418.5 [M+1]$^+$.

Preparation of Compound C0124M

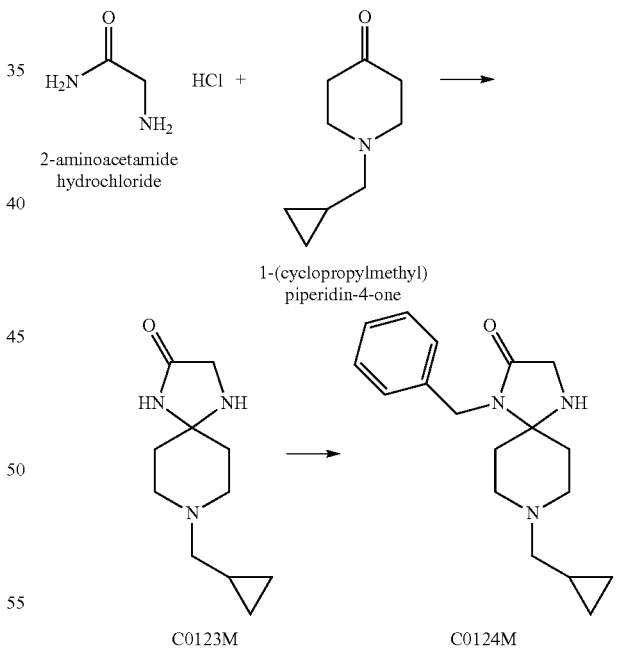

a. Preparation of Compound C0123M

2-Aminoacetamide hydrochloride (1 g, 9.09 mmol), 1-(cyclopropylmethyl)piperidin-4-one (1.4 g, 9.09) and triethylamine (1.26 mL, 9.09 mmol) in $CH_3OH$ (40 mL) were heated to reflux overnight (about 18 hours). The mixture was concentrated to afford the crude product. The crude product was purified via column chromatography ($CH_2Cl_2$:$CH_3OH$=100/1 to 5/1) to afford the final product (1.3 g, Yield: 71%).

b. Preparation of Compound C0124M

To a mixture of C0123M (300 mg, 1.44 mmol) in dimethylformamide (15 mL) was added NaH (574 mg, 14.4 mmol) slowly. The mixture was stirred for 1.5 hours. Benzyl chloride (146 mg, 1.15 mmol) was added slowly and the mixture was stirred overnight (about 18 hours). Water (15 mL) was added slowly to the mixture and the resulting mixture was extracted with dichloromethane. The organic layer was dried, concentrated to afford the impure product. The impure product was purified via column chromatography ($CH_2Cl_2$ to $CH_2Cl_2$: $CH_3COCH_3$=4/1 to 2/1 to $CH_2Cl_2$:$CH_3CO$=10/1 to $CHCl_3$/$CH_3OH$=1/1) to obtain the final product (45 mg, yield: 10%). The structure was confirmed by $^1$H NMR & LC-MS (target: M+1=300), purity: 95.3% by HPLC.

$^1$H NMR (400 MHz, $CDCl_3$): 7.30-7.22 (m, 5H); 4.46 (s, 2H); 3.54 (s, 2H); 2.98 (d, J=10.8 Hz, 2H); 2.29-2.26 (m, 4H); 2.05-20.2 (m, 2H); 1.43-1.40 (d, J=11.6 Hz, 2H); 0.86-0.83 (m, 1H); 0.54-0.49 (m, 2H); 0.10-0.06 (m, 2H). LCMS (ESI) calcd for $C_{18}H_{25}N_3O$ (m/z): 299.41. found: 300.4 [M+1]$^+$.

Preparation of Compound C0125M

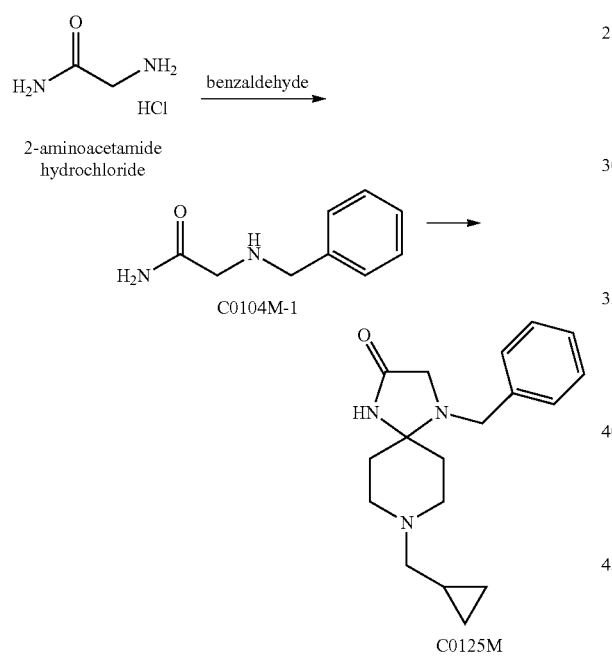

A mixture of C0104M-1 (350 mg, 2.13 mmol), 1-(cyclopropylmethyl)piperidin-4-one (326 mg, 2.13 mmol) and p-toluenesulfonic acid (10 mg) in methanol (15 mL) was heated to reflux overnight (about 18 hours). Thin-layer chromatography suggested the reaction complete. The solvent was removed. The residue was dissolved in DCM and washed with saturated aqueous $NaHCO_3$, dried, concentrated to afford the impure product (590 mg, yield: 930). 150 mg of the impure product was purified via pre-HPLC to obtain the final product (80 mg, yield: 60%).

$^1$H NMR (400 MHz, $CDCl_3$): 7.68 (s, 1H); 7.37-7.24 (m, 5H); 3.76 (s, 2H); 3.20 (s, 2H); 3.18 (d, J=8.8 Hz, 2H); 2.32 (d, J=6.0 Hz, 2H); 2.14-2.06 (m, 4H); 1.71 (d, J=10.0 Hz, 2H); 0.89-0.86 (m, 1H); 0.56-0.51 (m, 2H); 0.14-0.10 (m, 2H). LCMS (ESI) calcd for $C_{18}H_{25}N_3O$ (m/z): 299.41. found: 300.5 [M+1]$^+$.

Preparation of Compound C0126M

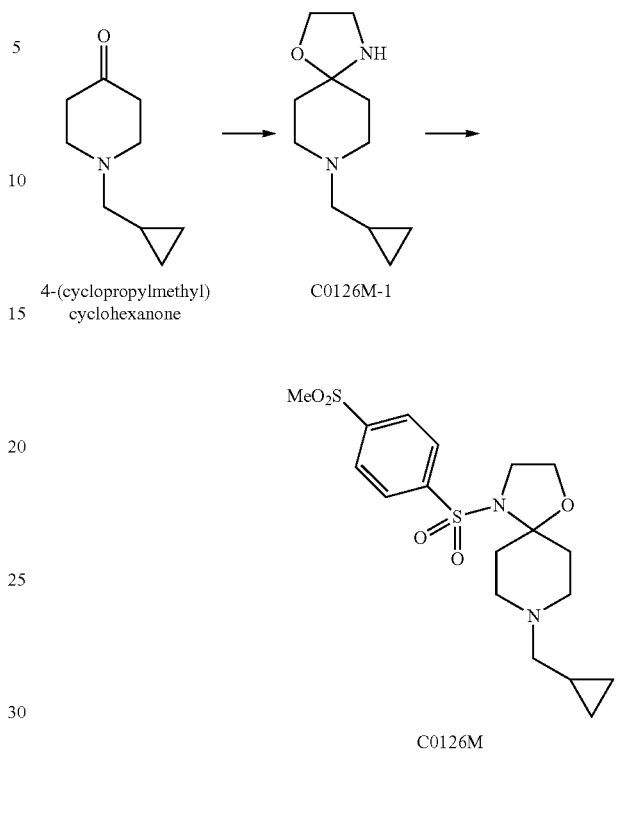

a. Preparation of Compound C0126M-1

A mixture of 4-(cyclopropylmethyl)-cyclohexanone (1 g, 6.5 mmol) and ethanolamine (4 mL, 65 mmol) in $CH_3CH_2OH$ (20 mL) was stirred overnight (about 18 hours) at room temperature. The mixture was concentrated to remove the solvent. The residue was dissolved in $CH_2Cl_2$ and washed with saturated aqueous of $Na_2CO_3$, dried, and concentrated to afford the final product without any purification (1.06 g, Yield: 84%). The product's identity was confirmed by $^1$H NMR and MS (target M+1=197).

b. Preparation of Compound C0126M

A mixture of C0126M-1 (122 mg, 0.63 mmol) and 4-(methyl sulfonyl)benzene-1-sulfonyl chloride (200 mg, 0.69 mmol) in triethylamine (0.1 mL, 0.69 mmol) and $CHCl_3$ (2.4 mL) was stirred overnight (about 18 hours) at room temperature. The solvent was removed. The residue was washed with diethyl ether (3×) and the 1N HCl was added to the residue until pH=1. The mixture wad washed with diethyl ether (2×). Then 1N NaOH was added until a precipitate formed (pH=12). The solid was filtered and dissolved in $CHCl_3$, dried with $Na_2SO_4$, and concentrated to afford the final product (28 mg, Yield: 11%). The structure was confirmed by $^1$H NMR & MS (target: M+1=415), purity 95.3% by HPLC.

$^1$H NMR (400 MHz, $CDCl_3$): 8.07 (s, 4H); 3.97 (t, J=6.4 Hz, 2H); 3.55 (t, J=6.4 Hz, 2H); 3.09 (s, 3H); 2.99 (dd, J=9.2 Hz, 2.4 Hz, 2H); 2.51 (td, J=12.8 Hz, 4 Hz, 2H); 2.27-2.19 (m, 4H); 1.56 (d, J=11.6 Hz, 2H); 0.87-0.84 (m, 1H); 0.52-0.48 (m, 2H); 0.09-0.07 (m, 2H). MS (ESI) calcd for $C_{18}H_{26}N_2O_5S_2$ (m/z): 414.54. found: 415.3 [M+1]$^+$.

Preparation of Compound C0128M

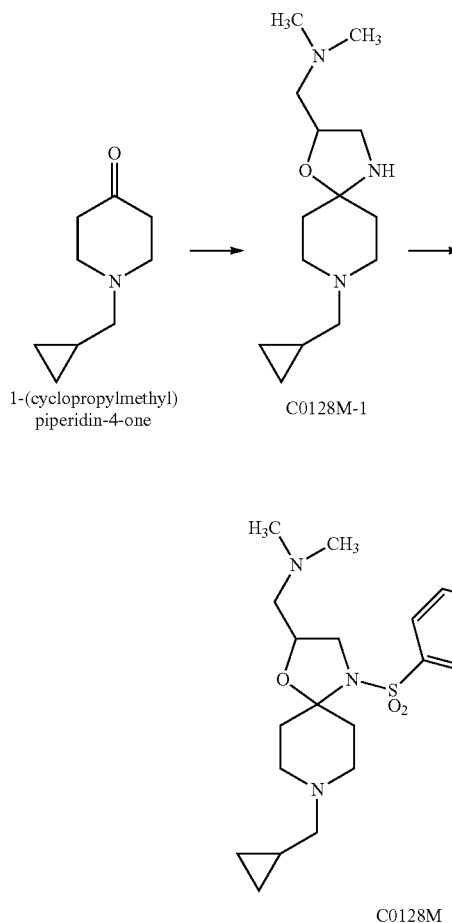

C0128M a. Preparation of Compound C0128M-1

Compound C0065-3 (213 mg, 1.8 mmol) was added N-(cyclopropylmethyl)-piperidine-4-one (306 mg, 2.1 mmol) in ethanol (2 mL). The mixture was stirred overnight (about 18 hours) at room temperature. The solvent was removed under reduced pressure to give the crude product as yellow oil. The crude product was used for next step without any further purification (519 mg; yield: 100%).

b. Preparation of Compound C0128M

To a solution of compound C0128M-1 (456 mg, 1.8 mmol) in pyridine (2 mL) was added 4-acetylbenzene-1-sulfonyl chloride (473 mg, 2.2 mmol). The mixture was stirred at room temperature overnight (about 18 hours). The solvent was removed under reduced pressure. The residue was diluted with $CH_2Cl_2$ (100 mL) and washed with saturated sodium carbonate solution (50 mL×3). Then the organic layer was dried and concentrated to get the crude product as dark oil (700 mg).

$^1$H NMR (400 MHz, $CDCl_3$): 8.05 (d, J=8.8 Hz, 2H); 7.97 (d, J=8.8 Hz, 2H); 4.26-4.19 (m, 1H); 3.76 (dd, J=8.7, 5.6 Hz, 1H); 3.11 (t, J=8.8 Hz, 1H); 2.97 (m, 2H); 2.66 (s, 3H); 2.61 (dd, J=12.8, 4.4 Hz, 1H); 2.45 (dd, J=5.6, 1.5 Hz, 2H); 2.39 (dd, J=13.0, 4.4 Hz, 1H); 2.26-2.15 (m, 10H); 1.75 (m, 1H); 1.44-1.37 (m, 1H); 0.86 (m, 1H); 0.54-0.45 (m, 2H); 0.09 (m, 2H); LCMS (ESI) calcd for $C_{22}H_{33}N_3O_4S$ (m/z): 435.58. found: 436.4 [M+1]$^+$.

Preparation of Compound C0129M

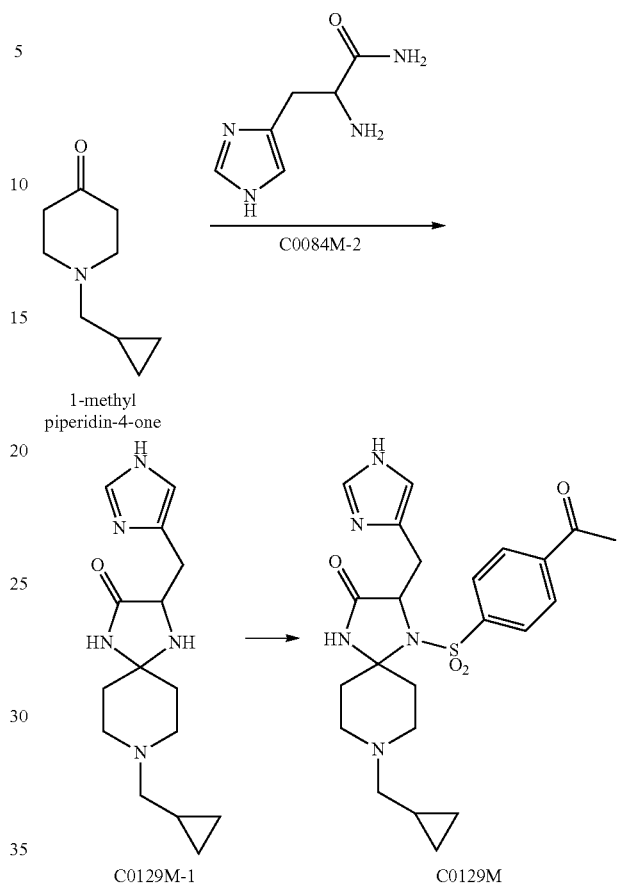

a. Preparation of Compound C0129M-1

Run 1: To a solution of compound C0084M-2 (617 mg, 4.0 mmol) in methanol (15 mL) was added 1-(cyclopropylmethyl)piperidin-4-one (307 mg, 2.0 mmol). The mixture was stirred at 70° C. overnight. The solvent was removed under reduced pressure. The residue was purified by column chromatography (dichloromethane:methanol=3:1) to obtain the unknown compound as yellow solid (300 mg).

Run 2: To a solution of compound C0084M-2 (309 mg, 2.0 mmol) in methanol (15 mL) was added 1-(cyclopropylmethyl)piperidin-4-one (341 mg, 2.2 mmol) and 4-methylbenzenesulfonic acid monohydrate (12 mg, 0.06 mmol). The mixture was stirred at room temperature overnight (about 18 hours). Then the reaction was refluxed for 7 hours. The solvent was removed under reduced pressure. The residue was purified by column chromatography (dichloromethane: methanol=3:1) to obtain the unknown compound as yellow solid (120 mg).

Preparation of Compound C0133M

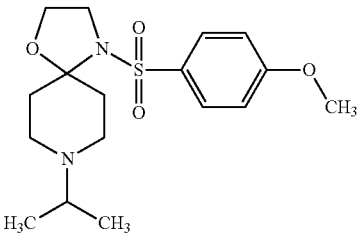 [SMILES: COc1ccc(S(=O)(=O)N2CCOC23CCN(C(C)C)CC3)cc1]

Prepared using methods discussed elsewhere herein.

$^1$H NMR (400 MHz, CDCl$_3$): 7.80 (d, J=9.2 Hz, 2H); 6.95 (d, J=8.8 Hz, 2H); 3.93 (t, J=5.6 Hz, 2H); 3.86 (s, 3H); 3.48 (t, J=6.8 Hz, 2H); 2.74 (m, 3H); 2.47-2.43 (m, 2H); 2.37-2.31 (m, 2H); 1.59 (d, J=11.6 Hz, 2H); 1.01 (d, J=6.0 Hz, 6H); MS (ESI) calcd for C$_{17}$H$_{26}$N$_2$O$_4$S (m/z): 354.16. found: 355.2 [M+1]$^+$.

Preparation of Compound C00134M

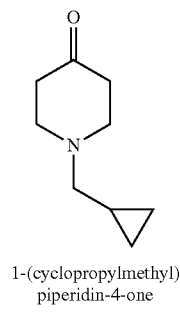

1-(cyclopropylmethyl)
piperidin-4-one

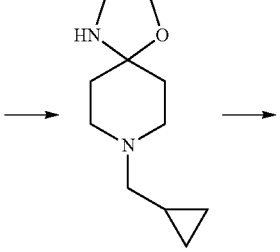

C0134M-1

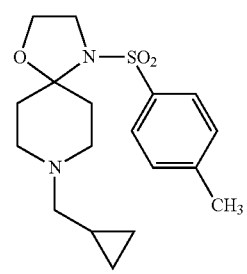

C0134M a. Preparation of Compound C0134M

A mixture of C0134M-1 (2.1 g, 10.7 mmol) and p-toluene-sulfonyl chloride (2.2 g, 11.8 mol) in triethylamine (1.64 mL, 11.8 mmol) and CHCl$_3$ (40 mL) was stirred overnight (about 18 hours) at room temperature. The mixture was washed with NaHCO$_3$, and the organic layer was concentrated to afford the crude product. The crude product was purified via column chromatography (CH$_2$Cl$_2$:CH$_3$COCH$_3$=100/1 to 1/1) to obtain the impure product as 2 samples. (210 mg, HPLC: 93%, yield: 6%; 400 mg, HPLC: 83%; yield: 11%). The impure product was further purified via preparative HPLC to obtain the final product (130 mg, yield: 3.7%).

$^1$H NMR (400 MHz, CDCl$_3$): 7.77 (d, J=8.0 Hz, 2H); 7.30 (d, J=8.0 Hz, 2H); 3.94 (t, J=6.4 Hz, 2H); 3.52 (t, J=6.4 Hz, 2H); 2.98 (m, 2H); 2.54 (td, J=13.2, 4.8 Hz, 2H); 2.42 (s, 3H); 2.27-2.21 (m, 4H); 1.58 (d, J=11.2 Hz, 2H); 0.89-0.84 (m, 1H); 0.53-0.49 (m, 2H); 0.10-0.04 (m, 2H). MS (ESI) calcd for C$_{18}$H$_{26}$N$_2$O$_3$S (m/z): 350.48. found: 351.2 [M+1]$^+$.

Preparation of Compound C0135M

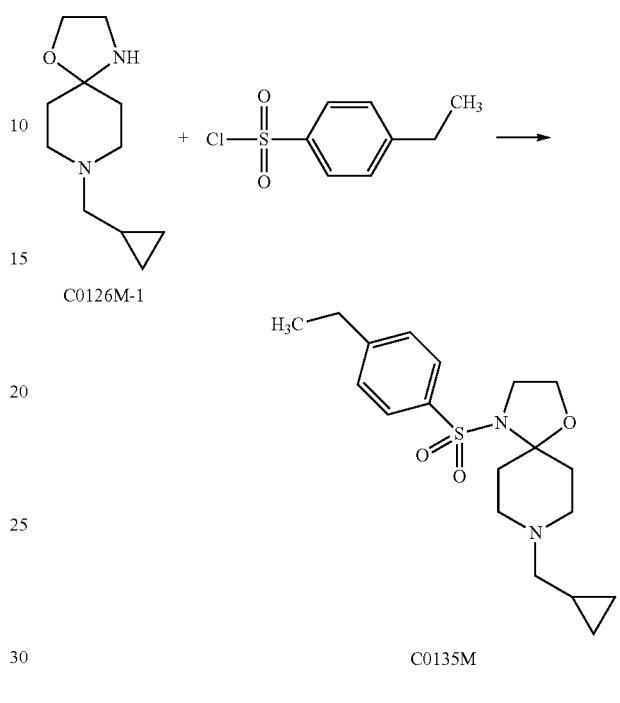

C0126M-1

C0135M

A mixture of compound C0126M-1 (378 mg, 1.92 mmol) and 4-ethylbenzene-1-sulfonyl chloride (433 mg, 2.12 mmol) in triethylamine (0.3 mL, 2.12 mmol) and CHCl$_3$ (7.6 mL) was stirred overnight (about 18 hours) at room temperature. The solvent was removed. The residue was dried to afford the impure product (630 mg). 360 mg of the impure product was purified via preparative thin-layer chromatography (ethyl acetate:ethanol=10/1) to afford the final product (25 mg, yield: 6%).

$^1$H NMR (400 MHz, CDCl$_3$): 7.79 (d, J=8.8 Hz, 2H); 7.31 (d, J=8.4 Hz, 2H); 3.94 (t, J=6.4 Hz, 2H); 3.52 (t, J=6.4 Hz, 2H); 3.00 (d, J=10.4 Hz, 2H); 2.70 (q, J=7.6 Hz, 2H); 2.56 (td, J=13.6, 4.4 Hz, 2H); 2.28-2.21 (m, 4H); 1.59 (d, J=11.6 Hz, 2H); 1.26 (t, J=7.6 Hz, 3H); 0.91-0.83 (m, 1H); 0.52-0.50 (m, 2H); 0.10-0.05 (m, 2H). MS (ESI) calcd for C$_{19}$H$_{28}$N$_2$O$_3$S (m/z): 364.5. found: 365.2 [M+1]$^+$.

Preparation of Compound C0136

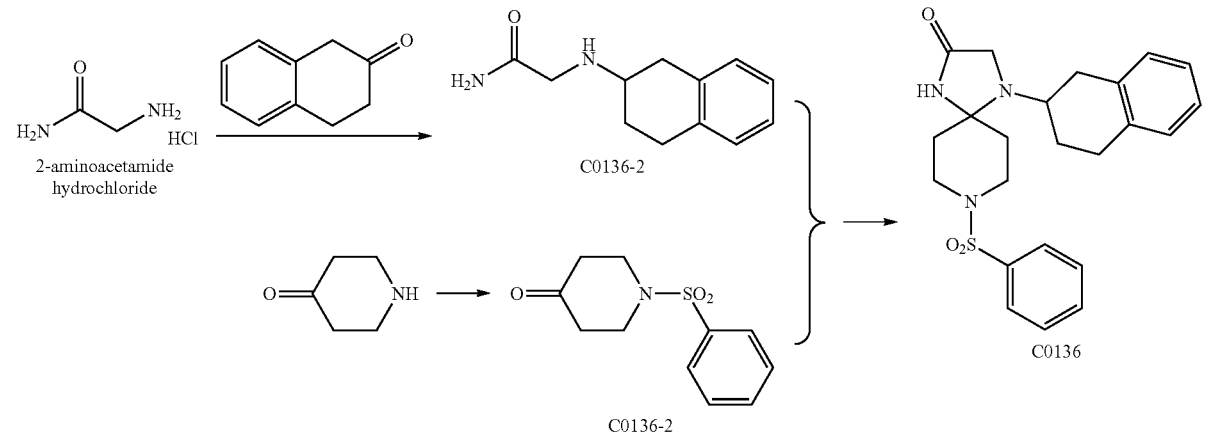

2-aminoacetamide
hydrochloride

C0136-2

C0136-2

C0136 a. Preparation of Compound C0136-1

Triethylamine (0.73 mL, 5.25 mmol) was added to the suspension of 2-aminoacetamide hydrochloride (553 mg, 5.0 mmol) in 10 mL of methanol at room temperature. Then, 2-tetralone (730 mg, 5.0 mmol) was added dropwise and the resulting mixture stirred overnight (about 18 hours) at room temperature. NaBH$_4$ (345 mg, 7.5 mmol) was added and stirred for 2 hours. After 2 hours, a white solid was removed via filtration and the filtrate was concentrated. Then 10 mL of water were added and the solution was extracted with ethyl acetate (EA) (20 mL×3). The organic phase was collected and dried over Na$_2$SO$_4$. The Na$_2$SO$_4$ was removed and ethyl acetate was removed via evaporation. 0.5 M HCl was added to the ether phase until the aqueous layer was pH=3. The aqueous phase was extracted with ether. Then 0.5 M NaOH was added to the aqueous phase until pH=8 and the aqueous phase was then extracted with ethyl acetate. The organic layer was collected and dried over Na$_2$SO$_4$. The Na$_2$SO$_4$ was removed and the filtrate was concentrated in vacuo to obtain the title product as purple solid (530 mg, yield: 52%).

b. Preparation of Compound C0136M-2

1.53 g of piperidin-4-one hydrochloride monohydrate was added in 50 mL of CHCl$_3$ and 4.2 mL of triethylamine was added. The mixture was heated to reflux for 0.5 hour. Then 1.28 mL of benzenesulfonyl chloride was added and the mixture was stirred at 70° C. for 4 hours. The solution was diluted with 50 mL of CHCl$_3$ and washed water (50 mL×3) and brine. The organic layer was dried over Na$_2$SO$_4$ and evaporated to dryness to obtain the title product as white solid. (1.76 g, yield: 74%).

c. Preparation of Compound C0136M

Compound C0136M-2 (251 mg, 1.05 mmol) was dissolved in isopropyl alcohol (10 mL) and C0136M-1 (204 mg, 1.00 mmol) was added. The reaction mixture was stirred at reflux for 3 days. The precipitate that formed was filtered and purified by column chromatography with CH$_2$Cl$_2$:CH$_3$OH=50:1 to 30:1 to obtain the title product as white solid (60 mg, yield: 13.4%). The structure was confirmed by $^1$H NMR and LC-MS, Purity: 95.7% by HPLC, shown as follows:

$^1$H NMR (400 MHz, CDCl$_3$): 7.76-7.69 (m, 3H); 7.54-7.51 (m, 3H); 7.15-7.05 (m, 3H); 3.88 (d, J=12.0 Hz, 2H); 3.37 (s, 2H); 3.10-3.09 (m, 1H); 2.91-2.85 (m, 3H); 2.77-2.72 (m, 1H); 2.42 (t, J=13.2 Hz, 2H); 2.12-2.03 (m, 2H); 1.92-1.89 (m, 1H); 1.81-1.78 (m, 1H); 1.68-1.56 (m, 2H); calcd for C$_{23}$H$_{27}$N$_3$O$_3$S (m/z): 425.18. found: 426.4 [M+1]$^+$.

Preparation of Compound C0137M

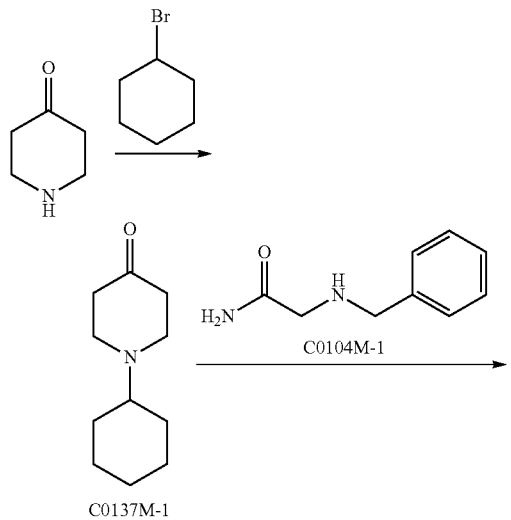

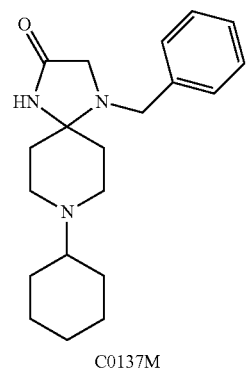

a. Preparation of Compound C0137M-1

Piperidin-4-one hydrochloride monohydrate (2.9 g) was added in 50 mL of acetonitrile and then 7.53 g of K$_2$CO$_3$ and 4.28 g of bromocyclohexane was added. The mixture was heated to reflux overnight (about 18 hours). The mixture was filtered and the filtrate was evaporated to dryness. The residue was diluted with CH$_2$Cl$_2$ and washed with water (3×) and brine. The organic layer was dried over Na$_2$SO$_4$ and evaporated to dryness to obtain 300 mg of the crude product as yellow solid (yield: 6%). The residue was washed with 40 mL of diethyl ether and filtered to obtain 150 mg of yellow solid (yield: 3%). The diethyl ether, which was used to wash the residue, was evaporated and 150 mg of yellow oil was obtained (yield: 3%)

b. Preparation of Compound C0137M

A solution of C0137M-1 (150 mg, 0.83 mmol), C0104M-1 (272 mg, 1.66 mmol) and p-toluenesulfonic acid monohydrate (8 mg, 0.0415 mmol) in CH$_3$OH (4 mL) was heated to reflux overnight (about 18 hours). The reaction solution was cooled to room temperature and the white solid was filtered and washed with CH$_3$OH dried in vacuo to obtain 55 mg of the impure product as white solid. The impure product was purified by preparative-HPLC to obtain the title product as white solid (13 mg, yield: 4.8%). The structure was confirmed by $^1$H NMR & LC-MS, (target M+1=328), purity: 98.8%.

$^1$H NMR (400 MHz, CDCl$_3$): 7.35-7.29 (m, 5H); 6.92 (s, 1H); 3.75 (s, 2H); 3.20 (s, 2H); 3.00 (d, J=11.2 Hz, 2H); 2.30 (m, 3H), 2.04 (dt, J=12.4, 4.0 Hz, 2H), 1.86-1.78 (m, 4H), 1.71 (d, J=11.4, 2H), 1.20 (m, 6H); MS (ESI) calcd for C$_{20}$H$_{29}$N$_3$O (m/z):327.46. found: 328.4 [M+1]$^+$.

Preparation of Compound C0141M-2

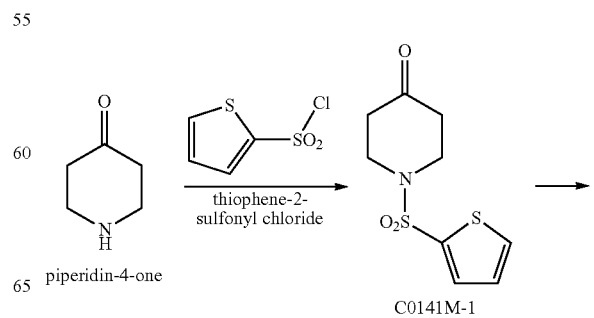

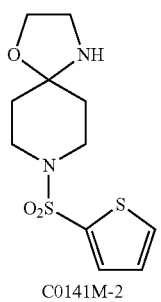

C0141M-2 a. Preparation of Compound C0141M-1

Piperidin-4-one (0.5 g) was dissolved in 25 mL of CHCl₃ and 1.4 mL of triethylamine was added. Then 915 mg of thiophene-2-sulfonyl chloride was added and the mixture was stirred at 70° C. overnight (about 18 hours). The solution was diluted with 50 mL of CHCl₃ and washed 0.1 M HCl (aq, 50 mL×3) and brine. The organic layer was dried over Na₂SO₄ and evaporated to obtain the title product as yellow solid (1.025 g, yield: 83.7%).

b. Preparation of Compound C0141M-2

The solution of C0141M-1 (1.02 g, 4.18 mmol), 2-aminoethanol (4.8 mL, 83.6 mmol), and p-toluenesulfonic acid-.monohydrate (24 mg, 0.125 mmol) in ethanol (30 ml) was stirred at room temperature for 2 days. The reaction solution was evaporated and the residue was dissolved in CHCl₃ and washed with sat.NaHCO₃ (aq) for (6×) and brine. The organic layer was dried over Na₂SO₄ and evaporated to obtain the title product as yellow oil. (1.175 g, yield: 98%). The structure was confirmed by MS (target M+1=289) and ¹H NMR.

Preparation of Compound C0142

30 mL×3) and brine. The organic layer was dried over Na₂SO₄ and evaporated to obtain the title product as yellow solid (580 mg, yield: 85.4%)

c. Preparation of Compound C0142M

The solution of C0142M-1 (540 mg, 2 mmol) and C0142M-2 (352 mg, 4 mmol) in CH₃OH (10 ml) was heated to reflux overnight. The reaction solution was cooled to RT and evaporated to dryness. The residue was purified by chromatography eluted with CH₂Cl₂:CH₃OH=50:1 to 10:1 to obtain the title product as white solid (32 mg, yield: 5%). The structure was confirmed by NMR & LC-MS (target M+1=340), purity: 98.2% by HPLC.

¹H NMR (400 MHz, CDCl₃): 7.70 (d, J=8.8 Hz, 2H); 7.01 (d, J=8.8 Hz, 2H); 6.10 (s, 1H); 3.89 (s, 3H); 3.46 (d, J=11.6 Hz, 2H); 2.99 (t, J=6.0 Hz, 2H); 2.80 (t, J=9.8 Hz, 2H); 2.28 (t, J=6.0 Hz, 2H); 1.87-1.78 (m, 4H); MS (ESI) calcd for C₁₅H₂₁N₃O₄S (m/z): 339.13. found: 340.4 [M+1]⁺.

Preparation of Compound C0143M

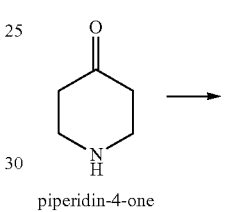

piperidin-4-one

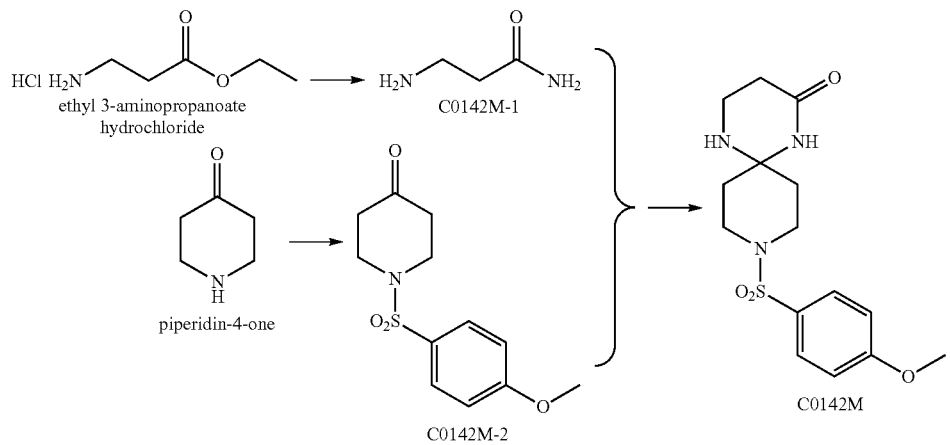

a. Preparation of Compound C0142M-1

Ethyl 3-aminopropanoate hydrochloride (5 g) was added to 50 mL of saturated NH₄OH (aq). The mixture was stirred at room temperature overnight (about 18 hours). Then the mixture was washed with CH₂Cl₂:CH₃OH=10:1 (6×). The resulting water layer was evaporated to obtain the title product as white solid (4.5 g; yield: 98%). The structure was confirmed by H NMR and LC-MS (target M+1=89)

b. Preparation of Compound C0142M-2

Piperidin-4-one (250 mg) was dissolved in 15 mL of CHCl₃ and 0.7 mL of triethylamine was added. Then 522 mg of 4-methoxybenzene-1-sulfonyl chloride was added and the mixture was stirred at 70° C. overnight. The solution was diluted with 30 mL of CHCl₃ and washed with 0.1 M HCl (aq, -continued

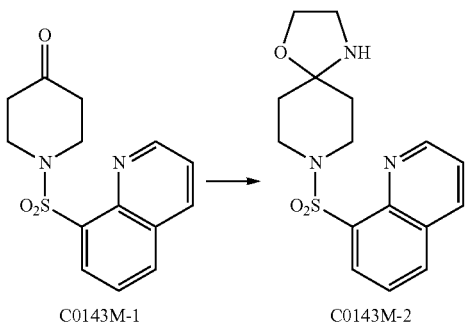

C0143M-1   C0143M-2 a. Preparation of Compound C0143M-1

8-Quinolinesulfonyl chloride (1.1 g, 4.8 mmol) and triethylamine (808 mg, 8 mmol) was added to a solution of piperidin-4-one (400 mg, 4 mmol) in CHCl$_3$ (20 mL). The mixture was stirred at room temperature overnight (about 18 hours). The mixture was diluted with CHCl$_3$, and washed with H$_2$O (10 mL×3) and 0.1N HCl (10 mL×3), dried over Na$_2$SO$_4$ and concentrated to give the title product as yellow solid (1.01 g, yield: 87%).

b. Preparation of Compound C0143M-2 p-Toluenesulfonic acid monohydrate (20 mg) and 2-aminoethanol (2.13 g, 35 mmol) was added to a solution of compound C0143M-1 (1.01 g, 3.5 mmol) in ethanol (30 mL). The mixture was stirred at room temperature overnight (about 18 hours). The mixture was concentrated in vacuo to dryness; the residue was diluted with dichloromethane, washed with saturated Na$_2$CO$_3$, dried over Na$_2$SO$_4$ and concentrated in vacuo to give the crude product as yellow solid (783 mg, yield: 67.2%).

Preparation of Compound C0144M-2

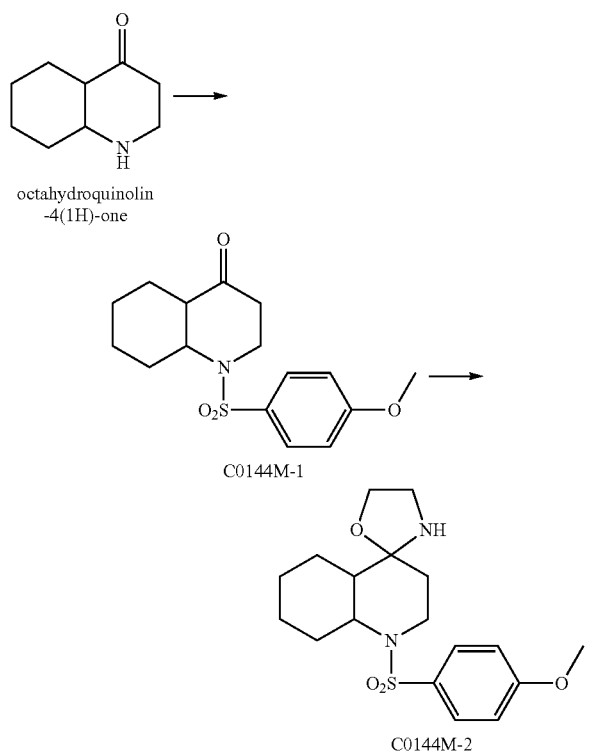

a. Preparation of Compound C0144M-1

4-Methoxybenzenesulfonyl chloride (453 mg, 2.2 mmol) and triethylamine (404 mg, 4 mmol) were added to a solution of octahydroquinolin-4(1H)-one (306 mg, 2 mmol) in CHCl$_3$ (15 mL). The mixture was stirred at room temperature overnight (about 18 hours). The mixture was diluted with CHCl$_3$, and washed with H$_2$O (10 mL×3) and 0.1N HCl (10 mL×3), dried over Na$_2$SO$_4$ and concentrated to give the title product as yellow oil (612 mg, yield: 95%).

b. Preparation of Compound C0144M-2 p-Toluenesulfonic acid monohydrate (10 mg) and 2-aminoethanol (1.15 g, 18.9 mmol) were added to a solution of compound C0144M-1 (612 mg, 1.89 mmol) in ethanol (20 mL). The mixture was stirred at room temperature overnight (about 18 hours). The mixture was concentrated in vacuo to dryness, the residue was diluted with dichloromethane, washed with saturated Na$_2$CO$_3$, dried over Na$_2$SO$_4$ and concentrated in vacuo to give the crude product as yellow gum (556 mg, yield: 80.4%).

Preparation of Compound C0145M

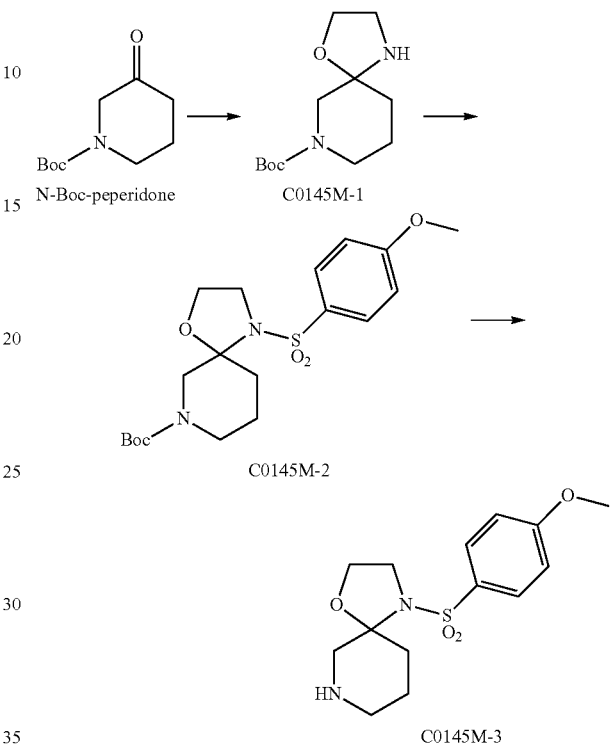

a. Preparation of Compound C0145M-1

A solution of N-Boc-piperidin-4-one (500 mg, 2.67 mmol) and 2-aminoethanol (0.55 mL, 9.34 mmol) in ethanol (4 mL) was stirred at room temperature overnight (about 18 hours). The solvent was removed under reduced pressure. The residue was diluted with CH$_2$Cl$_2$ (50 mL) and washed with saturated aqueous Na$_2$CO$_3$ (30 mL×6). The organic phase was dried over anhydrous Na$_2$SO$_4$, then concentrated to give target product as yellow oil (614 mg; yield: 95%).

b. Preparation of Compound C0145M-2

4-Methoxybenzene-1-sulfonyl chloride (626 mg, 3.04 mmol) and triethylamine (0.7 mL) were added to a solution of compound C0145M-1 (614 mg, 2.53 mmol) in chloroform (5 mL). The mixture was stirred at room temperature overnight (about 18 hours). The solvent was removed under reduced pressure. The residue was purified by column chromatography (petroleum ether:dichloromethane=1:1) to obtain target product as white solid (500 mg; yield: 48%).

c. Preparation of Compound C0145M-3

CF$_3$COOH (0.6 mL) was added to the solution of compound C0145M-2 (500 mg, 1.21 mmol) in 6 mL dichloromethane and the mixture was kept stirring for 0.5 hour at room temperature. Then CH$_3$CH$_2$OH/NH$_3$ (20 mL) was added to the reaction mixture. The solvent was removed under reduced pressure. The residue was diluted with dichloromethane (20 mL) and the white solid was precipitated. TLC showed that the solid was CF$_3$COONH$_4$. Then the mixture was filtered and the filtrate was concentrated. The residue was purified by column chromatography (CH$_2$Cl$_2$:CH$_3$OH=10:1) to obtain the product as yellow solid (290 mg; yield: 76%).

Preparation of Compound C0149M-2

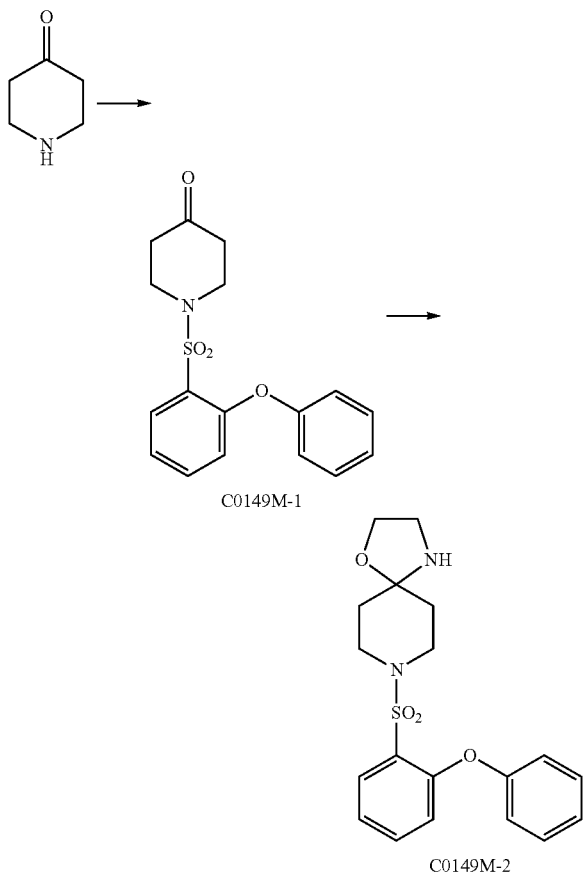

a. Preparation of Compound C0149M-1

4-Phenoxybenzenesulfonyl chloride (500 mg, 1.86 mmol) and triethylamine (404 mg, 4 mmol) were added to a solution of piperidin-4-one (202 mg, 2.05 mmol) in $CHCl_3$ (7 mL). The mixture was stirred at room temperature overnight (about 18 hours). The mixture was diluted with $CHCl_3$, and washed with $H_2O$ (10 mL×3) and 0.1 N HCl (10 mL×3), dried over $Na_2SO_4$ and concentrated to give 417 mg of the title product (67.8% yield).

b. Preparation of Compound C0149M-2

To a solution of C0149M-1 (417 mg, 1.26 mmol) in ethanol (15 mL) was added p-toluenesulfonic acid monohydrate (10 mg) and 2-aminoethanol (769 mg, 12.6 mmol). The mixture was stirred at room temperature overnight (about 18 hours). The mixture was concentrated in vacuo to dryness, the residue was diluted with $CH_2Cl_2$, washed with saturated $Na_2CO_3$, dried over $Na_2SO_4$ and concentrated in vacuo to give the crude product as white solid (434 mg, yield: 92.3%).

Preparation of Compound C0150M-2

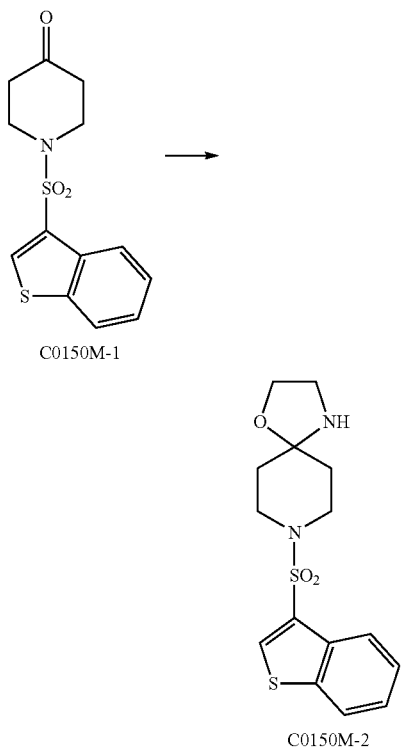

a. Preparation of Compound C0150M-1

A solution of piperidin-4-one (47 mg, 0.47 mmol) in chloroform (3 mL) was treated with 1-benzothiophene-3-sulfonyl chloride (100 mg, 0.43 mmol) and triethylamine (0.12 mL). The mixture was stirred at room temperature overnight (about 18 hours). Then, the solvent was removed under reduced pressure. The residue was diluted in dichloromethane (30 mL). The solution was washed by 0.1 N HCl (30 mL×2) and brine. The organic phase was dried over anhydrous $Na_2SO_4$ and concentrated to obtain target product as light yellow solid (120 mg; yield: 94%).

b. Preparation of Compound C0150M-2

A solution of C0150M-1 (217 mg, 0.74 mmol) in ethanol (10 mL) was treated with p-toluenesulfonic acid monohydrate (6 mg) and 2-aminoethanol (452 mg, 7.4 mmol). The mixture was stirred at room temperature for 5 hours. The mixture was concentrated in vacuo to dryness, the residue was diluted with dichloromethane, washed with saturated $Na_2CO_3$, dried over $Na_2SO_4$ and concentrated in vacuo to give the crude product as light yellow solid (228 mg, yield: 91.2%)

Preparation of Compound C0151M-2 piperidin-4-one

-continued

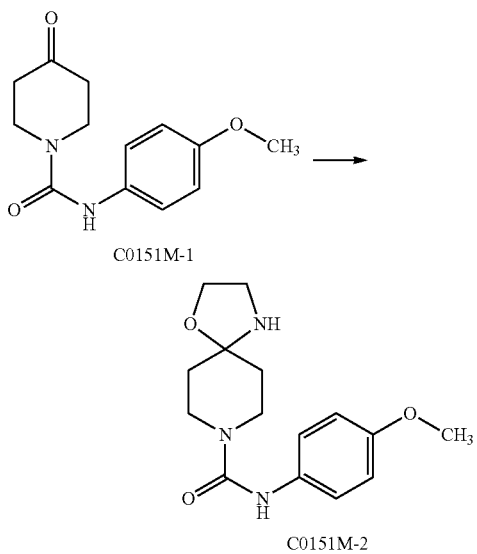

C0151M-1

C0151M-2 a. Preparation of Compound C0151M-1

A mixture of piperidin-4-one (643 mg, 6.5 mmol) and 1-isocyanato-4-methoxybenzene (500 mg, 3.4 mmol) and $K_2CO_3$ (1.1 g, 8.0 mmol) in $CH_2Cl_2$ (20 mL) was stirred overnight (about 18 hours) at room temperature. To the reaction mixture was added 5 mL water and the water phase was extracted with $CH_2Cl_2$. The combined organic layer was washed with 1 N HCl and brine, dried, and concentrated to obtain the product (800 mg, yield: 96%).

b. Preparation of Compound C0151M-2

To a solution of C0151M-1 (0.5 g, 2.0 mmol) in ethanol (5.0 mL) was added ethanolamine (0.4 mL). The mixture was stirred at room temperature for 4 hours. Then the solvent was removed under reduced pressure. The residue was diluted with $CH_2Cl_2$ and washed with saturated aqueous $Na_2CO_3$. The organic phase was dried over anhydrous $Na_2SO_4$, and concentrated to obtain the title product as white solid (530 mg, yield: 90%).

Preparation of Compound C0152M-4

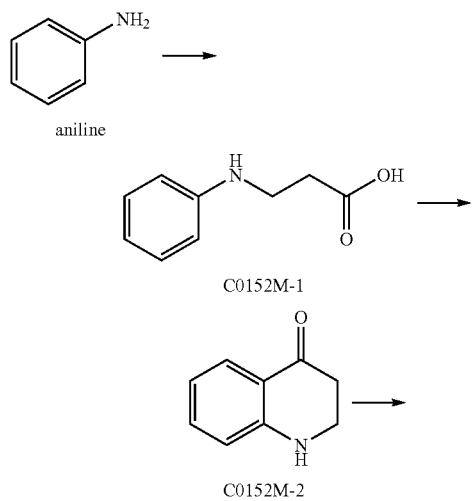

aniline

C0152M-1

C0152M-2

-continued

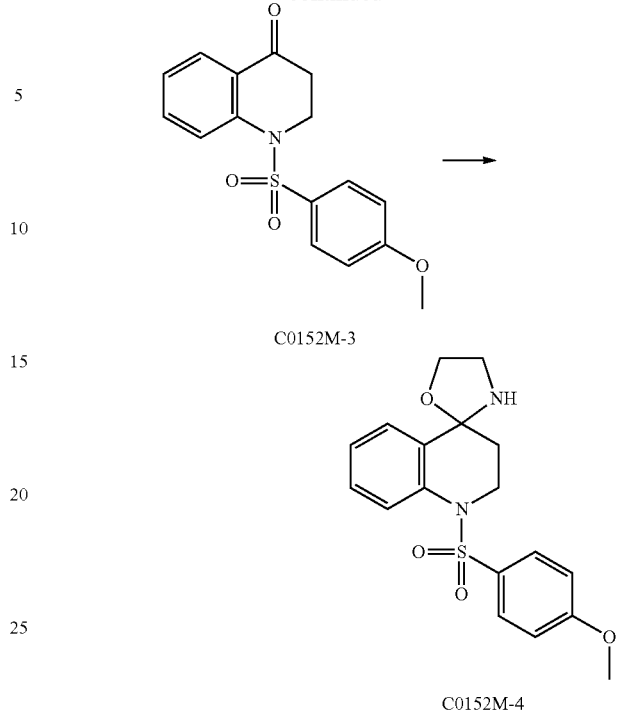

C0152M-3

C0152M-4 a. Preparation of Compound C0152M-1

A mixture of aniline (5 g, 53.8 mmol), 3-bromopropanoic acid (8.2 g, 53.8 mmol), triethylamine (10.8 g, 107.6 mmol), sodium iodide (0.05 g), and tetrahydrofuran (50 mL) was stirred at reflux overnight (about 18 hours). The reaction mixture was cooled down and filtered. The filtrate was concentrated under reduced pressure. The residue was diluted with dichloromethane (DCM) (100 mL) and washed with water once. The organic phase was dried over anhydrous $Na_2SO_4$ and concentrated. The residue was purified by column chromatography ($CH_2Cl_2$:$CH_3OH$:$CH_3COOH$=200:1:1) to obtain compound C0152M-1 as brown oil (3 g; yield: 33%)

b. Preparation of Compound C0152M-2

Compound C0152M-1 (1.5 g, 9 mmol) and polyphosphoric acid (1.5 g) were heated at 100° C. for 1 hour. After cooling to 0° C., ice-water was added into the reaction mixture. The aqueous phase was neutralized to pH 7 with saturated aqueous $KHCO_3$ at 0° C. and basified to pH 12 with saturated aqueous $K_2CO_3$. The aqueous layer was extracted with dichloromethane (150 mL×4). The organic layer were dried over anhydrous $Na_2SO_4$, filtered, and evaporated under reduced pressure to give a crude product which was purified by column chromatography (petroleum ether:ethyl acetate=5:1) to give product as yellow oil (94 mg; yield: 7.1%)

c. Preparation of Compound C0152M-3

To a solution of compound C0152M-2 (160 mg, 1.08 mmol) in pyridine (5 mL) was added 4-methoxy-benzene-1-sulfonyl chloride (159 mg, 0.77 mmol). The mixture was stirred at room temperature overnight (about 18 hours). The solvent was removed under reduced pressure. The residue was diluted in dichloromethane (30 mL). The solution was washed by 0.1 N HCl (30 mL×3) and brine. The organic phase was dried over anhydrous $Na_2SO_4$ and concentrated to obtain the crude product. The crude product was purified by column chromatography (petroleum ether:ethyl acetate=5:1) to obtain the title product as white solid (130 mg; yield: 64%)

d. Preparation of Compound C0152M-4

To a solution of C0152M-3 (170 mg, 0.536 mmol) and 2-aminoethanol (327 mg, 5.36 mmol) in ethanol (10 mL) was add 4-methylbenzenesulfonic acid monohydrate (3 mg, 0.016 mmol). The reaction was stirred at room temperature overnight (about 18 hours). The solvent was removed under reduced pressure. The residue was diluted with $CH_2Cl_2$ (50 mL) and washed with saturated aqueous $Na_2CO_3$ (30 ml×6). The organic phase was dried over anhydrous $Na_2SO_4$, then concentrated to give compound C0152M-4 as yellow solid (175 mg; yield: 90%)

Preparation of Compound C0153M

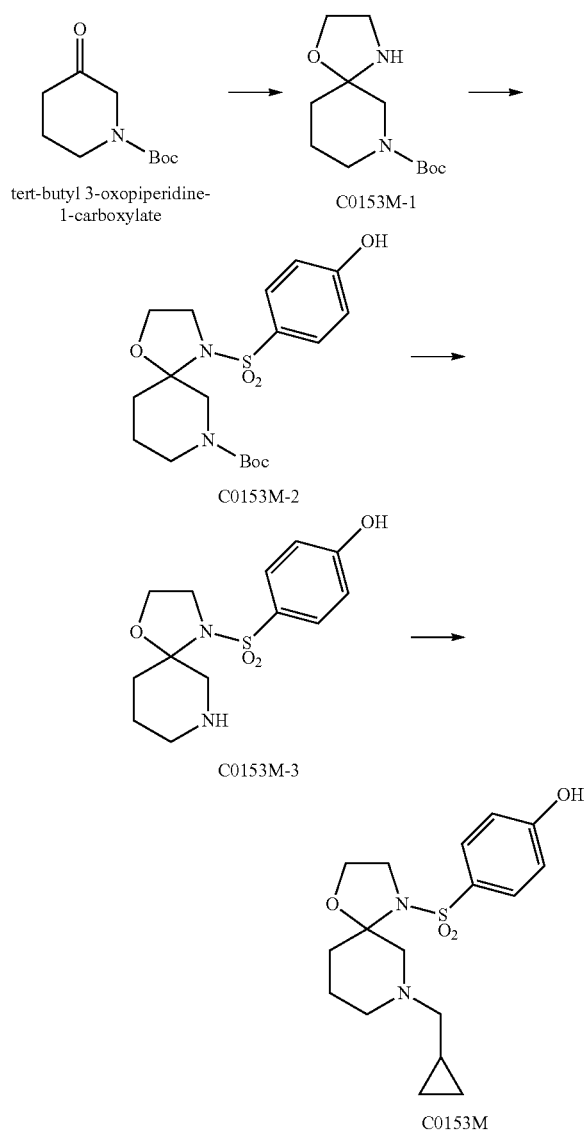

a. Preparation of Compound C0153M-1 t-Butyl-3-oxopiperidine-1-carboxylate (560 mg, 2.8 mmol) and 2-aminoethanol (599 mg, 9.8 mmol) in ethanol (4 mL) were stirred at room temperature overnight (about 18 hours). The reaction solution was evaporated and the residue was dissolved in dichloromethane and washed with saturated $Na_2CO_3$ (aq) (6×) and brine. The organic layer was dried over $Na_2SO_4$ and evaporated to obtain the title product as yellow oil (640 mg, yield: 94%.

b. Preparation of Compound C0153M-2

233 mg of C0153M-1 was dissolved in 1 mL of pyridine. A solution of 222 mg of 4-hydroxybenzene-1-sulfonyl chloride in 0.5 mL of pyridine was added and the mixture was stirred at room temperature overnight (about 18 hours).

Preparation of Compound C0153M-6

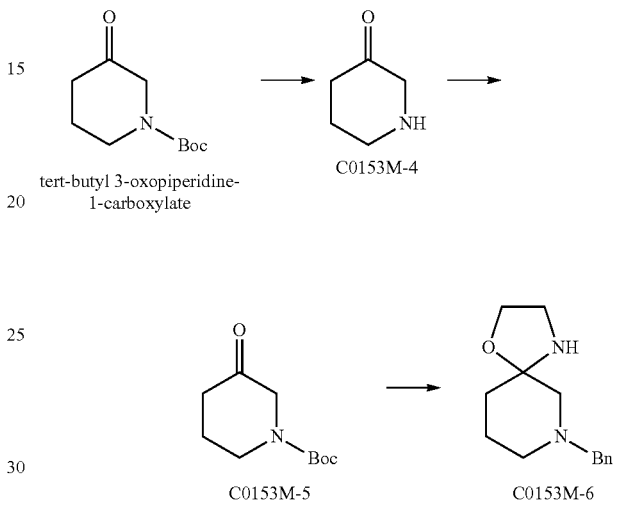

a. Preparation of Compound C0153M-4

A solution of tert-butyl 3-oxopiperidine-1-carboxylate (500 mg, 2.51 mmol) in $HCl/CH_3OH$ (12.5 mL) was heated to reflux for 0.5 hours. The solution was cooled to room temperature and evaporated to dryness to obtain the HCl salt of the title compound as yellow solid (330 mg, yield: 97%).

b. Preparation of Compound C0153M-5

Piperidin-3-one hydrochloride (330 mg) was added to 10 mL of acetonitrile. Then, 1.38 g of $K_2CO_3$ and 855 mg of bromobenzene were added to the solution. The mixture was heated at reflux overnight (about 18 hours). The mixture was filtered and the filtrate was evaporated to dryness. The residue was purified by chromatography eluted with dichloromethane:methanol=30:1 to obtain the title product as yellow oil (260 mg, yield: 58.3%).

c. Preparation of Compound C0153M-6

The solution of C0153M-5 (250 mg, 1.32 mmol), 2-aminoethanol (282 mg, 4.62 mmol) in $CH_3CH_2OH$ (3 mL) was stirred at room temperature overnight (about 18 hours). The reaction solution was evaporated to dryness and the residue was dissolved in dichloromethane and washed with saturated $Na_2CO_3$ (aq) (6×) and brine. The organic layer was dried over $Na_2SO_4$ and evaporated to dryness to obtain the title product as a yellow oil (301 mg, yield: 98%).

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed is:

1. A compound or its pharmaceutically acceptable salt that corresponds in structure to Formula III, wherein Z is C(O) and Q is CH$_2$,

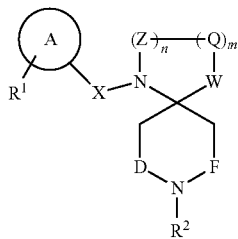

III wherein D and F are the same or different and are CH$_2$, CH(deuterium) or C(deuterium)$_2$, each of m and n is one, W is NR$^7$, X is CH$_2$, circle A is an aromatic or heteroaromatic ring system containing one ring or two fused rings;

R$^1$ is H,

R$^2$ is C(H)$_v$(deuterium)$_h$ where each of v and h is 0, 1, 2 or 3 and v+h=3, or C(H)$_q$(deuterium)$_r$-aliphatic C$_1$-C$_5$ hydrocarbyl where each of q and r is 0, 1, or 2 and q+r=0, 1 or 2, and R$^7$ is H.

2. The compound or its pharmaceutically acceptable salt according to claim 1, wherein said compound corresponds in structure to a formula selected from the group consisting of:

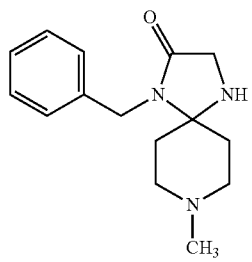

or

-continued

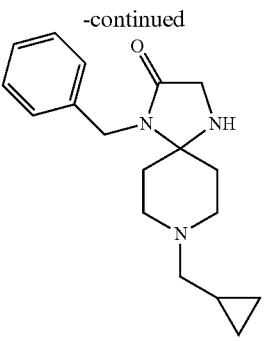

3. A pharmaceutical composition comprising an analgesic effective amount of a compound of claim 1 dissolved or dispersed in a physiologically tolerable carrier.

4. A compound or its pharmaceutically acceptable salt, wherein said compound corresponds in structure to the formula

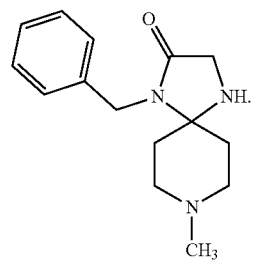 [SMILES: CN1CCC2(CC1)NCC(=O)N2Cc1ccccc1]

5. A compound or its pharmaceutically acceptable salt, wherein said compound corresponds in structure to the formula

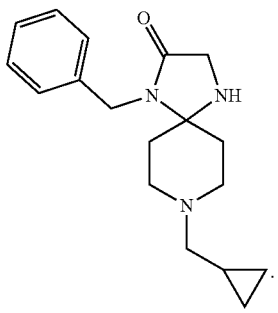 [SMILES: O=C1CNC2(CCN(CC3CC3)CC2)N1Cc1ccccc1]

* * * * *